US012691124B2

(12) United States Patent
Schaefer et al.

(10) Patent No.: US 12,691,124 B2
(45) Date of Patent: Jul. 28, 2026

(54) METHODS OF CONTROLLING AND IMPROVING BRAIN HEALTH

(71) Applicants: ICAHN SCHOOL OF MEDICINE AT MOUNT SINAI, New York, NY (US); THE ROCKEFELLER UNIVERSITY, New York, NY (US)

(72) Inventors: Anne Schaefer, New York, NY (US); Josefa Sullivan, New York, NY (US); Alexander Tarakhovsky, Amagansett, NY (US); Uwe Schaefer, New York, NY (US); Tuo Zhang, New York, NY (US)

(73) Assignees: Icahn School of Medicine at Mount Sinai, New York, NY (US); The Rockefeller University, New York, NY (US)

( * ) Notice: Subject to any disclaimer, the term of this patent is extended or adjusted under 35 U.S.C. 154(b) by 887 days.

(21) Appl. No.: 17/608,085

(22) PCT Filed: May 4, 2020

(86) PCT No.: PCT/US2020/031321
§ 371 (c)(1),
(2) Date: Nov. 1, 2021

(87) PCT Pub. No.: WO2020/227213
PCT Pub. Date: Nov. 12, 2020

(65) Prior Publication Data
US 2022/0305027 A1     Sep. 29, 2022

Related U.S. Application Data

(60) Provisional application No. 62/842,979, filed on May 3, 2019.

(51) Int. Cl.
| | |
|---|---|
| *A61K 31/5517* | (2006.01) |
| *A61K 31/437* | (2006.01) |
| *A61K 31/444* | (2006.01) |
| *A61K 31/4709* | (2006.01) |
| *A61K 31/472* | (2006.01) |
| *A61K 31/519* | (2006.01) |
| *A61K 31/538* | (2006.01) |
| *A61K 31/55* | (2006.01) |
| *A61K 31/551* | (2006.01) |
| *A61P 25/28* | (2006.01) |

(52) U.S. Cl.
CPC ........ *A61K 31/5517* (2013.01); *A61K 31/437* (2013.01); *A61K 31/444* (2013.01); *A61K 31/4709* (2013.01); *A61K 31/472* (2013.01); *A61K 31/519* (2013.01); *A61K 31/538* (2013.01); *A61K 31/55* (2013.01); *A61K 31/551* (2013.01); *A61P 25/28* (2018.01)

(58) Field of Classification Search
CPC .............. A61K 31/5517; A61K 31/437; A61K 31/444; A61K 31/4709; A61K 31/472; A61K 31/519; A61K 31/538; A61K 31/55; A61K 31/551; A61P 25/28
USPC ......................................................... 514/215
See application file for complete search history.

(56) References Cited

FOREIGN PATENT DOCUMENTS

| | | |
|---|---|---|
| WO | 2015/173133 A1 | 11/2015 |
| WO | 2016/196065 A1 | 12/2016 |
| WO | 2017031416 A1 | 2/2017 |

OTHER PUBLICATIONS

Sullivan et al., "Autism-Like Syndrome Is Induced By Pharmacological Suppression Of BET Proteins In Young Mice", J Exp Med (Sep. 15, 2015) 212 (11): 1771-1781 https://doi.org/10.1084/jem.20151271). (Year: 2015).*
Magistri et al., "The BET-Bromodomain Inhibitor JQ1 Reduces Inflammation and Tau Phosphorylation at Ser396 in the Brain of the 3xTg Model of Alzheimer's Disease", Current Alzheimer Research, 2016, 13, 985-995 (Year: 2016).*
Nicodeme et al., "Suppression of Inflammation By A Synthetic Histone Mimic" Nature. Dec. 23, 2010; 468(7327): 1119-1123. doi:10.1038/nature09589. (Year: 2010).*
International Search Report and Written Opinion for International Application No. PCT/US2020/031321 (mailed Aug. 17, 2020).
Sullivan et al., "Autism-Like Syndrome is Induced by Pharmacological Suppression of BET Proteins in Young Mice," The Journal of Experimental Medicine 212(11):1771-1781 (2015).
Magistri et al., "The BET-Bromodomain Inhibitor JQ1 Reduces Inflammation and Tau Phosphorylation at Ser396 in the Brain of the 3xTg Model of Alzheimer's Disease," Current Alzheimer Research 13:985-995 (2016).
Li et al., "BET Bromodomain Inhibition Promotes Neurogenesis While Inhibiting Gliogenesis in Neural Progenitor Cells," Stem Cell Research 17(2):212-221 (2016).
Nicodeme et al., "Suppression of Inflammation by a Synthetic Histone Mimic," Nature 468:1119-1123 (2010).

* cited by examiner

*Primary Examiner* — Kortney L. Klinkel
*Assistant Examiner* — Grace Ching Hsu
(74) *Attorney, Agent, or Firm* — Heslin Rothenberg Farley & Mesiti P.C.

(57) ABSTRACT

The present disclosure relates to a method of inducing a neuroprotective state comprising administering a Bromodomain and Extra-Terminal motif (BET) inhibitor under conditions effective to induce a neuroprotective state. Also disclosed are methods of preventing and/or treating neurodegenerative disease, methods of reducing microglial inflammation, and methods of restoring microglial homeostasis, where the methods include administering a Bromodomain and Extra-Terminal motif (BET) inhibitor.

4 Claims, 64 Drawing Sheets

| H2A | H2B | H3 | H4 |

WRITERS          ERASERS          READERS

CHEMOTAXIS
NfkB SIGNALING

IMMUNE RESPONSE
RESPONSE TO CYTOKINE
INTERFERON RESPONSE
INTERLEUKIN SIGNALING
APOPTOSIS

LPS INDUCED (747)
I-BET858 UP (3)
I-BET858 DOWN (484)

LPS INDUCED (960)
I-BET858 UP (12)
I-BET858 DOWN (514)

LPS INDUCED (204)
I-BET858 DOWN (17)

EXPRESSION

MIN　　MAX

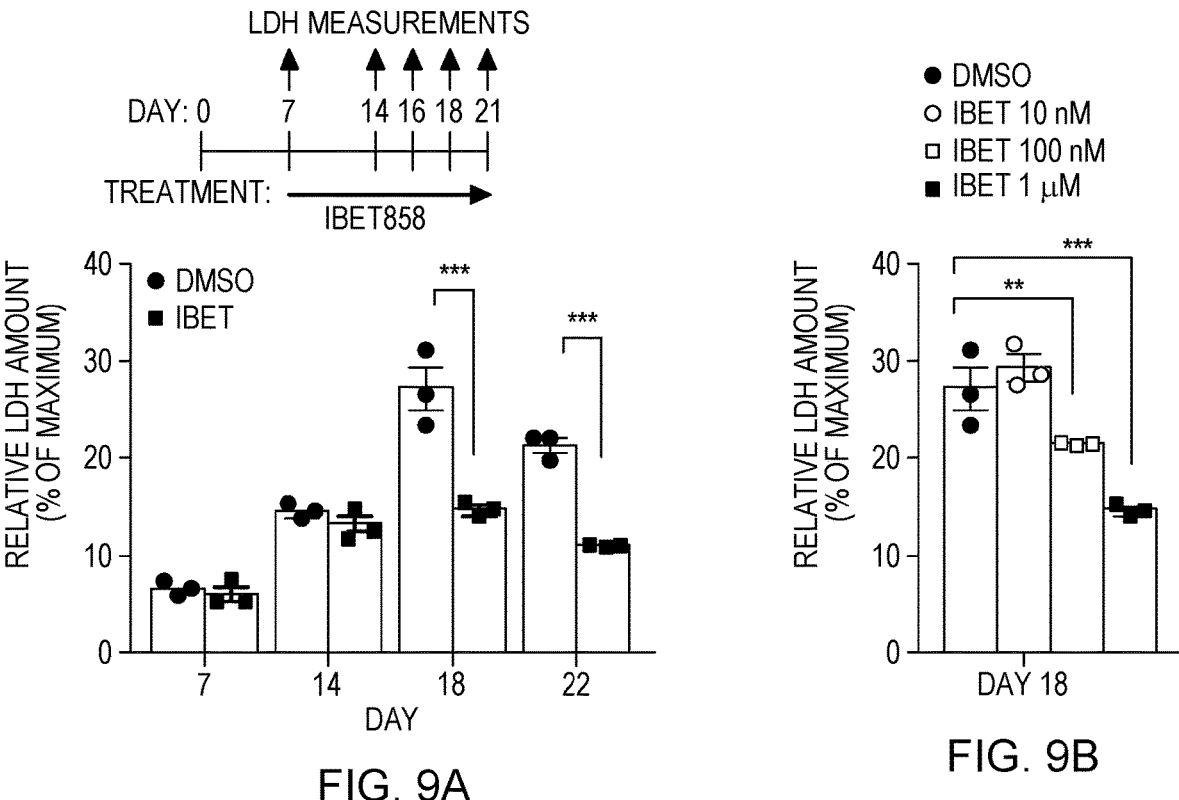
FIG. 9A
FIG. 9B
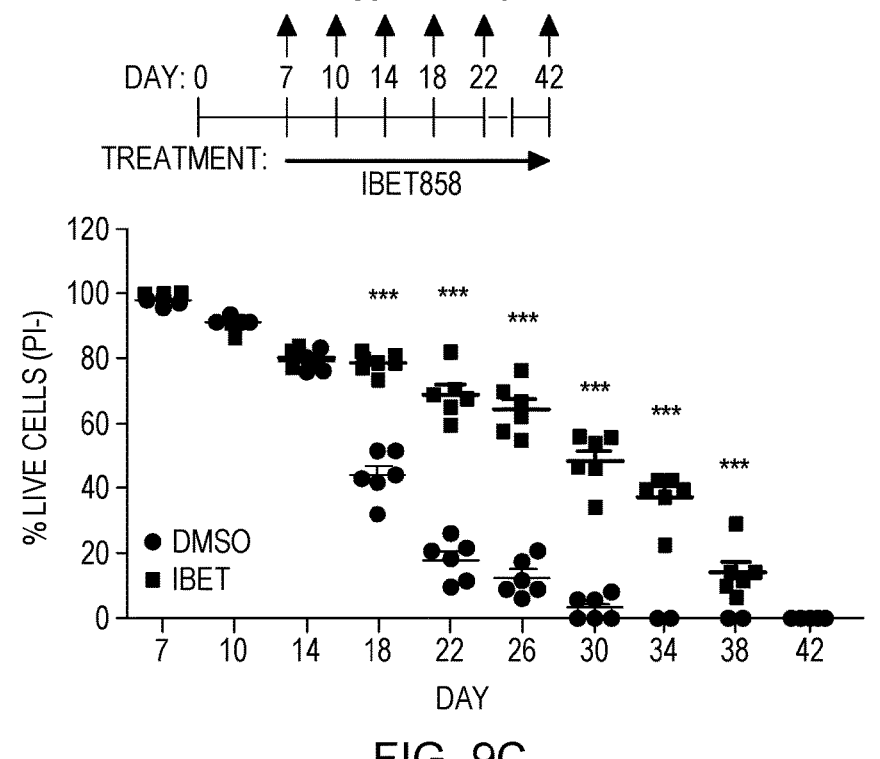
FIG. 9C

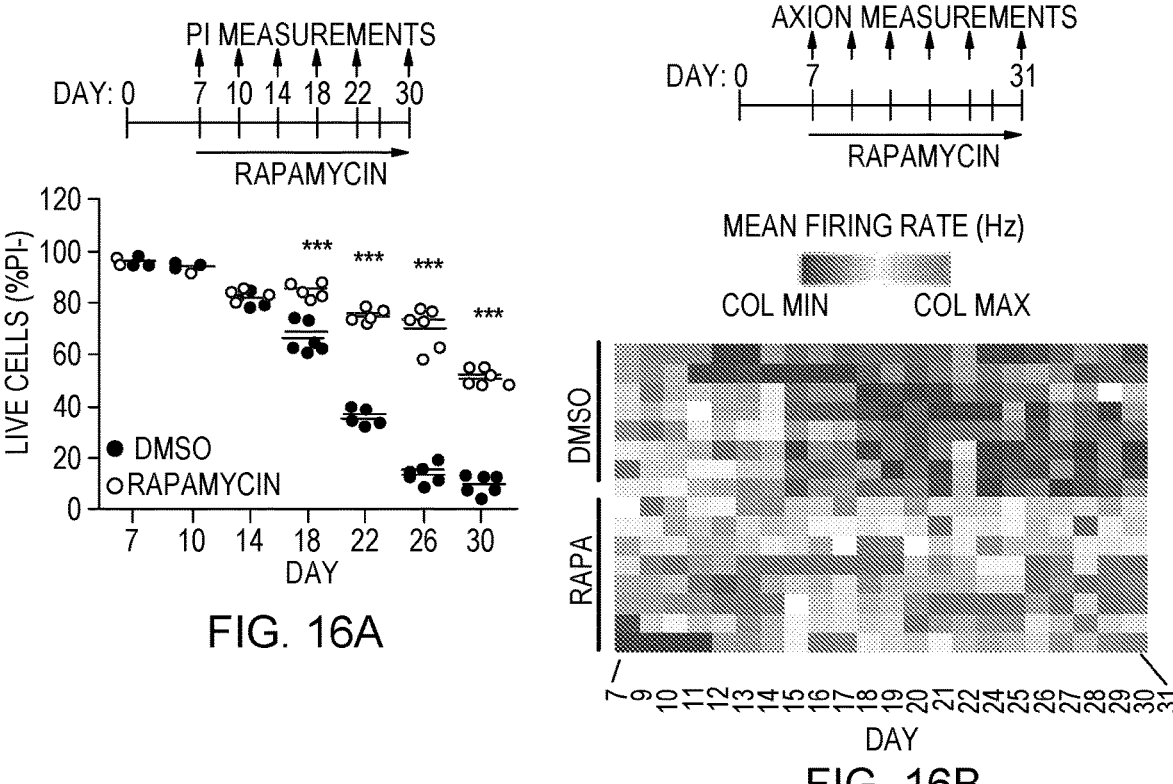
FIG. 16A
FIG. 16B
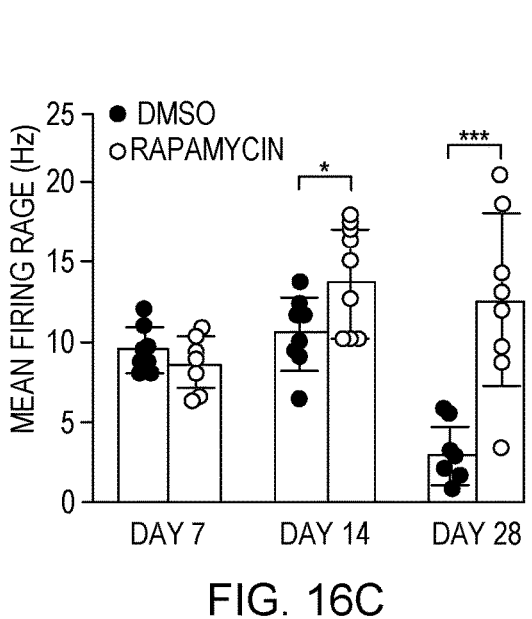
FIG. 16C
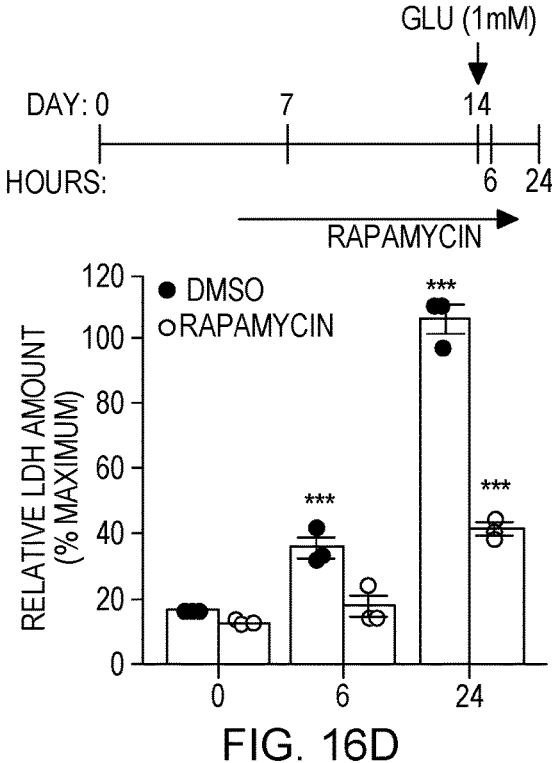
FIG. 16D

CASP 3
NS

CASP 3 (RPKM)

8

6

4

2

0
          CONTROL  IBET

-DOX   IBET (30 mg/kg IP)

AGE:           7    8         13

CONTROL + SALINE (n = 20)
CONTROL + IBET (n = 12)
CK-p25 + SALINE (n = 16)
CK-p25 + IBET (n = 15)

WT   P25   P25, IBET

α-GFP                          48 kDa

α-Gapdh                        37 kDa

200

150

100

50

0

NS

*          *

RELATIVE INTENSITY
(GFP/GAPDH)

WT   P25   P25,
                IBET 1.2

1.0

0.8

0.6

0.4

0.2

0

BRAIN WEIGHT
(% CONTROL)

***

IBET:   -        +        -        +
        CONTROL       CK-p25

METHODS OF CONTROLLING AND IMPROVING BRAIN HEALTH

This application is a national stage application under 35 U.S.C. § 371 of PCT Application No. PCT/US2020/031321, filed May 4, 2020, which claims benefit of U.S. Provisional Patent Application Ser. No. 62/842,979, filed May 3, 2019, each of which is hereby incorporated by reference in its entirety.

FIELD

The present disclosure relates generally to methods of controlling and improving brain health.

BACKGROUND

Gene transcription plays a major role in neuronal development and function. The acquisition of specific gene expression patterns during neuronal differentiation will determine the identity, morphology, and function of different neuron subtypes. Heiman et al., "A Translational Profiling Approach for the Molecular Characterization of CNS Cell Types," *Cell* 135:738-748 (2008) and Zeisel et al., "Molecular Architecture of the Mouse Nervous System Resource Molecular Architecture of the Mouse Nervous System," *Cell* 174:999-1014 (2018). For example, medium spiny neurons in the striatum are an intermingled population with nearly indistinguishable morphologies however gene expression analysis using ribosome profiling reveals two distinct cell types with differential transcriptomes. Heiman et al., "A Translational Profiling Approach for the Molecular Characterization of CNS Cell Types," *Cell* 135:738-748 (2008) and Doyle et al., "Application of a Translational Profiling Approach for the Comparative Analysis of CNS Cell Types," *Cell* 135:749-762 (2008). Single cell sequencing of the striatum further revealed that medium spiny neurons may have a higher degree of heterogeneity and exist as a continuous spectrum of functional states based on their transcriptional profiles. Gokce et al., "Cellular Taxonomy of the Mouse Striatum as Revealed by Single-Cell RNA-Seq," *Cell Reports* 16:1126-1137 (2016). This diversification is driven in part by the action of "terminal selector" transcription factors (TFs) that regulate cohorts of genes that drive neuronal identity. Hobert, "Regulatory Logic of Neuronal Diversity: Terminal Selector Genes and Selector Motifs," *Proceedings of the National Academy of Sciences of the United States of America* 105:20067-20071 (2008). In *Caenorhabditis elegans*, terminal selector TFs have been identified for over two-thirds of the 118 neuron classes (Hobert, "Terminal Selectors of Neuronal Identity," *Current Topics in Developmental Biology* 116:455-475 (2016) and Hobert, "Regulation of Terminal Differentiation Programs in the Nervous System," *Annual Review of Cell and Developmental Biology* 27:681-696 (2011)), although more work is required to understand how terminal selectors function in mammalian cells.

Highlighting this relationship between transcription and neurodevelopment, mutations in ubiquitously expressed transcriptional regulators or in non-coding regions have been causally linked to the development of Autism Spectrum Disorders (ASD). De Rubeis et al., "Synaptic, Transcriptional and Chromatin Genes Disrupted in Autism," *Nature* 515:209-215 (2014); An et al., "Genome-wide De Novo Risk Score Implicates Promoter Variation in Autism Spectrum Disorder," *Science* 362:eaat6576 (2018); Satterstrom et al., "Novel Genes for Autism Implicate Both Excitatory and Inhibitory Cell Lineages in Risk," *bioRxiv* 484113 (2018); and Iossifov et al., "De Novo Gene Disruptions in Children on the Autistic Spectrum," *Neuron* 74:285-299 (2012). Initially ASD was thought to be a synaptic disease (Zoghbi, "Postnatal Neurodevelopmental Disorders: Meeting at the Synapse?" *Science* 302:826-830 (2003)), but now more mutations have been identified in transcriptional regulator than synaptic genes. This indicates a potential causal role for gene transcription in ASD pathology where the disorder may be caused by a shift in the expression of global gene networks rather than alterations in a single pathway. Proper brain development therefore relies on tight transcriptional regulation of inducible genes to coordinate appropriate subtype specification and circuitry formation. Once these patterns are developed, they must be properly maintained, in neurons and in glia, throughout life to ensure normal brain health. Loss of this specification can lead to widespread brain dysfunction and degeneration. von Schimmelmann et al., "Polycomb Repressive Complex 2 (PRC2) Silences Genes Responsible for Neurodegeneration," *Nature Neuroscience* 19:1321-1330 (2016); Ayata et al., "Epigenetic Regulation of Brain Region-Specific Microglia Clearance Activity," *Nature Neuroscience* 21:1049-1060 (2018); Serrano-Saiz et al., "BRN3-type POU Homeobox Genes Maintain the Identity of Mature Postmitotic Neurons in Nematodes and Mice," *Current Biology* 28:2813-2823.e2 (2018); Wever et al., "EZH2 Influences mdDA Neuronal Differentiation, Maintenance and Survival," *Frontiers in Molecular Neuroscience* 11:491 (2019); and Hervás-Corpión et al., "Early Alteration of Epigenetic-Related Transcription in Huntington's Disease Mouse Models," *Science Reports* 8:9925 (2018). However, there is much that remains unknown about transcriptional regulation in the central nervous system.

DNA is the essential molecule in the cell that stores genetic information and passes it along to the next generation. It also provides the template for cellular functions by being copied into messenger RNA (mRNA) by RNA polymerases. The transcribed mRNA is then translated by the ribosome into proteins of diverse function and localization. Crick, "On Protein Synthesis," *Symposia of the Society for Experimental Biology* 12:138-163 (1958) and Crick, "Central Dogma of Molecular Biology," *Nature* 227:561-563 (1970). These key processes lay at the heart of all biological activity but each have their own challenges. In order to fit the length of the DNA strand into the nucleus, DNA is folded into an organized, three-dimensional structure. Aiding this process, 146 base pairs of DNA wraps 1.7 times around a protein complex termed the nucleosome. Richmond et al., "Structure of the Nucleosome Core Particle at 7 Å Resolution," *Nature* 311:532-537 (1984). The nucleosome is an octamer containing two copies of each core histone protein H2A, H2B, H3, and H4 which, due to their overall positive charge, tightly associate with negatively-charged DNA (Olins, A. L. and Olins, D. E., "Spheroid Chromatin Units (V Bodies)," *Science* 183:330-332 (1974)) (FIG. 1A). In eukaryotes, a fifth histone, H1, sits at the base of the nucleosome and binds to the entering and exiting DNA. This structure which Kornberg described as looking "rather like beads on a string," is the basic unit of chromatin and compacts DNA by 7-fold. Kornberg, "Chromatin Structure: A Repeating Unit of Histones and DNA," *Science* 184:868-871 (1974) and Finch and Klug, "Solenoidal Model for Superstructure in Chromatin," *Proceedings of the National Academy of Sciences of the United States of America* 73:1897-1901(1976). Present from archaea to eukaryotes, histones are among the most highly conserved proteins which illustrates their importance to cellular function. Chromatin exists as a continuum between two major states or phases, tightly compacted heterochromatin or loose euchromatin. In heterochromatin, the beads on the string condense further by a factor of 40 to form the solenoid, a secondary structure which comprises a 30 nm fiber of chromatin. Finch and Klug, "Solenoidal Model for Superstructure in Chromatin," *Proceedings of the National Academy of Sciences of the United States of America* 73:1897-1901 (1976). The nucleosome, while allowing for DNA compaction, presents a barrier for gene transcription. Heterochromatic DNA is inaccessible to the transcriptional machinery and is therefore transcriptionally inactive.

Even in euchromatin, nucleosomes can prevent gene transcription and need to be removed from promoters and gene bodies for transcription to proceed. Histones regulate gene transcription through an n-terminal domain that protrudes from the nucleosome core. This tail which is intrinsically disordered (Hansen et al., "Intrinsic Protein Disorder, Amino Acid Composition, and Histone Terminal Domains," *The Journal of Biological Chemistry* 281:1853-1856 (2006)) can be post-translationally modified with different moieties such as acetyl or methyl groups, to directly or indirectly alter nucleosome compaction (Bannister and Kouzarides, "Regulation of Chromatin by Histone Modifications," *Cell Research* 21:381-395 (2011)). Knowledge of these modifications continues to evolve as improving technologies identify novel histone marks such as acylation and monoaminylation. Chen et al., "Lysine Propionylation and Butyrylation are Novel Post-Translational Modifications in Histones," *Molecular & Cellular Proteomics* 6:812-819 (2007) and Farrelly et al., "Histone Serotonylation is a Permissive Modification that Enhances TFIID Binding to H3K4me3," *Nature* 567:535-539 (2019). The first modification identified and perhaps the best understood is histone acetylation. Phillips, "The Presence of Acetyl Groups of Histones," *The Biochemical Journal* 87:258-263 (1963) and Allfrey et al., "Acetylation and Methylation of Histones and Their Possible Role in the Regulation of Rna Synthesis," *Proceedings of the National Academy of Sciences of the United States of America* 51:786-794 (1964). When the histones tails are acetylated, the overall positive charge of the histone is reduced, decreasing the electrostatic interaction with DNA. In addition to direct structural changes, these modifications serve as a type of code, the so-called "histone code," for proteins to interact with the chromatin and regulate transcription. Jenuwein and Allis, "Translating the Histone Code," *Science* 293:1074-1080 (2001). Chromatin-interacting proteins can be grouped into three categories: writers which add modifications to histone tails (Taunton et al., "A Mammalian Histone Deacetylase Related to the Yeast Transcriptional Regulator Rpd3p," *Science* 272:408-411 (1996) and Brownell et al., "Tetrahymena Histone Acetyltransferase A: A Homolog to Yeast Gcn5p Linking Histone Acetylation to Gene Activation," *Cell* 84:843-851 (1996)), erasers which remove these marks, and readers which bind modifications to directly or indirectly modulate transcription (Tamkun et al., "Brahma: A Regulator of *Drosophila* Homeotic Genes Structurally Related to the Yeast Transcriptional Activator SNF2SWI2," *Cell* 68:561-572 (1992) and Dhalluin et al., "Structure and Ligand of a Histone Acetyltransferase Bromodomain," *Nature* 399:491-496 (1999)) (FIG. 1B). Together these proteins control the timing and specificity of gene transcription in response to diverse cellular stimuli by regulating protein interactions with the DNA, the most important being RNA polymerases.

While three classes of RNA polymerases transcribe various RNA species, RNA Polymerase II (RNAPII) catalyzes the transcription of messenger RNAs from the DNA template strand which are then translated into proteins by the ribosome. mRNA transcription occurs in three phases: initiation, elongation and termination. In order for gene transcription to occur, the promoter region must be cleared of nucleosomes to allow for the transcriptional machinery to bind (FIG. 1C). Once the promoter is free of nucleosomes, general transcription factors can recruit the polymerase to form the pre-initiation complex. In particular, TFIIH, dissociates the two DNA strands at the allowing PolII to initiate transcription. Kim et al., "Mechanism of ATP-dependent Promoter Melting by Transcription Factor IIH," *Science* 288:1418-1422 (2000).

Following these events, RNAPII will transcribe the first 20-120 nucleotides and then pause downstream of the transcriptional start site on the majority of metazoan genes (Rasmussen and Lis, "In Vivo Transcriptional Pausing and Cap Formation on Three *Drosophila* Heat Shock Genes," *Proceedings of the National Academy of Sciences of the United States of America* 90:7923-7927 (1993); Core et al., "Nascent RNA Sequencing Reveals Widespread Pausing and Divergent Initiation at Human Promoters," *Science* 322:1845-1848 (2008); Kwak et al., "Precise Maps of RNA Polymerase Reveal How Promoters Direct Initiation and Pausing," *Science* 339:950-953 (2013); and Nechaev et al., "Global Analysis of Short RNAs Reveals Widespread Promoter-Proximal Stalling and Arrest of Pol II in *Drosophila*," *Science* 327:335-338 (2010)) (FIG. 1D). In this initial elongation step, TFIIH phosphorylates the polymerase at Serine 5 and 7 of its c-terminal domain (CTD) to establish RNAPII pausing (Komarnitsky et al., "Different Phosphorylated Forms of RNA Polymerase II and Associated mRNA Processing Factors During Transcription," *Genes & Development* 14:2452-2460 (2000); Glover-Cutter et al., "TFIIH-Associated Cdk7 Kinase Functions in Phosphorylation of C-Terminal Domain Ser7 Residues, Promoter-Proximal Pausing, and Termination by RNA Polymerase II," *Molecular and Cellular Biology* 29:5455-5464 (2009); and Akhtar et al., "TFIIH Kinase Places Bivalent Marks on the Carboxy-Terminal Domain of RNA Polymerase II," *Molecular and Cellular Biology* 34:387-393 (2009)). The location of the downstream pausing site can vary based on polymerase escape speed and rate of pause factor recruitment as well as other undetermined factors. Kwak et al., "Precise Maps of RNA Polymerase Reveal How Promoters Direct Initiation and Pausing," *Science* 339:950-953 (2013). Two main factors NELF and DSIF also bind to RNAPII to prevent productive elongation. Wada et al., "DSIF, a Novel Transcription Elongation Factor that Regulates RNA Polymerase II Processivity, is Composed of Human Spt4 and Spt5 Homologs," *Genes & Development* 12:343-356 (1998); Yamaguchi et al., "NELF, a Multisubunit Complex Containing RD, Cooperates with DSIF to Repress RNA Polymerase II Elongation," *Cell* 97:41-51 (1999); Lee et al., "NELF and GAGA Factor Are Linked to Promoter-Proximal Pausing at Many Genes in *Drosophila*," *Molecular and Cellular Biology* 28:3290-3300 (2008); and Muse et al., "RNA Polymerase is Poised for Activation Across the Genome," *Nature Genetics* 39:1507-1511 (2007). RNAPII remains stably paused here and associated with the nascent RNA transcript awaiting further signals48.

In order for elongation to proceed, RNAPII must be phosphorylated at Ser2 of its CTD to be released from its pause site (Komarnitsky et al., "Different Phosphorylated Forms of RNA Polymerase II and Associated mRNA Processing Factors During Transcription," *Genes & Development* 14:2452-2460 (2000) and Ahn et al., "Phosphorylation of Serine 2 Within the RNA Polymerase II C-terminal Domain Couples Transcription and 3' End Processing," *Molecular Cell* 13:67-76 (2004)) (FIG. 1E). Additionally, phosphorylation of NELF and DSIF are also required alleviate pausing. Renner et al., "A Highly Purified RNA Polymerase II Elongation Control System," *The Journal of Biological Chemistry* 276:42601-42609 (2001); Wu et al., "NELF and DSIF Cause Promoter Proximal Pausing on the hsp70 Promoter in *Drosophila,"* *Genes & Development* 17:1402-1414 (2003); and Peterlin and Price, "Controlling the Elongation Phase of Transcription With P-TEFb," *Molecular Cell* 23:297-305 (2006). This is mainly accomplished by is positive transcription elongation factor b, P-TEFb. P-TEFb is a heterodimer of Cdk9 and either Cyclin T1, T2, or K which associates within three main complexes: the 7SK/Hexim1 snRNP, the super elongation complex (SEC), and a BET protein, Brd4. The 7SK complex represses transcription by sequestering P-TEFb via its interaction with Hexim1. Nguyen et al., "7SK Small Nuclear RNA Binds to and Inhibits the Activity of CDK9/cyclin T Complexes," *Nature* 414:322-325 (2001); Yang et al., "The 7SK Small Nuclear RNA Inhibits the CDK9/cyclin T1 Kinase to Control Transcription," *Nature* 414:317-322 (2001); and Michels et al., "MAQ1 and 7SK RNA Interact with CDK9/cyclin T Complexes in a Transcription-Dependent Manner," *Molecular and Cellular Biology* 23:4859-4869 (2003). Up to 90% of the total pool of P-TEFb is sequestered in the 7SK complex. Zhou et al., "RNA Polymerase II Elongation Control," *Annual Review of Biochemistry* 81:119-143 (2012). Therefore, active pools of P-TEFb are either associated with Brd4 (Jang et al., "The Bromodomain Protein Brd4 is a Positive Regulatory Component of P-TEFb and Stimulates RNA Polymerase II-dependent Transcription," *Molecular Cell* 19:523-534 (2005) and Yang et al., "Recruitment of P-TEFb for Stimulation of Transcriptional Elongation by the Bromodomain Protein Brd4," *Molecular Cell* 19:535-545 (2005)) or with SEC (Luo et al., "The Super Elongation Complex Family of RNA Polymerase II Elongation Factors: Gene Target Specificity and Transcriptional Output," *Molecular and Cellular Biology* 32:2608-2617 (2012)). Because interaction with Brd4 prevents P-TEFb from associating with the 7SK/Hexim1 complex, Brd4 can modulate the global levels of active P-TEFb within a cell which makes it a potent transcriptional regulator Wang et al., "The Bromodomain Protein Brd4 is a Positive Regulatory Component of P-TEFb and Stimulates RNA Polymerase II-dependent Transcription," *Molecular Cell* 19:523-534 (2005) and Yang et al., "Recruitment of P-TEFb for Stimulation of Transcriptional Elongation by the Bromodomain Protein Brd4," *Molecular Cell* 19:535-545 (2005)). This recruitment of P-TEFb to release RNAPII is required for transcriptional elongation to commence throughout the gene body. While much is known about the molecular dynamics of RNAPII function and regulation, many questions still exist as to how exactly a specific transcriptional responses is generated by a given stimulus. If the majority of genes have paused RNAPII, what triggers the expression of one gene over another? Additionally, do these regulatory mechanisms, identified in proliferating cells, also function similarly in postmitotic neurons?

The mammalian bromodomain and extraterminal domain containing protein (BET) family is comprised of four members, Brd2, Brd3, Brd4 and Brdt, which have diverse roles in the regulation of transcription. While expression of Brdt is restricted to the testes, the other BET family members are ubiquitously expressed in mouse and human somatic tissues including the brain (human protein atlas). The BET family is approximately 75% identical with each containing two tandem bromodomains, BD1 and BD2, and an extraterminal domain, ET (FIG. 2A). Filippakopoulos et al., "Histone Recognition and Large-scale Structural Analysis of the Human Bromodomain Family," *Cell* 149:214-231 (2012). Notably, the dominantly expressed Brd4 isoform has a unique, extended c-terminal domain that has been linked to multiple interaction partners which may confer additional functions that are distinct from other BET members. Bisgrove et al., "Conserved P-TEFb—Interacting Domain of BRD4 Inhibits HIV Transcription," *Proceedings of the National Academy of Sciences of the United States of America* 104:13690-13695 (2007).

The bromodomain was the first identified chromatin reader domain (Tamkun et al., "Brahma: A Regulator of *Drosophila* Homeotic Genes Structurally Related to the Yeast Transcriptional Activator SNF2SWI2," *Cell* 68:561-572 (1992) and Dhalluin et al., "Structure and Ligand of a Histone Acetyltransferase Bromodomain," *Nature* 399:491-496 (1999)) and comprises a ~110 amino acid protein domain that recognizes ε-N-lysine acetylation motifs on histones. Sixty-one bromodomains have been identified across 46 proteins in the human proteome which have diverse roles in the nucleus. Filippakopoulos and Knapp, "The Bromodomain Interaction Module," *FEBS Letters* 586:2692-2704 (2012). While sequences vary across bromodomains, all modules share a left-handed α-helical bundle linked by a loop region of variable length that determines binding specificity. The BET family bromodomains can bind to mono-acetylated lysine residues on histone H3 or H4 but have the highest affinity for multiply acetylated regions along histone H4 such as H4K5K8ac. Dey et al., "The Double Bromodomain Protein Brd4 Binds to Acetylated Chromatin During Interphase and Mitosis," *Proceedings of the National Academy of Sciences of the United States of America* 100:8758-8763 (2003); LeRoy et al., "The Double Bromodomain Proteins Brd2 and Brd3 Couple Histone Acetylation to Transcription," *Molecular Cell* 30:51-60 (2008); Morinière et al., "Cooperative Binding of Two Acetylation Marks on a Histone Tail by a Single Bromodomain," *Nature* 461:664-668 (2009); and Filippakopoulos et al., "Histone Recognition and Large-Scale Structural Analysis of the Human Bromodomain Family," *Cell* 149:214-231 (2012). BET bromodomains can also bind to histone propionylation and butyrylation although with a much weaker affinity. Vollmuth et al., "Structures of the Dual Bromodomains of the P-TEFb-activating Protein Brd4 at Atomic Resolution," *The Journal of Biological Chemistry* 284:36547-36556 (2009) and Goudarzi et al., "Dynamic Competing Histone H4 K5K8 Acetylation and Butyrylation Are Hallmarks of Highly Active Gene Promoters," *Molecular Cell* 62:169-180 (2016). In addition to binding to acetylated histones, the BET bromodomains can bind to certain transcription factors that are acetylated at histone-like motifs. Shi et al., "Disrupting the Interaction of BRD4 with Diacetylated Twist Suppresses Tumorigenesis in Basal-like Breast Cancer," *Cancer Cell* 25:210-225 (2014); Gamsjaeger et al., "Structural Basis and Specificity of Acetylated Transcription Factor GATA1 Recognition by BET Family Bromodomain Protein Brd3," *Molecular and Cellular Biology* 31:2632-2640 (2011); Lamonica et al., "Bromodomain Protein Brd3 Associates with Acetylated GATA1 to Promote its Chromatin Occupancy at Erythroid Target Genes," *Proceedings of the National Academy of Sciences of the United States of America* 108:E159-E168 (2011); and Huang et al., "Brd4 Coactivates Transcriptional Activation of NF-B via Specific Binding to Acetylated RelA," *Molecular and Cellular Biology* 29:1375-1387 (2009). In these interactions, BET proteins act as a scaffold to stabilize transcription factors at the chromatin by binding to acetylated histones with one bromodomain while simultaneously binding a transcription factor with the other.

Because constitutive loss of Brd2 or Brd4 is embryonically lethal (Houzelstein et al., "Growth and Early Postimplantation Defects in Mice Deficient for the Bromodomain-Containing Protein Brd4," *Molecular and Cellular Biology* 22:3794-3802 (2002) and Shang et al., "Double Bromodomain-Containing Gene Brd2 is Essential for Embryonic Development in Mouse," *Developmental Dynamics* 238: 908-917 (2009)), research on BET proteins was greatly facilitated by the development of the first small molecule BET inhibitors, IBET, and JQ1 (Nicodeme et al., "Suppression of Inflammation by a Synthetic Histone Mimic," *Nature* 468:1119-1123 (2010) and Filippakopoulos et al., "Selective Inhibition of BET Bromodomains," *Nature* 468:1067-1073 (2010)). These inhibitors mimic the structure of acetyllysine and prevent BET association with histones within 5 minutes. Zhan et al., "Development of Novel Cellular Histone-Binding and Chromatin-Displacement Assays for Bromodomain Drug Discovery," *Epigenetics and Chromatin* 8:1-19 (2015). Interference with acetylated histone binding alters gene expression with remarkable specificity and in a precisely controlled temporal fashion. Second and third generation inhibitors are now being developed to specifically target individual bromodomains (Picaud et al., "RVX-208, an Inhibitor of BET Transcriptional Regulators with Selectivity for the Second Bromodomain," *Proceedings of the National Academy of Sciences of the United States of America* 110: 19754-19759(2013) and Gacias et al., "Selective Chemical Modulation of Gene Transcription Favors Oligodendrocyte Lineage Progression," *Chemistry & Biology* 21:841-854 (2014)) or individual members of the BET family to improve understanding of BET functions. Alternatively, compounds to ablate BET function through selective protein degradation are now being developed. Sakamoto et al., "Protacs: Chimeric Molecules that Target Proteins to the Skp1-Cullin-F Box Complex for Ubiquitination and Degradation," *Proceedings of the National Academy of Sciences of the United States of America* 98:8554-8559 (2001); Lu et al., "Hijacking the E3 Ubiquitin Ligase Cereblon to Efficiently Target BRD4," *Chemistry & Biology* 22:755-763 (2015); and Winter et al., "Phthalimide Conjugation as a Strategy for In Vivo Target Protein Degradation," *Science* 348:1376-1381 (2015). These advances in chemistry can greatly inform understanding of basic BET function and may open new avenues for therapeutic targeting.

So how do BET proteins regulate transcription? As described above, BETs activate transcriptional elongation by recruiting P-TEFb to release paused RNAPII (FIG. 2B), however this is just one mechanism of BET action. Jang et al., "The Bromodomain Protein Brd4 is a Positive Regulatory Component of P-TEFb and Stimulates RNA Polymerase II-dependent Transcription," *Molecular Cell* 19:523-534 (2005) and Yang et al., "Recruitment of P-TEFb for Stimulation of Transcriptional Elongation by the Bromodomain Protein Brd4," *Molecular Cell* 19:535-545 (2005). BETs can directly phosphorylate RNAPII to activate transcription independent of p-TEFb. Bisgrove et al., "Conserved P-TEFb-Interacting Domain of BRD4 Inhibits HIV Transcription," *Proceedings of the National Academy of Sciences of the United States of America* 104:13690-13695 (2007). In addition, BET proteins bind to a host of other factors to regulate gene expression including chromatin remodelers like NSD2, JMJD6, and CHD4 (Wu et al., "Phospho Switch Triggers Brd4 Chromatin Binding and Activator Recruitment for Gene-specific Targeting," *Molecular Cell* 49:843-857 (2013); Rahman et al., "The Brd4 Extraterminal Domain Confers Transcription Activation Independent of pTEFb by Recruiting Multiple Proteins, Including NSD3," *Molecular and Cellular Biology* 31:2641-2652 (2011); and Liu et al., "Brd4 and JMJD6-associated Anti-Pause Enhancers in Regulation of Transcriptional Pause Release," *Cell* 155:1581-1595 (2013)) (FIG. 2C). Regulation at the gene promoter is only a small subset of transcriptional regulation and BETs importantly cooperate in enhancer-mediated transcription (Jiang et al., "Mammalian Mediator of Transcriptional Regulation and its Possible Role as an End-Point of Signal Transduction Pathways," *Proceedings of the National Academy of Sciences of the United States of America* 95:8538-8543 (1998); Lovén et al., "Selective Inhibition of Tumor Oncogenes by Disruption of Super-Enhancers," *Cell* 153:320-334 (2013); Delmore et al., "BET Bromodomain Inhibition as a Therapeutic Strategy to Target c-Myc," *Cell* 146:904-917 (2011); Zhang et al., "Bromodomain-containing Protein 4 (BRD4) Regulates RNA Polymerase II Serine 2 Phosphorylation in Human CD4+ T Cells," *The Journal of Biological Chemistry* 287: 43137-43155 (2012); Anand et al., "BET Bromodomains Mediate Transcriptional Pause Release in Heart Failure," *Cell* 154:569-582 (2013); Di Micco et al., "Control of Embryonic Stem Cell Identity by BRD4-dependent Transcriptional Elongation of Super-Enhancer-Associated Pluripotency Genes," *Cell Reports* 9:234-247 (2014); and Hsu et al., "The BET Protein BRD2 Cooperates with CTCF to Enforce Transcriptional and Architectural Boundaries," *Molecular Cell* 66:102-116.e7 (2017)) (FIG. 2D). Within the gene body, prominent BET binding may represent an additional role for BET proteins in transcriptional elongation separate from paused RNAPII release. LeRoy et al., "Proteogenomic Characterization and Mapping of Nucleosomes Decoded by Brd and HP1 Proteins," *Genome Biology* 13:R68 (2012). Indeed, BETs have intrinsic histone acetyltransferase activity to facilitate nucleosome eviction (Devaiah et al., "BRD4 is a Histone Acetyltransferase that Evicts Nucleosomes from Chromatin," *Nature Structural & Molecular Biology* 23:540-548 (2016) and Kanno et al., "BRD4 Assists Elongation of Both Coding and Enhancer RNAs by Interacting with Acetylated Histones," *Nature Structural & Molecular Biology* 21:1047-1057 (2014)) (FIG. 2E). In summary, multiple roles for BET proteins in the regulation transcription have been identified throughout the genome.

Given the broad pattern of BET binding and the multitude of interaction partners, there are still many remaining questions including why only a subset of genes are sensitive to BET inhibition. Nicodeme et al., "Suppression of Inflammation by a Synthetic Histone Mimic," *Nature* 468:1119-1123 (2010); Cheung et al., "Distinct Roles of Brd2 and Brd4 in Potentiating the Transcriptional Program for Th17 Cell Differentiation," *Molecular Cell* 65:1068-1080.e5 (2017); and Tyler et al., "Click Chemistry Enables Preclinical Evaluation of Targeted Epigenetic Therapies," *Science* 356:1397-1401 (2017). It also remains to be seen if these principles of BET-dependent transcription which were discovered in highly proliferative cells (Delmore et al., "BET Bromodomain Inhibition as a Therapeutic Strategy to Target c-Myc," *Cell* 146:904-917 (2011) and Dawson et al., "Inhibition of BET Recruitment to Chromatin as an Effective Treatment for MLL-fusion Leukaemia," *Nature* 478:529-533 (2011)), apply to non-dividing cells like neurons or if there are additional mechanisms regulating BET function. Furthermore, little work has been done on the BET proteins in the central nervous system. Currently, it is not even known which genes are direct targets of BET proteins in neurons let alone in glial cells.

Within the CNS, BET proteins are expressed in all major cell types although with some regional variability. Analysis of single cell sequencing datasets shows that Brd2 mRNA expression is enriched in microglia whereas Brd4 expression is highest in neurons. Emphasizing the importance of BET proteins in neuronal function, mutations were identified in human patients linking Brd2 and Brd4 to neurological diseases. A variant in Brd4 which results in a proline deletion was linked to autism spectrum disorders. Iossifov et al., "De Novo Gene Disruptions in Children on the Autistic Spectrum," *Neuron* 74:285-299 (2012). An association between Brd2 and juvenile myoclonic epilepsy (JME) has been identified in several Caucasian populations. Greenberg et al., "Reproducibility and Complications in Gene Searches: Linkage on Chromosome 6, Heterogeneity, Association, and Maternal Inheritance in Juvenile Myoclonic Epilepsy," *American Journal of Human Genetics* 66:508-516 (2000); Pal et al., "BRD2 (RING3) Is a Probable Major Susceptibility Gene for Common Juvenile Myoclonic Epilepsy," *American Journal of Human Genetics* 73:261-270 (2003); Cavalleri et al., "A Multicenter Study of BRD2 as a Risk Factor for Juvenile Myoclonic Epilepsy," *Epilepsia* 48:706-712 (2007); and Lorenz et al., "Association of BRD2 Polymorphisms with Photoparoxysmal Response," *Neuroscience Letters* 400:135-139 (2006). While no mutations have been identified in the coding regions of Brd2, the promoter may be highly methylated in JME patients compared to unaffected family members which may prevent Brd2 expression. Pathak et al., "DNA Methylation of the BRD 2 Promoter is Associated with Juvenile Myoclonic Epilepsy in Caucasians," *Epilepsia* 59:1011-1019 (2018) and Schulz et al., "No Evidence for a BRD2 Promoter Hypermethylation in Blood Leukocytes of Europeans with Juvenile Myoclonic Epilepsy," *Epilepsia* 60:e31-e36 (2019).

Evidence from genetic models also identifies a prominent role for BET proteins in proper brain function. Deletion of Fsh, the BET homolog in *Drosophila melanogaster*, reduces dendritic arborization complexity and decreases action potential frequency. Bagley et al., "Double-bromo and Extraterminal (BET) Domain Proteins Regulate Dendrite Morphology and Mechanosensory Function," *Genes & Development* 28:1940-1956 (2014). Constitutive loss of Brd4 in mice leads to lethality shortly after implantation while heterozygous mice have significant growth defects pre- and postnatally including head malformations. Houzelstein et al., "Growth and Early Postimplantation Defects in Mice Deficient for the Bromodomain-Containing Protein Brd4," *Molecular and Cellular Biology* 22:3794-3802 (2002). Homozygous loss of Brd2 also results in embryonic lethality although later at E11.5. Embryos exhibit neural tube malformations before death. Shang et al., "Double Bromodomain-Containing Gene Brd2 is Essential for Embryonic Development in Mouse," *Developmental Dynamics* 238:908-917 (2009). In support of the genetic associated data, Brd2 heterozygous mice develop spontaneous seizures as measured by long-term EEG. Brd2+/− mice are also more susceptible to seizures caused by a GABAa antagonist, flurothyl, which increases excitatory activity. Velíšek et al., "GABAergic Neuron Deficit As An Idiopathic Generalized Epilepsy Mechanism: The Role Of BRD2 Haploinsufficiency In Juvenile Myoclonic Epilepsy," *PLoS One*

6:e23656 (2011). Histological analysis showed fewer Gad67 or PV+ neurons in the basal ganglia indicating a decrease in GABAergic neurons in Brd2 heterozygous mice. This data suggests that loss of Brd2 function during neuronal development critically impairs neuronal subtype differentiation and may disrupt the excitation/inhibition balance in the brain resulting in epilepsy. Together these data highlight the important role for BET proteins during neurodevelopment but more work is required to understand the transcriptional and molecular mechanisms by BETs control brain maturation.

BET expression in the brain remains high after development which suggests a role for BET proteins in adult brain function. BET proteins contribute to addictive behaviors as Brd4-dependent transcription of BDNF is required for conditioned place preference for cocaine in mice. Sartor et al., "Epigenetic Readers of Lysine Acetylation Regulate Cocaine-Induced Plasticity," *The Journal of Neuroscience* 35:15062-15072 (2015). BET inhibition impaired memory in the novel object task (Korb et al., "BET Protein Brd4 Activates Transcription in Neurons and BET Inhibitor Jq1 Blocks Memory in Mice," *Nature Neuroscience* 18:1464-1473 (2015)) and can block the memory enhancement by HDAC3 knockdown (Sartor et al., "Enhancement of BDNF Expression and Memory by HDAC Inhibition Requires BET Bromodomain Reader Proteins," *The Journal of Neuroscience* 39:612-626 (2019)). Together these studies suggest that BET activity is required for memory formation however another study showed BET inhibition rather enhanced fear memory recall in wild type mice and the APP/PS1-21 mouse model of Alzheimer's disease (Benito et al., "The BET/BRD Inhibitor JQ1 Improves Brain Plasticity in WT and APP Mice," *Translation Psychiatry* 7:e1239 (2017)). These studies implicate BET proteins in the regulation of learning and memory however more work is needed to clarify BETs act positively or negatively on memory formation.

Lastly, this protein family can regulate transcription in other cell types including glia. Pharmacological inhibition of the first bromodomain of BETs in oligodendrocyte progenitors increases differentiation into mature oligodendrocytes. Gacias et al., "Selective Chemical Modulation of Gene Transcription Favors Oligodendrocyte Lineage Progression," *Chemistry & Biology* 21:841-854 (2014). This study is paralleled by the finding that neural progenitor cells increase neurogenesis and decrease astrogenesis after BET inhibition. Li et al., "BET Bromodomain Inhibition Promotes Neurogenesis While Inhibiting Gliogenesis in Neural Progenitor Cells," *Stem Cell Research* 17:212-221 (2016). These studies indicate BET proteins regulate differentiation processes in the CNS which is also true in other tissues. Di Micco et al., "Control of Embryonic Stem Cell Identity by BRD4-dependent Transcriptional Elongation of Super-Enhancer-Associated Pluripotency Genes," *Cell Reports* 9:234-247 (2014) and Cheung et al., "Distinct Roles of Brd2 and Brd4 in Potentiating the Transcriptional Program for Th17 Cell Differentiation," *Molecular Cell* 65:1068-1080.e5 (2017). BET proteins may also be required for inflammatory gene expression in microglia although current studies have addressed the role of BETs in immortalized cell lines. Jung et al., "RNA Sequencing Reveals Distinct Mechanisms Underlying BET Inhibitor JQ1-mediated Modulation of the LPS-induced Activation of BV-2 Microglial Cells," *Journal of Neuroinflammation* 12:36 (2015) and DeMars et al., "Selective Degradation of BET Proteins with dBET1, a Proteolysis-Targeting Chimera, Potently Reduces Pro-Inflammatory Responses in Lipopolysaccharide-Activated Microglia," *Biochemical and Biophysical Research Communications* 497:410-415 (2018).

Microglia, the resident macrophages of the central nervous system, are derived from myeloid progenitors in the yolk sac unlike other brain cells which are neuroectodermal. Ginhoux et al., "Fate Mapping Analysis Reveals That Adult Microglia Derive from Primitive Macrophages," *Science* 330:841-845 (2010); Schulz et al., "A lineage of Myeloid Cells Independent of Myb and Mematopoietic Stem Cells," *Science* 336:86-90 (2012); Kierdorf et al., "Microglia Emerge from Erythromyeloid Precursors via Pu.1- and Irf8-Dependent Pathways," *Nature Neuroscience* 16:273-280 (2013); and Gomez Perdiguero et al., "Tissue-Resident Macrophages Originate from Yolk-Sac-Derived Erythro-Myeloid Progenitors," *Nature* 518:547-551 (2015). As such, microglia perform unique roles to maintain brain function during homeostasis and disease. These highly dynamic cells continually survey the brain parenchyma (Nimmerjahn et al., "Resting Microglial Cells are Highly Dynamic Surveillants of Brain Parenchyma In Vivo," *Science* 308:1314-1318 (2005)) to sense changes in the environment with a multitude of cell-surface receptors (Haynes et al., "The P2Y12 Receptor Regulates Microglial Activation by Extracellular Nucleotides," *Nature Neuroscience* 9:1512-1519 (2006); Hickman et al., "The Microglial Sensome Revealed by Direct RNA Sequencing," *Nature Neuroscience* 16:1896-1905 (2013); and Fourgeaud et al., "TAM Receptors Regulate Multiple Features of Microglial Physiology," *Nature* 532:240-244 (2016)). In a homeostatic state, microglia perform many neurotrophic functions to promote proper neuronal development and function including synaptic pruning (Chu et al., "Enhanced Synaptic Connectivity and Epilepsy in C1q Knockout Mice," *Proceedings of the National Academy of Sciences of the United States of America* 107:7975-7980 (2010) and Schafer et al., "Microglia Sculpt Postnatal Neural Circuits in an Activity and Complement-Dependent Manner," *Neuron* 74:691-705 (2012)), secretion of growth factors (Trang et al., "Brain-derived Neurotrophic Factor from Microglia: A Molecular Substrate for Neuropathic Pain," *Neuron Glia Biology* 7:99-108 (2011); Ueno et al., "Layer V Cortical Neurons Require Microglial Support for Survival During Postnatal Development," *Nature Neuroscience* 16:543-551 (2013); and Parkhurst et al., "Microglia Promote Learning-Dependent Synapse Formation through Brain-Derived Neurotrophic Factor," *Cell* 155:1596-1609 (2013)), and phagocytosis of dead and dying cells. Ayata et al., "Epigenetic Regulation of Brain Region-Specific Microglia Clearance Activity," *Nature Neuroscience* 21:1049-1060 (2018); Marín-Teva et al., "Microglia Promote the Death of Developing Purkinje Cells," *Neuron* 41:535-547 (2004); and Sierra et al., "Microglia Shape Adult Hippocampal Neurogenesis through Apoptosis-Coupled Phagocytosis," *Cell Stem Cell* 7:483-495 (2010). These homeostatic functions are critical for the maintenance of proper brain health. Ayata et al., "Epigenetic Regulation of Brain Region-Specific Microglia Clearance Activity," *Nature Neuroscience* 21:1049-1060 (2018).

If an injury or infection is sensed, microglia initiate an inflammatory response which involves a dramatic, comprehensive change in morphology and function. To facilitate this transition, homeostatic gene networks are down-regulated while inflammatory gene networks are induced. Keren-Shaul et al., "A Unique Microglia Type Associated with Restricting Development of Alzheimer's Disease," *Cell* 169:1276-1290.e17 (2017) and Gosselin et al., "An Environment-Dependent Transcriptional Network Specifies Human Microglia Identity," *Science* 356:eaal3222 (2017). Other cell types such as astrocytes can be recruited by microglia to assist in this defense response. Liddelow et al., "Neurotoxic Reactive Astrocytes are Induced by Activated Microglia," *Nature* 541:481-487 (2017) and Gibson et al., "Methotrexate Chemotherapy Induces Persistent Tri-glial Dysregulation that Underlies Chemotherapy-Related Cognitive Impairment," *Cell* 176:43-55.e13 (2019). Microglia-mediated inflammation initially aids tissue recovery but can exacerbate or even initiate neuronal death if not properly regulated. Piani et al., "Murine Brain Macrophages Induced NMDA Receptor Mediated Neurotoxicity In Vitro by Secreting Glutamate," *Neuroscience Letters* 133:159-162 (1991); Marín-Teva et al., "Microglia Promote the Death of Developing Purkinje Cells," *Neuron* 41:535-547 (2004); and Frakes et al., "Microglia Induce Motor Neuron Death via the Classical NF-κB Pathway in Amyotrophic Lateral Sclerosis," *Neuron* 81:1009-1023 (2014). Hyperactive microglial activity has been implicated in almost all major neurodegenerative diseases. Tansey and Goldberg, "Neuroinflammation in Parkinson's Disease: Its Role in Neuronal Death and Implications for Therapeutic Intervention," *Neurobiology of Disease* 37:510-518 (2010) and Heneka et al., "Neuroinflammation in Alzheimer's Disease," *The Lancet. Neurology* 14:388-405 (2015).

In Alzheimer's disease (AD), microglia (McGeer et al., "Reactive Microglia in Patients with Senile Dementia of the Alzheimer Type are Positive for the Histocompatibility Glycoprotein HLA-DR," *Neuroscience Letters* 79:195-200 (1987); Rogers et al., "Expression of Immune System-Associated Antigens by Cells of the Human Central Nervous System: Relationship to the Pathology of Alzheimer's Disease," *Neurobiology of Aging* 9:339-349 (1988); Itagaki et al., "Relationship of Microglia and Astrocytes to Amyloid Deposits of Alzheimer Disease," *Journal of Neuroimmunology* 24:173-182 (1989); and McGeer, E. G. and McGeer, P. L., "The Role of the Immune System in Neurodegenerative Disorders," *Movement Disorders* 12:855-858 (1997)) can generate increased levels of pro-inflammatory cytokines such as MHCII, Il1B, and TNF. Eikelenboom and Stam, "Immunoglobulins and Complement Factors in Senile Plaques. An Immunoperoxidase Study," *Acta Neuropathologica* 57:239-242 (1982); Frautschy et al., "Microglial Response to Amyloid Plaques in APPsw Transgenic Mice," *The America Journal of Pathology* 152:307-317 (1998); and Akiyama et al., "Inflammation and Alzheimer's Disease," *Neurobiology of Aging* 21:383-421 (2001). These cytokines, which can be triggered by Aβ plaques (Itagaki et al., "Relationship of Microglia and Astrocytes to Amyloid Deposits of Alzheimer Disease," *J. Neuroimmunol.* 24:173-82 (1989) and Barger and Harmon, "Microglial Activation by Alzheimer Amyloid Precursor Protein and Modulation by Apolipoprotein E," *Nature* 388:878-881 (1997)) or dying neurons, can themselves cause neurodegeneration (Piani et al., "Murine Brain Macrophages Induced NMDA Receptor Mediated Neurotoxicity In Vitro by Secreting Glutamate," *Neuroscience Letters* 133:159-162 (1991); Marín-Teva et al., "Microglia Promote the Death of Developing Purkinje Cells," *Neuron* 41:535-547 (2004); and Frakes et al., "Microglia Induce Motor Neuron Death via the Classical NF-κB Pathway in Amyotrophic Lateral Sclerosis," *Neuron* 81:1009-1023 (2014)). Furthermore, mutations in microglia-enriched molecules such as Trem2 (Guerreiro et al., "TREM2 Variants in Alzheimer's Disease," *The New England Journal of Medicine* 368:117-127 (2012) and Jonsson et al., "Variant of TREM2 Associated with the Risk of Alzheimer's Disease," *The New England Journal of Medicine* 368:107-116 (2013)), C1R (Lambert et al., "Genome-wide Association Study Identifies Variants at CLU and CR1 Associated with Alzheimer's Disease," *Nature Genetics* 41:1094-1099 (2009)), and Cd33 (Naj et al., "Common Variants at MS4A4/MS4A6E, CD2AP, CD33 and EPHA1 are Associated with Late-Onset Alzheimer's Disease," *Nature Genetics* 43:436-441 (2011) and Hollingworth et al., "Common Variants at ABCA7, MS4A6A/MS4A4E, EPHA1, CD33 and CD2AP are Associated with Alzheimer's Disease," *Nature Genetics* 43: 429-435 (2011)) have been identified as risk factors for late-onset Alzheimer's disease indicating a significant role for microglia in AD pathology. Understanding the mechanisms that regulate the pro-inflammatory microglial state is therefore crucial to the development of novel therapeutic strategies for neurodegenerative disorders.

In peripheral macrophages, the induction of inflammatory gene networks is regulated by the BET protein family. Nicodeme et al., "Suppression of Inflammation by a Synthetic Histone Mimic," *Nature* 468:1119-1123 (2010) and Devaiah et al., "BRD4 is a Histone Acetyltransferase that Evicts Nucleosomes from Chromatin," *Nature Structural & Molecular Biology* 23:540-548 (2016). These BET proteins bind to acetylated lysine residues on histones H3/H4 and recruit factors that allow for the full elongation of mRNAs by RNAPII. Jang et al., "The Bromodomain Protein Brd4 is a Positive Regulatory Component of P-TEFb and Stimulates RNA Polymerase II-dependent Transcription," *Molecular Cell* 19:523-534 (2005) and Yang et al., "Recruitment of P-TEFb for Stimulation of Transcriptional Elongation by the Bromodomain Protein Brd4," *Molecular Cell* 19:535-545 (2005). Inhibition of the BET-dependent inflammatory gene expression profile in peripheral macrophages can completely prevent death from sepsis, a pathologically hyperactive immune response. Nicodeme et al., "Suppression of Inflammation by a Synthetic Histone Mimic," *Nature* 468: 1119-1123 (2010). In microglial cell lines, BET inhibition attenuates the induction of several pro-inflammatory genes after lipopolysaccharide, a bacterial wall component. Jung et al., "RNA Sequencing Reveals Distinct Mechanisms Underlying BET Inhibitor JQ1-mediated Modulation of the LPS-induced Activation of BV-2 Microglial Cells," *Journal of Neuroinflammation* 12:36 (2015) and DeMars et al., "Selective Degradation of BET Proteins with dBET1, a Proteolysis-Targeting Chimera, Potently Reduces Pro-Inflammatory Responses in Lipopolysaccharide-Activated Microglia," *Biochemical and Biophysical Research Communications* 497:410-415 (2018).

Neurons execute some of the most important functions for an organism's survival (e.g. central control of homeostatic processes like respiration) yet these cells are the most vulnerable. After cessation of circulation or an organism's death, irreversible neuronal damage occurs within 3 minutes. Safar, "Cerebral Resuscitation After Cardiac Arrest: A Review," *Circulation* 74:IV138-IV153 (1986) and Safar, "Resuscitation From Clinical Death: Pathophysiologic Limits and Therapeutic Potentials," *Critical Care Medicine* 16:923-941 (1988). Other organs like the heart, liver, or lungs survive much longer and some cell populations like muscle stem cells can continue to live for days after an organism dies. Latil et al., "Skeletal Muscle Stem Cells Adopt a Dormant Cell State Post Mortem and Retain Regenerative Capacity," *Nature Communications* 3:903 (2012). Even within the brain, certain neuronal populations are more susceptible than others, including the Purkinje cells, neurons in CA1 of the hippocampus, and Layers III and V of the cortex. Pulsinelli et al., "Temporal Profile of Neuronal Damage in a Model of Transient Forebrain Ischemia,"

*Annals of Neurology* 11:491-498 (1982); Sims, "Energy Metabolism and Selective Neuronal Vulnerability Following Global Cerebral Ischemia," *Neurochemical Research* 17:923-931 (1992); Sieber et al., "Global Incomplete Cerebral Ischemia Produces Predominantly Cortical Neuronal Injury," *Stroke* 26:2091-2096 (1995); and Wang and Michaelis, "Selective Neuronal Vulnerability to Oxidative Stress in the Brain," *Frontiers in Aging Neuroscience* 2:12 (2010). Understanding the factors that regulate neuronal survival is therefore essential both biologically and clinically as the population ages and the incidence of neurodegenerative disease increases.

One proposed explanation for this apparent vulnerability is the high metabolic demand of the brain. Although only 2% of total body weight, the brain consumes 20% of the body's oxygen and 25% of total glucose. Sokoloff, "Energetics of Functional Activation in Neural Tissues," *Neurochemical Research* 24:321-329 (1999). The majority of this energy is required for gene transcription, protein translation and the maintenance of ion gradients through the ATP-dependent Na/K transporter. Harris et al., "Synaptic Energy Use and Supply," *Neuron* 75:762-777 (2012); Frumkin et al., "Gene Architectures that Minimize Cost of Gene Expression," *Molecular Cell* 65:142-153 (2017); and Kafri et al., "The Cost of Protein Production," *Cell Reports* 14:22-31 (2016). Paradoxically, however, increased cellular and organismal survival is correlated with decreased food intake rather than increased nutrient availability. In fact, restricting caloric intake in a wide variety of species including yeast, mice, and non-human primates, can profoundly increase lifespan. Weindruch et al., "The Retardation of Aging in Mice by Dietary Restriction: Longevity, Cancer, Immunity and Lifetime Energy Intake," *The Journal of Nutrition* 116:641-654 (1986); Colman et al., "Caloric Restriction Delays Disease Onset and Mortality in Rhesus Monkeys," *Science* 325:201-204 (2009); McCay et al., "The Effect of Retarded Growth Upon the Length of Life Span and Upon the Ultimate Body Size," *The Journal of Nutrition* 10:63-79 (1935); and Mattison et al., "Caloric Restriction Improves Health and Survival of Rhesus Monkeys," *Nature Communications* 8:14063 (2017). Caloric restriction (CR) also decreases the incidence of age-related diseases like cancer and neurodegeneration (Mattison et al., "Caloric Restriction Improves Health and Survival of Rhesus Monkeys," *Nature Communications* 8:14063 (2017)) and can preserve cognitive functioning in aged mice. Ingram et al., "Dietary Restriction Benefits Learning and Motor Performance of Aged Mice," *Journal of Gerontology* 42:78-81 (1987); Means et al., "Mid-Life Onset of Dietary Restriction Extends Life and Prolongs Cognitive Functioning," *Physiology & Behavior* 54:503-508 (1993); and Parikh et al., "Caloric Restriction Preserves Memory and Reduces Anxiety of Aging Mice with Early Enhancement of Neurovascular Functions," *Aging* (Albany, NY) 8:2814-2826 (2016).

The beneficial effects of CR are thought to be caused by decreased metabolism and concomitant decrease in reactive oxygen species induced damage. Pearl, THE RATE OF LIVING (New York, Alfred A. Knopf Inc. (1928)) and Harman, "Aging: A Theory Based on Free Radical and Radiation Chemistry," *Journal of Gerontology* 11:298-300 (1956). In humans, a controlled clinical trial confirmed that CR decreases metabolic rate and oxidative stress and improves many aging biomarkers. Redman et al., "Metabolic Slowing and Reduced Oxidative Damage with Sustained Caloric Restriction Support the Rate of Living and Oxidative Damage Theories of Aging," *Cell Metabolism* 27:805-815.e4 (2018). Enforcing the idea that high metabolic states are detrimental to cell survival, ectopically increasing metabolic activity in neurons results in apoptosis. Herrero-Mendez et al., "The Bioenergetic and Antioxidant Status of Neurons is Controlled by Continuous Degradation of a Key Glycolytic Enzyme by APC/C-Cdh1," *Nature Cell Biology* 11:747-752 (2009) and Vilchez et al., "Mechanism Suppressing Glycogen Synthesis in Neurons and its Demise in Progressive Myoclonus Epilepsy," *Nature Neuroscience* 10:1407-1413 (2007). Additionally, immature neurons decrease energy consumption by 80% in response to stressful stimuli and survive significantly longer than mature neurons that cannot decrease metabolic rates to the same extent. Munns et al., "Primary Cortical Neuronal Cultures Reduce Cellular Energy Utilization During Anoxic Energy Deprivation," *Journal of Neurochemistry* 87:764-772 (2003). The pathways that sense nutrient availability and control cellular metabolism are therefore strongly implicated in the regulation of longevity.

The mechanistic target of rapamycin (mTOR) pathway incorporates nutrient availability and growth factor signaling to regulate cell growth and metabolism. Saxton and Sabatini, "mTOR Signaling in Growth, Metabolism, and Disease," *Cell* 168:960-976 (2017). In nutrient rich states, mTOR signaling promotes catabolic processes including protein translation, mitochondria biogenesis, lipid synthesis and increases glycolysis. When nutrients are scarce, mTOR signaling is naturally inhibited, decreasing these energetically demanding pathways in the cell. In turn anabolic pathways like autophagy are activated to generate nutrients from the self. Supporting the link between mTOR signaling and cell survival, rapamycin, a natural mTOR inhibitor increases the lifespan of yeast, *Drosophila* and mice (Powers et al., "Extension of Chronological Life Span in Yeast by Decreased TOR Pathway Signaling," *Genes Development* 20:174-184 (2006); Ravikumar et al., "Rapamycin Pretreatment Protects Against Apoptosis," *Human Molecular Genetics* 15:1209-1216 (2006); Medvedik et al., "MSN2 and MSN4 Link Calorie Restriction and TOR to Sirtuin-Mediated Lifespan Extension in *Saccharomyces cerevisiae,*" *PLoS Biology* 5:e261 (2007); Bjedov et al., "Mechanisms of Life Span Extension by Rapamycin in the Fruit Fly *Drosophila melanogaster,*" *Cell Metabolism* 11:35-46 (2010); and Harrison et al., "Rapamycin Fed Late in Life Extends Lifespan in Genetically Heterogeneous Mice," *Nature* 460:392 (2009)) and improves cognition in many animal models of neurodegeneration, including Alzheimer's Disease (Ravikumar et al., "Rapamycin Pre-treatment Protects Against Apoptosis," *Human Molecular Genetics* 15:1209-1216 (2006); Tain et al., "Rapamycin Activation of 4E-BP Prevents Parkinsonian Dopaminergic Neuron Loss," *Nature Neuroscience* 12:1129-1135 (2009); and Caccamo et al., "Molecular Interplay between Mammalian Target of Rapamycin (mTOR), Amyloid-β, and Tau," *Journal of Biological Chemistry* 285:13107-13120 (2010)).

While it is well known that inhibition of protein synthesis and cell metabolism either mTOR inhibition increases cell survival, less is known about how gene transcription, another energetically consuming process, impacts cell survival. Transcription is also intimately connected with cellular metabolism in that chromatin-modifying enzymes require metabolites as co-factors or substrates to post-translationally modify histone tails which regulate the rate of gene transcription. Lu and Thompson, "Metabolic Regulation of Epigenetics," *Cell Metabolism* 16:9-17 (2012). Additionally, these modifications, such as histone acetylation, change in response to metabolite availability importantly linking cellular metabolism to epigenetic regulation. Takahashi et al., "Nucleocytosolic Acetyl-Coenzyme A Synthetase Is Required for Histone Acetylation and Global Transcription," *Molecular Cell* 23:207-217 (2006); Wellen et al., "ATP-Citrate Lyase Links Cellular Metabolism to Histone Acetylation," *Science* 324:1076-1080 (2009); Cai et al., "Acetyl-CoA Induces Cell Growth and Proliferation by Promoting the Acetylation of Histones at Growth Genes," *Molecular Cell* 42:426-437 (2011); Donohoe et al., "The Warburg Effect Dictates the Mechanism of Butyrate-Mediated Histone Acetylation and Cell Proliferation," *Molecular Cell* 48:612-626 (2012); Lee et al., "Akt-dependent Metabolic Reprogramming Regulates Tumor Cell Histone Acetylation," *Cell Metabolism* 20:306-319 (2014); and Moussaieff et al., "Glycolysis-Mediated Changes in Acetyl-CoA and Histone Acetylation Control the Early Differentiation of Embryonic Stem Cells," *Cell Metabolism* 21:392-402 (2015). In a metabolically low cell state, gene transcription is decreased in some organisms and it is conceivable that this may contribute to cell survival during starvation. Vogel et al., "Decreasing Transcription Elongation Rate in *Escherichia coli* Exposed to Amino Acid Starvation," *Molecular Microbiology* 6:2191-2200 (1992); Jona et al., "Glucose Starvation Induces a Drastic Reduction in the Rates of Both Transcription and Degradation of mRNA in Yeast," *Biochimica et Biophysica Acta* 1491:37-48 (2000); and Salem et al., "Effect of Starvation on Global Gene Expression and Proteolysis in Rainbow Trout (*Oncorhynchus mykiss*)," *BMC Genomics* 8:328 (2007).

Complete blockade of transcription by RNAPII inhibitors is highly detrimental to neuronal survival (Brusés and Pilar, "Effect of Cycloheximide and mRNA Synthesis Inhibition on Death of Trophically Deprived Ciliary Ganglion Neurons in Culture," *Journal of Neurophysiology* 74:2487-2499 (1995)), however, inhibiting the P-TEFb-dependent subset of transcription increases neuronal survival suggesting that specific gene networks may regulate longevity. Park et al., "Inhibitors of Cyclin-dependent Kinases Promote Survival of Post-mitotic Neuronally Differentiated PC12 Cells and Sympathetic Neurons," *Journal of Biological Chemistry* 271:8161-8169 (1996); Park et al., "G1/S Cell Cycle Blockers and Inhibitors of Cyclin-Dependent Kinases Suppress Camptothecin-Induced Neuronal Apoptosis," *Journal of Neuroscience* 17:1256-1270 (1997); and Verdaguer et al., "Inhibition of Cell Cycle Pathway by Flavopiridol Promotes Survival of Cerebellar Granule Cells After an Excitotoxic Treatment," *The Journal of Pharmacology and Experimental Therapeutics* 308:609-616 (2004). The specificity of P-TEFb transcription is regulated by the BET protein family which binds to acetylated histones and recruits P-TEFb to stimulate signal-dependent gene transcription. Therefore, it is hypothesized that BET-dependent transcription may impact cell survival.

In support of this hypothesis, mTOR inhibition and caloric restriction decrease specific histone acetylation marks that are recognized by the BET proteins. Füllgrabe et al., "The Histone H4 Lysine 16 Acetyltransferase hMOF Regulates the Outcome of Autophagy," *Nature* 500:468-471 (2013); Gong et al., "Histone Modifications Change with Age, Dietary Restriction and Rapamycin Treatment in Mouse Brain," *Oncotarget* 6:15882-15890 (2015); Workman et al., "*Saccharomyces cerevisiae* TORC1 Controls Histone Acetylation by Signaling Through the Sit4/PP6 Phosphatase to Regulate Sirtuin Deacetylase Nuclear Accumulation," *Genetics* 203:1733-1746 (2016); and Sakamaki et al., "Bromodomain Protein BRD4 Is a Transcriptional Repressor of Autophagy and Lysosomal Function," *Molecular Cell* 66:517-532.e9 (2017). Additionally, BET mRNA expression is decreased in several tissues including the brain after caloric restriction in mice (Swindell, "Genes and Gene Expression Modules Associated with Caloric Restriction and Aging in the Laboratory Mouse," *BMC Genomics* 10:585 (2009)). This indicates that the pro-survival effects of rapamycin may, at least in part, be caused by decreased BET-dependent transcription. Further evidence linking BET-dependent transcription to cell survival, a Crispr-Cas9 screen in human cells identified Brd2, a member of the BET family, as a negative regulator of neuronal survival. Kramer et al., "CRISPR-Cas9 Screens in Human Cells and Primary Neurons Identify Modifiers of C9ORF72 Dipeptide-Repeat-Protein Toxicity," *Nature Genetics* 50:603-612 (2018). Finally, pharmacological inhibition of BET proteins was recently shown to ameliorate NMDA-induced apoptosis in retinal neurons. Li et al., "Epigenetic Intervention with a BET Inhibitor Ameliorates Acute Retinal Ganglion Cell Death in Mice," *Molecular Vision* 23:149-159 (2017). Together, these data suggest a negative role for BET proteins in neuronal survival.

As postmitotic cells, neurons are incapable of replacing themselves and, while adult neurogenesis can occur (Bayer et al., "Neurons in the Rat Dentate Gyms Granular Layer Substantially Increase During Juvenile and Adult Life," *Science* 216:890-892 (1982) and Cameron et al., "Differentiation of Newly Born Neurons and Glia in the Dentate Gyms of the Adult Rat," *Neuroscience* 56:337-344 (1993)), this limited capacity cannot compensate for large-scale neuronal loss during neurodegeneration. Therefore in order to preserve brain function, it is of the utmost importance to understand the mechanisms that cause neuronal death and dysfunction. Inflammation can exacerbate and even initiate neuronal death. Piani et al., "Murine Brain Macrophages Induced NMDA Receptor Mediated Neurotoxicity In Vitro by Secreting Glutamate," *Neuroscience Letters* 133:159-162 (1991); Marín-Teva et al., "Microglia Promote the Death of Developing Purkinje Cells," *Neuron* 41:535-547 (2004); and Frakes et al., "Microglia Induce Motor Neuron Death via the Classical NF-κB Pathway in Amyotrophic Lateral Sclerosis," *Neuron* 81:1009-1023 (2014). In Alzheimer's Disease (AD), the most common form of neurodegeneration, mutations in immune molecules such as TREM2 (Guerreiro et al., "TREM2 Variants in Alzheimer's Disease," *The New England Journal of Medicine* 368:117-127 (2012) and Jonsson et al., "Variant of TREM2 Associated with the Risk of Alzheimer's Disease," *The New England Journal of Medicine* 368:107-116 (2013)) and CD33 (Naj et al., "Common Variants at MS4A4/MS4A6E, CD2AP, CD33 and EPHA1 are Associated with Late-Onset Alzheimer's Disease," *Nature Genetics* 43:436-441 (2011) and Hollingworth et al., "Common Variants at ABCA7, MS4A6A/MS4A4E, EPHA1, CD33 and CD2AP are Associated with Alzheimer's Disease," *Nature Genetics* 43: 429-435 (2011)) have been identified indicating a causal role for microglia in late onset AD pathology. Postmortem AD tissue, as well as many other neurodegenerative diseases, also shows increased microglial proliferation and expression of pro-inflammatory cytokines. Tansey and Goldberg, "Neuroinflammation in Parkinson's Disease: Its Role in Neuronal Death and Implications for Therapeutic Intervention," *Neurobiology of Disease* 37:510-518 (2010) and Heneka et al., "Neuroinflammation in Alzheimer's Disease," *The Lancet. Neurology* 14:388-405 (2015). These cytokines, which initially benefit host survival, can have extremely deleterious effects on tissue health if their expression is left unchecked. In peripheral macrophages, the induction of pro-inflammatory cytokines in response to danger signals requires a shift in transcriptional programs which is controlled by the bromodomain and extraterminal domain containing (BET) protein family. Nicodeme et al., "Suppression of Inflammation by a Synthetic Histone Mimic," *Nature* 468:1119-1123 (2010) and Tasdemir et al., "BRD4 Connects Enhancer Remodeling to Senescence Immune Surveillance," *Cancer Discovery* 6:613-629 (2016). These BET proteins bind to acetylated lysine residues on histones H3/H4 allowing transcription of stimulus-induced genes.

Preservation of postmitotic neurons throughout an organism's life is critical for the proper maintenance of neuronal circuitries and cognition. The unique vulnerability of these cells may arise from the high metabolic demand required to maintain ion gradients which allow for appropriate neuronal activity. Sokoloff, "Energetics of Functional Activation in Neural Tissues," *Neurochemical Research* 24:321-329 (1999) and Harris et al., "Synaptic Energy Use and Supply," *Neuron* 75:762-777 (2012). Paradoxically, decreasing nutrient availability and cellular metabolism increases neuronal survival in response to toxic stimuli. Bruce-Keller et al., "Food Restriction Reduces Brain Damage and Improves Behavioral Outcome Following Excitotoxic and Metabolic Insults," *Annals of Neurology* 45:8-15 (1999); Duan and Mattson, "Dietary Restriction and 2-deoxyglucose Administration Improve Behavioral Outcome and Reduce Degeneration of Dopaminergic Neurons in Models of Parkinson's Disease," *Journal of Neuroscience Research* 57:195-206 (1999); Yu and Mattson, "Dietary Restriction and 2-deoxyglucose Administration Reduce Focal Ischemic Brain Damage and Improve Behavioral Outcome: Evidence for a Preconditioning Mechanism," *Journal of Neuroscience Research* 57:830-839 (1999); and Caccamo et al., "Molecular Interplay Between Mammalian Target of Rapamycin (mTOR), Amyloid-Beta, and Tau: Effects on Cognitive Impairments," *The Journal of Biological Chemistry* 285: 13107-13120 (2010). However the effects on gene transcription, which is intimately coupled to cellular metabolism, are not well understood.

The present disclosure is directed to overcoming these and other deficiencies in the art.

SUMMARY

A first aspect of the present disclosure relates to a method of inducing a neuroprotective state. The method includes administering a Bromodomain and Extra-Terminal motif (BET) inhibitor under conditions effective to induce a neuroprotective state.

A second aspect of the present disclosure relates to a method of preventing and/or treating neurodegenerative disease. The method includes administering a Bromodomain and Extra-Terminal motif (BET) inhibitor under conditions effective to prevent and/or treat neurodegenerative disease.

A third aspect of the present disclosure relates to a method of reducing microglial inflammation. The method includes administering a Bromodomain and Extra-Terminal motif (BET) inhibitor under conditions effective to reduce microglial inflammation.

A fourth aspect of the present disclosure relates to a method of restoring microglial homeostasis. The method includes administering a Bromodomain and Extra-Terminal motif (BET) inhibitor under conditions effective to restore microglial homeostasis.

The mammalian brain is a highly complex organ that integrates diverse sensory inputs, allowing mammals to adapt to changes in the environment. The intricate architecture of the brain mimics its diverse functionality and is composed of numerous neuronal and glial subtypes. How this diversity in form and function arises in cells with the same genome is thought to be coordinated by specific programs of gene expression. It is becoming increasingly clear that dysregulation of these transcriptional programs during development and in adulthood has a profoundly detrimental impact on brain health. In peripheral cells, the induction of cell-type specific gene networks is controlled by the bromodomain and extra-terminal domain containing (BET) protein family (Nicodeme et al., "Suppression of Inflammation by a Synthetic Histone Mimic," *Nature* 468: 1119-1123 (2010), which is hereby incorporated by reference in its entirety) however their function in the central nervous system is largely unknown. The present disclosure identifies fundamental roles for BET proteins in postnatal brain development and in the adult brain. It is shown that by using pharmacological inhibition BETs are epigenetic regulators of neuronal and synaptic genes involved in ASD-like behaviors in mice. Second, the transcriptional control of microglial inflammation by BETs is described which highlights the cell-type specificity of this regulation. Lastly it is shown that BETs negatively regulate neuronal survival likely via the expression of metabolic genes. This disclosure provides a comprehensive examination of the role of BET-dependent transcription in the central nervous system and offers a novel strategy for the treatment of neurodegenerative disorders.

Based on the data presented herein, it is hypothesized that BET proteins regulate inflammatory gene expression in microglia and that BET inhibition may be a potential therapeutic strategy to restrain hyperactive microglial activation during neurodegeneration.

Using the brain permeable BET inhibitor, IBET858, it is confirmed herein that BET proteins control the inflammatory activation of microglia by LPS in vitro. Moreover, it is shown that chronic BET inhibition in an AD mouse model prevents the expression of key inflammatory mediators without negatively impacting homeostatic gene expression profiles. Furthermore, chronic administration of IBET858 decreases microgliosis, preserves hippocampal neuron numbers, and significantly rescues memory in an AD mouse model. These data importantly identify BET inhibition as a promising therapeutic strategy for the treatment of neurodegenerative disease.

The BET proteins are identified herein as critical transcriptional regulators of long, synaptic genes, many of which are risk genes for Autism Spectrum Disorders. Pharmacological inhibition of BET proteins in young mice causes an autism-like phenotype, suggesting the key role of the BET-controlled gene network in the disorder. The BET-dependent initiation of inflammatory gene networks in microglia is discussed and the impact of these gene networks on brain health using two mouse models of neurodegenerative disease is addressed. Finally a novel role for BET proteins as negative regulators of neuronal survival in the adult brain is identified. Inhibition of BET-dependent transcription initiates a protective state in neurons characterized by decreased metabolic activity, increased protein degradation pathways and increased lifespan. Importantly, it is shown that pharmacological BET inhibition decreases microglial-mediated inflammation while increasing neuronal resilience to toxic stimuli and therefore has promising therapeutic potential in the treatment of neurodegenerative diseases. As described herein, the genes that require BET proteins for their proper transcription in both the developing and adult brain are identified. Furthermore the first genome-wide dataset of Brd2 and Brd4 chromatin occupancy from neurons is generated. Critically the importance of BET proteins in proper brain function is highlighted by showing that inhibition of BET-dependent transcription during postnatal brain development initiates an autism-like phenotype. Blockade of BET-mediated transcription in adulthood induces a neuroprotective state that preserves brain function during neurodegeneration. Novel roles for BET proteins in the regulation of gene transcription that contribute to diseases both during development and in the adult brain are described herein.

Analogous to their role in macrophages, here it is shown that the BET proteins are required for the microglial expression of pro-inflammatory genes in vitro and in vivo. Furthermore, pharmacological inhibition of the BET proteins decreases microgliosis, prevents brain atrophy, and rescues fear memory in an Alzheimer's mouse model. These data identify BET proteins as critical regulators of pathological microglial activation and demonstrate an exciting therapeutic potential for BET inhibition in neurodegenerative disease.

Here it is shown that inhibition of the bromodomain and extraterminal domain containing (BETs) proteins promotes neuronal longevity and resilience to lethal stimuli by inducing a cellular state similar to that of mTOR inhibition. It is proposed that BET-dependent transcription of metabolic genes is a previously underappreciated component of the feed-forward cycle linking nutrient availability, cellular metabolism and epigenetic regulation of gene expression.

Here it is shown that pharmacological inhibition of the BET family of transcriptional regulators significantly increases neuron survival at baseline and in response to toxic stimuli. This is accomplished by inhibiting gene expression networks that stimulate neuronal metabolism and inducing autophagy and pro-survival gene programs. It is proposed that BET inhibition induces a protective state reminiscent to that after mTOR inhibition. These data describe a novel contribution of transcriptional regulation to cell survival and directly implicate the BET proteins as negative regulators of survival which have direct therapeutic implications for neurodegenerative disease.

BRIEF DESCRIPTION OF THE DRAWINGS

FIG. 1A shows the crystal structure of the nucleosome structure containing two copies of H2A, H2B, H3, and H4. In FIG. 1B, the histone code proposes three types of chromatin interacting proteins. In the Left section, Writers add post-translational modifications (PTMs). In the Middle section, Erasers remove these modifications. In the Right section, Readers bind to histone PTMS to either directly or indirectly regulate transcription. FIGS. 1C-1E show initiation and elongation phases of RNAPII transcription. In FIG. 1C, initiation begins by the clearing the promoter so transcriptional machinery can bind. In FIG. 1D, TFIIH phosphorylates RNAPII (orange) at Ser5 which causes the polymerase to pause proximal to the promoter. In FIG. 1E, elongation proceeds after RNAPII is phosphorylated at Ser2 by kinases, usually P-TEFb (green).

In FIG. 2A, three BET proteins, Brd2, Brd3, and Brd4 are expressed in somatic cells. Brd4 has an extended c-terminus. In FIG. 2B, BETs release paused RNAPII from the promoter either by direct phosphorylation or by recruiting P-TEFb. In FIG. 2C, BETs recruit chromatin remodelers to facilitate transcription. In FIG. 2D, BETs control enhancer-mediated transcription. In FIG. 2E, BETs have histone acetyltransferase activity that can evict nucleosomes.

FIG. 3A shows primary microglia that were cultured from mouse forebrain and treated with 1 μM IBET858 for 1 hour, 4 hours, or 12 hours. IBET858 significantly down-regulates 1245 and 1175 genes at 4 hours or 12 hours respectively. In FIG. 3B, down-regulated genes at 4 hours are enriched for immune response and cell activation pathways (−log 10p value). In FIG. 3C, key microglia identity genes are unaffected by BET inhibition indicating IBET858 does not affect microglial differentiation. FIG. 3D shows that phagocytosis genes are also largely unaffected by IBET858. FIG. 3E shows that IBET858 significantly decreases the expression of pro-inflammatory genes. (*$p<0.05$, ***$p<0.0001$)

In FIG. 4B, BET inhibition does not affect the expression of microglial identity genes after LPS stimulation. In FIGS. 4C-4E, LPS induces a time-dependent pro-inflammatory gene network at 1 hour (FIG. 4C), 4 hours (FIG. 4D), and 12 hours (FIG. 4E) including cytokine, interferon signaling, proliferation, and cell death genes. (Circle plots) Of the LPS induced genes (white), IBET858 significantly suppresses the majority (blue) and induces very few genes (red) by more than two-fold compared to LPS. Heatmaps of the LPS induced genes show that IBET858 suppresses immune response, interferon, and apoptosis gene expression but does not affect chemotaxis or NFkB signaling pathways.

In FIG. 5A, mice were injected once per day intraperitoneally with 30 mg/kg of IBET858 or vehicle for two weeks then TRAP was performed on striatum (ST) and cerebellum (CB). In FIG. 5B, BET inhibition does not affect key microglial identity genes or (FIG. 5C) the region-specific transcriptional profiles of cerebellar or striatal microglia in vivo. In FIG. 5D, however, pro-inflammatory genes are suppressed by IBET858 in the striatum (p adj<0.05).

In FIG. 6A, p25 was overexpressed for two weeks to initiate neurodegeneration before mice were treated daily i.p. with either IBET858 (30 mg/kg) or vehicle. Gene expression and histology were assessed after five weeks of injections. In FIG. 6B, BET inhibition suppresses inflammatory gene expression in the hippocampus of the P25 AD mouse model. In FIG. 6C, histology of the dentate gyms (NeuN green, Iba1 red) shows fewer microglia after IBET858 treatment. (n=3-5 animals, ***$p<0.0001$)

In FIG. 7A, hippocampal Psd95 and NeuN protein levels were decreased in the P25 model but rescued in mice treated with IBET858 (n=5, *$p<0.05$, $p<0.01$) (FIG. 7B and FIG. 7C) NeuN immunofluorescence reveals IBET858 treatment prevents neuron loss (FIG. 7D) IBET858 prevents brain atrophy in the P25 model. In FIG. 7E, contextual (left) and Cued (right) recall was rescued by IBET858 (n=12-20, $p<0.01$, ***$p<0.0001$).

In FIG. 8A, microglia numbers after PLX5622 treatment in the dentate gyms. In FIG. 8B, neuron numbers in the dentate gyms. In FIG. 8C, PSD95 and NeuN protein levels after PLX5622. In FIG. 8D, contextual recall after PLX5622 treatment and Cued (right) recall was rescued by IBET858 (n=5-11, **$p<0.01$).

FIGS. 9A-9E shows that BET proteins negatively regulate neuronal survival. In FIG. 9A, LDH release was measured over time in neuronal cultures treated with IBET858. In FIG. 9B, the decrease in LDH release is dose-dependent. As shown in FIG. 9C, propidium iodide staining reveals the number of cells that survive over time after IBET858. In FIG. 9D, mean firing rate (Hz) in neuronal cultures after BET inhibition is not different at day 14 but IBET858 treated neurons exhibit electrical activity longer than control neurons. FIG. 9E shows that IBET858 and Rapamycin increase neuronal longevity to the same extent.

FIG. 10A shows that neurons were stimulated with 50 μM Glutamate and their activity was recorded immediately after. In FIG. 10B, neurons were treated with IBET858 for 2 hours, 24 hours, 72 hours, or 1 week and then survival was measured in response to 1 mM Glutamate. In FIG. 10C, propidium iodide staining confirms that BET inhibition prevents neuronal death after 1 mM glutamate. FIG. 10D shows that 1 week of IBET858 (1 μM) and Rapamycin (20 nM) protect neurons equally against 1 mM Glutamate. FIGS. 10E and 10F show that IBET858 prevents neuronal death caused by (FIG. 10E) 1% oxygen and (FIG. 10F) exposure to Aβ1-43 oligomers. Experiments in FIGS. 10C-10F were repeated a minimum of three times.

In FIG. 11C, expression heatmaps show that gene expression strengthens over time. In FIG. 11D, selected heatmaps showing individual gene changes in specific pathways.

In FIG. 12A, pathway enrichment analysis of differentially changed metabolites after IBET858 in neurons. (red: up, blue: down). FIG. 12B shows correlation of enriched pathways from gene expression timecourse and metabolic data. FIG. 12C shows that principal component analysis of metabolite samples shows divergence of IBET858 and Rotenone.

In FIG. 13A, seahorse assay quantifies mitochondrial activity and glycolysis after acute and chronic IBET858. In FIG. 13B, quantification of Map2+ cell area reveals decreased somatic area after BET inhibition. In FIG. 13C, total protein content was measured using the BCA assay. FIG. 13D shows that autophagy marker, LC3II, is increased after IBET858. In. FIG. 13E, IBET858 leads to a time-dependent decrease in mTOR signaling.

In FIG. 14A, Brd4$^{fl/fl}$ neuronal cultures were infected with AAV(Php.EB)-SynGFP or AAV (Php.EB)-SynCre on day 1. Deletion was confirmed by western blot and immunofluorescence. In FIG. 14B, on day 7, neurons were treated with IBET858 and Glutamate toxicity was measured using the LDH assay at day 14. FIG. 14C shows increased survival of Brd4 deficient cultures was confirmed using propidium iodide staining.

FIGS. 16A-16F illustrate that rapamycin treatment promotes neuronal longevity/survival and is associated with rapid gene expression changes in metabolic genes that are associated with a displacement of BRDs from chromatin. Rapamycin has neuroprotective activity. In FIG. 16A, primary cortical neurons were treated with rapamycin (20 nM) at day 7 and propidium iodide (PI) staining was carried out every 3-4 days to evaluate the percentage of living cells. Two-way repeated measures ANOVA with multiple comparisons, n=6 for each condition. In FIG. 16B, the heatmap shows mean firing rate (Hz) normalized by column in neuronal cultures over time for rapamycin and control treated cells. In FIG. 16C, dot plots show the average mean firing rate (Hz) of control and rapamycin-treated neurons at day 7, 14 and day 28. Unpaired, two-tailed t-test, n=8, p<0.0001. In FIG. 16D, dot plots show the percentage of cells that are releasing LDH after 6 hours and 24 hours of exposure to 1 mM glutamate upon pre-treatment with either control or rapamycin for 1 week. In FIG. 16E, rapamycin triggers rapid changes in metabolic gene expression. MA plots and KEGG pathway enrichment for primary cortical neurons treated with rapamycin (20 nm) for 4 h, 6 h, 24 h and 1 w. In FIG. 16F, rapamycin treatment leads to changes in Brd4 chromatin association associated with gene networks involved in metabolism (down) and neuronal longevity (up). Brd4 Chip sequencing experiments have been performed in saline and rapamycin treated primary cortical neurons six hours after treatment.

FIG. 18A shows genomic distribution of loci that have reduced occupancy of BRD2 (2099 loci) or BRD4 (4756 loci) at DIV7 after 6 h of IBET858 treatment. FIG. 18B shows that IBET sensitive genes lose BRD2 and BRD4 at the transcriptional start site of 1497 and 2226 genes, respectively. FIG. 18C shows representative traces of three genes, Atp5e, Akt1, and Idh2, that lose both BRD2 and BRD4 at the transcriptional start site. Of the genes that have reduced occupancy BRD2 or BRD4 at the promoter after 6 h of IBET858, 528 are also transcriptionally downregulated and these overlapping genes are enriched (KEGG enrichment) for metabolic pathways including oxidative phosphorylation, PPAR signaling, and pyruvate metabolism. Chi square test, p<0.0001; OR=3.363. FIG. 18D shows genomic distribution of loci that have increased occupancy of BRD2 (1680 loci) or BRD4 (1827 loci) at day 7 after 6 h of IBET858 treatment. In FIG. 18E, there is a gain of BRD2 at the transcriptional start sites of 828 genes and a gain of BRD4 at 295 genes. FIG. 18F shows representative traces of three genes, that gain both BRD2 and BRD4 (Atg4d), gain only BRD2 (Foxo1), or gain only BRD4, (Txnip). Of the genes that have increased occupancy of BRD2 or BRD4 at the promoter after 6 h of IBET858, 212 are also transcriptionally upregulated and these overlapping genes are enriched for neuroprotective pathways including longevity regulating pathway, FoxO signaling, and autophagy. Chi square test, p<0.0001; OR=5.234.

In FIG. 20A, MA plots and KEGG pathway enrichment for primary cortical neurons treated with IBET858 for 24 h, 72 h, and 1 w are shown. FIG. 20B shows that rapamycin and IBET control the expression of similar genes. Venn diagram shows degree of overlap between rapamycin and IBET-induced gene expression changes at 24 hrs and 1 week show significant overlap. In FIG. 20C, the heatmap shows genes that display equal downregulation by IBET and rapamycin and combined treatment has similar effect, suggesting that rapamycin-mediated suppression of these genes occurs via BRD displacement from chromatin. FIG. 20D shows that IBET treatment for one week induces changes in mTor activity as measured by S6K phosphorylation.

FIGS. 21A-21L illustrate that IBET858 treatment induces a metabolic switch in primary cortical neurons. In FIG. 21A, primary cortical neurons treated with IBET858 for 1 week have decreased glycolysis (p=1.22E−15; OR=48.8) and amino acid metabolites. In FIG. 21B, there is significant correlation between the decreased metabolites and genes downregulated after 72 hours to 1 week of IBET858 treatment. Spearman coefficient, 72 h: r=0.59; 1 w: r=0.56). FIG. 21C shows a summary of gene expression and metabolite data highlighting downregulation of solute carriers and metabolites that support anabolic and oxidative metabolic programs and an upregulation of neuroprotective metabolites and programs, such as autophagy. FIGS. 21D-21H show the glycolytic capacity of primary cortical neurons treated with acute (24 h) or chronic (1 w) of IBET858. IBET treated neurons was evaluated using the Seahorse assay. A progressive decrease in basal mitochondrial respiration (FIG. 21D) and ATP production (FIG. 21E) was observed, suggesting a decreased reliance on energy production by the oxidative phosphorylation. The mitochondria also display decreased proton leak (FIG. 21F) and increased coupling efficiency (FIG. 21G), suggesting increased mitochondrial integrity. Further, FIG. 21H shows that the neurons display a decrease in glycolytic capacity as measured by the extracellular acidification rate (ECAR). Two-way repeated measures ANOVA with multiple comparisons, *p<0.001. In FIGS. 21I-21J**, 1 w of IBET858 treatment increases autophagy as measured by an increase in the LC3 II/I ratio and a decrease in overall protein content by BCA assay. Unpaired two-tailed t-test, *p<0.05. In FIGS. 21K-21L, CAG-RFP-EGFP-Map11c3b mice expressing the LC3 protein together with RFP and a pH-dependent eGFP were used to evaluate the number of autophagic vesicles by immunofluorescence. In FIG. 21K, primary cortical neurons of these mice were treated with IBET858 for 1 w and an increase in autophagic vesicles was observed. In FIG. 21L, frequency distribution of autophagic vesicles after 24 h (left) or 1 w (right) treatment with IBET858. The histogram was fitted with a gaussian distribution graph for each condition. Control: n=291 and IBET858: n=222 for 24 h, p=0.0426 and control: n=654 and IBET858: n=615 for 1 w, p<0.0001, Kolmogorov-Smirnov test.

As shown in FIG. 22A, IBET promotes longevity of neurons in culture. Primary cortical neurons were treated with iBET858 (1 uM) at day 7 and propidium iodide (PI) staining was carried out every 3-4 days to evaluate the percentage of living cells. Two-way repeated measures ANOVA with multiple comparisons, n=6 for each condition. In FIG. 22B, long-lived IBET treated neurons maintain normal activity patterns. The heatmap shows mean firing rate (Hz) normalized by column in neuronal cultures over time. Dot plots show the average mean firing rate (Hz) of control and IBET858-treated neurons at day 14 (left) and day 28 (right). Unpaired, two-tailed t-test, n=6-7, p<0.0001. FIGS. 22C-22E illustrate that IBET treatment protects neurons from neurotoxin-induced cell death. Dot plots show the percentage of cells that are propidium iodide negative after different neurotoxic insults when pre-treated with either control or iBET for 1 week. FIG. 22C shows results of 6 h and 24 h after 1 mM glutamate exposure. FIG. 22D shows results of 18 h, 24 h, and 48 h of hypoxia (1% 02). FIG. 22E shows results of 48 h and 72 hours of Aβ1-43 oligomer exposure (10 μM). Two-way repeated measures ANOVA with multiple comparisons, n=3 per group, *p<0.001. Experiments were repeated a minimum of three times. FIG. 22F shows that extended—but not acute—IBET pre-treatment protects neurons from neurotoxin-induced cell death. Primary cortical neurons were pre-treated with either IBET858 (1 μM) or control for 2 hours, 24 hours, 72 hours, or 1 week before glutamate exposure (1 mM) at day 14. LDH release was measured 6 hours, 24 hours, and 72 hours after initial glutamate exposure. Two-way repeated measures ANOVA with multiple comparisons, n=3 per group, *p<0.001. FIG. 22G shows that temporary, one week of IBET treatment mediates prolonged neuronal survival that is maintained even in the absence of IBET. The heatmap shows mean firing rate (Hz) normalized by column in neuronal culture treated with control, IBET858 (1 uM) continuously and IBET858 (1 uM) for 1 week followed by washout at day 14, n=7-8. As shown in FIG. 22H, temporary IBET pretreatment establishes a neuroprotective phenotype that is maintained even in the absence of IBET. Primary cortical neurons were pre-treated with either 1 week IBET858 (1 μM) or 72 hours or followed by wash out and 4 days on DMSO before glutamate exposure (1 mM) at day 14. Propidium iodine staining was used to assess numbers of live/dead cells. Two-way repeated measures ANOVA with multiple comparisons.

In FIG. 23A, IBET treatment induces neuroprotective gene expression changes in the hippocampus of mice in vivo. The heatmap shows gene expression analysis of striatum of IBET858 treated mice compared to vehicle. Autophagy and proteostasis genes are increased, while many genes involved in different metabolic pathways are downregulated. Selected GO terms for up- and down-regulated genes are shown. Arrowheads indicate p=0.05. FIG. 23B shows that IBET treatment protects neurons from glutamate-induced toxicity in vivo. C57bl/6 mice were daily treated with IBET858 (30 mg/kg, i.p.) for 1 week, followed by stereotaxic injection of kainic acid in the hippocampus. Mice were perfused 24 h after kainic acid injection and brains were immunostained for cCASP3 to identify dying cells. Both conditions n=4, p=0.0074, unpaired two-tailed t-test. FIGS. 23C and 23D show that IBET treatment prevents neuronal death and neuroinflammation in a mouse model of Alzheimer disease. FIG. 23C shows immunofluorescence of IBA1=microglia (yellow, quantified in FIG. 23D) and NEUN=neurons (purple, quantified in FIG. 23D) in the dentate gyms after 7 weeks of P25 transgene expression (scale bar=100 μM, n=2-3 images per animal, 3-5 animals per group) shows a significant rescue of neuronal numbers and microglia activation in the hippocampus. FIG. 23E shows that IBET treatment prevents loss of memory in a mouse model of Alzheimer disease. Classical fear conditioning assay was used to assess learning and memory in mice. Percent time freezing during contextual and cued recall one week after classic fear conditioning is shown. One-way ANOVA, n=12-20 per group, p<0.01, *p<0.001.

In FIG. 24A, IBET treatment does not affect Caspase 3 expression. Gene expression levels for Casp3 are unaffected by 5-week IBET858 treatment in vivo. n=3, unpaired two-tailed t-test. FIGS. 24B and 24C show that IBET treatment does not affect p25 transgene expression. In. FIG. 24B, scheme of IBET treatment in P25 mouse is shown. To generate the p25 neurodegenerative mouse model, tetOCDK5R1/GFP were bred to CamK2a-tTA mice ("CK-p25"). Transgene overexpression was induced at 6 weeks of age by removing doxycycline from the diet. In FIG. 24C, after two weeks, mice were daily injected with IBET858 (30 mg/kg, i.p.) or vehicle. Gene expression and protein levels of GFP reflecting transgene expression are unchanged (n=3-5, One-way ANOVA with Tukey's multiple comparisons, *p<0.05). FIGS. 24D and 24E show that IBET treatment rescues neuronal loss in p25 model. In FIG. 24D, Brain weight of control and CKp25 mice treated with vehicle or IBET858 are shown as percentage of control brains. In FIG. 24E, NEUN and PSD95 protein levels in the hippocampus of CK-p25 mice are restored by IBET858 treatment (One-way ANOVA, n=5-6 per group, *p<0.05, p<0.01). FIG. 24F shows that IBET treatment reduces inflammatory gene expression and rescues neuronal gene expression in p25 mice. Total RNA was isolated from the hippocampus of p25 overexpressing mice that were daily injected with IBET858 (30 mg/kg, i.p.) and sequenced (n=3 per group). Heatmaps show normalized expression of 365 genes induced by P25 overexpression that are significantly suppressed by IBET858 and normalized expression of 373 genes suppressed by P25 overexpression that are significantly induced by IBET858. FIG. 24G** shows that temporary IBET treatment rescued survival in Huntington's (neurodegeneration) but not in Rett syndrome neurodevelopmental syndrome) in mice. Survival graph of R6/2 mice treated daily with either vehicle or IBET858 (30 mg/kg, i.p.) at 6 weeks of age for 5 weeks. Survival curves were compared with the Log-rank (Mantal-Cox) test, p=0.0190, n=15 for control and n=11 for IBET858. Survival graph of Mecp2 mice treated daily with either vehicle or IBET858 (30 mg/kg, i.p.) at 6 weeks of age for 5 weeks. Survival curves were compared with the Log-rank (Mantal-Cox) test, p=0.4690, n=10 for control and n=6 for IBET858.

DETAILED DESCRIPTION

Figure 1A:
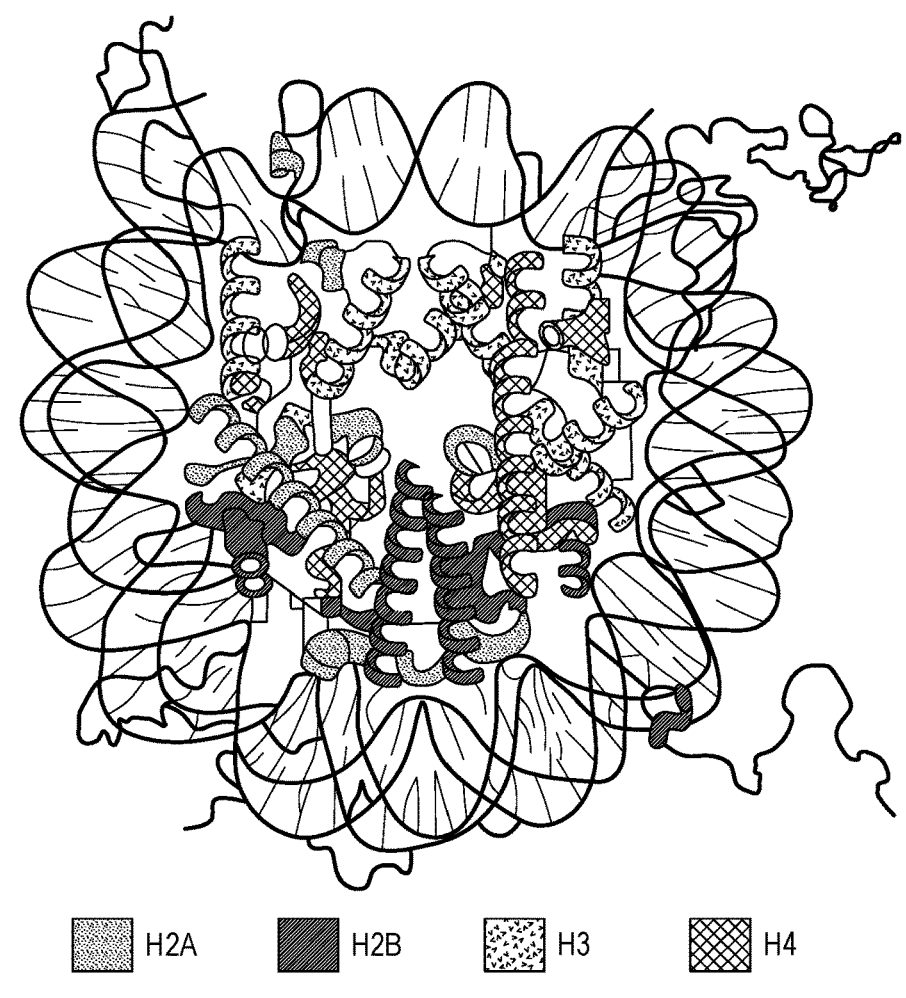
FIGS. 1A-1E show principles of transcriptional regulation.
Figure 1B:
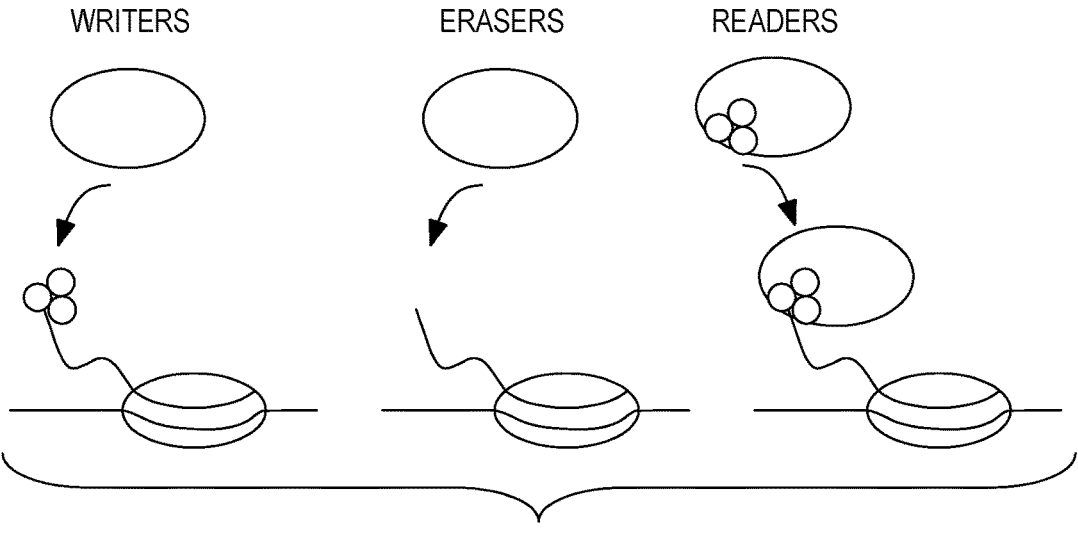
Figure 1C:
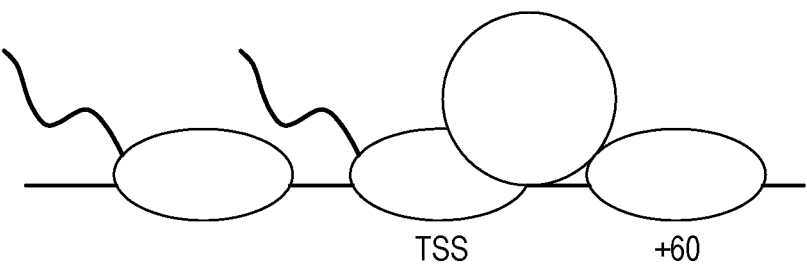
Figure 1D:
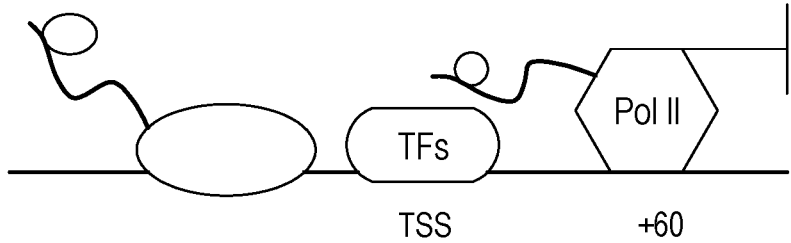
Figure 1E:
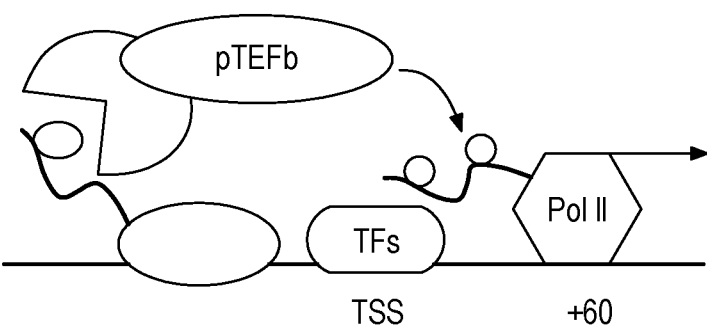
Figure 2A:
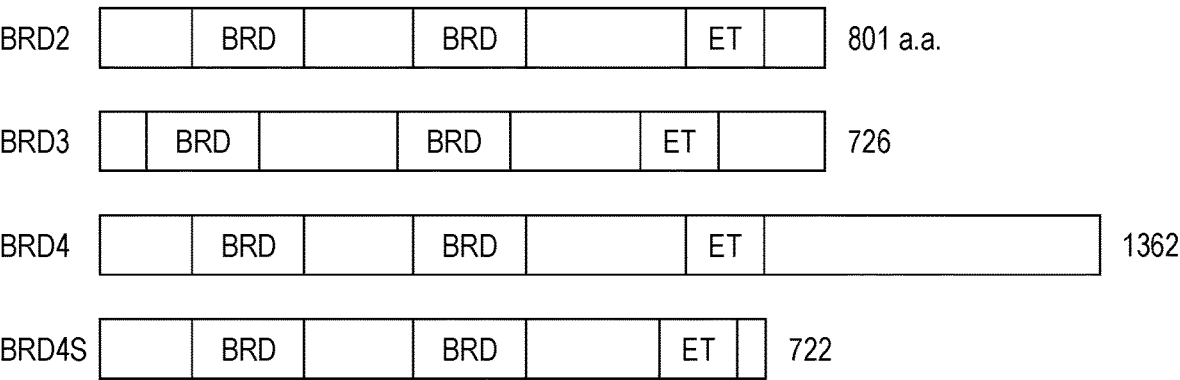
FIGS. 2A-2E show structure and function of the BET proteins.
Figure 2B:
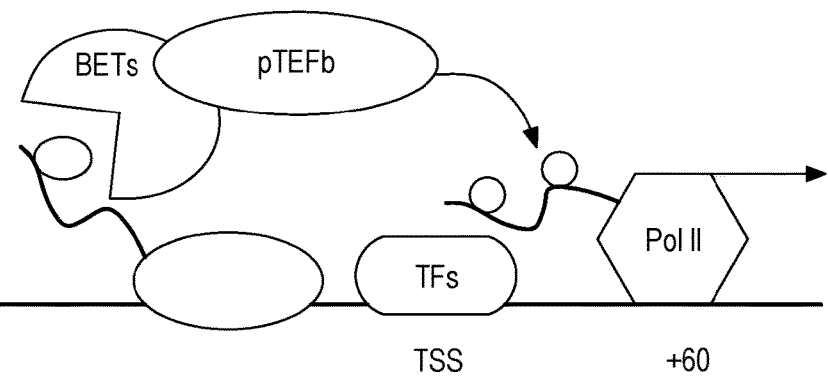
Figure 2C:
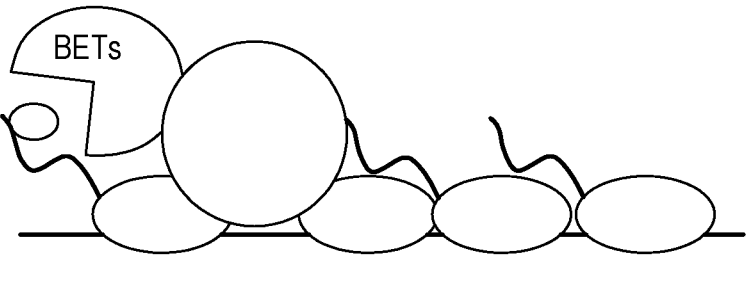
Figure 2D:
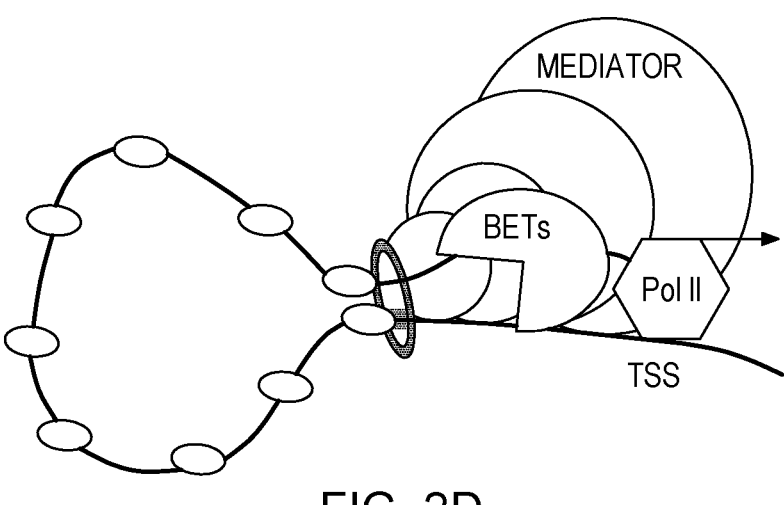
Figure 2E:
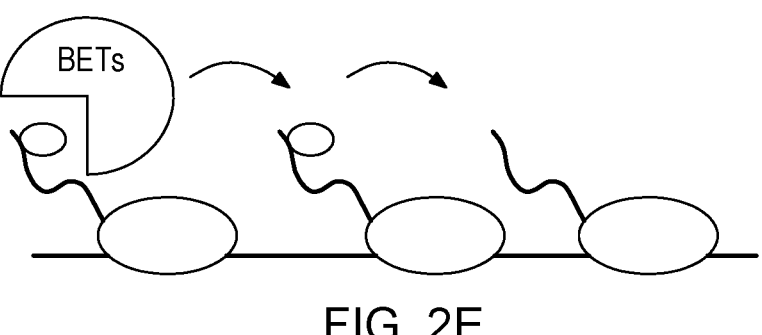

A first aspect of the present disclosure relates to a method of inducing a neuroprotective state. The method includes administering a Bromodomain and Extra-Terminal motif (BET) inhibitor under conditions effective to induce a neuroprotective state.

It is to be appreciated that certain aspects, modes, embodiments, variations and features of the present invention are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this invention belongs.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Where a range of values is described, it should be understood that intervening values, unless the context clearly dictates otherwise, between the upper and lower limit of that range and any other stated or intervening value in other stated ranges, may be used in the embodiments described herein.

As used herein, the terms "subject," "individual" or "patient," used interchangeably, means any animal, including mammals, such as mice, rats, other rodents, rabbits, dogs, cats, swine, cattle, sheep, horses, or primates, such as humans.

As used herein, the term "purified" means that when isolated, the isolate contains at least 90%, at least 95%, at least 98%, or at least 99% of a compound described herein by weight of the isolate.

As used herein, the phrase "substantially isolated" means a compound that is at least partially or substantially separated from the environment in which it is formed or detected.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable sub-combination.

In accordance with this and all aspects of the present disclosure, a subject suitable for treatment using the methods of the present disclosure includes any animal, preferably a mammal, e.g., human, non-human primate, rodent, cow, horse, sheep, pig, goat, deer, elk, bison, etc. Preferably, the subject is a human. Particularly susceptible subjects include adults and elderly adults. However, any infant, juvenile, adult, or elderly adult can be treated in accordance with the methods of the present disclosure.

In certain embodiments, the present disclosure encompasses use of one or more BET targeting compounds for modulating the activity of a BET protein. In one embodiment, modulating the activity comprises use of a BET targeting agent that can affect the function of one or more BET proteins, including but not limited to the function of Brd2 and Brd4. Without intending to be limited by any particular theory, it is generally considered that BET-targeting compounds function by modulating protein-protein interaction between one or more BET proteins and acetylated histones and/or transcription factors. In one embodiment, modulating a BET protein comprises use of a BET targeting compound to fully, or only partially inhibit one or more functions of the BET protein. In one embodiment, modulating a BET protein comprises use of a BET targeting protein for stimulating, enhancing, and/or activating one or more functions of the BET protein. A BET inhibitor as described herein is also interchangeably referred to herein as "IBET treatment" and "IBET."

In one embodiment, the BET modulator (i.e., BET inhibitor) prevents BET-dependent transcription. Inhibition of BET-dependent transcription may in one embodiment initiates a protective state in neurons characterized by decreased metabolic activity, increased protein degradation pathways, and increased lifespan. Pharmacological BET inhibition, in one embodiment, decreases microglial-mediated inflammation while increasing neuronal resilience to toxic stimuli. An example of a toxic stimuli includes excessive glutamate.

BET modulators as described herein include, for example, all BET inhibitors that are known to those skilled in the art. The BET modulator may include, for example, IBET858, JQ1, OTX015, BET-d246, ABBV-075, ABBV-744, IBET151, IBET762, CP203, CPI-0610, PFI-1, RVX-208, DINACICLIB, INCB057643, ZEN003694, PLX51107, CC-90010, RO6870810, and any combination thereof. See, e.g., WO 2017/031416, which is hereby incorporated by reference in its entirety.

In one embodiment, the method may comprise administering a BET inhibitor in an in vitro sample, for example in neurons obtained from a living system or subject. As used herein, a sample may include any sample obtained from a living system or subject, including, for example, blood, serum, and/or tissue. In one embodiment, a sample is obtained through sampling by minimally invasive or non-invasive approaches (for example, by urine collection, stool collection, blood drawing, needle aspiration, and other procedures involving minimal risk, discomfort, or effort). Alternatively, samples may be gaseous (for example, breath that has been exhaled) or liquid fluid. Liquid samples may include, for example, urine, blood, serum, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, nasal excretions, and other liquids. Samples may also include a clinical sample such as serum, plasma, other biological fluid, or tissue samples, and also includes cells in culture, cell supernatants and cell lysates. In one embodiment, the sample is selected from the group consisting of whole blood, serum, urine, and nasal excretion. Samples may be in vivo or ex vivo.

The method in certain embodiments may comprise administering a BET inhibitor in an in vivo sample, for example in the brain of a subject thought to be in need thereof. In one embodiment, the method includes comprises administering a composition comprising an effective amount of a BET targeting compound, such as a BET inhibitor, to an individual in need of prophylaxis and/or therapy of a condition that would benefit from induction of a neuroprotective state. In one embodiment, the administering of the BET inhibitor is such that one or more symptoms of a condition are improved.

In one embodiment, the method includes selecting subject as a candidate for treatment with a BET targeting compound, such as a BET inhibitor, for a condition which would benefit from induction of a neuroprotective state, such correlation being established by discoveries and implementations as described herein. The method may, in one embodiment, include testing a subject to determine whether the subject has a condition that would benefit from induction of a neuroprotective state, and optionally, subsequent to determining the subject has such a condition, administering to the subject a therapeutically effective amount of the BET modulating compound (e.g., a BET inhibitor). In one embodiment, a subject selected for treatment with a BET modulator (e.g., a BET inhibitor) is selected based on a determination of whether a subject has neurodegeneration or is at risk of having neurodegeneration. In one embodiment, a determination that a subject is a candidate for treatment with a BET targeting compound due to the presence of a neurodegeneration or a subject has a risk of having neurodegeneration (i.e., the subject is diagnosed with a neurodegenerative condition) can be represented in a written and/or digitized report which can also be provided to a health care provider.

Blockade of BET-mediated transcription in a subject may induce a neuroprotective state to preserve brain function during neurodegeneration. Accordingly, in one embodiment, the method includes selecting a subject having or at risk of having neurodegeneration. In one embodiment, the method includes comprises administering a composition comprising an effective amount of a BET targeting compound, such as a BET inhibitor, to an individual in need of prophylaxis and/or therapy to induce a neuroprotective state. In one embodiment, the administering of the BET inhibitor is such that one or more symptoms of a condition such a neurodegeneration are improved.

In one embodiment, the subject has a neurodegenerative condition, for example, Alzheimer's Disease (AD), Huntington's Disease, frontotemporal dementia, senile dementias, dementia with lewy bodies, and mild cognitive impairment.

Neurodegeneration as described herein may appear as impairment to thought processes, including, for example, loss of higher reasoning, forgetfulness, learning disabilities, concentration difficulties, decreased intelligence, and any other reduction in mental function. Neurodegeneration may begin in utero, at birth, or can occur at any point in a person's lifespan. Accordingly, suitable subjects for administration in accordance with the methods of the present disclosure include infants, children, adolescents, young adults, adults, and elderly. In one embodiment, the subject is of advanced age or is elderly.

Causes of neurodegeneration in infants and small children include chromosome abnormalities and genetic syndromes, malnutrition, prenatal drug exposure, poisoning due to lead or other heavy metals, hypoglycemia (low blood sugar), neonatal jaundice (high bilirubin levels developing after birth), hypothyroidism (underactive thyroid), complications of prematurity, trauma or child abuse such as shaken baby syndrome, or oxygen deprivation in the womb or during or after birth.

Neurodegeneration that develops in childhood or adolescence can result from many conditions. Examples include side effects of cancer therapy, malnutrition, heavy metal poisoning, autism (abnormal development of communication and social skills), metabolic conditions, and systemic lupus erythematosus (disorder in which the body attacks its own healthy cells and tissues.

BET inhibition is known to cause an Autism-like phenotype in young mice. As identified in Sullivan et al., "Autism-Like Syndrome is Induced by Pharmacological Suppression of BET Proteins in Young Mice," *J. Exp. Med.* 212:1771-1781(2015), which is hereby incorporated by reference in its entirety, the bromodomain and extraterminal domain-containing proteins (BETs) are epigenetic regulators of genes involved in ASD-like behaviors in mice. Moreover, Sullivan et al., "Autism-Like Syndrome is Induced by Pharmacological Suppression of BET Proteins in Young Mice," *J. Exp. Med.* 212:1771-1781(2015), which is hereby incorporated by reference in its entirety, further found that the pharmacological suppression of BET proteins in the brain of young mice, by the novel, highly specific, brain-permeable inhibitor I-BET858 leads to selective suppression of neuronal gene expression followed by the development of an autism-like syndrome. Many of the I-BET858-affected genes have been linked to ASD in humans, thus suggesting the key role of the BET-controlled gene network in the disorder. Sullivan et al., "Autism-Like Syndrome is Induced by Pharmacological Suppression of BET Proteins in Young Mice," *J. Exp. Med.* 212:1771-1781(2015), which is hereby incorporated by reference in its entirety. The present disclosure suggests that environmental factors controlling BET proteins or their target genes may contribute to the epigenetic mechanism of ASD.

Neurodegeneration may occur in young adults, adults, and elderly adults. This may be an age-related phenomenon (i.e., not associated with any disease state or with any neurodegeneration), for example, or due to age-related memory loss. Alternatively, neurodegeneration may cause various cognitive impairments and may be associated with or resulting from a disease or other condition such as Alzheimer's Disease, Huntington's Disease, frontotemporal dementia, senile dementias, dementia with lewy bodies, and mild cognitive impairment. In one embodiment, the neurodegenerative disease is prevented. In another embodiment, the neurodegenerative disease is treated.

The administration to a subject having or at risk of having neurodegeneration may be useful in inducing a neuroprotective state and thereby improve cognition of a subject having a or at risk of having neurodegeneration, including, for example, Alzheimer's Disease and Huntington's Disease. In one embodiment, the subject has or is at risk of having Alzheimer's Disease. In one embodiment, the subject has or is at risk of having Huntington's Disease. In another embodiment, the subject may not have or be at risk of having neurodegeneration. In one embodiment, the neurodegeneration or risk of neurodegeneration occurs after exposure to one or more neurotoxic agents.

Individuals suffering from neurodegeneration may be unable to think well enough to do normal activities, such as dressing or eating. Other manifestations of neurodegeneration include a loss of problem solving capacity, memory impairment, and difficulty with recall of information and remembering new experiences and past events. Individuals suffering from neurodegeneration may be unable to differentiate between real and unreal experiences. There may be a loss of a train of thought, a phenomenon known as "word salad", social withdrawal at least in part because of fear, disorganized thinking, loss of long-term memory, and loss of responsiveness. Other individuals may experience difficulty concentrating amid distractions and may be slower at processing new information, experience a loss of recent memory, have difficulty with new learning, and/or lose executive function ability in starting tasks and setting goals. Still other individuals with neurodegeneration may experience difficulty with decision making, control of inhibitions, planning, and memory, may have problems with concentration, sifting different thoughts, application to problems, and general mental activities. These symptoms and signs are purely for illustration and it is understood by one of skill in the art that there are many other medical manifestations arising from neurodegeneration and cognitive decline. In one embodiment, the BET targeting compound (e.g., the BET inhibitor) is administered to a subject, optionally a subject having or at risk of having neurodegeneration, prior to onset of one or more cognitive deficits in the subject. In one embodiment, by administering a composition comprising a BET targeting compound to a subject in need thereof, the severity of at least one symptom in the subject is reduced, and/or there is a slowing of the progression of the symptom(s), and/or a cessation of the progression of the symptom(s), and/or an elimination of the symptom(s).

Neurodegeneration caused by age-associated cognitive decline as described herein may include, for example, the progressive loss of physiological functions in multiple organs and systems that occurs during aging (Lopez-Otin et al., "The Hallmarks of Aging," *Cell* 153:1194-1217 (2013), which is hereby incorporated by reference in its entirety). The brain is particularly susceptible to the effects of aging. Mammalian cognitive function, especially learning and memory, gradually declines with aging (Glisky, E. L. "Changes in Cognitive Function in Human Aging," *In Brain Aging: Models, Methods, and Mechanisms* D. R. Riddle, editor Boca Raton (FL) (2007) and Harada et al., "Normal Cognitive Aging," *Clin. Geriatr. Med.* 29:737-752 (2013), which are hereby incorporated by reference in their entirety). Aging is known to induce gradual deterioration of the adaptive immune system and to increase susceptibility to infectious diseases, termed immunosenescence (Goronzy et al., "Understanding Immunosenescence to Improve Responses to Vaccines," *Nat. Immunol.* 14:428-436 (2013), which is hereby incorporated by reference in its entirety). Many tissue-resident innate immune cells, such as microglia, display hyperactivation phenotypes with aging (Dilger et al., "Aging, Microglial Cell Priming, and the Discordant Central Inflammatory Response to Signals From the Peripheral Immune System," *J. Leukoc. Biol.* 84:932-939 (2008) and Spittau, B. "Aging Microglia-Phenotypes, Functions and Implications for Age-Related Neurodegenerative Diseases," *Front Aging Neurosci.* 9:194 (2017), which are hereby incorporated by reference in their entirety). In addition, subsets of memory or memory-like T and B cells with innate-like properties have been observed to accumulate with aging (Fukushima et al., "The Impact of Senescence-Associated T Cells on Immunosenescence and Age-Related Disorders," *Inflamm. Regen.* 38:24 (2018); Goronzy et al., "Successful and Maladaptive T Cell Aging," *Immunity* 46:364-378 (2017); Hao et al., "A B-cell Subset Uniquely Responsive to Innate Stimuli Accumulates in Aged Mice," *Blood* 118:1294-1304 (2011); Ratliff et al., "In Senescence, Age-associated B Cells Secrete TNFalpha and Inhibit Survival of B-Cell Precursors," *Aging Cell* 12:303-311 (2013); Rubtsov et al., "Toll-like Receptor 7 (TLR7)-driven Accumulation of a Novel CD11c(+) B-cell Population is Important for the Development of Autoimmunity," *Blood* 118: 1305-1315 (2011); and Rubtsova et al., "Age-Associated B Cells: A T-bet-Dependent Effector with Roles in Protective and Pathogenic Immunity," *J. Immunol.* 195:1933-1937 (2015), all of which are incorporated by reference in their entirety).

Compositions for performing any method described herein may be prepared by mixing any suitable BET modulating compound (i.e., a BET inhibitor) with any suitable pharmaceutically acceptable carriers, excipients, and/or stabilizers. Examples of compositions suitable for mixing with the compounds are described in Remington: The Science and Practice of Pharmacy, 21st Edition, Philadelphia, PA. Lippincott Williams & Wilkins (2005), which is hereby incorporated by reference in its entirety.

Administration of a BET targeting compound (i.e., a BET inhibitor or IBET) may result in a reduction in one or more symptoms by at least 10%, 20%, 30%, 50% or greater, up to a 75-90%), or 95% or greater, reduction in the one or more symptoms in a subject, compared to placebo-treated or other suitable control subjects, or any other suitable reference. In one embodiment, the method includes administering a composition comprising a therapeutically effective amount of a compound described herein.

As used herein, the phrase "therapeutically effective amount" means an amount of active compound or pharmaceutical agent (i.e., a BET targeting compound, preferably a BET inhibitor) that elicits the biological or medicinal response that is being sought in a tissue, system, animal, individual or human by a researcher, veterinarian, medical doctor, or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size, and sex of the subject. Optimal amounts can also be determined based on monitoring of the subject's response to treatment.

Administration of a BET targeting compound, such as a BET inhibitor, can be performed in conjunction with conventional therapies that are intended to induce a neuroprotective state. For example, a composition comprising a BET inhibitor could be administered prior to, concurrently, or subsequent to conventional therapies known to those skilled in the art for prophylaxis or therapy for conditions that may benefit from induction of a neuroprotective state, conditions that may benefit from a reduction in microglial inflammation, conditions that may benefit from restoration of microglial homeostasis, and/or a condition such as neurodegeneration. Such therapies include but are not limited to combining treatment with a BET inhibitor with other pharmaceutical agent(s) known to be effective against the particular condition being treated, behavioral and physical therapies, cognitive therapies, and the like. In one embodiment, an additional agent may be administered in addition to the BET inhibitor.

As used herein, the term "simultaneous" therapeutic use refers to the administration of at least one additional agent beyond the BET targeting compound (i.e., BET inhibitor), optionally, by the same route and at the same time or at substantially the same time. As used herein, the term "separate" therapeutic use refers to an administration of at least one additional agent beyond the BET targeting compound (i.e., BET inhibitor) at the same time or at substantially the same time by different routes. As used herein, the term "sequential" therapeutic use refers to administration of at least one additional agent beyond the BET targeting compound (i.e., BET inhibitor) at different times, the administration route being identical or different. More particularly, sequential use refers to the whole administration of the additional agent before administration of the BET targeting compound (i.e., BET inhibitor). It is thus possible to administer the additional agent over several minutes, hours, or days before applying the BET targeting compound (i.e., BET inhibitor).

In one embodiment, the additional agent may include, for example, any treatments that are useful in treating a subject having or at risk of having neurodegeneration. For example, any treatments known by those skilled in the art for Alzheimer's Disease (AD), Huntington's Disease, frontotemporal dementia, senile dementias, dementia with lewy bodies, and mild cognitive impairment, could be useful as an additional agent. The additional agent may, for example, be one or more antibiotic compound; one or more antimicrobial compound; one or more antibody; one or more biocidal agent; one or more nanoparticle; one or more self-assembling nanoparticle; one or more viral particle; one or more bacteriophage particle; one or more bacteriophage DNA; genetic material including but not limited to a plasmid, RNA, mRNA, siRNA, and an aptamer; one or more chemotherapy agent; one or more growth factor; one or more synthetic scaffold including but not limited to hydrogel and others; one or more natural scaffold including but not limited to collagen gel and decellularized tissue (whole, dissolved, denatured, or powdered); one or more electrode; one or more drug or pharmaceutical compound including but not limited to an anti-inflammatory agent, an inflammatory agent, a pain blocking agent, and a numbing agent; one or more microbes; and one or more bacteria.

In one embodiment, administering the BET targeting compound (i.e., the BET inhibitor) further comprises a pharmaceutically acceptable carrier. "Pharmaceutically acceptable carriers" as used herein refer to conventional pharmaceutically acceptable carriers. See *Remington's Pharmaceutical Sciences*, by E. W. Martin, Mack Publishing Co., Easton, Pa., 15th Edition (1975), which is hereby incorporated by reference in its entirety, describes compositions suitable for pharmaceutical delivery of the inventive compositions described herein. In particular, a pharmaceutically acceptable carrier as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits. In one embodiment, the pharmaceutically acceptable carrier is selected from the group consisting of a liquid filler, a solid filler, a diluent, an excipient, a solvent, and an encapsulating material.

Pharmaceutically acceptable carriers (e.g., additives such as diluents, immunostimulants, adjuvants, antioxidants, preservatives, and solubilizing agents) are nontoxic to the cell or subject being exposed thereto at the dosages and concentrations employed. Examples of pharmaceutically acceptable carriers include water, e.g., buffered with phosphate, citrate and another organic acid. Representative examples of pharmaceutically acceptable excipients that may be useful in the present disclosure include antioxidants such as ascorbic acid; low molecular weight (less than about 10 residues)

polypeptides; proteins, such as serum albumin, gelatin, or immunoglobulins; adjuvants (selected so as to avoid adjuvant-induced toxicity, such as a (3-glucan as described in U.S. Pat. No. 6,355,625, which is hereby incorporated by reference in its entirety, or a granulocyte colony stimulating factor (GCSF)); hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

In addition, in various embodiments, the BET targeting compound (i.e., the BET inhibitor) according to the present disclosure may be formulated for delivery via any route of administration. The route of administration may refer to any administration pathway known in the art, including but not limited to aerosol, nasal, oral, transmucosal, transdermal, subcutaneous, or parenteral. Parenteral refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or in the form of lyophilized powders.

The BET targeting compound (i.e., the BET inhibitor) may be formulated as appropriate for such administration, which may be tailored to a given purpose, such as in a tablet, capsule, or other form for oral administration or injectable formulation for injection, or gel, cream, powder, ointment, or other composition for rectal or dermal application, etc. Any suitable approach for delivery of BET targeting compound (i.e., the BET inhibitor) can be utilized to practice this aspect. Typically, the BET targeting compound (i.e., the BET inhibitor) will be administered to a patient in a vehicle that delivers the agent(s) to the target cell, tissue, or organ. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, intracranially, intrathecally, intracerebroventricularly, intraspinally, by application to mucous membranes (such as that of the nose, throat, bronchial tubes, genitals, and/or anus), or implantation of a sustained release vehicle.

Some non-limiting examples include oral, parenteral, subcutaneous, intraperitoneal, intrapulmonary, intranasal, intracranial, and can be performed using an implantable device, such as an osmotic pump. Parenteral infusions include intramuscular, intravenous, intraarterial, intraperitoneal, pulmonary instillation as mist or nebulization, and subcutaneous administration. In one embodiment, the administering is carried out intraperitoneally, orally, parenterally, nasally, subcutaneously, intravenously, intramuscularly, intracerebroventricularly, intraparenchymally, by inhalation, intranasal instillation, by implantation, by intracavitary or intravesical instillation, intraocularly, intraarterially, intralesionally, transdermally, topically, intradermally, intraplurally, intrathecally, or by application to mucous membranes.

In one embodiment, the composition that may be administered in accordance with the methods described herein may further comprise an adjuvant. Suitable adjuvants are known in the art and include, without limitation, flagellin, Freund's complete or incomplete adjuvant, aluminum hydroxide, lysolecithin, pluronic polyols, polyanions, peptides, oil emulsion, dinitrophenol, iscomatrix, and liposome polycation DNA particles.

In one embodiment, the administering may be conducted via aerosol inhalation. In some embodiments, an agent can be incorporated into pharmaceutical compositions suitable for administration, as described herein.

The BET targeting compound, may, in one embodiment, be administered under an extended dosing and/or an intermittent dosing protocol.

An extended dosing protocol as described herein may include administering the BET targeting compound (i.e., BET inhibitor) more than once, and for a period of time beyond a single dose or a short dosing protocol. For example, an extended dosing protocol may include administering one or more doses of the BET targeting compound (i.e., BET inhibitor) to a sample or a subject each consecutive day for a period of more than one day. Alternatively, an extended dosing protocol may, for example, include administering one or more doses of the BET targeting compound (i.e., BET inhibitor) to a sample or a subject at a predetermined interval with one or more days between each administration.

An intermittent dosing protocol as described herein may include administering the BET targeting compound (i.e., BET inhibitor) more than once, and optionally at periodic intervals that are determined to be useful in inducing the effect of inhibiting BET (e.g., and inducing a neuroprotective state). An intermittent dosing protocol as described herein may be useful in managing and mitigating toxicity risks to a subject or a sample, as it may administer more than one dose but also provides a period of time between each dose is administered sufficient to reduce toxicity in a subject or a sample. Under an intermittent dosing protocol, the BET targeting compound (i.e., BET inhibitor) may be administered in one or more doses for a set period of time ("on period") followed by a set period of time with no doses being administered ("off period"), followed by repeating the "on period" and "off period" one or more times for a sustained period of time effective to of inhibit BET (and induce a neuroprotective state).

In one embodiment, the method includes repeating administration of the BET targeting compound (i.e., BET inhibitor) any number of times necessary to create a desired effect. For example, the BET targeting compound may be administered once daily for a set period of time (i.e., an extended dosing protocol) or may be administered for one or more "on periods" where each "on period" may be followed by an "off period" (i.e., an intermittent dosing protocol). In one embodiment, the BET inhibitor is administered once daily for a period of time of at least about 1 week. For example, the BET inhibitor may be administered once daily for about 1 week, about 2 weeks, about 3 weeks, about 4 weeks, about 5 weeks, about 6 weeks, about 7 weeks, about 8 weeks, about 9 weeks, about 10 weeks, about 12 weeks, about 15 weeks, about 20 weeks, about 25 weeks, about 30 weeks, about 35 weeks, about 40 weeks, about 45 weeks, about 50 weeks, about 52 weeks, about 1 year, or more than about 1 year. In one embodiment, the BET inhibitor is administered for a time of between about 1 week and about 12 weeks.

In one embodiment, the BET inhibitor is administered under an intermittent dosing protocol, for example, once daily for one week (i.e., "on period"), followed by 3 weeks with no administration (i.e., "off period"), and this may optionally be repeated. Alternatively, in one embodiment, the BET inhibitor is administered under an intermittent dosing protocol, for example, once daily for one week (i.e., "on period"), followed by 8 weeks with no administration (i.e., "off period"), and this may optionally be repeated. In another embodiment, the BET inhibitor is administered under an intermittent dosing protocol, for example, once daily for one week (i.e., "on period"), followed by 6 months off with no administration (i.e., "off period"), and this may optionally be repeated.

The terms dose and dosage are used interchangeably herein. A dose refers to the amount of active ingredient given to an individual at each administration. The dose will vary depending on a number of factors, including the range of normal doses for a given therapy, frequency of administration, size and tolerance of the individual, severity of the condition, risk of side effects, and the route of administration. One of skill will recognize that the dose can be modified depending on the above factors or based on therapeutic progress. The term dosage form refers to the particular format of the pharmaceutical or pharmaceutical composition, and depends on the route of administration. Dosage, toxicity, and therapeutic efficacy of the agents or compositions of the present disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices may be desirable. While compositions that exhibit toxic side effects may be used, care should be taken to design a delivery system that targets such compositions to the site of affected tissue in order to minimize potential damage to uninfected cells and, thereby, reduce side effects.

The amount to be administered will, of course, vary depending upon the treatment regimen. Generally, an agent is administered to achieve an amount effective for prevention and/or treatment of a subject having a condition that could benefit from induction of a neuroprotective state (e.g., a subject having or at risk of having neurodegeneration). Thus, a therapeutically effective amount can be an amount which is capable of at least partially treating or preventing such a condition. This includes, without limitation, delaying the onset of infection. The dose required to obtain an effective amount may vary depending on the agent, formulation, and individual to whom the agent is administered. In one embodiment, the BET targeting compound (i.e., the BET inhibitor) is administered in an amount between about 10 mg/kg and about 100 mg/kg. The amount of BET targeting compound (i.e., BET inhibitor) may be below 10 mg/kg in one embodiment, or in an alternative embodiment, may be above 100 mg/kg. For example, the BET targeting compound may be administered in an amount of less than 1 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, above 100 mg/kg, or any amount therebetween. In one embodiment, the BET targeting compound (i.e., the BET inhibitor) is administered in an amount between about 10 mg/kg and about 60 mg/kg.

As described herein, inhibition of BET-dependent transcription initiates a protective state in neurons characterized by decreased metabolic activity, increased protein degradation pathways, and increased lifespan. Importantly, BET inhibition decreases microglial-mediated inflammation while increasing neuronal resilience to toxic stimuli and therefore has promising therapeutic potential in the treatment of neurodegenerative diseases. In one embodiment, the BET inhibitor increases neuronal survival. In another embodiment, the BET inhibitor prevents and/or treats neuronal aging. In yet another embodiment, the BET inhibitor prevents and/or treats neuronal degeneration.

The BET inhibitor, in another embodiment, suppresses microglial inflammatory gene expression, metabolic gene expression, and/or a combination thereof. In another embodiment, the BET inhibitor suppresses immune response, interferon activity, apoptosis gene expression in microglia, and/or a combination thereof. In one embodiment, the BET inhibitor prevents neuronal loss, brain atrophy, and/or a combination thereof. In yet another embodiment, the BET inhibitor promotes memory formation.

A second aspect of the present disclosure relates to a method of preventing and/or treating neurodegenerative disease. The method includes administering a Bromodomain and Extra-Terminal motif (BET) inhibitor under conditions effective to prevent and/or treat neurodegenerative disease.

This aspect is carried out in accordance with the previously described aspect.

A third aspect of the present disclosure relates to a method of reducing microglial inflammation. The method includes administering a Bromodomain and Extra-Terminal motif (BET) inhibitor under conditions effective to reduce microglial inflammation.

This aspect is carried out in accordance with the previously described aspects.

In one embodiment, the method further includes selecting a subject having or at risk of having microglial inflammation. Microglial inflammation in accordance with the present disclosure may exacerbate neurodegeneration. Inflammation, particularly inflammation in the microglia, can exacerbate and even initiate neuronal death. Piani et al., "Murine Brain Macrophages Induced NMDA Receptor Mediated Neurotoxicity In Vitro by Secreting Glutamate," *Neuroscience Letters* 133:159-162 (1991); Marín-Teva et al., "Microglia Promote the Death of Developing Purkinje Cells," *Neuron* 41:535-547 (2004); Frakes et al., "Microglia Induce Motor Neuron Death via the Classical NF-κB Pathway in Amyotrophic Lateral Sclerosis," *Neuron* 81:1009-1023 (2014), which are hereby incorporated by reference in their entirety. In Alzheimer's Disease (AD), the most common form of neurodegeneration, mutations in immune molecules such as TREM2 (Guerreiro et al., "TREM2 Variants in Alzheimer's Disease," *The New England Journal of Medicine* 368:117-127 (2012) and Jonsson et al., "Variant of TREM2 Associated with the Risk of Alzheimer's Disease," *The New England Journal of Medicine* 368:107-116 (2013), both of which are hereby incorporated by reference in their entirety) and CD33 (Naj et al., "Common Variants at MS4A4/MS4A6E, CD2AP, CD33 and EPHA1 are Associated with Late-Onset Alzheimer's Disease," *Nature Genetics* 43:436-441 (2011) and Hollingworth et al., "Common Variants at ABCA7, MS4A6A/MS4A4E, EPHA1, CD33 and CD2AP are Associated with Alzheimer's Disease," *Nature Genetics* 43: 429-435 (2011), which are hereby incorporated by reference in their entirety) have been identified indicating a causal role for microglia in late onset AD pathology. If an injury or infection is sensed, microglia initiate an inflammatory response which involves a dramatic, comprehensive change in morphology and function. To facilitate this transition, homeostatic gene networks are down-regulated while inflammatory gene networks are induced. Keren-Shaul et al., "A Unique Microglia Type Associated with Restricting Development of Alzheimer's Disease," *Cell* 169:1276-1290.e17 (2017) and Gosselin et al., "An Environment-Dependent Transcriptional Network Specifies Human Microglia Identity," *Science* 356:eaal3222 (2017), which are hereby incorporated by reference in their entirety.

A fourth aspect of the present disclosure relates to a method of restoring microglial homeostasis. The method includes administering a Bromodomain and Extra-Terminal motif (BET) inhibitor under conditions effective to restore microglial homeostasis.

This aspect is carried out in accordance with the previously described aspects.

Administration of a BET inhibitor (via, for example IBET treatment) may, for example, restore microglia homeostasis (represses inflammatory activation) and restore the microglia-mediated neuro-suppression of excessive neuronal activity, which may otherwise be neurotoxic. In one embodiment, the BET inhibitor restores microglia-mediated neuro-suppression of excessive neuronal activity. This is particularly useful since many of neurodegenerative diseases are characterized by an early hyperexcitability of neurons at the beginning of the disease preceding many of the other symptoms, and increased seizures are a common symptom of neurodegenerative diseases.

In the following description, reference is made to the accompanying drawings that form a part hereof, and in which is shown by way of illustration specific embodiments which may be practiced. These embodiments are described in detail to enable those skilled in the art to practice the disclosure, and it is to be understood that other embodiments may be utilized and that structural, logical and electrical changes may be made without departing from the scope of the present disclosure. The following description of example embodiments is, therefore, not to be taken in a limited sense.

The present disclosure may be further illustrated by reference to the following examples.

EXAMPLES

The following examples are intended to illustrate, but by no means are intended to limit, the scope of the present disclosure as set forth in the appended claims.

Example 1

Materials and Methods

Animals. 4-week-old male C57Bl/6 mice were purchased from The Jackson Laboratory. Mice were housed at five animals per cage on a 12-hour light/dark cycle (lights on from 0700 to 1900 hours) at constant temperature (23° C.) with ad libitum access to food and water. All animal protocols were approved by IACUC at Icahn School of Medicine at Mount Sinai. All studies were conducted in accordance with the GSK Policy on the Care, Welfare and Treatment of Laboratory Animals and were reviewed the Institutional Animal Care and Use Committee either at GSK or by the ethical review process at the institution where the work was performed.

Cx3Cr1$^{CreErt2/+}$; Efl10a mice were orally gavaged 5 times with tamoxifen to induce the expression of gfp-labelled ribosome. Mice were intraperitoneally injected with IBET858 (30 mg/kg) or vehicle control once daily for two weeks. Four hours after either an acute (1 injection) or chronic (2 weeks) injection, mice were decapitated and used for TRAP.

Cdk$^{5tetO/+}$; Camk$^{2atTa/+}$ model of Alzheimer's disease uses the Camk2a promoter-driven tetracycline-controlled transactivator system (tTA) to overexpress human p25 fused to GFP in forebrain projection neurons after the removal of doxycycline from the diet. To avoid potential developmental effects of p25 expression, all mice were conceived and raised in the presence of doxycycline until 6-8 weeks of age.

Brd4$^{fl/fl}$ mice were donated by Dr. Keiko Ozato and Brd2$^{fl/fl}$ mice were generated by Drs. Enyuan Shang and Debra Wolgemuth who kindly gifted them to us.

In vivo I-BET858 treatment. IBET858 was developed and validated by GlaxoSmithKline. I-BET858 solutions used for in vivo studies (3 mg/ml) were prepared in 10% Kleptose buffer with 5% DMSO (pH 6.5) and maintained at 4° C. I-BET858 was made fresh daily, buffers were made fresh each week. 30 mg/kg I-BET858 or vehicle (Kleptose buffer pH=6.5) was delivered by i.p injection. For acute treatment, 6-week-old mice received a single I-BET858 injection. For chronic I-BET858 treatment, 4-week-old mice received a total of 14 i.p. injections (one per day) over two weeks. Gene expression and behavioral changes were assessed in 6 weeks old mice at 4 h (acute, n=8-10 for behavior, n=2 for gene expression analysis) or 12 h (chronic, n=10 for behavior, n=2 for gene expression analysis) after the (last) I-BET858 injection, respectively.

Primary Cortical Neuron Culture. Embryonic day 18 (E18) timed-pregnant female mice were anesthetized with CO2 and sacrificed by cervical dislocation. In a dissection hood, 24-26 embryos per experiment were collected through an incision of the mother's abdomen, taken out of the amniotic sacs and decapitated in ice cold Hank's Balanced Salt Solution (HBSS). Using fine scissors and forceps, brains were rapidly dissected and the cortex cleared from meninges and isolated under a dissection microscope. Cortices were collected in ice cold HBSS and kept on ice until all embryos had been dissected. In a tissue culture hood, HBSS was removed and the cortex tissue digested by 0.25% Trypsin-EDTA for 12 minutes at 37° C., followed by DNase1 treatment for 10 minutes at 37° C. The tissue was dissociated by serial trituration with a 25 ml serological pipette, followed by trituration with 10 ml and 5 ml serological pipettes. Cell suspension was washed once with DMEM medium, supplemented with 10% FBS and 1% penicillin/streptomycin and passed through a 40 M cell strainer before counted on a hemocytometer. Single cells were seeded on poly-D-lysine (0.1 mg ml-1) coated wells at a density of 1×106 cells per well on a 12-well plate. Cells were grown in Neurobasal medium, complemented with B27 supplement, N2 supplement, and 0.5 mM L-glutamine and maintained at 37° C. in 5% CO2 for 1 week. Cultures were treated with DMSO (0.2%), I-BET858 (1 μM, 0.2% DMSO), BDNF (50 ng/ml), or BDNF+I-BET858 for 2 and 12 h on day 7 in vitro. Cultures were washed with phosphate-buffered saline (PBS) on ice and processed for RNA isolation using TRIzol/Chloroform extraction.

Primary Microglia Culture. Postnatal day 0 C57/Bl6 mice were decapitated in ice cold HBSS. The forebrain was rapidly dissected and treated as above in order to generate a single cell suspension. 60,000 cells per cm2 were seeded in vented, Poly-D-lysine coated flasks. Mixed glial cultures were maintained in DMEM containing 10% FBS and 1% penicillin/streptomycin for 3 weeks. After three weeks, microglia were isolated by shaking the mixed glial cultures for 4 hours at 360 rpm and re-plated at density on 100,0000 cells/cm2. Cultures were given 24 hours to settle before treatment. Cultures were pre-treated for 30 minutes with either DMSO (0.01%) or 1 uM IBET858. After 30 minutes, LPS (100 ng/ml) was added to the cultures. RNA was isolated with Trizol LS according to the manufacturer's recommendations after 1, 4 and 12 hours of LPS treatment.

Axion Recordings. A 48-well multielectrode array plate (Axion) was coated with 0.1% PEI for 1 hour at 37 degrees and washed four times with deionized water. Plates were dried overnight at room temperature in a sterile hood. Plates were incubated with 20 ug/ml laminin for one hour at 37 degrees before cells were seeded onto the plate. Primary cortical neurons were plated 50,000 per well. Plates were equilibrated on the Axion Maestro system at 37 degrees C. for 5 minutes before each 10 minute recording session. Baseline activity was recorded at day 7 before cells were treated with either I-BET858 (1 um) or DMSO. Electrical activity was recorded every day until day 21 and then at regular intervals until activity was no longer detected.

RNA Isolation. For in vitro gene expression analysis, neuronal culture plates were washed once with PBS, and TRIzol was added directly to cultures to isolate RNA (n=3 per group). For in vivo gene expression analysis, mice were anesthetized with CO2 and decapitated. The striata from two control and acute or chronic I-BET treated mice were rapidly dissected on ice and frozen in liquid nitrogen. RNA extraction from frozen samples was performed using TRIzol/Chloroform according to manufacturer's instructions (Invitrogen Corporation, Carlsbad, CA). RNA was precipitated overnight at −80° C. in isopropanol with 0.15 M sodium acetate, washed twice with 70% ethanol, air-dried, and resuspended in RNase-free water. RNA samples were purified using Rneasy Micro columns (Qiagen) with on-column DNAse treatment as specified by manufacturer. RNA integrity was assayed using nanodrop and RNA Pico chip on Bioanalyzer 2100 (Agilent, Santa Clara, CA) for quality RIN>9.

Microarray analysis. Total RNA samples were prepared for microarray analysis as described previously. Briefly, total RNA was converted to cDNA using the Superscript GeneChip Expression 3'-Amplification Reagents Two-Cycle cDNA Synthesis Kit (Affymetrix) and the GeneChip T7-Oligo(dT) Primer. Affymetrix Mouse Genome 430 2.0 arrays were used in all experiments. Mouse Genome 430 2.0 arrays were scanned using the GeneChip Scanner 3000 (Affymetrix, Santa Clara, CA) and globally scaled to 150 using the Affymetrix GeneChip Operating Software (GCOS v1.4). Three biological replicates were performed for each experiment. GeneChip CEL files were imported into Gene-Spring GX 13.0 (Agilent Technologies, Santa Clara, CA), processed with the GC-RMA algorithm, and expression values on each chip were normalized to that chip's 50th percentile. Statistical analysis was carried out to determine which genes are differentially expressed in BDNF-, I-BET858-, or BDNF, I-BET858-treated neurons as compared to the DMSO controls. Genes were filtered for a raw expression level of >20 and a fold change of >2, followed by moderate t-test with a p-value cutoff of 0.05. P-values were adjusted using the Benjamini-Hochberg correction. Gene expression changes are shown using Volcano plots where the corrected p-value (−log 10) is plotted versus fold-change (log 2). Heatmaps were created by hierarchical gene clustering on entities using the Euclidean distance metric and the Ward's linkage rule using GeneSpring GX 13.0.

RNA Sequencing. Double-stranded cDNA was generated from 1-5 ng purified RNA using Nugen Ovation V2 kit (NuGEN, San Carlos, CA) following manufacturer's instructions. 500 ng of cDNA per sample were sonicated to obtain fragments of 200 bp using Covaris-S2 system (Duty cycle: 10%, Intensity: 5.0, Bursts per second: 200, Duration: 120 seconds, Mode: Frequency sweeping, Power: 23W, Temperature: 5.5° C.-6° C., Covaris Inc., Woburn, MA). These fragments were then used to produce sequencing libraries with the TruSeq DNA Sample kit (Illumina, San Diego, CA, USA). The quality of the libraries was ensured using the 2200 TapeStation (Agilent). Duplexed libraries were sequenced on HiSeq 2000, typically yielding on average 60 million, 100 bp long single-end reads per sample (Illumina). All samples were mapped at a rate of 79-80%. After filtering out adaptor and low quality reads, reads were mapped using TopHat (version 2.0.8) to the mm9 mouse genome. The Cufflinks/Cuffdiff suite was used to estimate gene-level expression values as fragments per kilobase of exon model per million mapped fragments (FPKM). Differentially expressed autosomal genes between control and acute I-BET858 or chronic I-BET858 libraries were determined using a p-value <0.05 and fold change of >2. Values with a FPKM less than 0.5 were excluded.

Gene List Statistics. Overlaps between gene sets were tested for statistical significance using the $\chi 2$ test by using GraphPad Prism 5.01. The total number of expressed genes in neurons as measured by microarray (25,788) was used to calculate the $\chi 2$ test for all lists generated by microarray. For RNA sequencing data, the total number of protein-coding genes in the mouse genome according to Mouse Genome Informatics (24,979) was used for the $\chi 2$ test. The ASD candidate gene list (n=1193) was obtained from the SFARI homepage (Basu et al., "AutDB: A Gene Reference Resource for Autism Research," *Nucleic Acids Research* 37:D832-D836 (2009), which is hereby incorporated by reference in its entirety) and supplemented with the list from (King et al., "Topoisomerases Facilitate Transcription of Long Genes Linked to Autism," *Nature* 501:58-62 (2013), which is hereby incorporated by reference in its entirety).

Pathway analysis. Bioinformatic network and pathway analyses of I-BET858 suppressed genes have been performed using the Database for Annotation, Visualization and Integrated Discovery (DAVID) version 6.7. Representative biological pathways from the top 25 enriched categories are shown. Pathway enrichment was calculated as −log 10 p-value. The p-value cut-off (0.05) for significance is indicated by red dashed line.

Gene Length Analysis. Gene Symbols were annotated with their gene start and end (in bp) using the mm9 database. Gene length was then calculated from these values. Replicate symbols were filtered out. To determine the relationship between fold-change (e.g. I-BET858 vs DMSO) and gene length, the log 2 fold-change was plotted versus length for all genes expressed in neurons. Pearson correlation coefficients and p-values were calculated from the resulting scatter plot using linear regression. Genes were binned by length and a sliding window was employed to calculate the average of the log 2 fold-changes for the genes within each length window (in vitro: window: 200, step: 40; in vivo: window: 800, step: 20). For the BDNF induced, I-BET858 suppressed gene list, different parameters were necessary due to the significantly smaller list size (625 genes, window: 80, step: 1). To assess changes in gene expression levels in regards to length, raw microarray values were transformed using log 10 and plotted versus length for each condition. A running average was calculated as above using window size of 400 and a step size of 20.

Chromatin Immunoprecipitation with Sequencing. Primary cortical neuronal cultures were washed once with PBS then fixed for 10 minutes with a 1% formaldehyde solution in PBS with protease inhibitors (Sigma #P8340) at room temperature. Fixation was quenched adding glycine to a final concentration of 0.125M (5 minutes, room temperature). 10e6 fixed cells were resuspended in 1 ml of lysis buffer (50 mM Hepes KOH, pH7.5, 140 mM NaCl, 1 mM EDTA, 10% glycerol, 0.5% NP-40, 0.25% Triton X-100) and 10 ul of protease inhibitor cocktail (PIC). Samples were rotated for 10 minutes at 4 degrees then spun at 1350 g at 4 C for 10 minutes. Pellets were resuspended in 1 ml of lysis buffer 2 (10 mM Tris-HCl pH8.0, 200 mM NaCl, 1 mM EDTA, 0.5 mM EGTA) and 10 ul PIC.). 5e6 nuclei were sonicated in lysis buffer 3 (10 mM Tris-HCl pH8.0, 100 mM NaCl, 1 mM EDTA, 0.5 mM EGTA, 0.1% Na-Deoxicholate, 0.5% N-Lauroylsarcosine) at 4 degrees for 5 cycles of 30 seconds ON/30 seconds OFF using the Diagenode bioruptor. After, 30 ul of 10% Triton-X100 was added to each sample and then spun for 15 minutes at 20,000 g at 4 degrees. Sonication efficiency was checked by running the samples on a 2% agarose gel to confirm enrichment for fragments from 200-500 bps.

Streptavidin M-280 dynabeads were blocked with 0.5% BSA solution and coupled to 7 ug of antibody (Brd4 #Ab84778, Brd2 Bethyl #A302-583A, Pol2 Ser5 #Ab5408) for at least 8 hours at 4 degrees, rotating. Antibody-coupled beads were then added to sonicated chromatin (20e6 cells for Brd2/Brd4, 10e6 for Pol2) and incubated overnight at 4 degrees. After washing the IPs eight times with wash buffer (50 mM Hepes-KOH pH7.6, 100 mM LiCl, 1 mM EDTA, 1% NP-40, 0.7% Na-Deoxycholate) and once with TE buffer (10 mM Tris-HCl, 1 mM EDTA, 50 mM NaCl), Chromatin was eluted from magnetic beads in 200 ul elution buffer (50 mK Tris-HCl pH8.0, 10 mM EDTA, 1% SDS) for 45 minutes at 65 degrees. Samples were de-crosslinked overnight at 65 degrees and proteins and RNA were removed by incubating with RNAse and proteinase k. Samples were purified using the Qiagen PCR purification kit according to the manufacturers protocol.

Samples were end-repaired using the End-IT DNA End-Repair Kit (#ER0720). After 45 minutes incubation, samples were purified using the Qiagen PCR Clean up kit as described above. Samples were adenylated using a reaction mix (200 uM dATP, 1× Klenow buffer NEB2, Klenow Fragment (3' to 5' exo-), NEB M0212L) and incubating at 37 degrees for 30 minutes. After, samples were purified as above except using the Minelute columns to minimize sample loss. Adapters were ligated to samples using a reaction mix containing T4 DNA ligase buffer, Solexa adapter oligo mix and 1200 units of T4 DNA ligase. The samples were incubated according to the following PCR program: 1) 20 C for 15 min, 2) 4 C for 2 h, 3) 0.1 C/sec to 16 C, 4) 16 C for 20 min, 5) 0.1 C/sec to 4 C, 6) back to step 2 for 6 cycles. Samples were purified using the Minelute kit as described above. Samples were amplified using a reaction mix containing the Phusion HF buffer, 300 uM dNTP mix, 3% DMSO, diluted Solexa primers 1.0 and 2.0, and 1 unit of Phusion polymerase. Samples were amplified according to the following program: 1) 30 sec at 98 C, 2) 18 cycles of: 10 sec at 98 C, 30 sec at 65 C, 30 sec at 72 C, 3) 5 min 72 C. Prepared samples were then sequenced on the HiSeq 2000 platform by Rockefeller's Genomic Core Facility. Bioinformatic analysis was performed by the Shen Lab. Briefly, raw sequencing data was processed by using Illumina bcl2fastq2 Conversion Software v2.17. The ChIP-seq data was first checked for quality using the various metrics generated by FastQC. Raw sequencing reads were then aligned to the mouse mm9 genome using the default settings of Bowtie (v2.2.0)87. Only uniquely mapped reads were retained, and the alignments were subsequently filtered using the SAMtools package (v0.1.19)88 to remove duplicate reads. Peak-calling was performed using MACS (v2.1.1)89 with default settings. Annotation of called peaks and differential regions to their genomic features (promoters, gene bodies, intergenic, etc.) was performed using region-analysis (v0.1.2)90, and read alignment profile plots and heatmaps were generated using ngsplot (v2.47)91 and Multiple Experiment Viewer 4.8.

Bioinformatic analysis of RNA and Chip sequencing was done in collaboration with Dr. Yong-Hwee E. Loh, Aarthi Ramakrishnan, and Dr. Li Shen.

Behavioral Analysis. All behavioral tests were performed between 7 AM and 7 PM. For all behavioral experiments, experimenters were blinded to the treatment of the animals. GraphPad Prism version 5.01 for Windows (Graph-Pad Software) was used for statistical analysis of the data. Samples corresponding to data points that are more than 2 standard deviations from the sample mean were excluded from analyses. All procedures were conducted in strict accordance with the National Institutes of Health Guide for the Care and Use of Laboratory Animals and were approved by the IACUC at Icahn School of Medicine at Mount Sinai.

Locomotion, exploratory, and thigmotaxis/anxiety behavior was measured using the open field analysis as previously described (Schaefer et al., 2009). Mice were assessed for 60 minutes and data was collected in 5 minute intervals (n=10). Locomotor activity was assessed by total distance traveled (m), anxiety like behavior was defined by counts of rearing (number of vertical episodes in counts), and the ratio of the distance moved in the center versus the periphery (thigmotaxis), and stereotypical behavior (time spent). Mice were tested in the open field 4 h after acute (n=8) and 12 h after chronic (n=10) I-BET858 or vehicle treatment.

Memory and learning in mice acutely treated with I-BET858 or vehicle (n=10) was analyzed using a standard fear conditioning paradigm (Med Associates, St. Albans, VT) as described previously (Schaefer et al., "Control of Cognition and Adaptive Behavior by the GLP/G9a Epigenetic Suppressor Complex," Neuron 64:678-691 (2009), which is hereby incorporated by reference in its entirety). Briefly, a mouse was placed in the test chamber (house lights on) and allowed to explore freely for 2 min. A white noise (80 dB) was then presented for 30 s, co-terminating with a mild foot shock (2 s, 0.5 mA). Two minutes later the same sequence of auditory cue-shock pairing was repeated. The mouse was removed from the chamber 30 s later and returned to its home cage. Freezing behavior was continuously recorded during the time spent in the test chamber. Mice were injected with either I-BET858 (30 mg/kg) or vehicle 10 minutes after the training. Twenty-four hours later, the mouse was placed back into the test chamber for 5 min and freezing behavior was recorded (context test). Two hours later, the mouse was tested for freezing in response to the auditory cue. Environmental and contextual cues were changed for the auditory cue test. The auditory cue test was divided into two phases: 3 min in the absence of the auditory cue and 3 min of the auditory cue. The time freezing during each test was converted to a percentage of freezing value.

Social preference and social memory was performed as previous described (Ellegood and Crawley, "Behavioral and Neuroanatomical Phenotypes in Mouse Models of Autism," Neurotherapeutics 12:521-533 (2015), which is hereby incorporated by reference in its entirety) using a plexiglass chamber divided into three-compartments. The two edge compartments contain an empty wire cup. Mice were habituated to the testing room for at least 1 hour prior to the experiment. Stimulus mice are 6-8 week old C67Bl/6 male mice that were housed in separate areas of the animal facility and had no prior contact with the test mice. Stimulus mice were habituated to the wire cup prior to testing. For the sociability test, the test mouse is introduced to the middle chamber and allowed to freely move and habituate to all three compartments for 10 minutes. Then, the mouse is restricted to the middle chamber using the dividers while a novel object (Lego) is placed under the wire cup in one chamber and an unfamiliar mouse in the other. The test mouse is then allowed to investigate the whole apparatus for 10 minutes. After, the mouse is again restricted to the middle chamber while the object is replaced by a second, unfamiliar mouse. The test mouse is allowed 10 minutes to investigate. Data is acquired using the Ethovision system (Noldus) to automatically track motion while manual scoring is used to quantify time spent sniffing the stimuli. Counter-balancing was used to control for potential left-right preferences.

$$= \left( \frac{\text{Time}_{target} - \text{Time}_{object}}{\text{Time}_{total}} \times 100 \right).$$

Social preference index is
Social novelty index is $$= \left( \frac{\text{Time}_{new} - \text{Time}_{old}}{\text{Time}_{total}} \times 100 \right).$$

Olfaction was tested by exposing mice (n=5) to a small amount of palatable food (Cinnamon Toast Crunch cereal) once per day for two days. Mice were deprived of food overnight before the test. A clean cage was filled with roughly 3 inches of fresh bedding and the stimulus food was buried in the bedding until it was not visible. Mice were then placed in the cage one at a time and allowed to freely explore. The latency to localize and retrieve the food was measured. Bedding was mixed in between trials and tested mice were placed in a new holding cage until all cage-mates had been tested. After which, all mice were returned to their original cage and ad libitum food access was restored. All mice retrieved the food within 2 minutes.

Accession numbers. The data discussed in this publication have been deposited in NCBI's Gene Expression Omnibus (GEO) and are accessible through GEO SuperSeries accession number GSE72149.

LDH Assay. LDH activity was measured using the Pierce LDH Cytotoxicity Assay Kit. Culture media was incubated with an equal volume of LDH master mix and incubated for 30 minutes at room temperature in the dark. After, the same volume of stop reagent was added and the absorbance was measured at 490 and 680 nm. Maximum LDH measurements were obtained by adding lysis buffer to release the total amount of LDH in the sample. LDH release is calculated as a percent of the maximum.

Propidium Iodide Assay. Propidium iodide (1 mg/ml, Life Technologies #P3566) was added to each culture well at a final concentration of 0.5 µg/ml. Cultures were incubated for 30 minutes at 37 degrees then washed with PBS. Cells were then fixed with 4% paraformaldehyde in PBS for 15 minutes at room temperature. After fixation, cells were washed with PBS and then mounted using mounting media containing DAPI.

Immunostaining. Mice were anesthetized with ketamine (120 mg/kg) and xylazine (24 mg/kg) and perfused transcardially with 10 ml PBS and 40 ml 4% paraformaldehyde (Electron Microscopy Sciences). Fixed brains were removed and dehydrated in 5%, 15% and 30% sucrose in PBS. Following dehydration, brains were frozen in Neg-50 (Thermo Scientific) on dry ice and stored at −80° C. until further processing. Brains were cut using a cryostat and 25-μm sections were mounted on Superfrost Plus microscope slides (Fisher Scientific). Slides were stored at −80° C. until staining. Slides were washed with PBS, permeabilized with PBS+0.2% Triton X-100 (PBST) and blocked with 2% normal goat serum in PBST for one hour at room temperature. Slides were incubated with primary antibodies (IBA1, 1:500, 019-19741, Waco; NeuN) in 2% normal goat serum in PBST overnight at 4° C. Slides were washed in PBST and incubated in Alexa Fluor-conjugated secondary antibodies (Alexa Fluor 488-, 546-, and 568- and 647-labeled goat anti-mouse, goat anti-rat, goat anti-chicken, goat anti-rabbit or donkey anti-goat IgGs (H+L); 1:500, Thermo Scientific) in 2% normal goat serum in PBST for 1 h at RT. Slides were washed and cover-slipped using Prolong Gold anti-fade with DAPI (Invitrogen) and dried overnight. Imaging was performed using a Zeiss LSM 780 Confocal Microscope (Zeiss, Oberkochen, DE). For z-stack images, 20-μm z-stack confocal images were acquired at 2-μm intervals, with 40×/1.3 oil objective at 0.6 or 1× zoom. For single plane images, 4.6 μm images were acquired at 20×/0.8 or 40×/1.3 objectives 0.6 or 1× zoom. Image processing was performed using Zen 2011 software (Zeiss).

Immunoblotting. Mice were anesthetized with CO2 followed by decapitation, and the region of interest was rapidly dissected and frozen in liquid nitrogen and stored at −80° C. until further processing. Samples were sonicated at 4° C. in 1% SDS solution supplemented with protease, Trichostatin A (500 ng/ml) and PhosStop phosphatase inhibitor (Roche, Switzerland), and boiled for ten minutes. The protein concentration was determined using a BCA protein assay kit (ThermoFisherScientific, USA) according to the manufacturer's instructions. Protein samples were diluted in equal volume of 2×LDS sample buffer (Invitrogen) and supplemented with DTT to a final concentration of 200 mM (Sigma).

Mass Spectrometry. Cell culture plates (2e6 cells per well n=7-8 per group) were washed with 75 mM Ammonium bicarbonate, pH 7.4, warmed to 37 degrees. Plates were quenched on liquid nitrogen for 10 seconds and then placed on dry ice. 1 ml of 70% Ethanol in MS-grade water was warmed to 75 degrees and added to each well. Plates were incubated in a 75 degree water bath for 3 minutes, shaking gently every minute. After 3 minutes, plates were placed on dry ice and once cooled, supernatants were lyophilized using the speed vacuum and stored at −80 degrees. Samples were shipped on dry ice to Cellzome who processed the samples for mass spectrometry and performed the initial analysis annotating metabolites. A semi-quantitative approach was used which determines the metabolite levels relative to a control rather than absolute concentrations. All detected ions were used for statistical analysis regardless of how many samples they were detected. This allows for the identification of low-abundant metabolites that may be present in only a subset of samples. Comparison of untreated neuron cultures to vehicle-treated cultures revealed no effect of vehicle on the cellular metabolome.

Seahorse Mitochondrial Stress Test. In this assay, two fluorescent probes that detect the concentration of oxygen or protons are added to the culture media. Cellular metabolism causes rapid changes in the concentration of these molecules in the media which can be detected by changes in sensor fluorescence. The oxygen consumption rate (OCR) indicates mitochondrial respiration and the extracellular acidification rate (ECAR) is largely due to glycolysis. Certain pathways can be analyzed by the sequential addition of inhibitors to the media and measuring ensuing changes to the OCR and ECAR. First baseline readings are measured to give an understanding of basal metabolic rates. Then the last step of oxidative phosphorylation, the ATP synthase, is inhibited by oligomycin to determine how much oxygen is being used for ATP production. FCCP is next added to decouple the electron transport chain from the ATP synthase by increasing proton permeability of the membrane which drives oxidative phosphorylation to its maximum. Lastly, complex I is inhibited by rotenone to completely shut down mitochondrial respiration. Any oxygen that is consumed after rotenone is due to other cellular processes such as fatty acid metabolism. On the day of the assay, cultures were washed times with artificial CSF (aCSF) [120 mM NaCl, 3.5 mM KCl, 1.3 mM CaCl2, 1 mM MgCl2, 0.4 mM KH2PO4, 5 mM HEPES, 0.4% BSA, 10 mM Sodium-pyruvate, 15 mM Glucose], and incubated at 37° C. without CO2 for one hour prior to assay. Oxygen Consumption rate (OCR) was measured using the Seahorse XFe24 Analyzer (Agilent), under basal conditions and after the sequential addition of 2 mM oligomycin, 4 mM FCCP [carbonyl cyanide p-(trifluoromethoxy) phenylhydrazone], 0.5 mM rotenone and 4 mM antimycin A. Metrics were calculated according to the following equations. All values were calculated per well and normalized to cell number for each experiment. Each experiment was normalized to the average of all controls across all experiments (n=3) performed.

$$\text{Basal Respiration} = OCR_{baseline} - \text{Lowest } OCR_{R+A}$$

$$\text{Maximum Respiration} = \text{Highest } OCR_{FCCP} - \text{Lowest } OCR_{R+A}$$

$$ATP \text{ Production} = \text{Lowest } OCR_{oligomycin} - \text{Basal Respiration}$$

$$\text{Proton Leak} = OCR_{baseline} - \text{Lowest } OCR_{R+A}$$

$$\text{Coupling Efficiency} = \frac{Atp \text{ Production}}{\text{Basal Respiration}} \times 100$$

Example 2

BETs Regulate LPS-Mediated Microglial Activation In Vitro

Figure 3A:
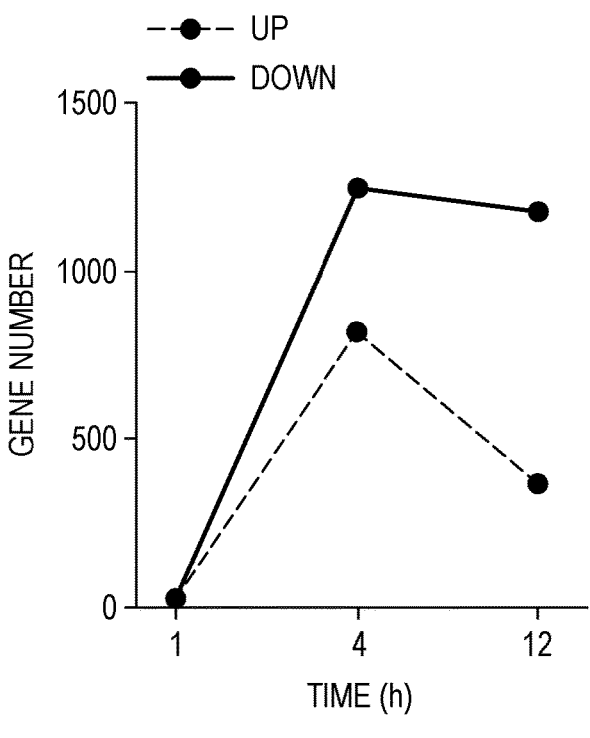
FIGS. 3A-3E show that BETs regulate inflammatory genes in primary microglia.
Figure 3B:
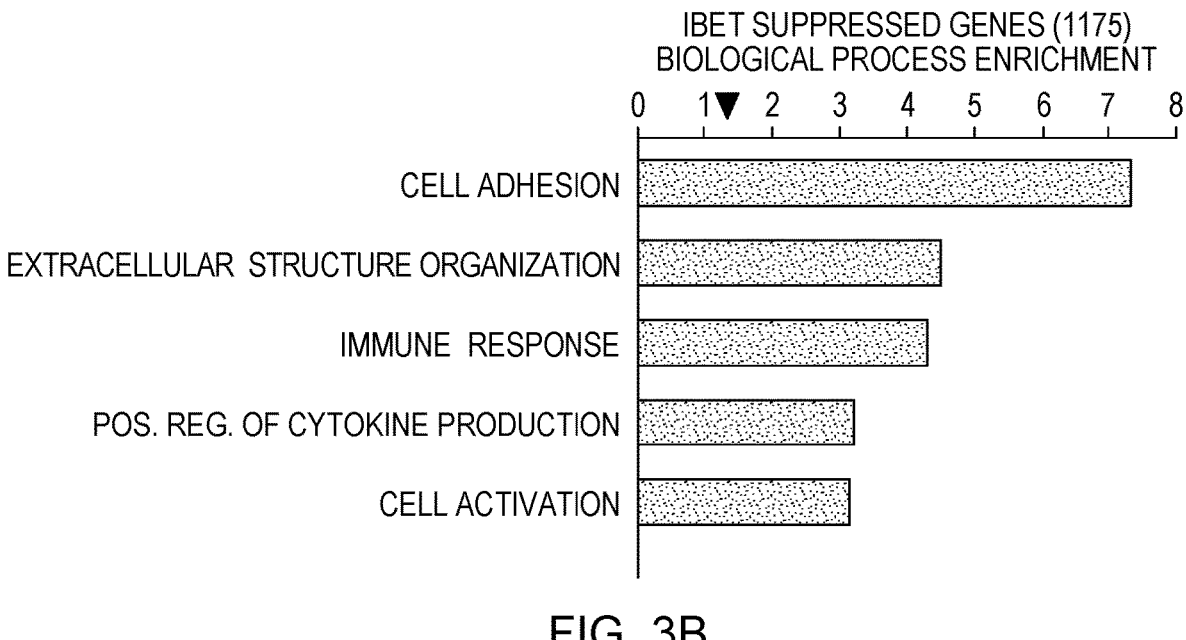
Figures 3C, 3D, 3E:
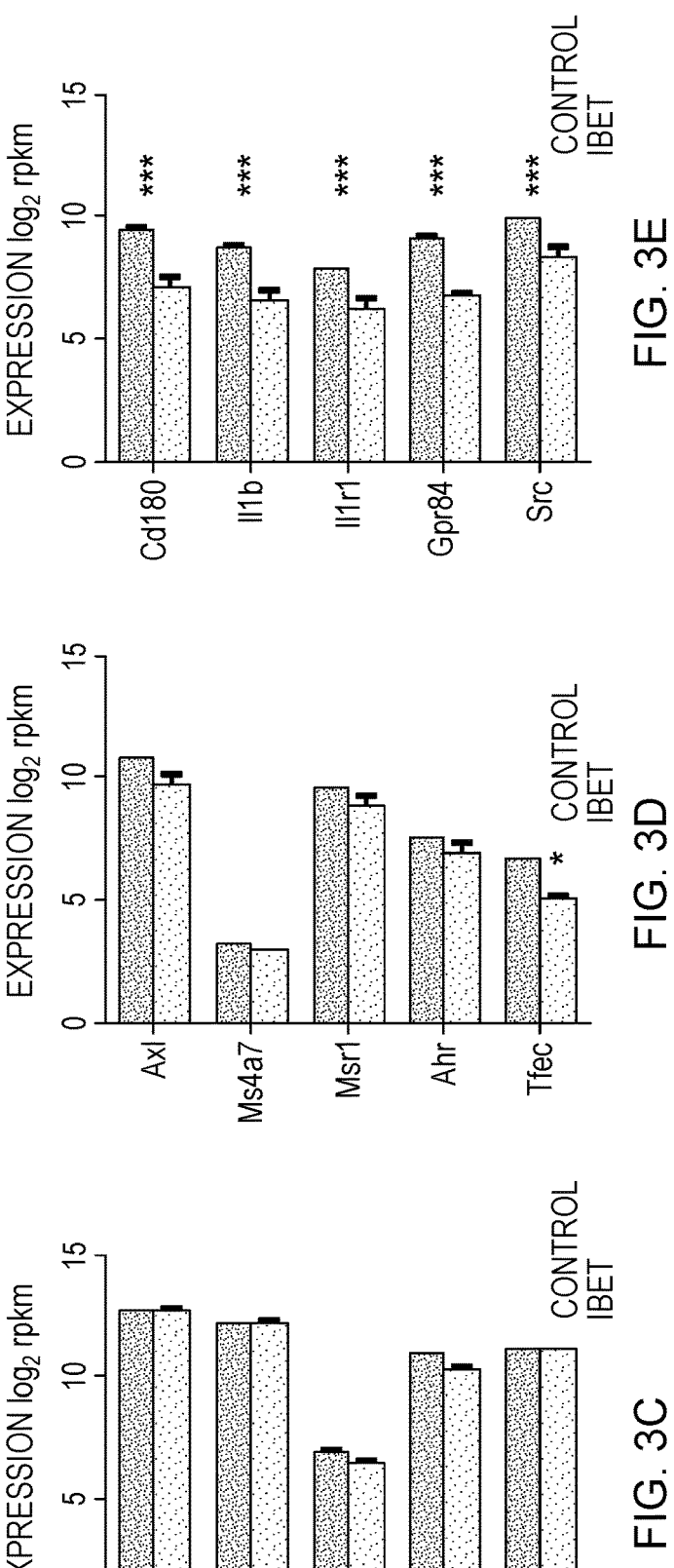

To test the role of BET proteins in microglial gene expression, primary microglia cultures from mouse forebrain were treated with the brain-permeable BET inhibitors IBET858 (1 μM) for 1, 4, or 12 hours (FIG. 3A). Because loss of BET activity in macrophages negatively impacts differentiation and proliferation189, microglia identity genes were examined to understand if microglial lineage is regulated by BET proteins (FIG. 3C). Hexb, Fcrls, and Fcer1g expression was unaffected by IBET858 indicating microglial differentiation is unaffected. Likewise it was found that phagocytosis genes, which were previously shown as controlled by a separate epigenetic complex PRC2, are also unaffected by IBET858 treatment at all time points (FIG. 3D). However, it was found that IBET858 suppresses genes enriched for immune response and cell activation pathways (FIG. 3B). These genes encode regulators of every step of the pro-inflammatory response from signal recognition (Ccr5, Il1r1, and Tlr2/3/7), to signal transduction (Irak2, Src, and Traf1) and cytokines (Il1b) (FIG. 3E) suggesting that BETs may be critical for the initiation and maintenance of an inflammatory response.

Figures 4A, 4B:
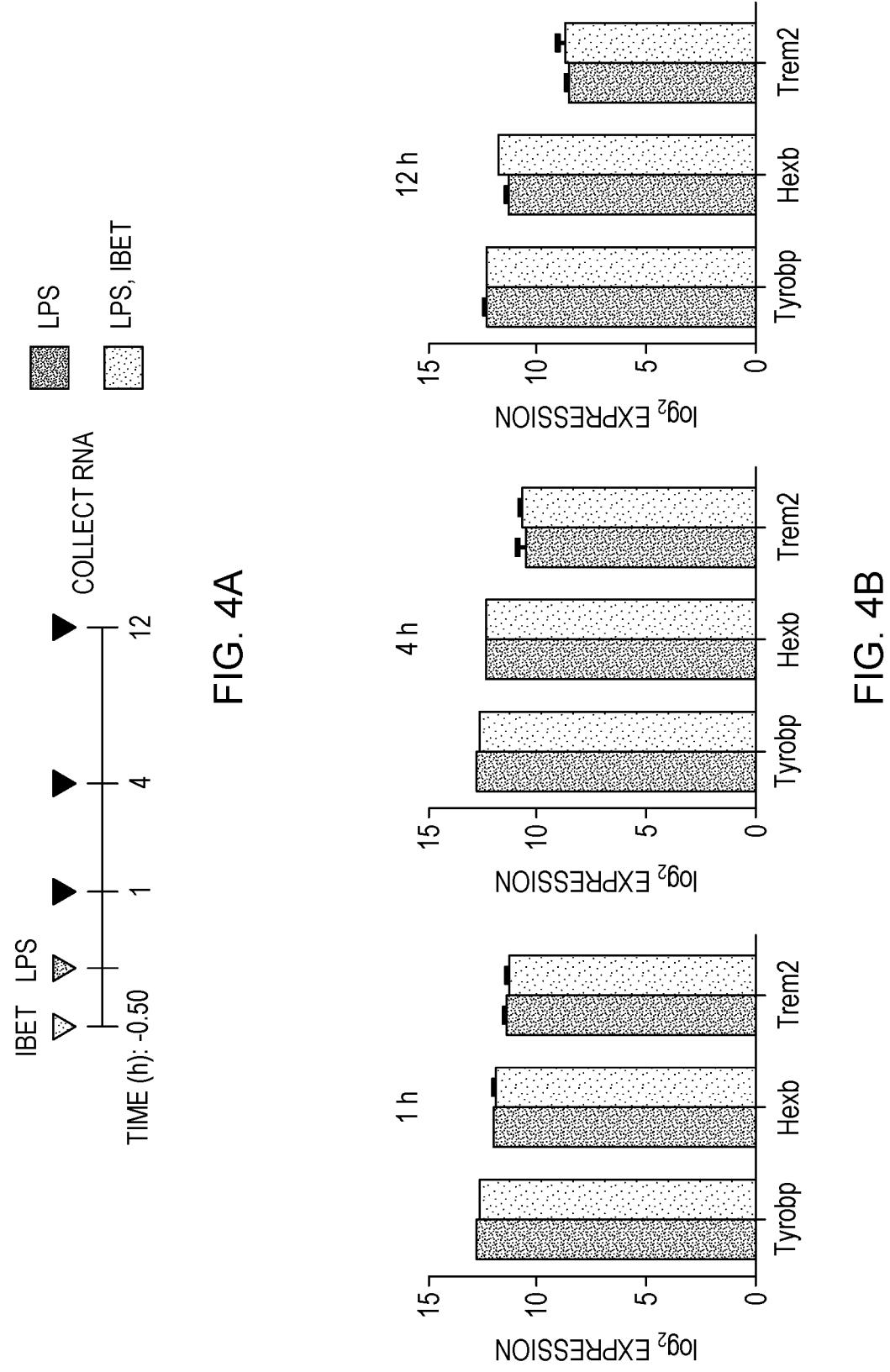
FIGS. 4A-4E show that BETs regulate the induction of inflammatory genes in microglia In FIG. 4A, primary microglia pretreated with IBET858 for 30 minutes were exposed to lipopolysaccharide (LPS) for 1 hour, 4 hours, or 12 hours.
Figure 4E:
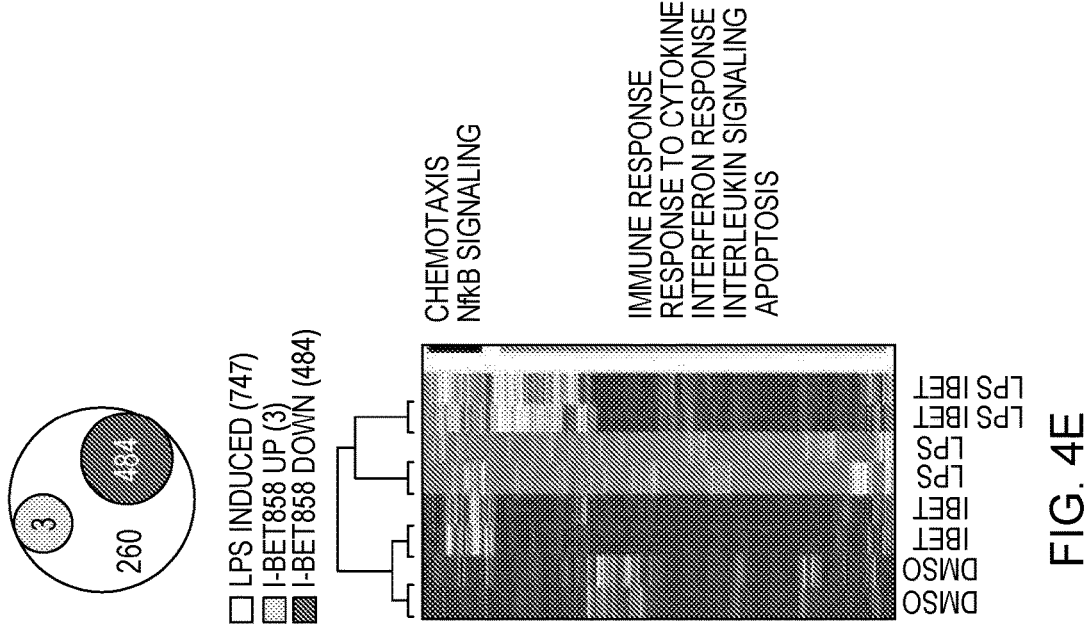
Figure 4D:
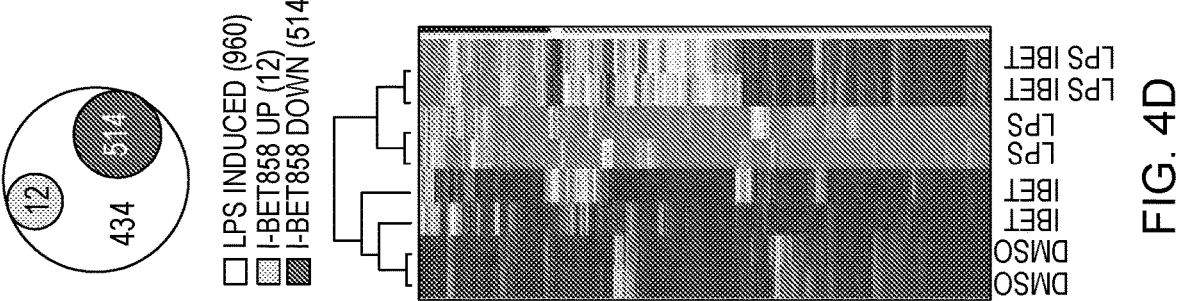
Figure 4C:
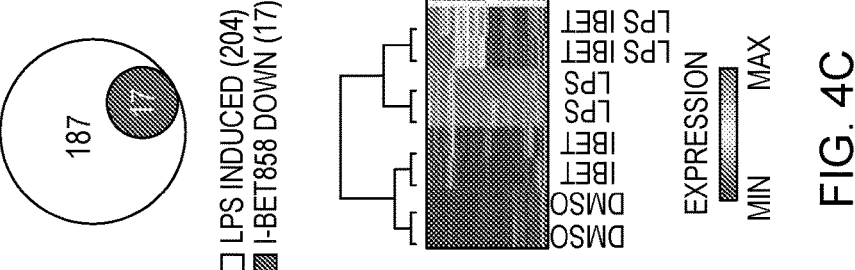

To understand if BET proteins regulate the dynamic induction of pro-inflammatory gene networks, primary microglia were exposed to the bacterial cell wall component lipopolysaccharide, LPS. T, which is recognized by Tlr4, triggers a signal cascade that leads to an extensive increase in cytokine and chemokine production which causes significant damage to host tissues if left unrestrained. Nicodeme et al., "Suppression of Inflammation by a Synthetic Histone Mimic," Nature 468:1119-1123 (2010), which is hereby incorporated by reference in its entirety. As before, microglial identity genes Tyrobp, Hexb and Trem2 were unaffected by IBET858 (FIG. 4B). As expected, LPS causes a time-dependent increase in pro-inflammatory gene expression in microglia (FIGS. 4C-4E). Specifically, proliferation (Cdk6, Cdk14), cell death (Casp1/4/7/12, Bid, Fas) and cytokine production pathways (Nfkb1/2, Il1a/b, Ifnb1, Tnf) are strongly and rapidly induced by LPS in primary microglia. IBET858 has little effect on gene induction at 1 h (FIG. 4C) which indicates that BET inhibition does not prevent microglia from sensing and responding to LPS. However IBET858 selectively inhibits the majority of genes (514/960 at 4 hours and 484/747 at 12 hours) at the peak of the LPS response which are the main effectors of the inflammatory response (FIGS. 4D and 4E). BET inhibition specifically decreases the expression of inflammatory genes (Il6, Cd33, and Nlrp3), interferon response pathway (Ifnb, Irf2/9, Mx1) and cell death mediators (Bid, Casp1/4/7/12, Traf1). Notably, a proportion of genes are insensitive to IBET858 which enriched for chemotaxis (Ccl2/3/4/5, Cxcl1/2) cell proliferation (Csf1, Kitl) and NFkB (Rel, Relb, Nfkb1/2) pathways which is expected given previous work in macrophages. Nicodeme et al., "Suppression of Inflammation by a Synthetic Histone Mimic," Nature 468:1119-1123 (2010), which is hereby incorporated by reference in its entirety. In summary, it is concluded that BETs do not impact signal induced cell migration or proliferation but instead specifically regulate the induction of the pro-inflammatory cascade in microglia. These results reflect the unique specificity of BETs in different cell types and suggest IBET858 as potential approach to selectively suppress inflammatory gene expression in microglia.

Example 3

Figure 5A:
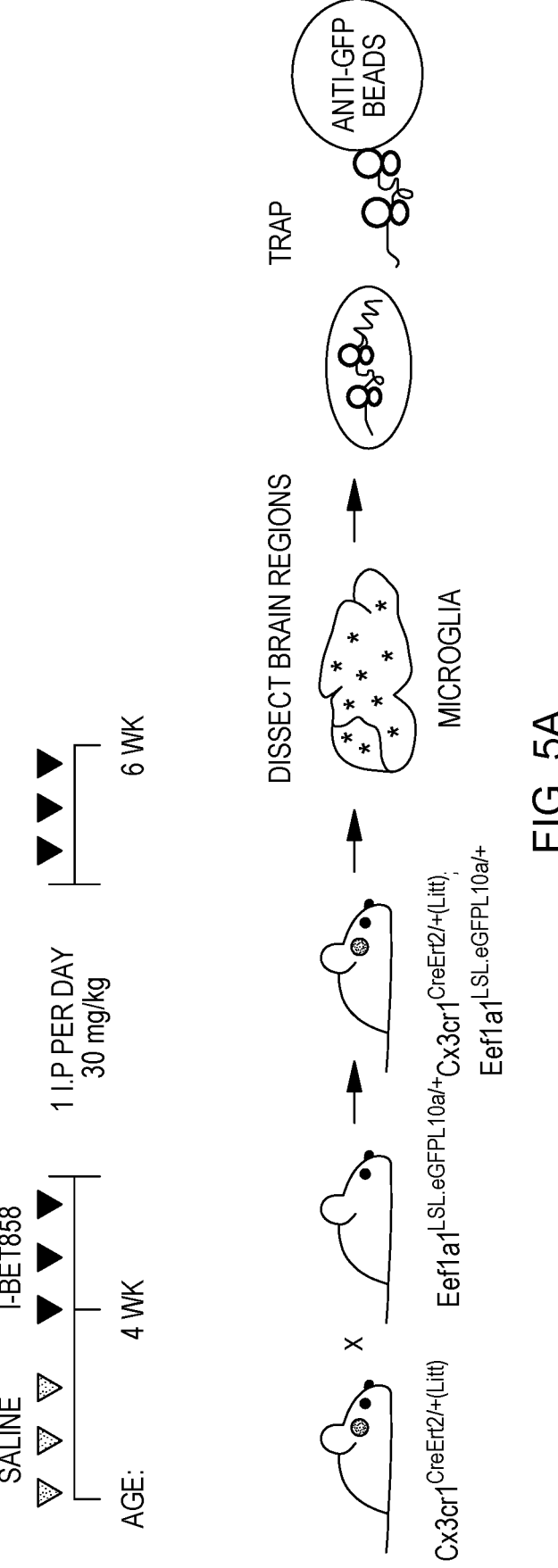
FIGS. 5A-5D show that homeostatic microglial states in the brain are BET independent.
Figure 5D:
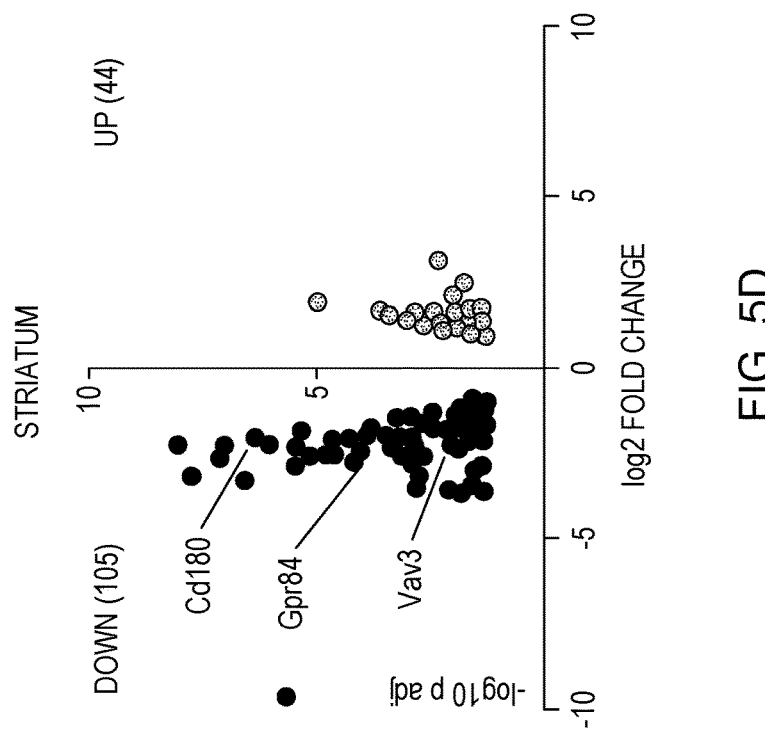
Figure 5C:
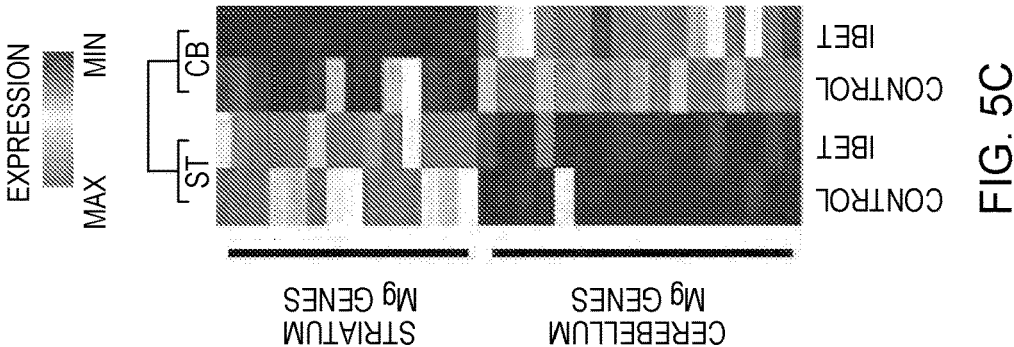
Figure 5B:
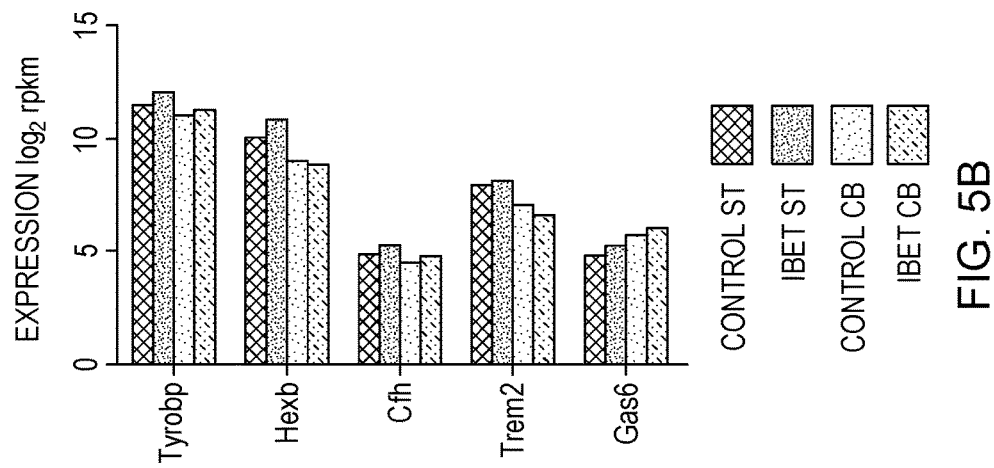

Loss of BET Function In Vivo does not Disrupt Homeostatic Microglia Functions While this data is highly indicative of a role for BETs in inflammation, cultured microglia do not fully recapitulate gene expression profiles of microglia in vivo. To better understand how IBET858 affects microglia in their homeostatic state, translating ribosome affinity purification (TRAP) after chronic IBET858 administration was used. TRAP is ideal because it prevents the induction of immediate early and pro-inflammatory genes caused by other isolation protocols which can occlude homeostatic transcriptional profiles. Ayata et al., "Epigenetic Regulation of Brain Region-Specific Microglia Clearance Activity," Nature Neuroscience 21:1049-1060 (2018), which is hereby incorporated by reference in its entirety. As observed in vitro, microglial lineage is maintained after chronic BET inhibition IBET858 as indicated by expression of Hexb, Fcrls, and Fcer1g in either the striatum or cerebellum (FIG. 4B). Moreover, the regional microglial transcriptomic heterogeneity is also unaffected by chronic BET inhibition in vivo. This is especially important because loss of these region-specific gene expression signatures is highly detrimental to brain function. Ayata et al., "Epigenetic Regulation of Brain Region-Specific Microglia Clearance Activity," Nature Neuroscience 21:1049-1060 (2018), which is hereby incorporated by reference in its entirety. Striatal gene expression shows inflammatory genes such as Ccr5 and Cd180, Gpr84, and Wdfy1 which collaborate with TLR4/Trif signaling to induce inflammation are suppressed after chronic BET inhibition in microglia in vivo (FIG. 5D). Together these data indicate that chronic BET inhibition does not impact microglial differentiation or homeostatic gene expression but may regulate inflammatory pathways in the brain. Therefore it is likely that BET inhibition can prevent or modulate pathological microglial activation in vivo as occurs during neurodegeneration.

Example 4

BET Inhibition Rescues Microgliosis and Neurodegeneration In Vivo

The ideal model to test the therapeutic potential of IBET858 in vivo would exhibit transcriptomic, cellular and behavioral phenotypes reminiscent of human neurodegenerative disease and have a rapid symptom onset of in order to limit the amount of drug required for the study and the length of time animals received daily intraperitoneal injections. Based on these criteria, two neurodegenerative mouse models were chosen to assess the neuroprotective role of IBET858 in vivo, the p25 model of Alzheimer's and the R6/2 model of Huntington's disease. In the p25 model, inducible over-expression of human p25 closely mimics the pathology and symptoms seen in AD patients. Fischer et al., "Opposing Roles of Transient and Prolonged Expression of p25 in Synaptic Plasticity and Hippocampus-Dependent Memory," Neuron 48:825-838 (2005); Patrick et al., "Conversion of p35 to p25 Deregulates Cdk5 Activity and Promotes Neurodegeneration," Nature 402:615-622 (1999); Lee et al., "Elevated Neuronal Cdc2-like Kinase Activity in the Alzheimer Disease Brain," Neuroscience Research 34:21-29 (1999); and Swatton et al., "Increased MAP Kinase Activity in Alzheimer's and Down Syndrome but Not in Schizophrenia Human Brain," The European Journal of Neuroscience 19:2711-2719 (2004), all of which are hereby incorporated by reference in their entirety. Increased p25 levels increases Aβ accumulation, neurofibrillary tangles and neuron loss similar to AD. In this model, microglia rapidly proliferation and inflammatory genes are dramatically increased as early as 2 weeks after p25 induction. Gjoneska et al., "Conserved Epigenomic Signals in Mice and Humans Reveal Immune Basis of Alzheimer's Disease," Nature 518:365-369 (2015), which is hereby incorporated by reference in its entirety. This "microgliosis" is followed by severe hippocampal neuron loss, brain atrophy, and cognitive deficits after six to seven weeks of transgene expression. Fischer et al., "Opposing Roles of Transient and Prolonged Expression of p25 in Synaptic Plasticity and Hippocampus-Dependent Memory," *Neuron* 48:825-838 (2005); Fischer et al., "Recovery of Learning and Memory is Associated with Chromatin Remodelling," *Nature* 447: 178-182 (2007); Giusti-Rodriguez et al., "Synaptic Deficits are Rescued in the p25/Cdk5 Model of Neurodegeneration by the Reduction of β-Secretase (BACE1)," *The Journal of Neuroscience* 31:15751-15756 (2011); and Gräff et al., "An Epigenetic Blockade of Cognitive Functions in the Neuro-degenerating Brain," *Nature* 483:222-226 (2012), all of which are hereby incorporated by reference in their entirety. Importantly, microgliosis in this model precedes cognitive deficits, placing hyperactive microglia as a key contributor to the etiology of degeneration which makes it an ideal model to test if BETs regulate the pathological, inflammatory activity of microglia. Gjoneska et al., "Conserved Epigenomic Signals in Mice and Humans Reveal Immune Basis of Alzheimer's Disease," *Nature* 518:365-369 (2015), which is hereby incorporated by reference in its entirety.

Figures 6A, 6B:
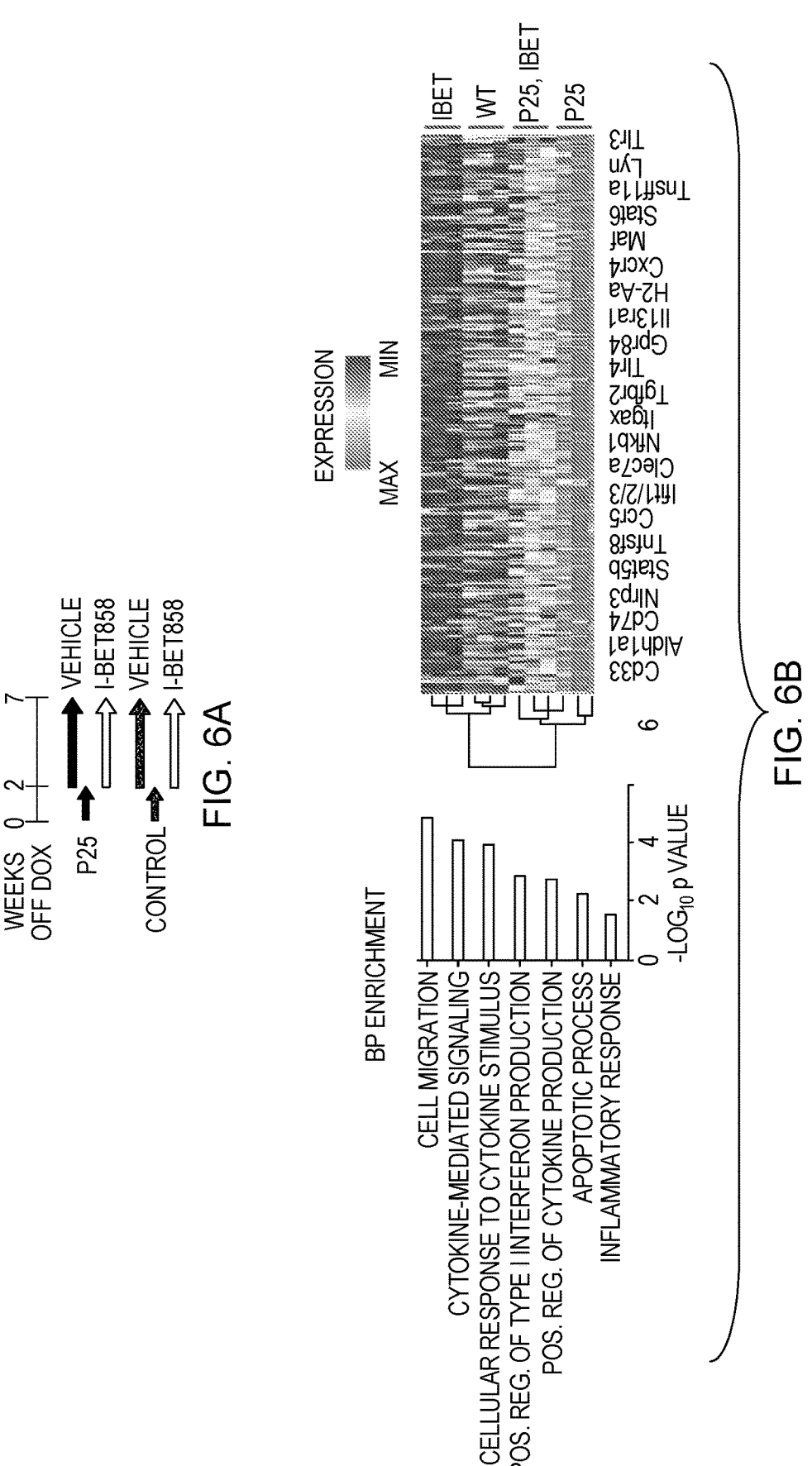
FIGS. 6A-6C illustrate that BETs regulate inflammation in vivo.

Therefore to test the therapeutic effect of IBET858, p25 was overexpressed for two weeks in adult mice to initiate microgliosis and gene expression deficits before administration of daily IBET858 (30 mg/kg, i.p.) treatment for five weeks (FIG. 6A).

Figure 6C:
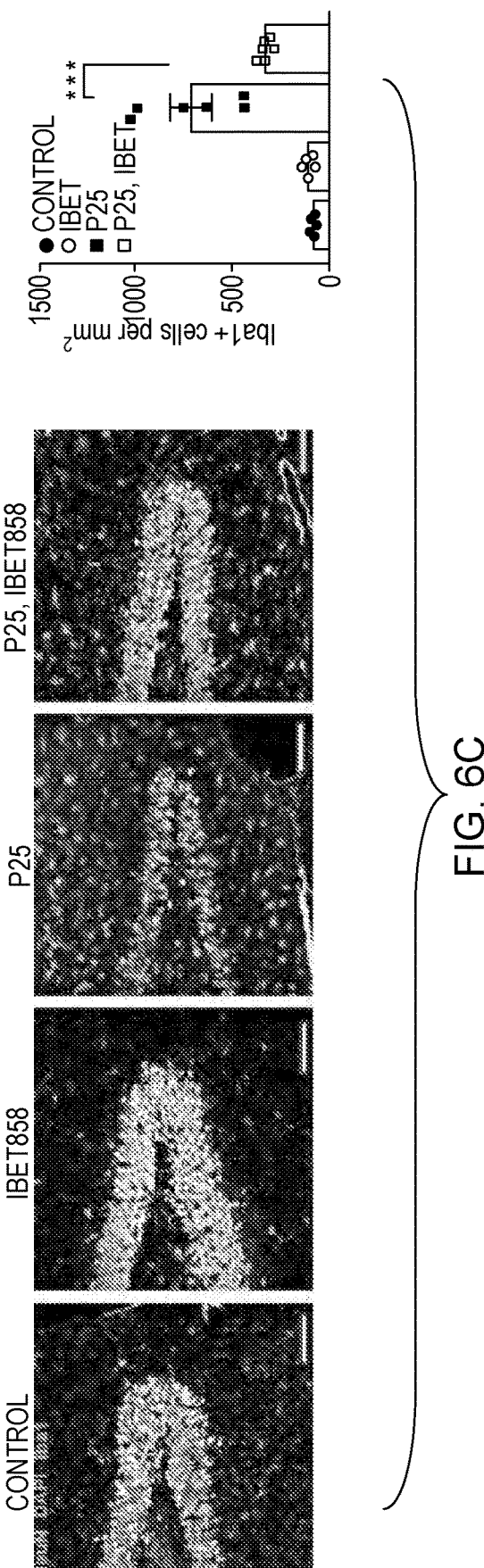

Because this line is driven by a Camk$^{2atTa/+}$ line and BET inhibition can affect expression of neuronal function genes, it was confirmed that IBET858 administration does not affect the expression of the transgene by western blot. P25 overexpression dramatically increases the expression inflammatory genes in the hippocampus. A subset of these genes is suppressed after BET inhibition including inter-feron, cytokine pathways, and apoptosis confirming the BET-dependent regulation of pro-inflammatory genes in vivo (FIG. 6B). Furthermore, histological analysis reveals that chronic BET inhibition significantly decreases the number of microglia in the hippocampus in p25 mice from 713.9+/−106 Iba1+ cells per mm$^2$ to 332.9+/−12.6 Iba1+ cells per mm$^2$ (FIG. 6C). This suggests that BET inhibition can prevent that pathological activation of microglia during neurodegeneration.

Figure 7A:
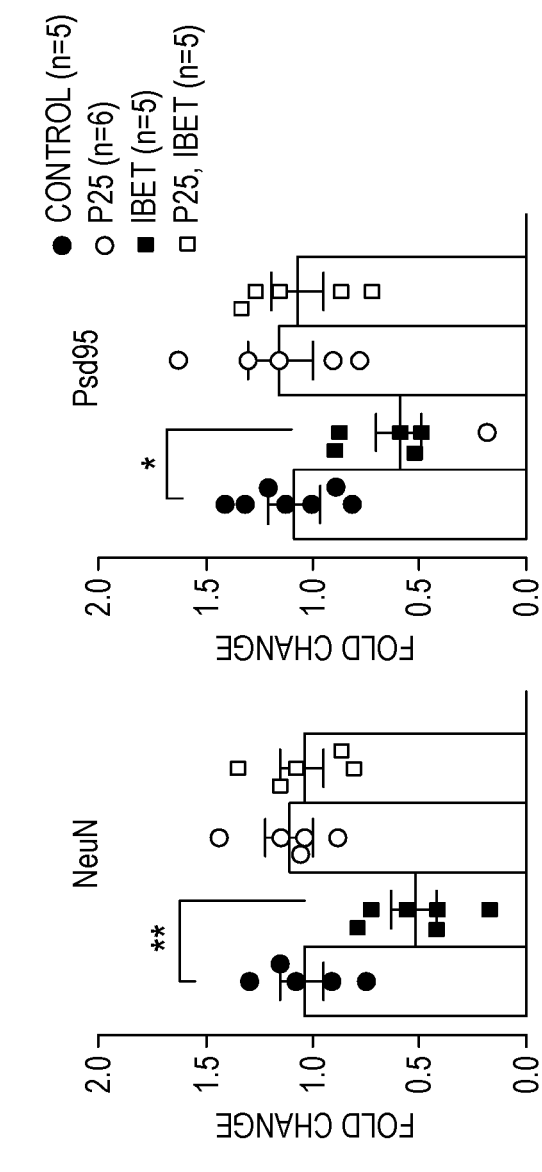
FIGS. 7A-7E shows that BET inhibition prevents neuron loss and cognitive impairment in an Alzheimer's mouse model.
Figure 7B:
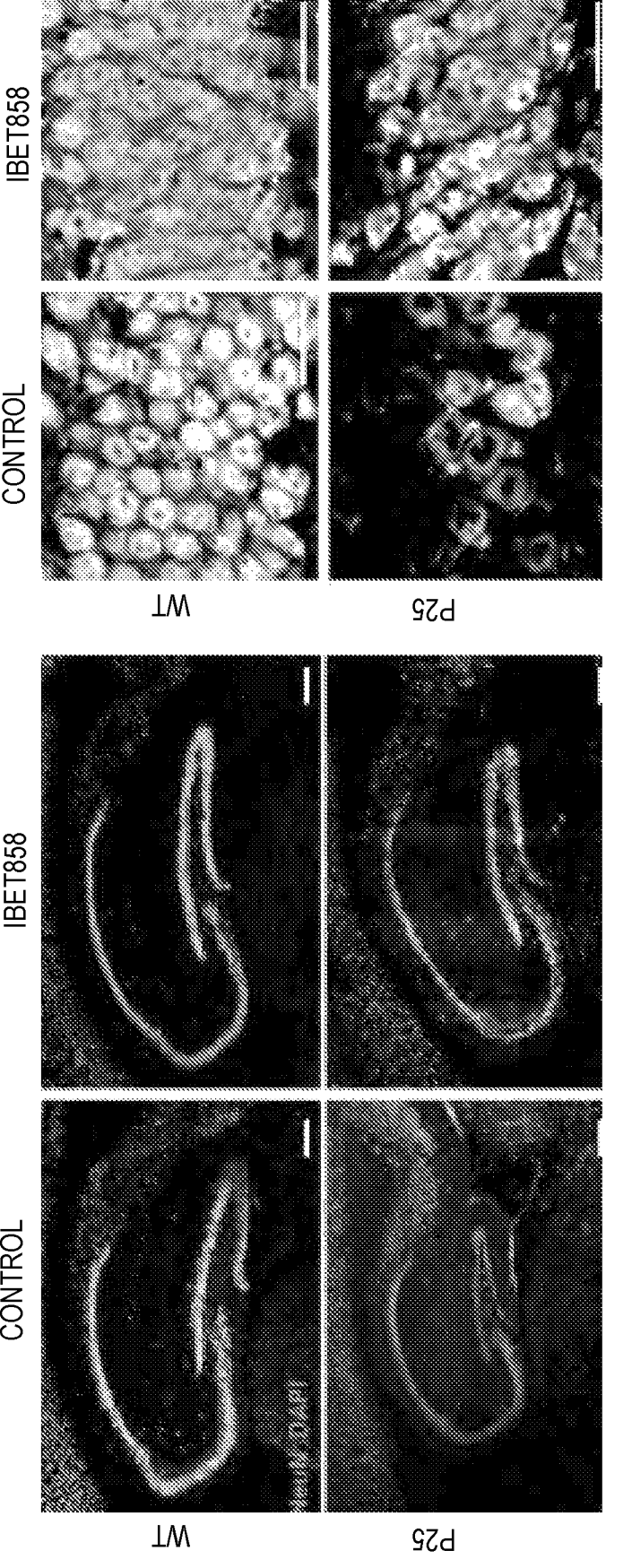
Figures 7C, 7D, 7E:
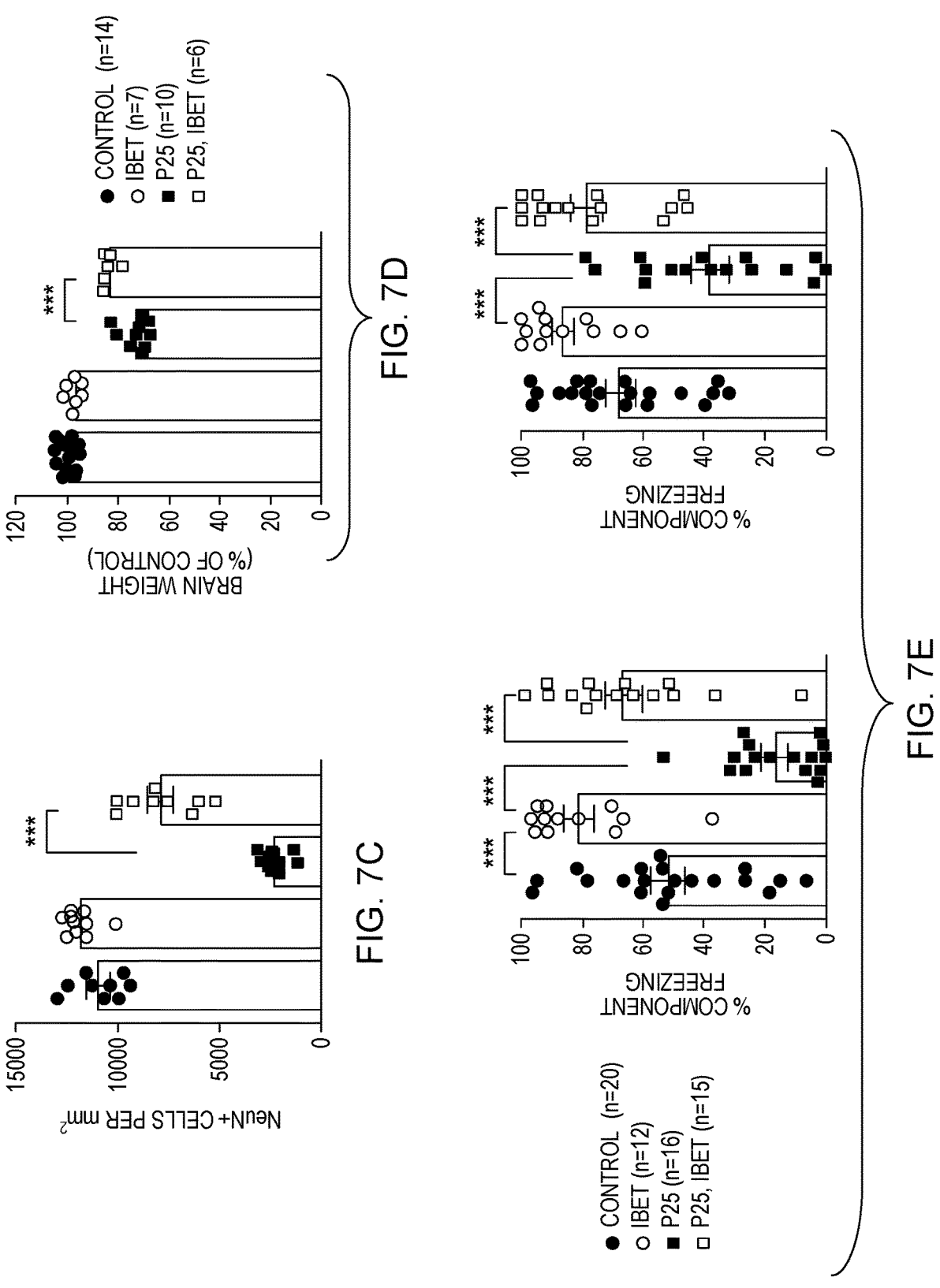
Figure 8D:
FIGS. 8A-8D depicts that reducing microglia numbers does not fully rescue neurodegeneration.
Figure 8B:
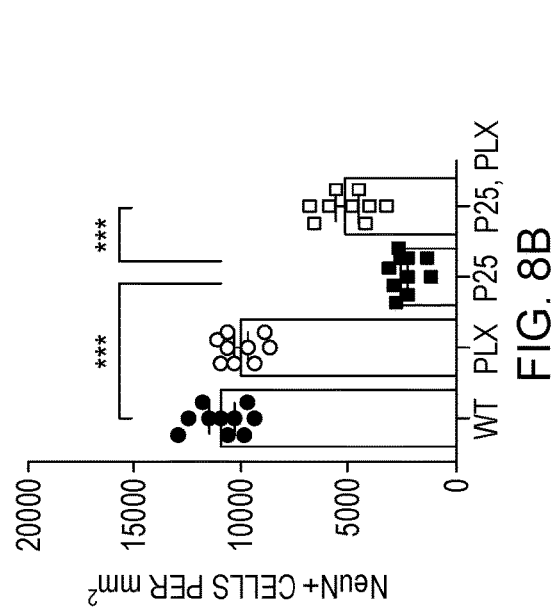
Figure 8A:
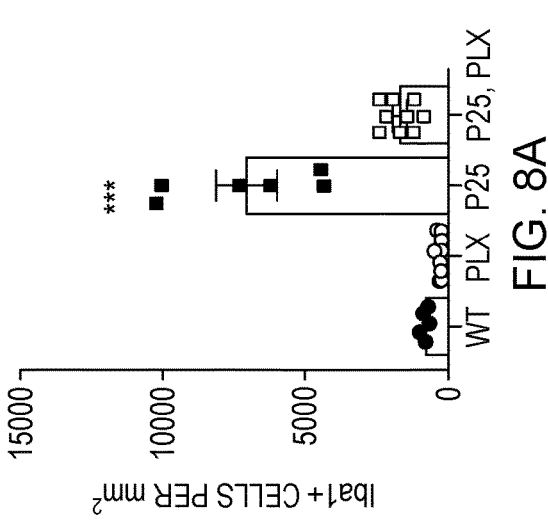
Figure 8C:
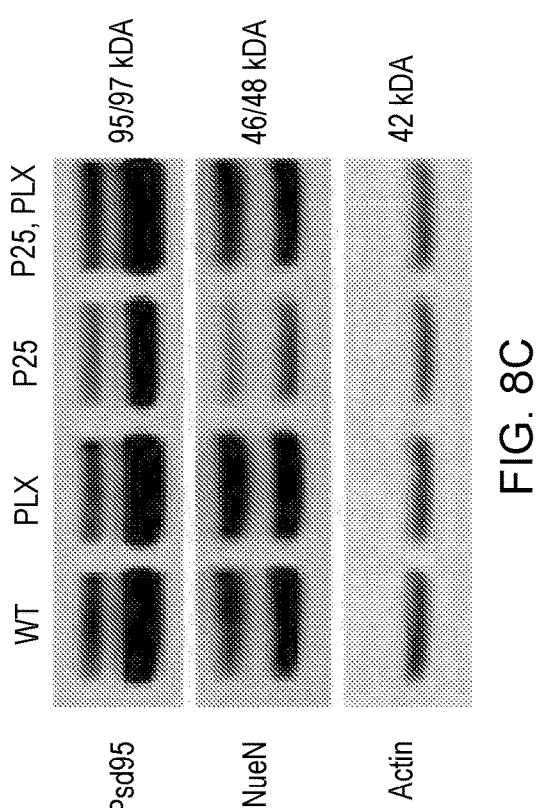
Figures 9D, 9E:
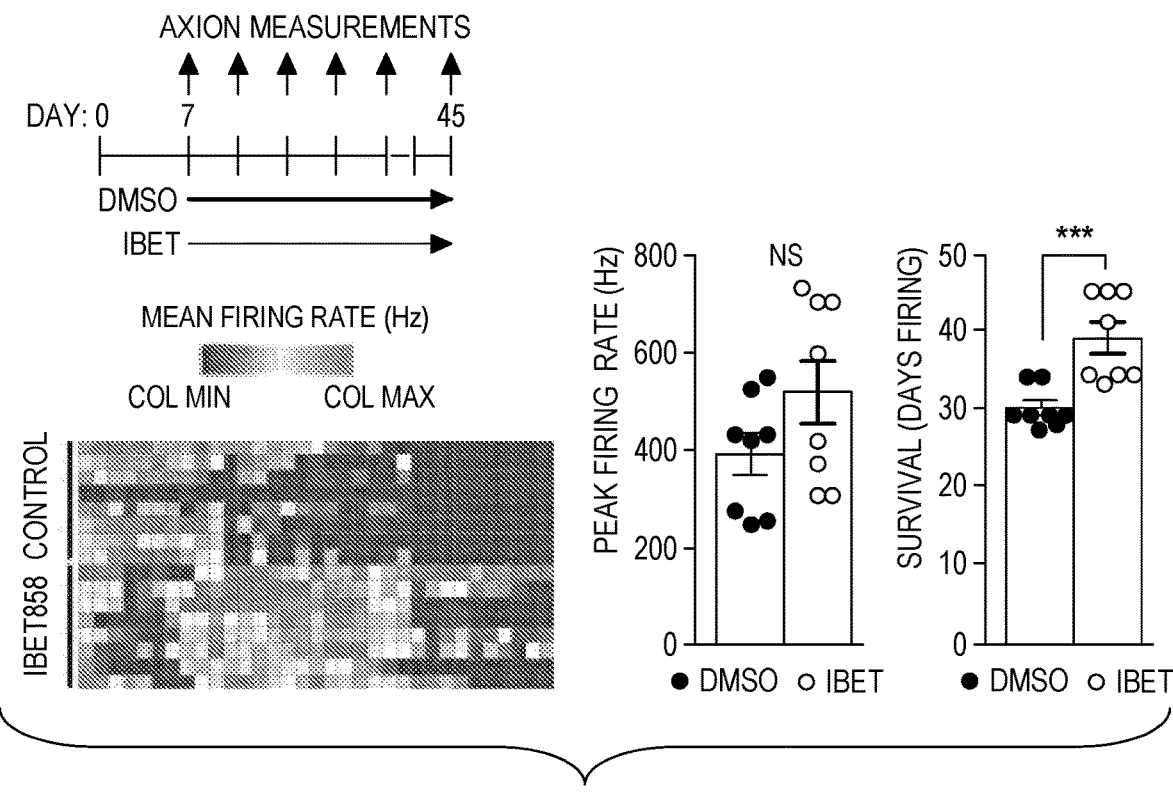

The current hypothesis is that microglial inflammation exacerbates neurodegeneration. It is therefore important to understand if decreasing inflammation positively affects neuronal survival and function. In the hippocampus of P25 mice, there is significant loss of both synapses and neurons as indicated by a reduction in the levels of Psd95 (42+/− 10.7%) and NeuN (49+/−9.3%) compared to wild type controls (FIG. 7A). In P25 mice chronically treated with IBET858, Psd95 (106+/−11.9%) and NeuN (105+/−9.8%) protein levels were the same as wild type controls suggest-ing that BET inhibition preserves neuron and synapses. Furthermore, neuronal density in the dentate gyms was significantly increased in P25, IBET858 mice (7880+/−587 NeuN+ cells per mm2) compared to p25 mice (2254+/− 223.8 NeuN+ cells per mm$^2$) (FIG. 7B, 7C). In accordance with this data, there was less brain atrophy in the p25 model after IBET858 treatment (27% vs 17% loss) (FIG. 7D). Therefore, chronic BET inhibition prevents neuronal loss in an Alzheimer's mouse model, possibly by decreasing inflammation.

To understand if these cellular and molecular improve-ments impact behavior, memory was assessed using the classic fear conditioning paradigm. Surprisingly, it was found that five weeks of daily IBET858 injections signifi-cantly increased the contextual recall of wild-type mice suggesting IBET858 may promote memory formation (FIG. 7E). There is almost a complete loss of contextual and cued recall in p25 mice however P25, IBET858 mice exhibit freezing behavior that is indistinguishable from controls (FIG. 7E). Together these data indicate that BETs control the pro-inflammatory activation of microglia in vivo and that suppression of this pathway can preserve neuronal health and function during neurodegeneration.

To understand if the therapeutic potential of IBET858 could be generalized to other degenerative diseases, the efficacy of BET inhibition in a Huntington's mouse model was assessed. Illustrating the key role of microglia dysfunc-tion in Huntington's disease, reactive microglia are observed in HD patients and mutant Huntington protein, HTT, pro-motes the expression of pro-inflammatory genes in micro-glia. Pavese et al., "Microglial Activation Correlates with Severity in Huntington Disease: A Clinical and PET Study," *Neurology* 66:1638-1643 (2006); Tai et al., "Microglial Activation in Presymptomatic Huntington's Disease Gene Carriers," *Brain* 130:1759-1766 (2007); Sapp et al., "Early and Progressive Accumulation of Reactive Microglia in the Huntington Disease Brain," *Journal of Neuropathology and Experimental Neurology* 60:161-72 (2001); and Crotti et al., "Mutant Huntingtin Promotes Autonomous Microglia Acti-vation via Myeloid Lineage-Determining Factors," *Nature Neuroscience* 17:513-521 (2014), all of which are hereby incorporated by reference in their entirety. The R6/2 mouse model recapitulates several aspects of the human disease including motor deficits, tremors and premature death around 12 weeks. It was found that chronic daily injections with IBET858 (30 mg/kg) extended the lifespan of R6/2 mice by five weeks. These data indicate that IBET858 may have broad therapeutic potential in neurodegenerative dis-orders.

These models both have strong inflammatory components to their pathology; however it is important to understand the mechanism by which IBET858 improves symptoms. If the pathology is driven by microglial-mediated inflammation, it was hypothesized that depleting microglia from the brain should prevent neuronal degeneration and memory deficits as well. Therefore a pharmacological approach was used to deplete microglia in vivo by inhibiting the colony stimulat-ing factor receptor 1 (CSF1R) which is required for micro-glial survival and kills 99% of microglia in one week in wild type mice. Elmore et al., "Colony-Stimulating Factor 1 Receptor Signaling is Necessary for Microglia Viability, Unmasking a Microglia Progenitor Cell in the Adult Brain," *Neuron* 82:380-397 (2014), which is hereby incorporated by reference in its entirety.

While microglia were fully depleted after PLX in wild type mice, microglia remained after PLX treatment in the CK-p25 mice. In fact there was twice the number of micro-glia in Ck-p25 mice treated with PLX as compared to wild-type controls. Decreasing the number of microglia in the P25 model using PLX5622 prevented neuronal and synapse loss in the p25 model. However, this was not sufficient to rescue memory deficits and in fact made con-textual recall worse. These data could suggest two different possibilities. First, the PLX5622-mediated mediated reduc-tion in microglia numbers is not sufficient to reduce inflam-matory gene expression to the level that not only allows neuronal survival but also normal function. Second, while IBET858 clearly dampens microglia-mediated inflamma-tion, its neuroprotective effect cannot be solely attributed to microglia and may in fact be a combinatorial effect on other cell types in the brain.

Example 5

Discussion of Examples 2-4

Microglia perform many functions necessary for healthy brain homeostasis such as tissue remodeling and neurotrophic support. These cells rapidly switch their functional program to an activated, pro-inflammatory state after brain injury or infection. This transition is essential for the elimination of pathogens and the removal of dead or dying brain cells. However, excessive microglial activation can be devastating for the brain is thought to exacerbate neurodegeneration. Such a complete shift in cellular state must require dynamic gene regulatory networks but little is known about the mechanisms underlying transcriptional control in microglia. Understanding the molecular mechanisms that regulate the excessive pro-inflammatory activation of microglia may elucidate new therapeutic strategies for the treatment of neurodegenerative diseases.

Here it is shown that the BET proteins are key mediators of pro-inflammatory gene expression in microglia. Pharmacological inhibition of these proteins in vitro and in vivo prevents the induction of inflammation without disrupting microglia lineage or region-specific transcriptomes which are required to maintain proper brain health. Most importantly, it is shown that BET inhibition can rescue symptoms of neurodegeneration in two distinct mouse models emphasizing the therapeutic potential of IBET858.

The neuroprotective effect of IBET858 however is not completely mediated by microglia and may also improve neuronal or glial functions as well. BET inhibition has been shown to stimulate neurogenesis in vitro (Li et al., "BET Bromodomain Inhibition Promotes Neurogenesis While Inhibiting Gliogenesis in Neural Progenitor Cells," *Stem Cell Research* 17:212-221 (2016), which is hereby incorporated by reference in its entirety) which, if also occurring in vivo, could compensate for neuron loss in the P25 mouse model of AD. Additionally, IBET858 may prevent astrocyte-mediated inflammation by disrupting the instructive communication between microglia and astrocytes (Liddelow et al., "Neurotoxic Reactive Astrocytes are Induced by Activated Microglia," *Nature* 541:481-487 (2017), which is hereby incorporated by reference in its entirety). Moreover, BET inhibition can decrease retinal neuron death after NMDA stimulation (Li et al., "Epigenetic Intervention with a BET Inhibitor Ameliorates Acute Retinal Ganglion Cell Death in Mice," *Molecular Vision* 23:149-159 (2017), which is hereby incorporated by reference in its entirety) and, given its pro-cognitive effect in wild-type animals, IBET858 may also increase neuronal survival intrinsically. Future work should delineate the potential protective effects of BET inhibition in the different cell populations using both pharmacological and genetic deletion models.

The efficacy of BET inhibition in the treatment of neurodegeneration has been tested previously although many of these studies use the BET inhibitor JQ1 which was not originally designed to be brain permeable. Prolonged JQ1 treatment in the 3xTg mouse model of Alzheimer's disease decreased the level of phosphorylated tau but did not have any effect on memory and learning deficits. Magistri et al., "The BET-Bromodomain Inhibitor JQ1 Reduces Inflammation and Tau Phosphorylation at Ser396 in the Brain of the 3xTg Model of Alzheimer's Disease," *Current Alzheimer Research* 13:985-995 (2016), which is hereby incorporated by reference in its entirety. This mild effect may be explained by the intermittent treatment schedule (5 days on, 2 days off) and the cessation of JQ1 treatment two weeks before behavioral testing. A separate study found, similar to the findings presented here, that JQ1 treatment enhanced memory using the fear conditioning paradigm in wild type mice and rescued cognitive deficits in the APP/PS1-21 mouse model of Alzheimer's disease. Benito et al., "The BET/BRD Inhibitor JQ1 Improves Brain Plasticity in WT and APP Mice," *Translation Psychiatry* 7:e1239 (2017), which is hereby incorporated by reference in its entirety. BET inhibition has also been showed to modestly improve recovery after spinal cord injury (Wang et al., "BRD4 Inhibition Attenuates Inflammatory Response in Microglia and Facilitates Recovery After Spinal Cord Injury in Rats," *Journal of Cellular and Molecular Medicine* 23:3214-3223 (2019), which is hereby incorporated by reference in its entirety), ischemic stroke (DeMars et al., "Neuroprotective Effects of Targeting BET Proteins for Degradation with dBET1 in Aged Mice Subjected to Ischemic Stroke," *Neurochemistry International* 127:94-102 (2019), which is hereby incorporated by reference in its entirety), and delay the onset of experimental autoimmune encephalomyelitis (Barrett et al., "I-BET151 Selectively Regulates IL-6 Production," *Biochimica et Biophysica Acta* 1842:1549-1555 (2014), which is hereby incorporated by reference in its entirety). Of these studies, the data presented here show the strongest neuroprotective effect which may be due to differences in brain permeability and treatment schedules. Clearly BET inhibition represents a novel and exciting treatment strategy for a broad range of neurodegenerative disorders.

While several mechanisms including the recruitment of super-enhancers have been proposed for the BET-dependent regulation of cytokine gene expression in peripheral immune cells. Nicodeme et al., "Suppression of Inflammation by a Synthetic Histone Mimic," *Nature* 468:1119-1123 (2010); Tasdemir et al., "BRD4 Connects Enhancer Remodeling to Senescence Immune Surveillance," *Cancer Discovery* 6:613-629 (2016); and Hargreaves et al., "Control of Inducible Gene Expression by Signal-Dependent Transcriptional Elongation," *Cell* 138:129-145 (2009), all of which are hereby incorporated by reference in their entirety), the present study does not offer much insight into how BET proteins specifically regulate the expression of inflammatory genes in microglia. Unlike BET-dependent genes in neurons, the genes sensitive to BET inhibition in microglia are not of extended length. As in peripheral macrophages, interferon-response genes are especially susceptible to BET inhibition in microglia while NFkB genes are largely MET-insensitive. Going forward, it will be important to understand how BET proteins are recruited to the chromatin during inflammation and why selective loci preferentially lose BET binding after IBET858.

In summary, it was found that the BET proteins are required for the induction of a pro-inflammatory transcriptional program in microglia. Inhibition of this gene network in vivo does not disrupt homeostatic microglial gene networks but rather can ameliorate neurodegeneration in response to excessive microglial activation. These findings have broad therapeutic potential and may allow for the treatment of various neurodegenerative disorders.

Example 6

BETs Negatively Regulate Neuronal Survival In Vitro

In order to understand the effect of chronic BET inhibition on neuronal survival, primary cortical mouse neurons were cultured in the presence or absence of the brain permeable BET inhibitor IBET858 (1 μM). To quantify cell death over time, the levels of lactate dehydrogenase (LDH) were measured in culture media which is presumably released during cell death as the membranes become permeable. It was found that LDH activity is equivalent between conditions until day 16 in vitro when IBET858-treated neurons have significantly less LDH activity than control neurons suggesting that BET inhibition increases neuronal survival in vitro (FIGS. 9A-9E). The observed decrease in LDH activity after BET inhibition occurs in a dose-dependent manner. LDH activity, which is an indirect measure of cell death, may be affected by other factors such as changes in metabolism or expression of the LDH genes. Therefore in order to confirm these findings, propidium iodide (PI) staining was used to directly quantify the number of dead neurons over time. This membrane impermeable dye increases in fluorescence 20-30 fold after intercalating DNA265. Using the propidium iodide assay, it was confirmed that IBET858 treated neurons survive significantly longer than control. Lastly, the number of cells positive for cleaved caspase 3, a marker of apoptosis, is also decreased after IBET858 treatment. To give context to the magnitude of this effect on survival, this experiment was repeated with a direct comparison to the mTOR inhibitor, rapamycin (20 nM). Impressively, BET inhibition increases neuronal lifespan to the same extent as rapamycin if not more. This data excitingly shows that BETs negatively regulate neuronal survival and represent a potential and novel therapeutic strategy for neuronal aging and perhaps degeneration.

Increasing neuronal survival does not necessarily mean neuronal function is preserved over time as well. Therefore to determine the effect of chronic BET inhibition on electrical activity, neurons were cultured on the Axion Microelectrode array system in the presence of IBET858. Primary cortical neurons first show electrical activity at day 7 which gradually increases over time, peaking around day 14 consistent with published time courses of synaptogenesis and electrical activity in vitro. Notably it was observed that while control neurons ceased firing on average at day 29, IBET858-treated neurons continued to fire up until day 45. In one experiment, IBET858 treated neurons lived until day 77, 86% longer than control neurons. LDH measurements were lower after BET inhibition over time in these cultures indicating that IBET858 increased neuronal survival correlates with increased maintenance of neuronal function.

In conclusion, BET inhibition significantly increases neuronal survival without any detrimental effect on neuronal activity in vitro (FIGS. 9A-9E).

In addition to increasing longevity, rapamycin treatment protects neurons from toxic stimuli such as excessive glutamate. Zheng et al., "Alleviation of Neuronal Energy Deficiency by mTOR Inhibition as a Treatment for Mitochondria-Related Neurodegeneration," *eLife* 5: e13378 (2016); Malagelada et al., "Rapamycin Protects against Neuron Death in In Vitro and In Vivo Models of Parkinson's Disease," *The Journal of Neuroscience* 30:1166-1175 (2010); Berger et al., "Rapamycin Alleviates Toxicity of Different Aggregate-Prone Proteins," *Human Molecular Genetics* 15:433-442 (2005), all of which are hereby incorporated by reference in their entirety. Because IBET858 increased neuronal lifespan to the same extent as rapamycin, it was hypothesized that BET inhibition could also induce a protective state in neurons. To test if IBET858 can prevent neuronal death, the neurons were exposed to excitotoxic levels of glutamate, a common in vitro assay that mirrors neuronal death observed in vivo after stroke or neurodegeneration. High levels of glutamate cause a strong influx of calcium into the neuron ultimately leading to necrosis followed by apoptosis. Olney, "Brain Lesions, Obesity, and Other Disturbances in Mice Treated with Monosodium Glutamate," *Science* 164:719-721 (1969) and Ankarcrona et al., "Glutamate-Induced Neuronal Death: A Succession of Necrosis or Apoptosis Depending on Mitochondrial Function," *Neuron* 15:961-973 (1995, both of which are hereby incorporated by reference in their entirety.

Figure 10A:
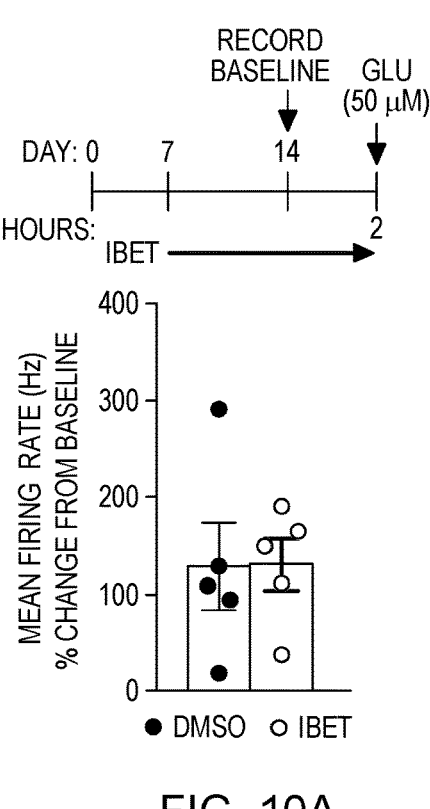
FIGS. 10A-10F BET inhibition protects neurons from toxic stimuli.

An important caveat is that it has been previously shown that neurotransmitter receptors such as Gria1 were down-regulated after BET inhibition. One could argue that the protective effect of IBET858 was caused by a decreased sensing of glutamate levels. If so, 12 hours of IBET858 treatment should protect neurons, however, this is not the case. To further explore this hypothesis, neuronal firing in response to a sub-lethal dose of glutamate (50 μM) was measured using the Axion system (FIG. 10A). At day 14, neurons treated with 50 μM glutamate increased their firing rate 127.4+/−44.4% compared to baseline. IBET858 showed the same increase in firing rate (129.3+/−26.2%) after glutamate treatment implying that BET inhibition does not decrease glutamate-induced neuronal activity (FIG. 10A). Therefore, it is appropriate to use glutamate as a neuronal death assay.

Figure 10B:
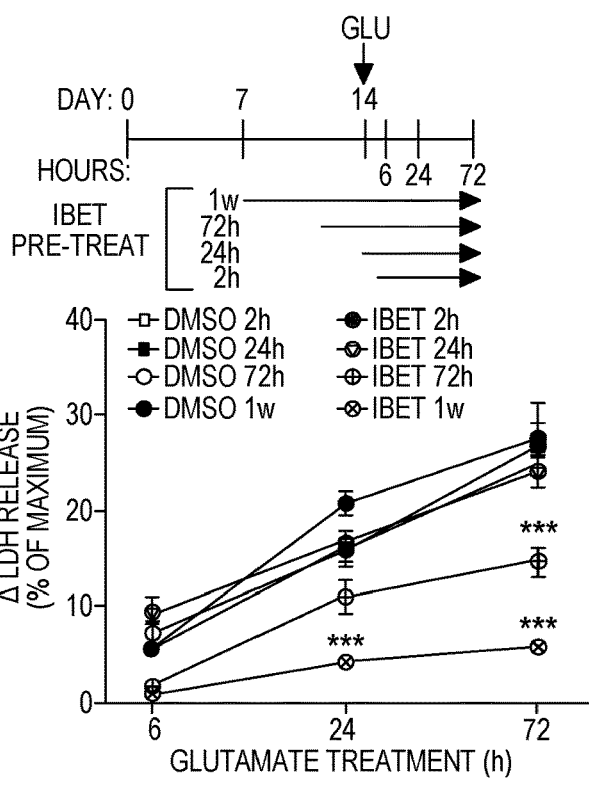
Figure 10C:
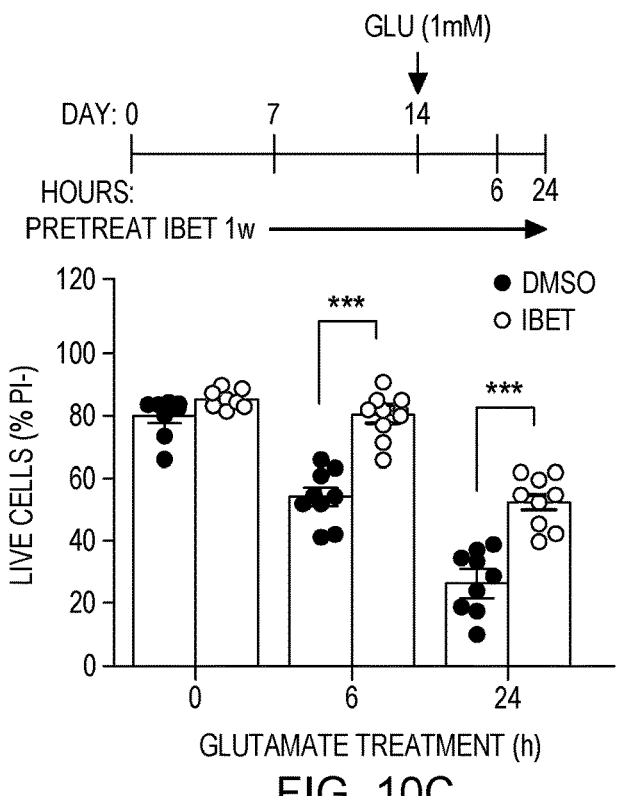
Figure 10D:
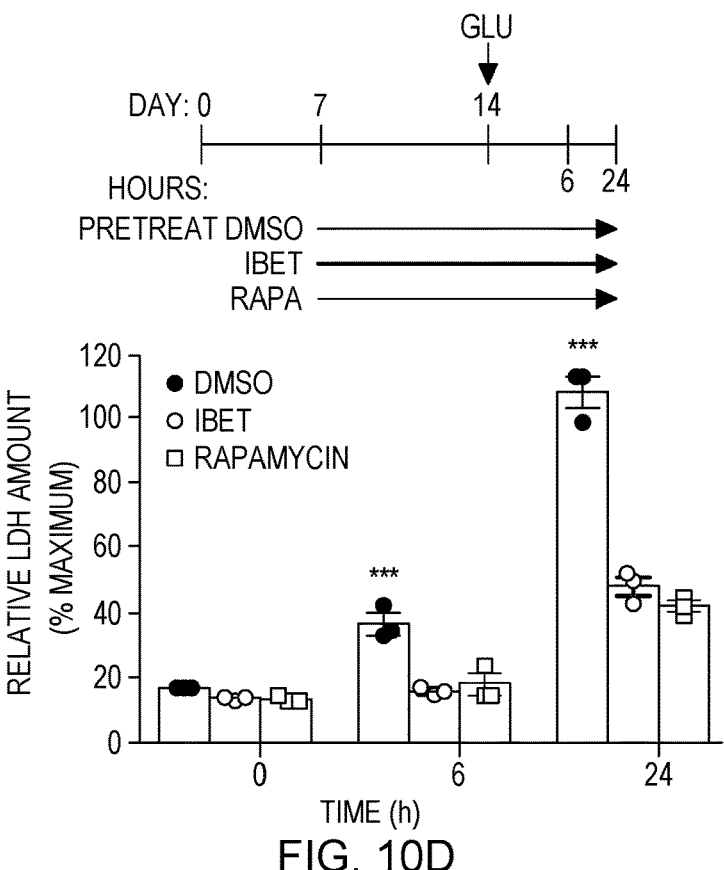

Neurons were treated with IBET858 for increasing durations (2 h, 24 h, 72 h or 1 week) before stimulation with an excitotoxic amount of glutamate (1 mM) on day 14 when mature synapses fully express glutamate receptors. Chronic but not acute BET inhibition increases neuronal survival in response to glutamate toxicity, as measured by the LDH assay. While a mild protective effect is observed at 72 h, 1 week of BET inhibition almost completely prevents excitotoxicity-induced neuronal death (FIG. 10B). Therefore a 1 week treatment time point was used for all subsequent experiments. It was confirmed that fewer neurons treated with IBET858 die after glutamate exposure compared to controls using propidium iodide to directly quantify cell death (FIG. 10C). As observed with neuronal lifespan, IBET858 protected neurons from excitotoxicity as well as rapamycin, the current gold standard for neuroprotective agents (FIG. 10D). This data excitingly shows that suppressing BET-dependent transcription increases neuronal survival and protects them from toxic stimuli.

Figure 10E:
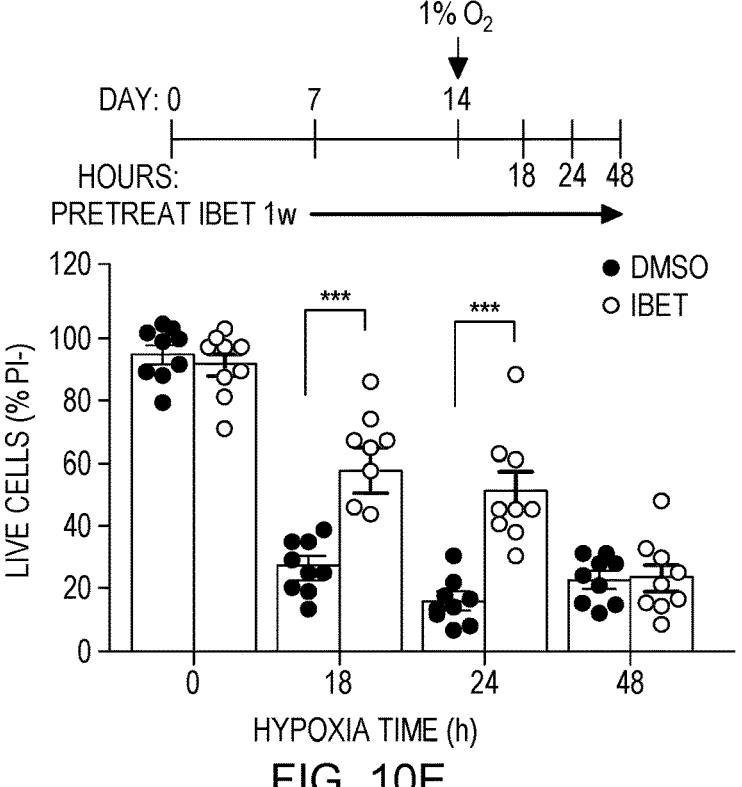
Figure 10F:
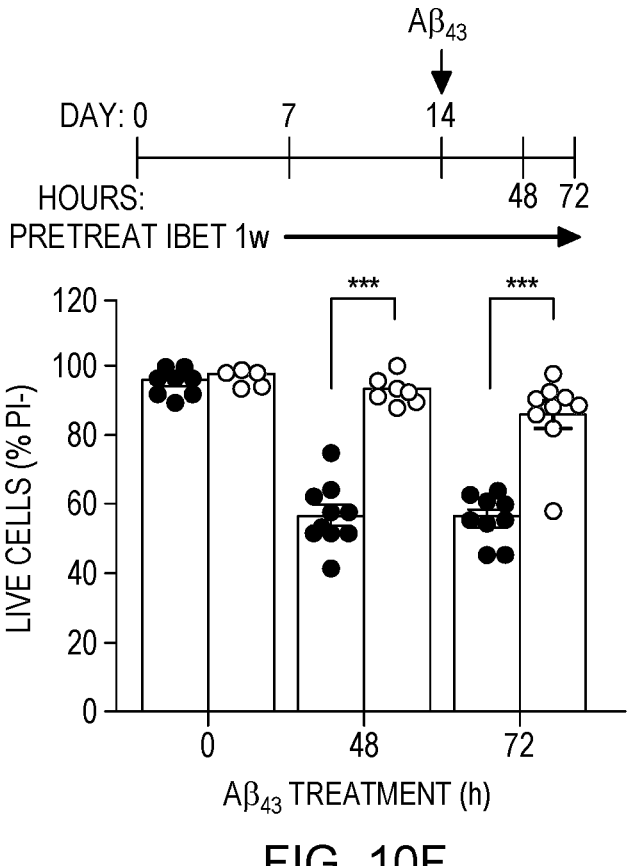

While glutamate toxicity is a widely used and clinically relevant assay, there are other factors that contribute to neuronal death in vivo such as lack of oxygen which occurs after stroke or protein aggregates which are observed in many neurodegenerative disorders. To understand if the observed protective effect is specific to glutamate toxicity, neurons were exposed to either hypoxic (1% O2) environments or Aβ1-43 oligomers (FIGS. 10E and 10F). BET inhibition significantly prevents loss of neurons due to both hypoxia and toxic Aβ oligomers, emphasizing the broad nature of the neuroprotective state induced by BET inhibition.

Example 7

BET Inhibition Suppresses Metabolism and Stimulates Autophagy

Figure 11A:
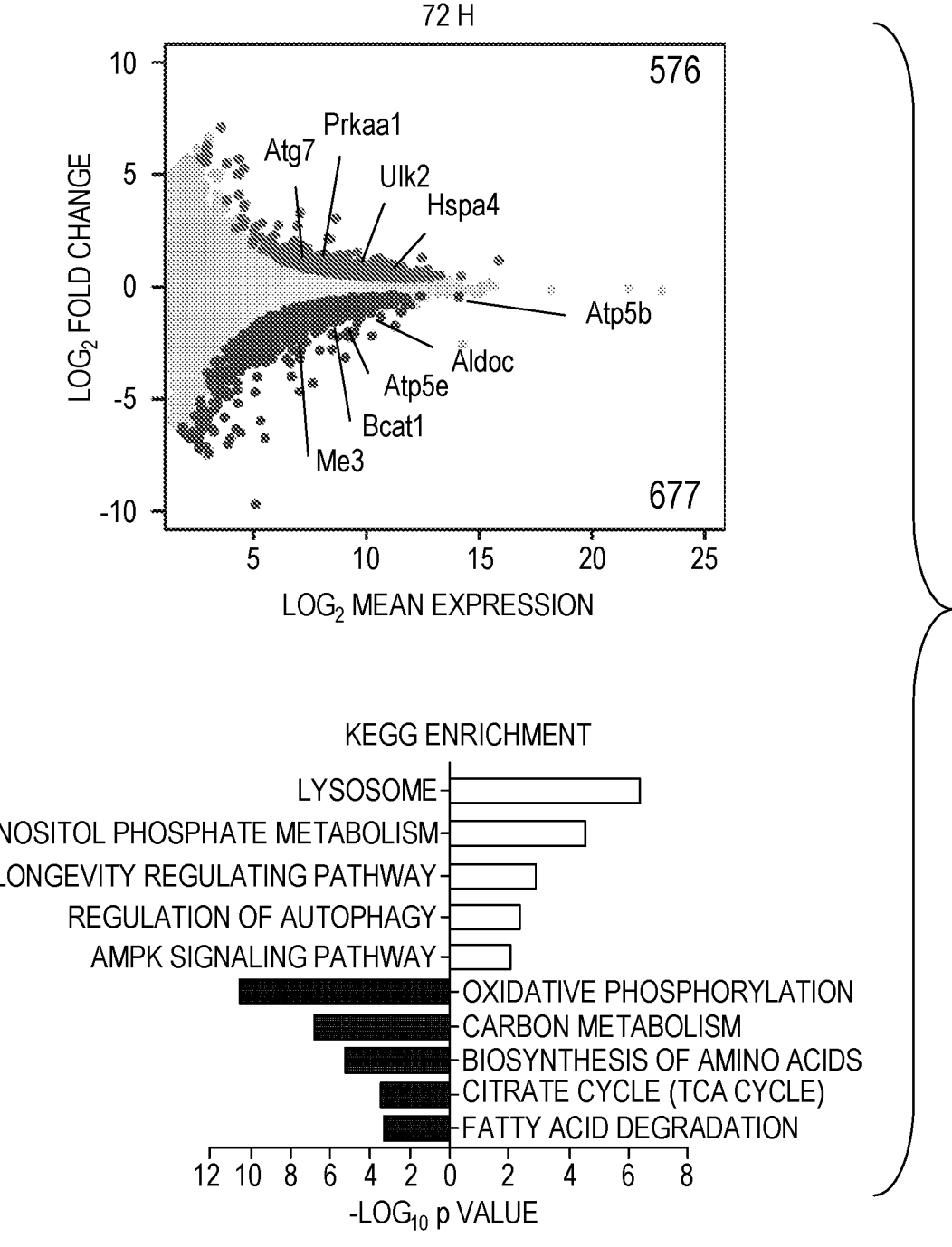
FIGS. 11A-11D show that metabolic genes are suppressed after IBET858 in neurons. Gene expression changes in primary neuronal cultures after 72 hours (FIG. 11A) and 1 week (FIG. 11B) of IBET858. MA plots (top) highlight significantly changed genes (padj<0.05) while the pathway enrichments for up (red) and down (blue) genes are shown below (−log 10 p value).
Figure 11B:
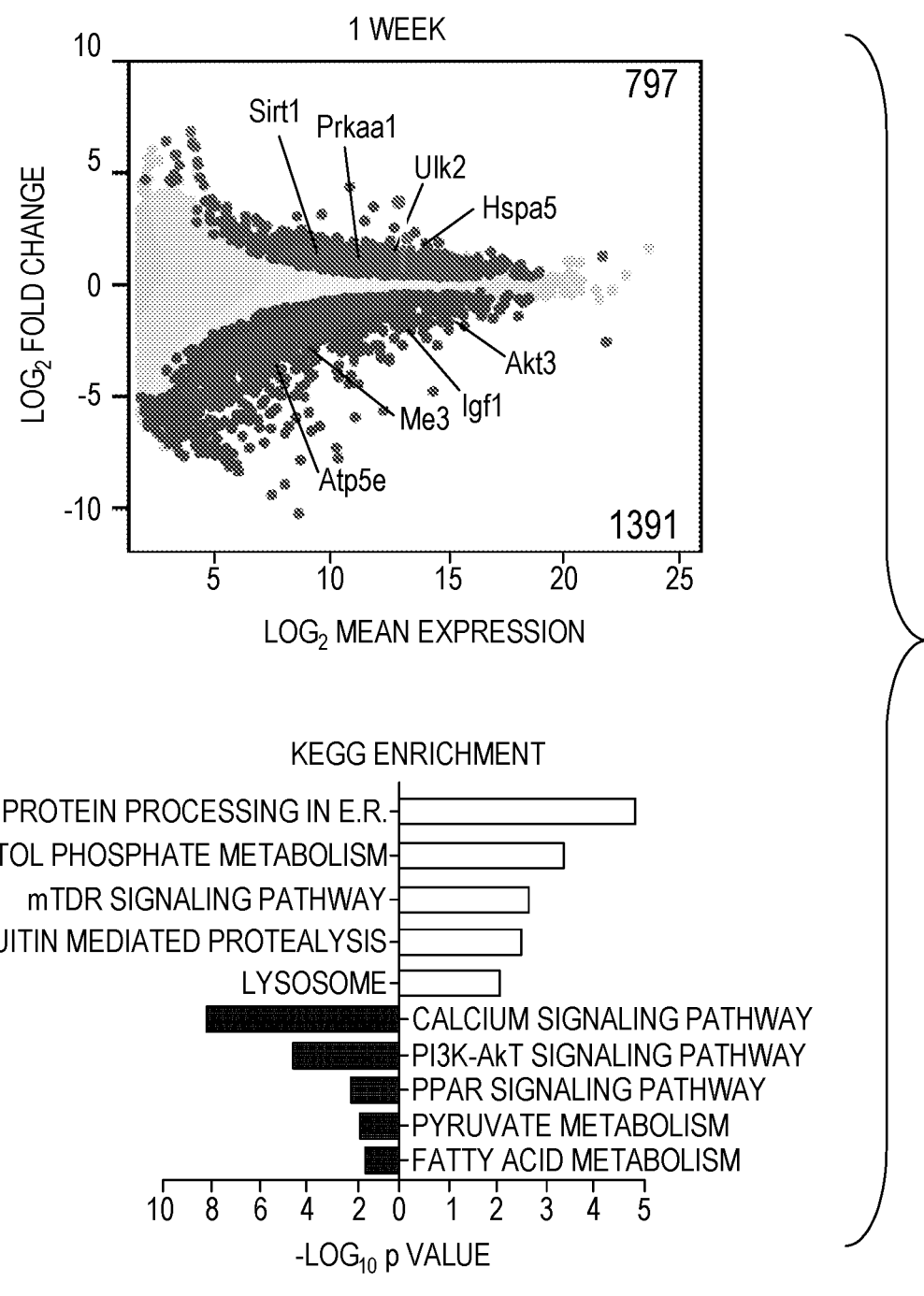
Figure 11C:
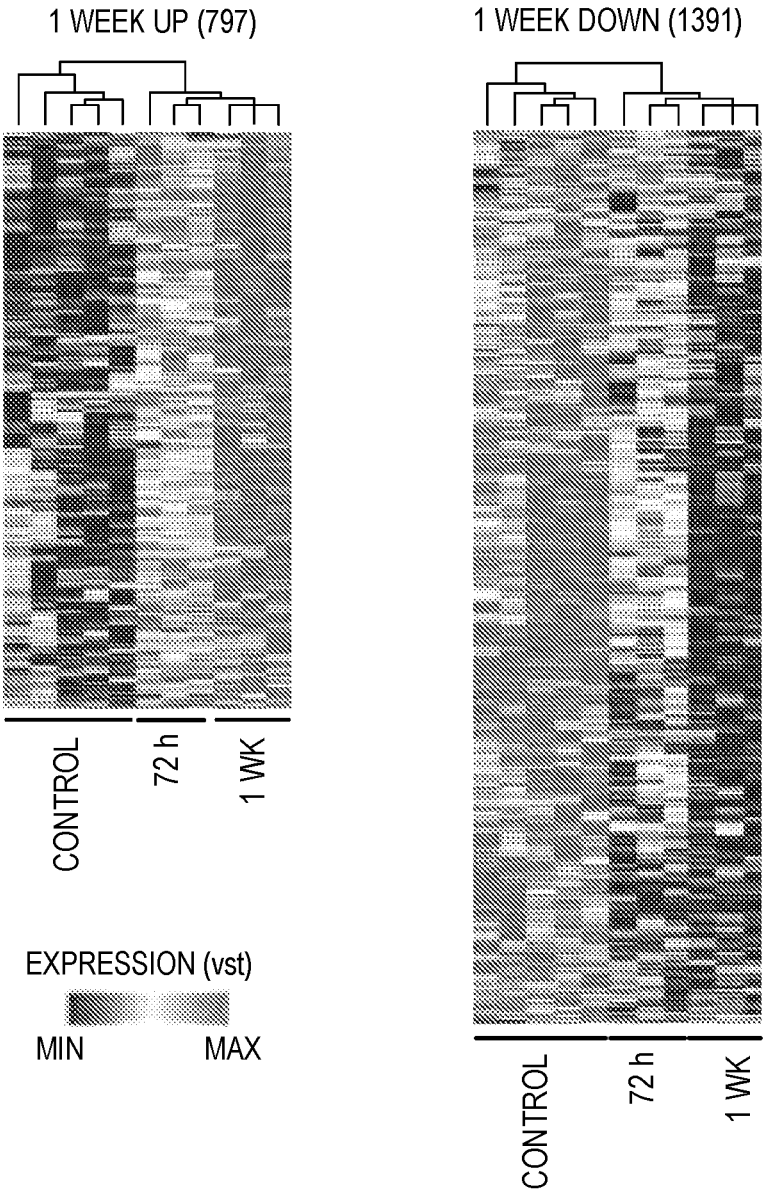
Figure 11D:
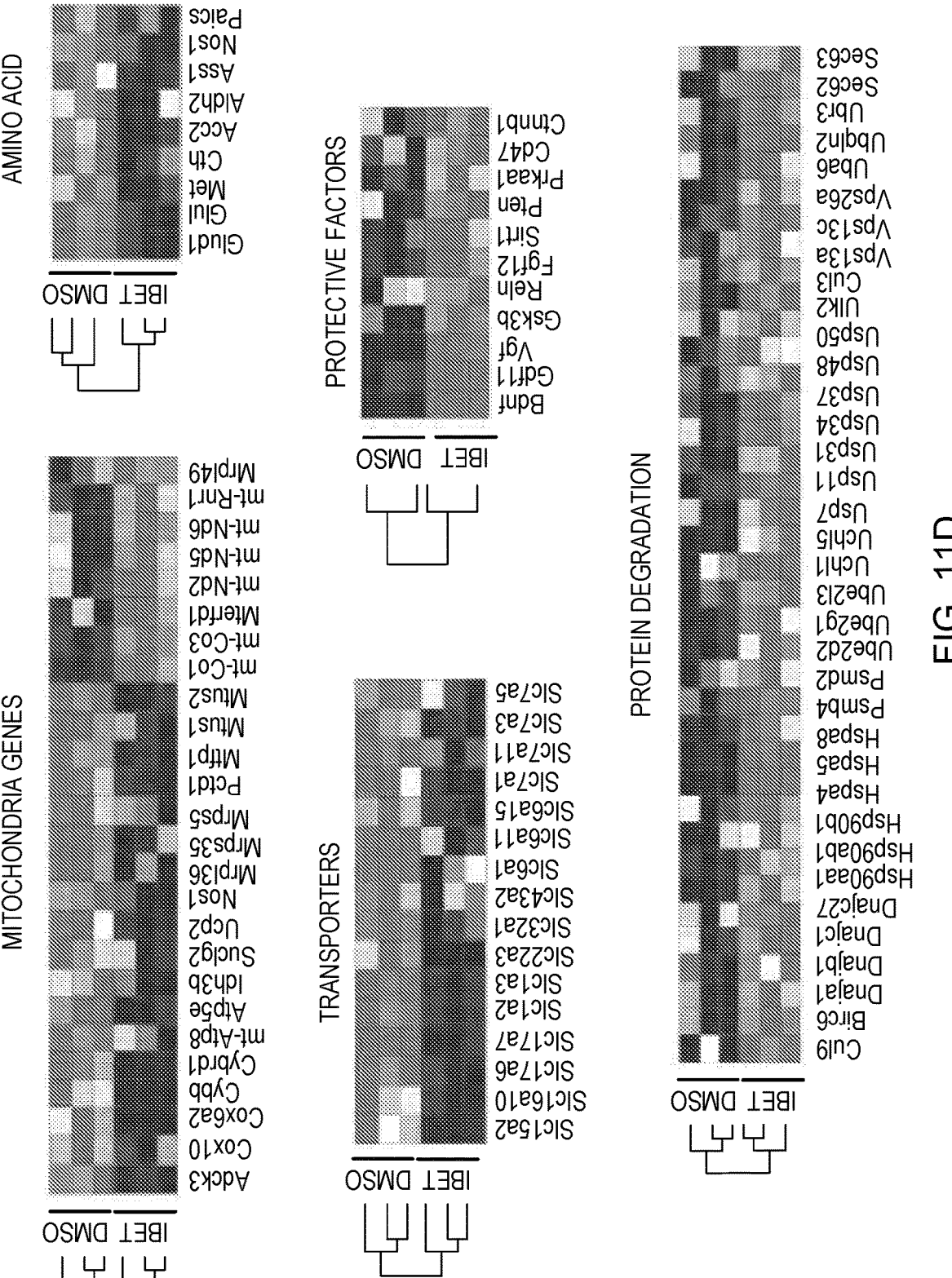

To understand how IBET858 increases neuronal survival and given the primary role of BET proteins in transcriptional regulation, how gene expression changes over time was analyzed after BET inhibition (FIGS. 11A-11D). Because BETs are mainly thought to be transcriptional activators, the focus was first on the down-regulated genes. Ion channels and synaptic genes such as Gria1, Nlgn3, and Shank2 which was previously showed to be BET-dependent at day 7 are still decreased after chronic BET inhibition at day 14. However, the majority of down-regulated genes after chronic BET inhibition are metabolic genes spanning several pathways (FIGS. 11A-11C). Specifically, genes important for amino acid synthesis and import (Bcat1, Glud1, Glu1, Slc7a5, Slc6a15, and Slc43a2), glycolysis/TCA cycle (Eno1/2, Idh3b, Suclg2, and Me1/3), oxidative phosphorylation (Apt5e, Cox6a2, and Cox10) and fatty acid metabolism (Crot, Fads2, Fabp5/7, and Lpl) are down-regulated (FIG. 11D, upper). Because previous work suggested mTOR inhibition may lead to decreased BET-dependent gene expression, gene expression profiles were compared of neurons treated with either rapamycin or IBET858 for one week and found that 56% (93/165) of genes decreased by rapamycin were also decreased by IBET858. These data suggest BET proteins regulate metabolic gene expression similar to mTOR and, therefore, the protective effect of IBET858 may be caused by lowering neuronal metabolism similar to rapamycin.

Furthermore, given the recently described role for Brd4 as a negative regulator of autophagy gene expression in cancer cells (Sakamaki et al., "Bromodomain Protein BRD4 Is a Transcriptional Repressor of Autophagy and Lysosomal Function," *Molecular Cell* 66:517-532.e9 (2017), which is hereby incorporated by reference in its entirety), the genes that were induced after chronic BET inhibition were examined. Here, there is an up-regulation of autophagy and proteolysis pathways as well as a pro-survival program that includes growth factors (Bdnf, Gdf11, Gsk3b) and genes that encode proteins (Prkaa1: the AMPK catalytic subunit, Sirt1, Acss2, Ulk2) thought to mediate the protective effects of mTOR inhibition (FIGS. 11A-11D). Howitz et al., "Small Molecule Activators of Sirtuins Extend *Saccharomyces cerevisiae* Lifespan," *Nature* 425: 191-196 (2003) and Cantó et al., "AMPK Regulates Energy Expenditure by Modulating NAD+ Metabolism and SIRT1 Activity," *Nature* 458: 1056-1060 (2009), both of which are hereby incorporated by reference in their entirety. It was previously observed that BET inhibition protects neurons from glutamate in a time-dependent manner. Accordingly, it is seen that the gene expression patterns strengthen over time with BET inhibition for both induced and suppressed genes and may induce the observed neuroprotective state (FIG. 11C). Together this data suggests that BET inhibition may mimic mTOR inhibition by modulating gene expression networks such that neuronal metabolism is suppressed while inducing autophagy.

Figure 12A:
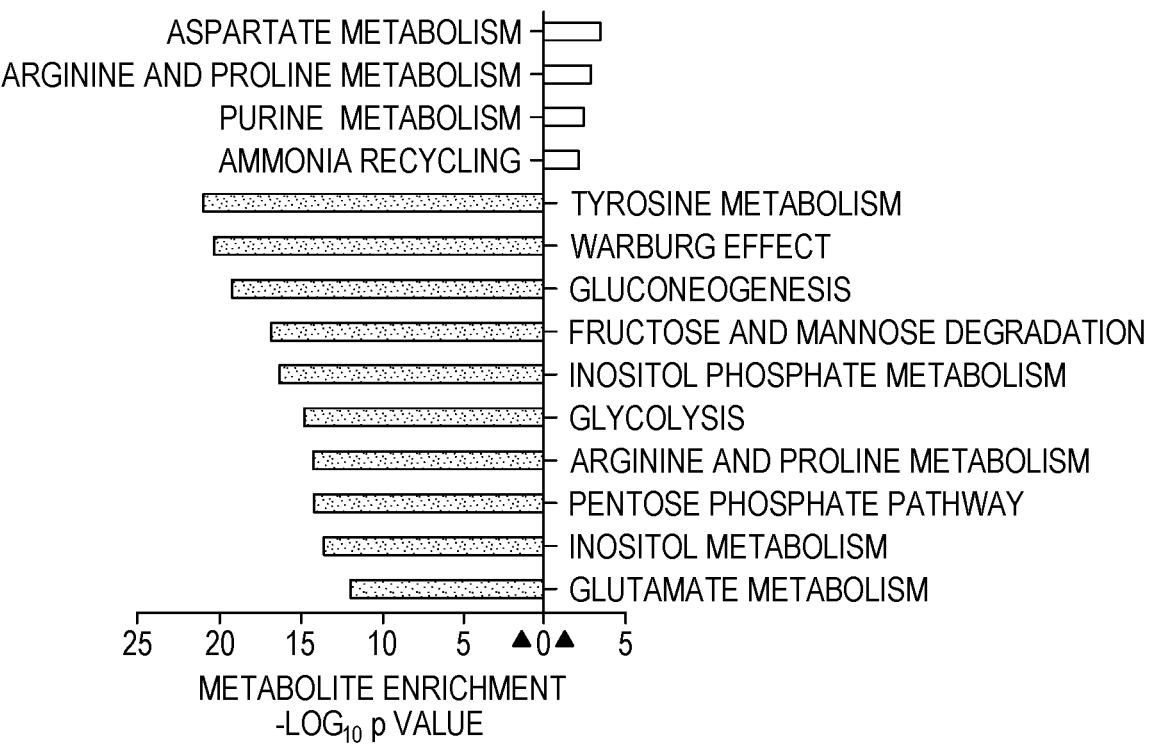
FIGS. 12A-12C illustrate that chronic BET inhibition decreases amino acids and glycolytic metabolites.
Figures 12B, 12C:
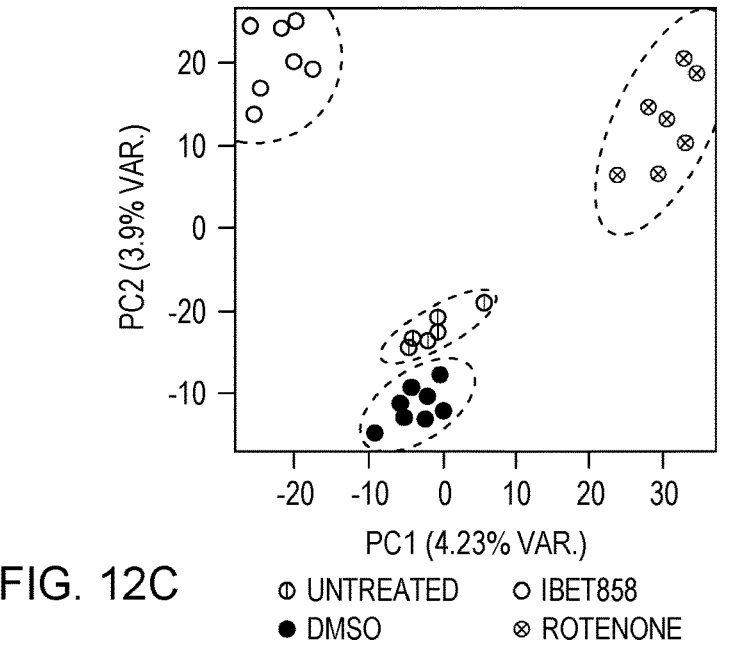

If IBET858 is indeed decreasing metabolism as indicated, comprehensive metabolic changes after BET inhibition should be observed. Therefore, an unbiased analysis of polar metabolites via mass spectrometry was employed (FIGS. 12A-12C). Accordingly, the levels of 100-150 unique metabolites are changed by chronic BET inhibition in primary cortical neurons. The increased metabolites showed minimal enrichment except for a clear increase in the aspartate metabolism pathway (p=0.000379, OR: 23.5) (FIG. 12A). The decreased ions, however, showed strong enrichment in various metabolic including amino acid metabolism (Tyrosine OR: 30.33, Arginine/Proline OR: 26.8, Glutamate OR: 24.4), glycolysis (p=1.22e-15, OR: 48.8), and the pentose phosphate pathway (p=5e-15, OR: 42). Strikingly, 65% (13/20) of amino acids are significantly decreased after IBET858 including methionine, glutamine and glutamate while only aspartate is increased (FIG. 12A).

Correlation of the enriched pathways for gene expression and metabolomics data reveals a strong agreement between the decreased metabolites and the down-regulated genes after chronic but not acute BET inhibition (FIG. 12B). This implies that these metabolic adaptations are directly related to loss of BET-dependent transcription. To give perspective to these metabolic adaptations, 2-3 times more metabolites (300-500) are changed after an acute exposure to Rotenone, (24 h, 50 nM) an inhibitor of mitochondrial respiration which is highly toxic to cells. Li et al., "Mitochondrial Complex I Inhibitor Rotenone Induces Apoptosis Through Enhancing Mitochondrial Reactive Oxygen Species Production," *The Journal of Biological Chemistry* 278:8516-8525 (2003), which is hereby incorporated by reference in its entirety. This is best illustrated by principle component analysis where the divergence of the two conditions is clear (FIG. 12C). These data strongly suggest that BET proteins regulate neuronal metabolism via gene transcription. Given the decrease in amino acids, especially methionine which is required for protein translation, and glycolysis intermediates, mTOR signaling may be reduced after BET inhibition. If so, this would imply a convergence of transcription and translation pathways in the regulation of neuronal survival during times of stress.

These metabolic changes give a static impression of the metabolic state of neurons after BET inhibition. Decreased metabolism could be caused by either decreased nutrient intake or decreased utilization via metabolic processes or a combination. Several amino acid transporters (Slc7a5, Slc7a3, Slc7a11, and Slc6a15) and the major glucose transporter GLUT1 are down-regulated after BET inhibition suggesting that decreased neuronal metabolism after IBET858 may be in part due to decreased nutrient uptake. It was hypothesized that metabolic activity would also be decreased because, after 1 week of BET inhibition when neuron numbers are equivalent, the culture media was less acidic than the control suggesting decreased nutrient utilization.

To understand if this was the case, the major energetic pathway in neurons, mitochondrial respiration, after BET inhibition was assessed using Seahorse technology. As expected, chronic BET inhibition significantly decreases basal mitochondrial respiration rates and decreases ATP production by 50% (FIG. 13A) indicating mitochondria are less metabolically active after IBET858. The maximum mitochondrial activity of IBET858-treated neurons is also decreased indicating the total metabolic capacity of neurons is suppressed after BET inhibition. In addition to lower mitochondrial activity, proton leak which contributes to the production of reactive oxygen species (ROS) is lower after BET inhibition. Because increased ROS levels are detrimental to neuronal health, lower ROS production could also increase neuronal survival after BET inhibition. Together these data confirm that mitochondrial activity is depressed after chronic BET inhibition.

Figure 13A:
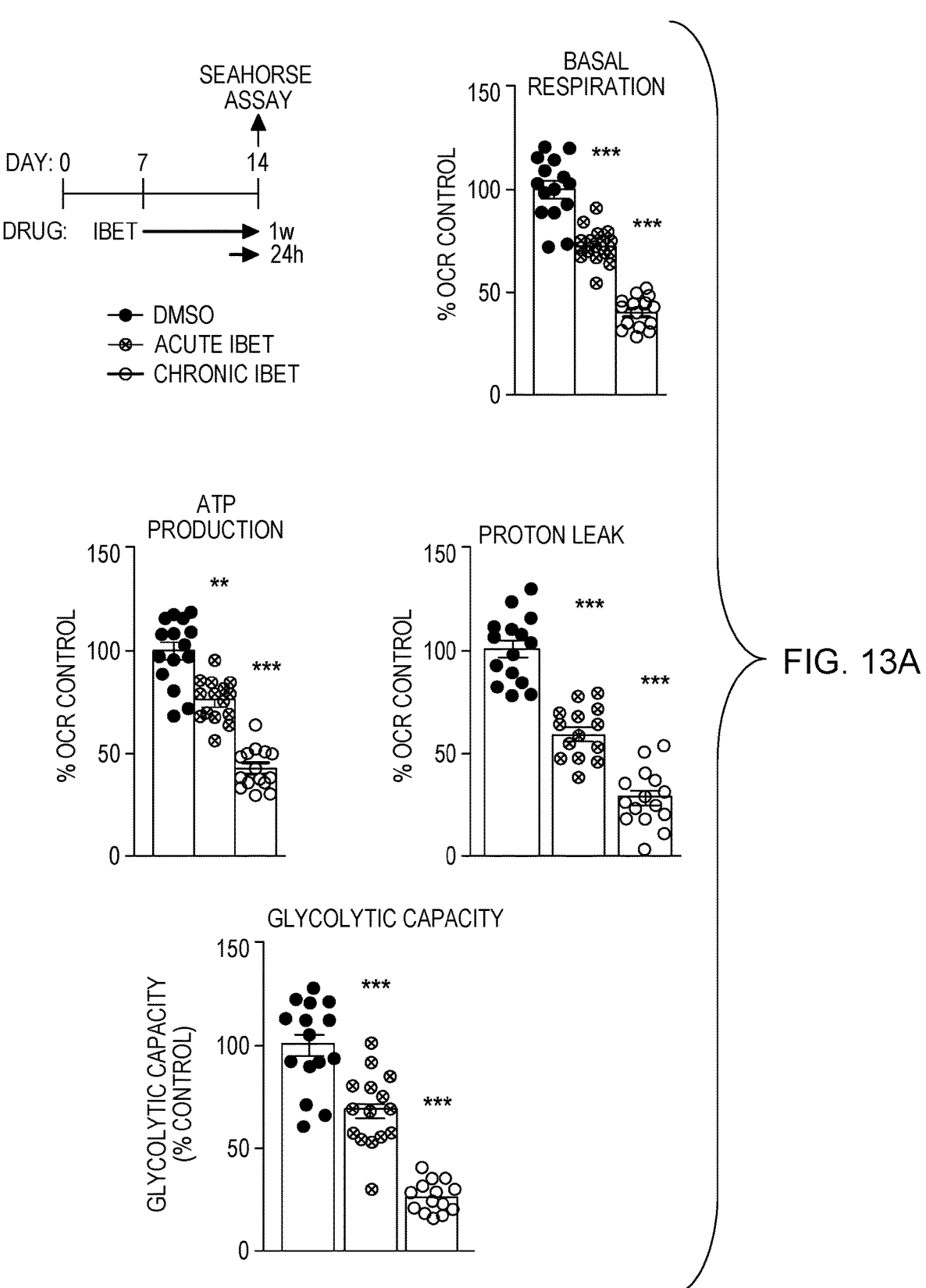
FIGS. 13A-13E show that chronic BET inhibition suppresses neuronal metabolism and increases autophagy.

Glycolysis also contributes to neuronal metabolism and several key glycolytic metabolites (Fructose 6-phosphate, Glucose-6-phosphate, Phosphoenolpyruvate) were decreased after IBET858. Basal glycolysis as measured by extracellular acidification rate is slightly decreased by chronic BET inhibition suggesting glycolysis may be suppressed. More striking, however, was the maximum glycolytic rate is significantly attenuated after BET inhibition (FIG. 13A). These baseline changes show that IBET858 decrease neuronal metabolism as predicted by the observed gene expression changes. Additionally, the decreased maximal responses indicate that this metabolic state is relatively stable. This decrease in metabolic activity happens gradually as an acute IBET858 treatment (24 h) does not impact respiration and glycolysis to the same magnitude as chronic BET inhibition. The time-dependent decrease in metabolic activity correlates with the time-dependent increase in neuroprotection and gene expression profiles, suggesting that the metabolic reprogramming by IBET858 contributes to its protective effect. These results confirm that BET inhibition lowers rate of oxidative phosphorylation and glycolysis in neuronal cultures which could contribute to the increased lifespan caused by IBET858.

Figures 13B, 13C:
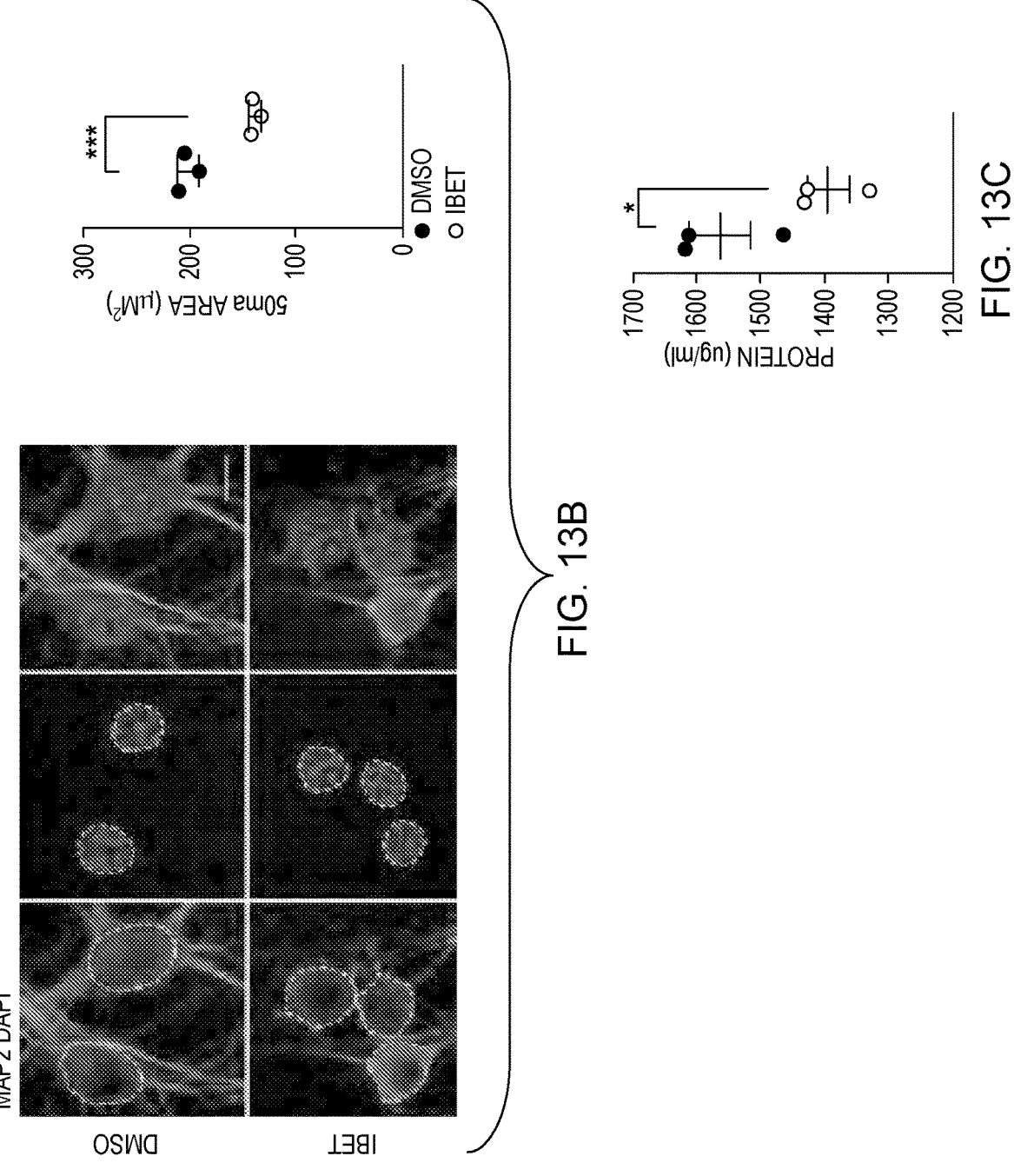
Figure 13D:
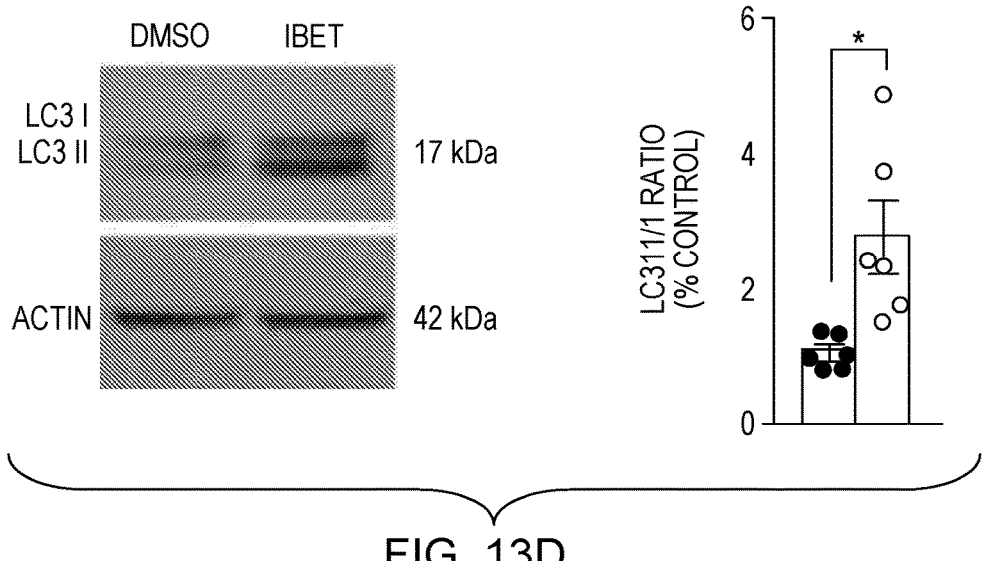

Metabolic gene suppression was also accompanied by increased protein degradation suggesting autophagy is increased after IBET858. Because autophagy increases lipid species which are mostly non-polar, they are not detected in the polar metabolite data. However, if autophagy is, in fact, activated after BET inhibition, the neurons would be smaller and possibly contain less protein. Indeed, total protein content is decreased by 13% as measured by the BCA assay after one week of BET inhibition (FIG. 13C). Furthermore, cell morphological analysis revealed that BET inhibition decreases somatic area (Map2+ area) by 25% (FIG. 13B). Moreover, BET inhibition causes an almost three-fold increase in autophagy as measured by the ratio of LC3II to LC3I, a common autophagic marker (FIG. 13D). Together these data confirm that, in addition to lowering metabolism, IBET858 increases autophagy in neurons.

This cellular phenotype is remarkably similar to that reported for the mTOR inhibitor, rapamycin. Decreasing amino acid availability, which is seen in the metabolite data, is known to inhibit mTOR signaling.

Figure 13E:
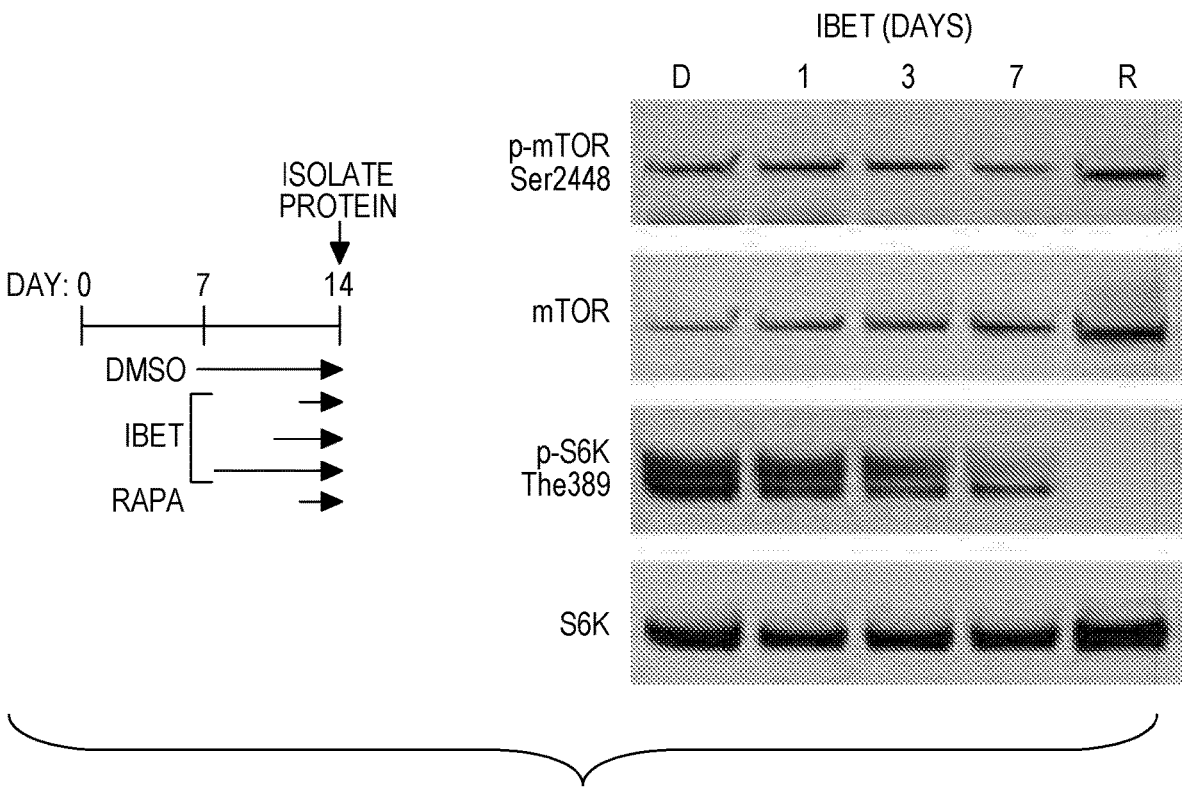

Additionally, there is significant agreement between genes sensitive to BET inhibition and mTOR inhibition. These data suggested to that, although IBET858 does not decrease its expression, mTOR signaling may be lower after BET inhibition which would represent a convergence of the two pathways. While BET inhibition does not affect the mTOR protein levels, there is a significant, time-dependent decrease in mTOR activity as indicated by phosphorylation of p70-S6k at Thr389 (FIG. 13E). These data suggest BET inhibition converges on the same cellular phenotype induced by mTOR inhibition.

Example 8

BETs Directly Regulate Synaptic and Metabolic Gene Expression

The defined transcriptional changes after BET inhibition strongly correlate with observed changes in cellular phenotype including decreased metabolism. However it is possible that these changes are secondary to loss of BET binding especially because of the extended treatment duration. For example, these gene expression changes could be caused by loss of a transcription factor that coordinates metabolic gene expression rather than direct loss of BETs from these loci. To understand if these changes are primarily caused by loss of BET activity, the following must be understood: 1) what genes are directly bound by BET proteins in neurons and 2) which genes lose BETs after IBET858.

To first address direct interactions with the BET proteins, chromatin immunoprecipitation was performed with sequencing for Brd2, Brd4 and Pol2 in neurons. The BET proteins Brd2 and Brd4 bind to 9100 promoters in wild-type neurons. Most of these loci (68%, 6173) are co-bound by Brd2 and Brd4 but 981 and 1946 promoters appear to be bound only by Brd2 or Brd4 respectively. As expected from proteins that promote transcriptional elongation, BET proteins display modest, intermittent binding along gene bodies (10-20% of loci) and Brd2 and Brd4 are also present at numerous intergenic sites including active enhancers (596 and 980 respectively). The BET-bound genes encode proteins that contribute to axon guidance, glutamatergic and GABAergic synapse development but also metabolic pathways including mTOR signaling, oxidative phosphorylation, and amino acid biosynthesis. The majority of genes downregulated after 12 h (63%, 733/1158) and 1 week (61%, 844/1391) IBET858 are bound by Brd2 or Brd4 which indicates the observed phenotypes are likely due to direct inhibition/loss of BET proteins at these loci. Indeed short-term treatment (6 h) of neurons with IBET858 reduces BET binding at approximately 1000 gene promoters which encode proteins that 1) regulate axon and synapse development like Shank2, Rbfox1, and Dscam and 2) include several metabolic genes such as Atp5e, Me1, and Cox20. In conclusion, BET proteins bind to metabolic gene loci and are lost after IBET858 indicating that BETs control neuronal metabolism via direct transcription of metabolic genes.

Example 9

Loss of Brd4 Protects Neurons from Glutamate Toxicity

Figure 14A:
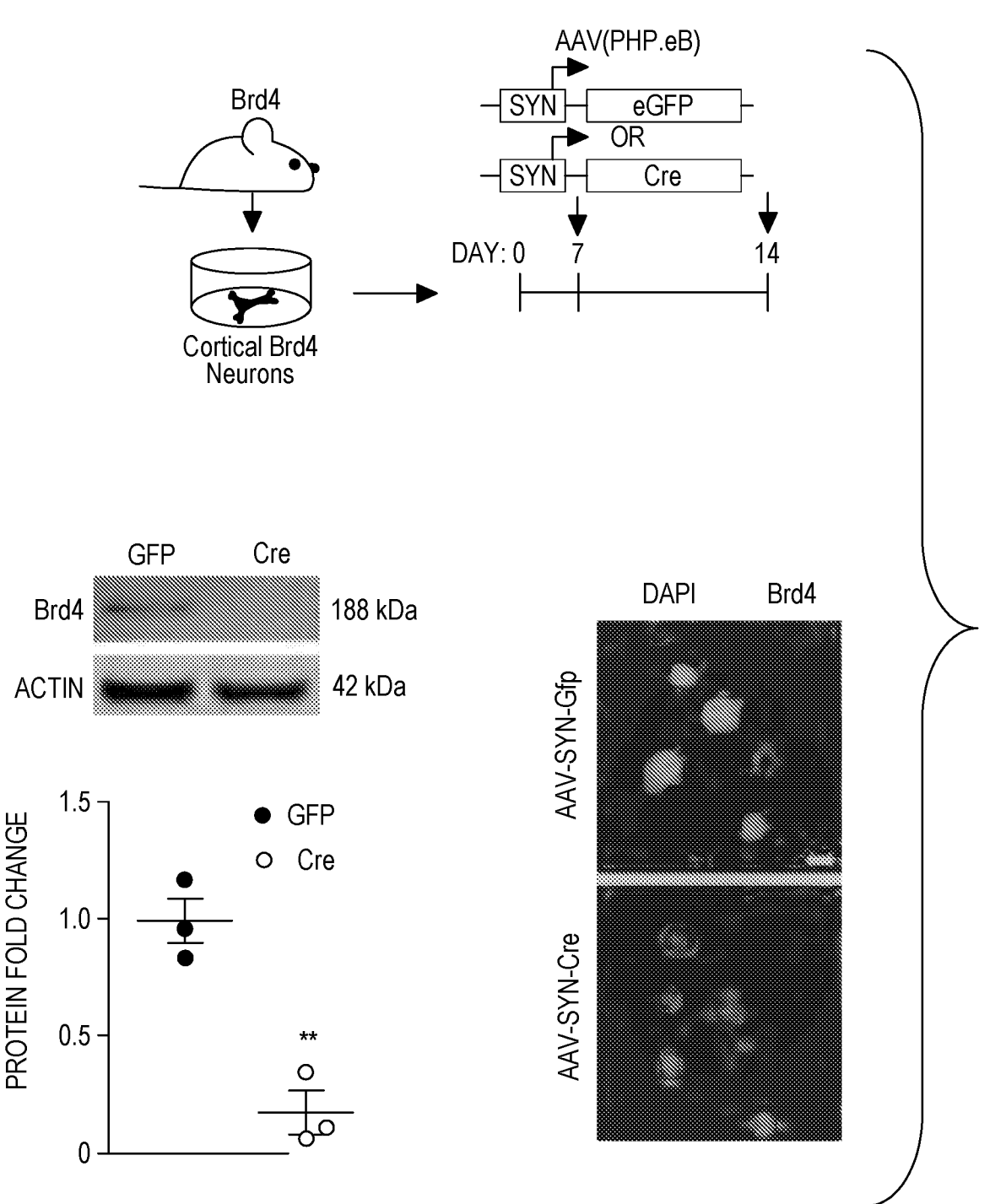
FIGS. 14A-14C depict that loss of Brd4 protects neurons from glutamate toxicity.
Figure 14B:
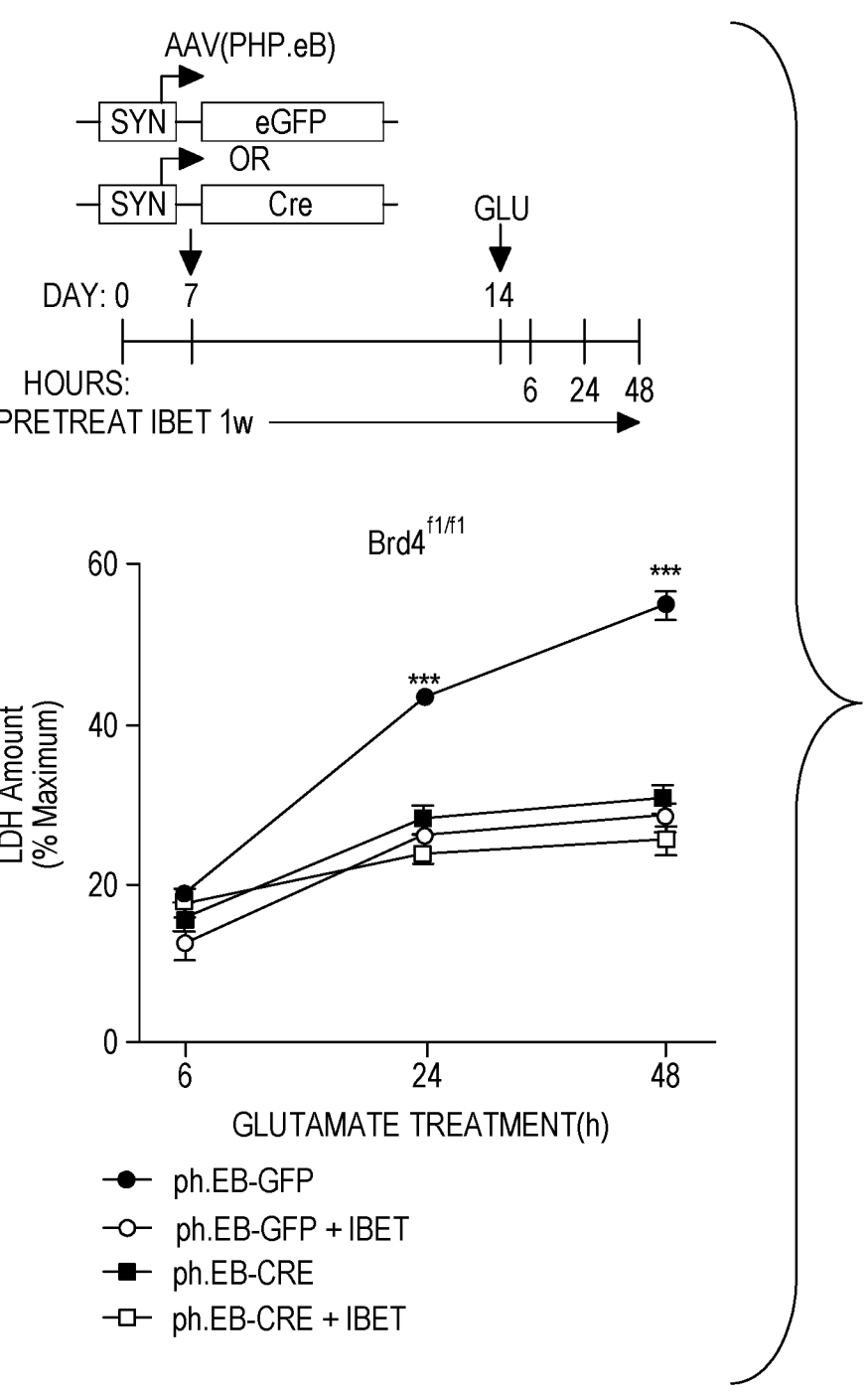
Figure 14C:
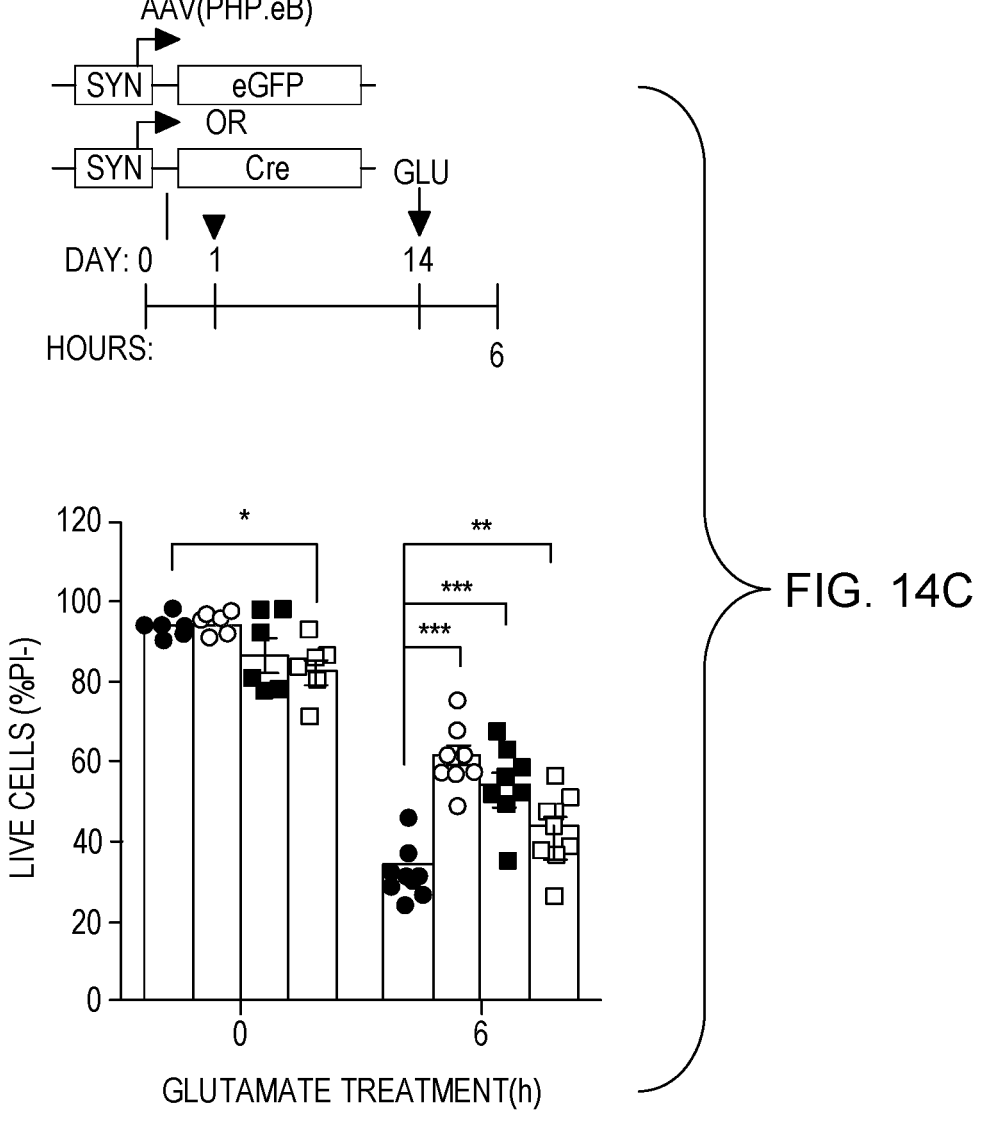

Notably, IBET858 is a pan-BET family inhibitor which displaces all three BET proteins from the chromatin. While the majority of direct target genes (75%) are shared between Brd2 and Brd4 in neurons, there are genes that are unique to either member. Furthermore, there is evidence that Brd2 and Brd4 have distinct interaction partners and may have unique, alternative functions. Shi et al., "Disrupting the Interaction of BRD4 with Diacetylated Twist Suppresses Tumorigenesis in Basal-like Breast Cancer," *Cancer Cell* 25:210-225 (2014); Bisgrove et al., "Conserved P-TEFb-Interacting Domain of BRD4 Inhibits HIV Transcription," *Proceedings of the National Academy of Sciences of the United States of America* 104:13690-13695 (2007); and Cheung et al., "Distinct Roles of Brd2 and Brd4 in Potentiating the Transcriptional Program for Th17 Cell Differentiation," *Molecular Cell* 65:1068-1080.e5 (2017), all of which are hereby incorporated by reference in their entirety. Understanding which BET contributes to the neuroprotective effect of IBET858 may help identify the mechanism underlying this phenomenon. Therefore to determine which BET member is required for the neuroprotective effect of IBET858, survival was measured in neuronal cultures deficient for either Brd2 or Brd4 after glutamate toxicity. Primary neuronal cultures were generated from either Brd4$^{fl/fl}$ mice or the newly developed Brd2$^{fl/fl}$ mouse line (kind gift from Drs. Debra Wolgemuth and Enyuan Shang). After plating, cultures were infected with either with AAV (PHP.eB)-Synapsin-Cre or AAV (PHP.eB)-Synapsin-GFP which overexpress Cre recombinase or GFP specifically in neurons. Complete culture infection was confirmed by GFP expression and by the loss of mRNA and protein. Immunofluorescence for Brd4 showed complete protein depletion from neurons at day 7 in culture which matches exactly the time point for IBET858 treatment. In three independent experiments, neuronal loss of Brd2 does not protect neurons from glutamate toxicity. Similarly loss of Brd2 does not impact the protective effect of IBET858 (GFP+IBET858). However, neuron-specific deletion of Brd4 protects neurons from glutamate toxicity to the same magnitude as IBET858 (two experimental replicates) (FIGS. 14A-14C). This effect was confirmed using propidium iodide staining after 6 hours of glutamate treatment. This assay confirmed that Brd4 deletion prevents cell death in response to glutamate toxicity and that this effect is similar in magnitude to that of IBET858. This data strongly suggests that Brd4 mediates the protective effect of IBET858 in neurons.

Example 10

Discussion of Examples 6-9

As the human population continues to age, the incidence of age-related diseases like cancer and neurodegeneration likewise increases. Neurons, which perform critical functions required for organism health and survival, are among the most susceptible cell type to lack of trophic support and toxic stimuli. While several therapeutic strategies have been developed over the last few decades to treat different cancers, there are no approved therapies that can reverse or even halt cognitive decline in neurodegeneration. It is therefore imperative to understand the molecular and cellular mechanisms that regulate neuronal survival if effective treatments for diseases such as Alzheimer's or Huntington's disease are to be developed.

Here a novel role for the BET proteins in the negative regulation of neuronal survival is identified. Pharmacological inhibition of these proteins increases neuronal lifespan and protects neurons from lethal agents including high concentrations of glutamate, hypoxia, and $A\beta 1$-43 oligomers. Chronic BET inhibition decreases neuronal metabolism, increases autophagy and ultimately leads to decreased mTOR signaling. The pro-survival phenotype may be neuron-intrinsic because pharmacological depletion of microglia using PLX5622 did not alter longevity after IBET858. It is also possible that, given the cognate interactions between neurons and glial cells, that the protective state in neurons by IBET858 may increase neurotrophic support by glia. Specifically Gdf11 is known to increase longevity but is thought to be mainly produced by astrocytes. Expression of Gdf11 is increased after BET inhibition and it would be interesting to determine if this is produced by neurons or originates from the few astrocytes which are 5% of all cells in the culture. Alternatively, the protective effect observed in vivo in Examples 2-5 herein may result from a combination of the neuroprotective effect detailed here and the anti-inflammatory effect of BET inhibition. Interestingly, BET inhibition in microglia suppresses metabolic gene expression (Bcat1, Igf1, Me3, and Lpl) and induces protein degradation pathways (Ulk2, Atg12/14, and Hspa1a/1b) similar to neurons. This suggests that BET control of metabolic gene expression is not neuron-specific and that potentially any cell type could be driven into the protective state induced by IBET858.

The neuroprotective effect of IBET858 is similar to that of the mTOR inhibitor, rapamycin, which is the best-known agent to increase neuronal survival. Other small molecules that mimic caloric restriction such as resveratrol, a SIRT1 agonist, or metformin, which activates AMPK, also have neuroprotective effects. Kim et al., "SIRT1 Deacetylase Protects Against Neurodegeneration in Models for Alzheimer's Disease and Amyotrophic Lateral Sclerosis," *The EMBO Journal* 26:3169-3179 (2007) and Bastianetto et al., "Neuroprotective Action of Resveratrol," *Biochimica et Biophysica Acta* 1852:1195-1201 (2015), both of which are hereby incorporated by reference in their entirety. IBET858 may be superior because it increases expression of Sirt1 and Prkaa1, an AMPK subunit, expression as well as other pro-survival factors like Bdnf and Gdf11. Hetman et al., "Neuroprotection by Brain-Derived Neurotrophic Factor is Mediated by Extracellular Signal-Regulated Kinase and Phosphatidylinositol 3-Kinase," *The Journal of Biological Chemistry* 274:22569-22580 (1999); Almeida et al., "Neuroprotection by BDNF Against Glutamate-Induced Apoptotic Cell Death is Mediated by ERK and PI3-Kinase Pathways," *Cell Death and Differentiation* 12:1329-1343 (2005); and Katsimpardi et al., "Vascular and Neurogenic Rejuvenation of the Aging Mouse Brain by Young Systemic Factors," *Science* 344:630-634 (2014), all of which are hereby incorporated by reference in their entirety. Resveratrol has been shown to weakly inhibit BET proteins suggesting that part of its protective effect may be due to BET inhibition. Dutra et al., "Dietary Compound Resveratrol Is a Pan-BET Bromodomain Inhibitor," *Nutrients* 9:1172 (2017), which is hereby incorporated by reference in its entirety. Similar to rapamycin, BET inhibition may be an endogenous survival strategy as a naturally-occurring inhibitor of the BET proteins was recently identified. Kim, "A Natural Compound, Aristoyagonine, Is Identified as a Potent Bromodomain Inhibitor by Mid-throughput Screening," *Biochemical and Biophysical Research Communications* 503:882-887 (2018), which is hereby incorporated by reference in its entirety. As such, BET inhibition represents a novel and powerful strategy for neuroprotection.

Future work should focus on expanding the efficacy of BET inhibition in other mouse models of neurodegeneration but also on human induced pluripotent stem cell-derived neurons. Examining whether BET proteins negatively regulate the survival in human neurons is especially important as many therapeutic strategies identified in pre-clinical studies fail to as clinical trials progress. Additionally, this study largely quantified late apoptosis and necrotic cell death but did not fully examine the effects of IBET858 on specific cell death pathways. This may be especially useful because autophagy, which is strongly induced by BET inhibition, can also lead to cell death but the mechanisms that distinguish pro-survival vs pro-death autophagy are poorly understood. Therefore it is likely that the protective effect of IBET858 is multifactorial and depends on multiple cell types possibly even those in the periphery.

Overall this study shows that inhibition of BET-dependent transcription induces a neuroprotective state that is highly reminiscent of mTOR inhibition. Indeed, BETs regulate the majority of rapamycin-sensitive genes and may therefore represent a previously unappreciated aspect of the protective mechanism of mTOR inhibition. It is proposed here that nutrient availability, cell metabolism, and transcriptional regulation work together in a self-enforcing cycle where inhibition at any stage (Caloric restriction, mTOR inhibition, or IBET858) can induce a cell state beneficial for survival and longevity.

Example 11

Overarching Discussion and Future Perspectives

Here the role of BET-dependent gene networks in diverse cellular and developmental contexts within the central nervous system are presented. BET-mediated transcriptional control of long, synaptic genes implicated in Autism Spectrum Disorder (ASD) is described in Sullivan et al., "Autism-Like Syndrome is Induced by Pharmacological Suppression of BET Proteins in Young Mice," *J. Exp. Med.* 212:1771-1781(2015), which is hereby incorporated by reference in its entirety. Dysregulation of these networks during development causes an autism-like phenotype in young mice providing support to the proposed epigenetic mechanism underlying ASD. In Examples 2-5, it is shown that BET proteins are required for microglia-mediated inflammation. Pharmacological inhibition of the BET proteins prevents neurodegeneration in various mouse models which is at least partly due to blunted pro-inflammatory microglia activity. Lastly in Examples 6-10, a novel role for the BET proteins as negative regulators of neuronal survival is elucidated. While these roles may be distinct at face-value, these data highlight the main role of BET proteins in the definition and regulation of transcriptional networks in response to cellular stimuli. Nicodeme et al., "Suppression of Inflammation by a Synthetic Histone Mimic," *Nature* 468:1119-1123 (2010) and Hargreaves et al., "Control of Inducible Gene Expression by Signal-Dependent Transcriptional Elongation," *Cell* 138:129-145 (2009), which are hereby incorporated by reference in their entirety. This is in accordance with other data that show BETs regulate the induction of cell-type and stimulus-specific gene expression in peripheral cells. These disparate roles for BETs in neurodevelopment, inflammation, and neurodegeneration can be unified by applying the attractor state model of gene network regulation, which has been widely discussed in the context of differentiation.

Example 12

Autism Spectrum Disorder as a Novel Cellular Attractor States

In ASD it is unclear how the many diverse mutations in genes which encode synaptic and transcriptional regulators converge onto the same phenotypes. De Rubeis et al., "Synaptic, Transcriptional and Chromatin Genes Disrupted in Autism," *Nature* 515:209-215 (2014) and Zoghbi, "Postnatal Neurodevelopmental Disorders: Meeting at the Synapse?" *Science* 302:826-830 (2003), which are hereby incorporated by reference in their entirety. Here it is shown that altering transcriptional efficiency in developing neurons disrupts synaptic gene networks and leads to an autism-like phenotype similar to that induced by direct loss of synaptic proteins like Shank3. Peça et al., "Shank3 Mutant Mice Display Autistic-Like Behaviours and Striatal Dysfunction," *Nature* 472:437-442 (2011), which is hereby incorporated by reference in its entirety. If the idea of attractor states is considered, which, in physics, would be defined by low potential energy, how diverse mutations act as different signals that drive neuronal development towards a common disease state will begin to be understood.

Gene expression is a complex, dynamic system where the coordinated transcription of thousands of individual genes gives rise to a particular cell state or function. Pope and Medzhitov, "Emerging Principles of Gene Expression Programs and Their Regulation," *Molecular Cell* 71:389-397 (2018), which is hereby incorporated by reference in its entirety. While a cell can theoretically express any combination of the 20,000 genes in the genome, not all of these gene networks lead to a viable or stable cell state. von Schimmelmann et al., "Polycomb Repressive Complex 2 (PRC2) Silences Genes Responsible for Neurodegeneration," *Nature Neuroscience* 19:1321-1330 (2016), which is hereby incorporated by reference in its entirety. Thinking of gene networks and their associated stability, a landscape with hills can be imagined, which have high potential energy, and valleys with low potential energy, representing unstable and stable states respectively.

Figure 15A:
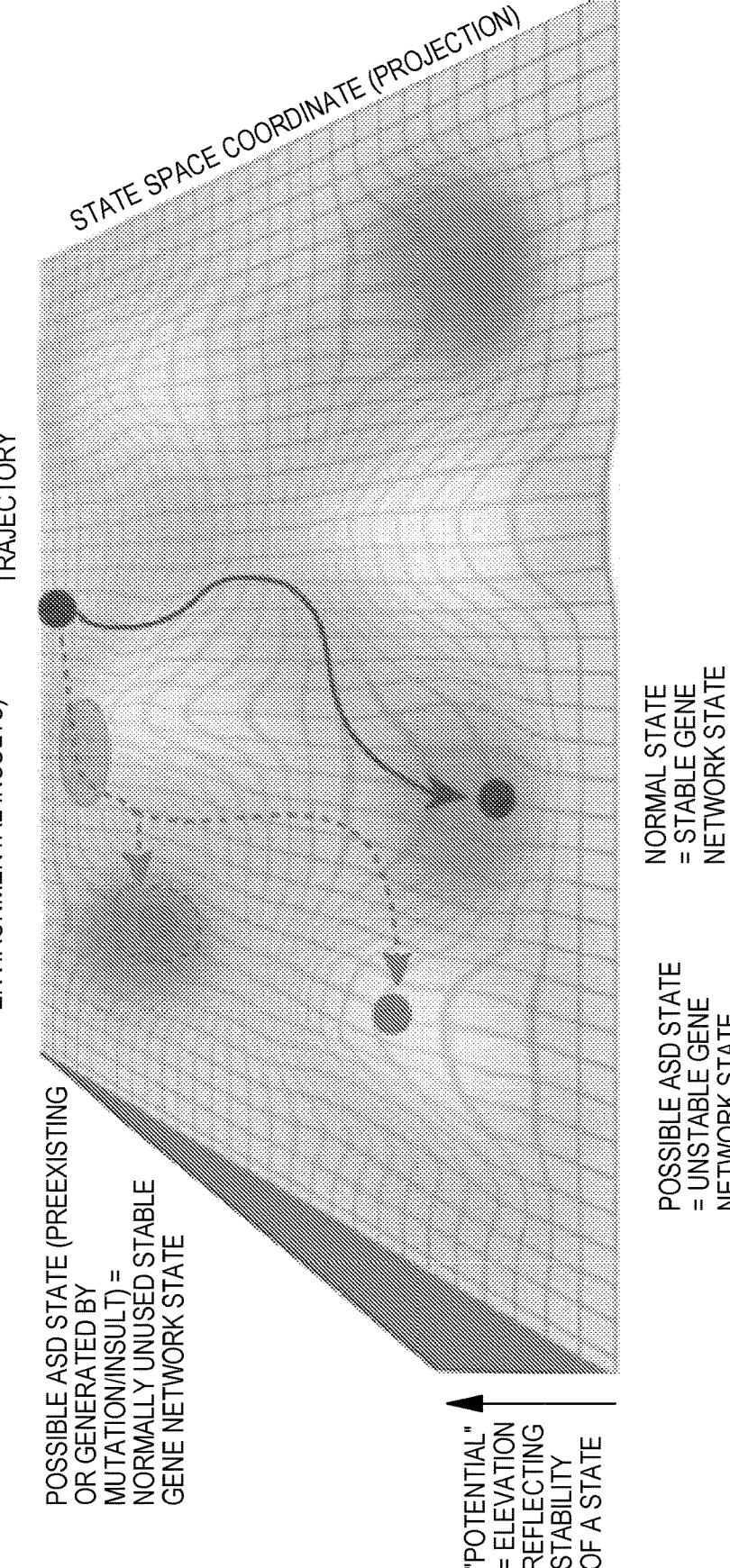
FIGS. 15A-15C show cellular differentiation in normal and neurodegeneration-associated gene regulatory network states (FIG. 15A), neurodegeneration versus healthy brain function (FIG. 15B), and homeostasis versus protected (FIG. 15C).
Figure 15B:
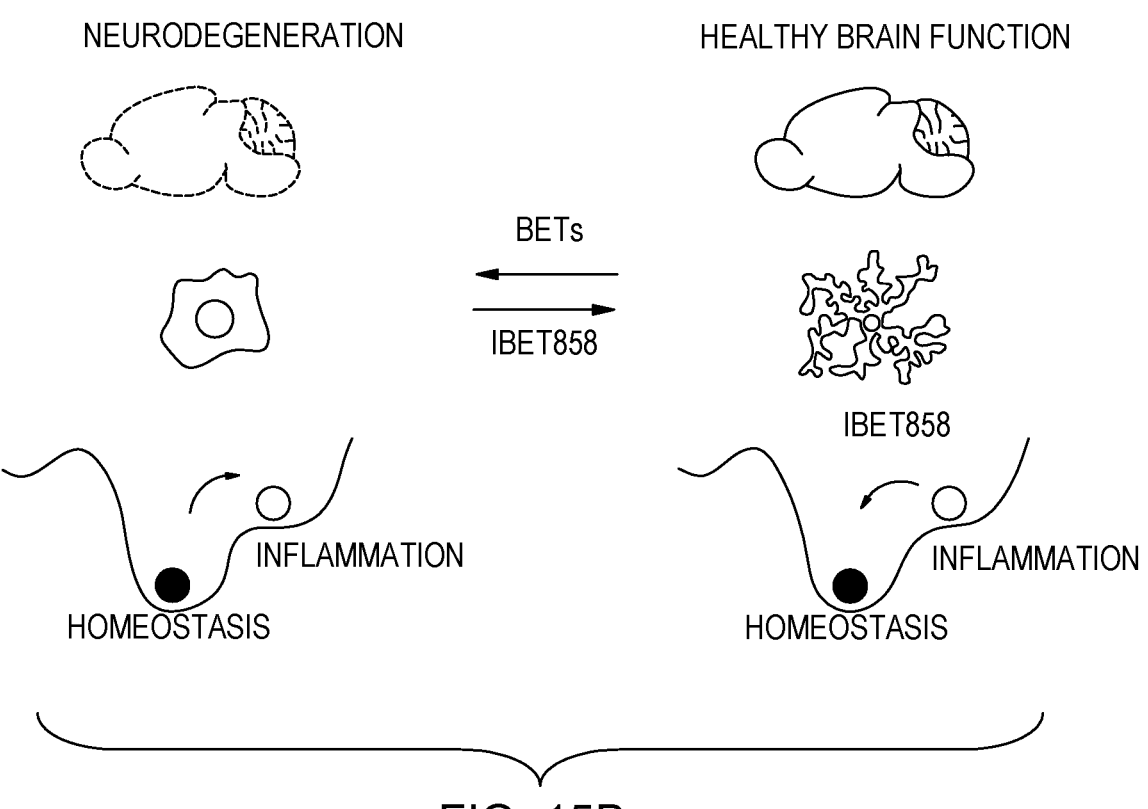
Figure 15C:
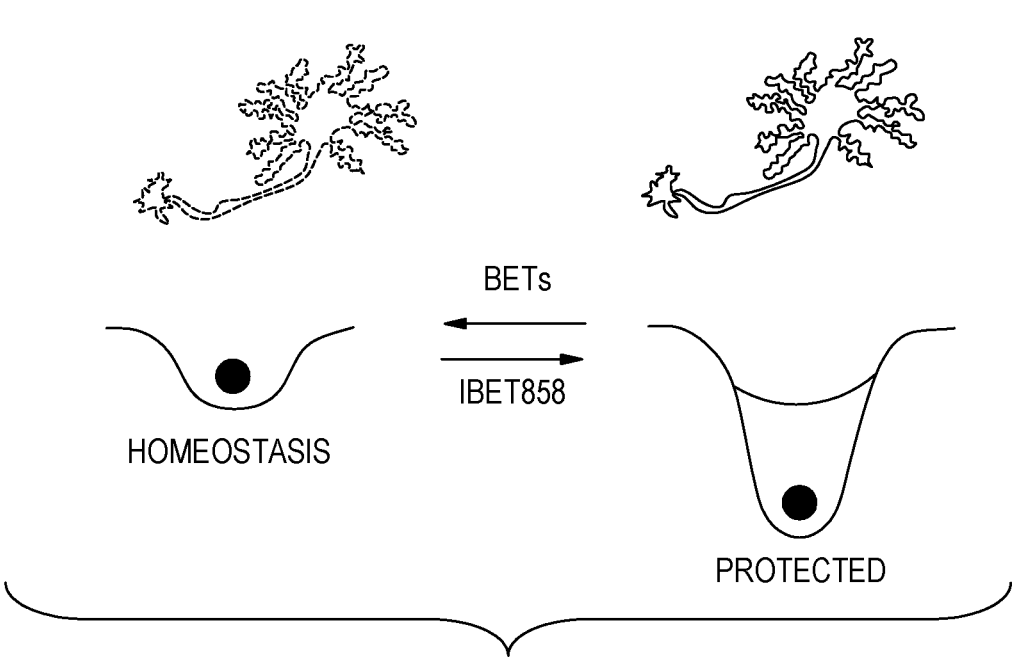

Perhaps the best known example of this notion is Waddington's epigenetic landscape, where the metaphor of a ball rolling down a hill into deep valleys is used to explain the cellular differentiation process. A multipotent stem cell, beginning at the top of the metaphorical hill, follows a "canalization" process towards a specific outcome which is guided by exposure to both external and internal signals. Waddington, "Canalization of Development and Genetic Assimilation of Acquired Characters," *Nature* 183:1654-1655 (1959), which is hereby incorporated by reference in its entirety. As differentiation proceeds, the now progenitor cell is drawn towards terminal differentiation as a mature cell type like a medium spiny neuron. This process is defined by the precise coordination of specific transcription factors (Hobert, "Regulatory Logic of Neuronal Diversity: Terminal Selector Genes and Selector Motifs," *Proceedings of the National Academy of Sciences of the United States of America* 105:20067-20071 (2008), which is hereby incorporated by reference in its entirety), gene regulatory networks (Heiman et al., "A Translational Profiling Approach for the Molecular Characterization of CNS Cell Types," *Cell* 135:738-748 (2008) and Doyle et al., "Application of a Translational Profiling Approach for the Comparative Analysis of CNS Cell Types," *Cell* 135:749-762 (2008), which are hereby incorporated by reference in their entirety), and epigenetic modifiers (von Schimmelmann et al., "Polycomb Repressive Complex 2 (PRC2) Silences Genes Responsible for Neurodegeneration," *Nature Neuroscience* 19:1321-1330 (2016) and Ayata et al., "Epigenetic Regulation of Brain Region-Specific Microglia Clearance Activity," *Nature Neuroscience* 21:1049-1060 (2018), which are hereby incorporated by reference in their entirety) that maintain and enforce the cell state (FIGS. 15A-15C).

These attractor states are the defined, common outcome of numerous interactions within any given network. MacArthur et al., "Systems Biology of Stem Cell Fate and Cellular Reprogramming," *Nature Reviews. Molecular Cell Biology* 10:672-681(2009), which is hereby incorporated by reference in its entirety. For example, progenitor cells in culture stimulated with different signals will reach the same differentiation state because the gene expression networks, despite being initiated by distinct signaling pathways, eventually converge onto the same attractor state or transcriptional profile 285. However, these attractor states can be hijacked during disease like the case of malignancy where mutations in various, discrete genes cause the same immortal and invasive cell state similar to that observed in cancer. Huang et al., "Cancer Attractors: A Systems View of Tumors From a Gene Network Dynamics and Developmental Perspective," *Seminars in Cell & Developmental Biology* 20:869-876 (2009); Huang and Kauffman, "How to Escape the Cancer Attractor: Rationale and Limitations of Multi-Target Drugs," *Seminars in Cancer Biology* 23:270-278 (2013); and Li et al., "Dynamics Inside the Cancer Cell Attractor Reveal Cell Heterogeneity, Limits of Stability, and Escape," *Proceedings of the National Academy of Sciences of the United States of America* 113:2672-2677(2016), all of which are hereby incorporated by reference in their entirety. In this model, mutations or environmental factors contributing to ASD risk could lower the barriers defining cell states and divert the neuron from its normal developmental trajectory towards a new neuronal attractor state that induces the formation of a new phenotype. Li et al., "Dynamics Inside the Cancer Cell Attractor Reveal Cell Heterogeneity, Limits of Stability, and Escape," *Proceedings of the National Academy of Sciences of the United States of America* 113:2672-2677 (2016) and Muñoz-Descalzo et al., "Wnt-Notch Signalling: An Integrated Mechanism Regulating Transitions Between Cell States," *BioEssays* 34:110-118 (2012), which are hereby incorporated by reference in their entirety. This model switches the focus from the impact of individual genes to ASD pathology towards that of impaired gene regulatory networks. Importantly, these ASD attractor states could be stable or unstable and, if so, the induced phenotype may be reversible. This is supported by recent studies including the data presented here that report reversal of transcriptional and behavioral changes after reinstating ASD risk gene function in the adult brain. Guy et al., "Reversal of Neurological Defects in a Mouse Model of Rett Syndrome," *Science* 315:1143-1147 (2007); Sullivan et al., "Autism-Like Syndrome is Induced by Pharmacological Suppression of BET Proteins in Young Mice," *The Journal of Experimental Medicine* 212:1771-1781 (2015); Sztainberg et al., "Reversal of Phenotypes in MECP2 Duplication Mice Using Genetic Rescue or Antisense Oligonucleotides," *Nature* 528:123-126 (2015); Mei et al., "Adult Restoration of Shank3 Expression Rescues Selective Autistic-Like Phenotypes," *Nature* 530:481-484 (2016); and Creson et al., "Re-expression of SynGAP Protein in Adulthood Improves Translatable Measures of Brain Function and Behavior in a Model of Neurodevelopmental Disorders," *bioRxiv* 474965 (2018), all of which are hereby incorporated by reference in their entirety. Given this model, it would be interesting to understand how BET inhibition alters gene expression on a single cell level because cortical cultures contain heterogeneous neuron subtypes similar to that observed in the cortex in vivo. Kriegstein and Dichter, "Morphological Classification of Rat Cortical Neurons in Cell Culture," *The Journal of Neuroscience* 3:1634-1647 (1983), which is hereby incorporated by reference in its entirety. If BET inhibition induces a new attractor state, it may be observed that these neuron subtype specific gene expression profiles are replaced or superseded by a common transcriptional profile.

In accordance with the BET-dependent regulation of synaptic gene expression described in Sullivan et al., "Autism-Like Syndrome is Induced by Pharmacological Suppression of BET Proteins in Young Mice," *J. Exp. Med.* 212:1771-1781(2015), which is hereby incorporated by reference in its entirety, BET inhibition delays the development of neuronal firing in vitro that eventually normalizes in Examples 6-10. Others have also shown the requirement of BET activity for proper dendritic and spine development106,146. This data provides a crucial functional link between the observed transcriptional and behavioral changes discussed previously and highlight the need for more investigation. Remarkably, despite the significant down-regulation of solute-carriers, ion channels and neurotransmitter receptors, IBET858 treated neurons exhibit wild-type levels of electrical activity after recovering from this initial developmental delay. Proteomics analysis has not been performed to validate that the transcriptional changes are recapitulated at the protein level however targeted analysis shows this to be likely. As such, there must be robust mechanisms of homeostatic plasticity that compensate for the loss of these channels and receptors and it would be interesting to investigate the mechanism underlying this phenomenon. This highlights the critical importance of neuronal activity such that even in a starvation-like state, appropriate electrical activity is maintained.

Example 13

Inflammation as an Attractor State

The attractor state framework is useful because it can apply to any cell state that is defined by transcriptional networks. For instance, during homeostasis microglia the brain's immune cells survey neuronal tissues in a quiescent state which is directed by a unique transcriptional profile. Gosselin et al., "An Environment-Dependent Transcriptional Network Specifies Human Microglia Identity," *Science* 356:eaal3222 (2017), which is hereby incorporated by reference in its entirety. When an injury is sensed, microglia completely switch morphology, function and gene expression profiles. Keren-Shaul et al., "A Unique Microglia Type Associated with Restricting Development of Alzheimer's Disease," *Cell* 169:1276-1290.e17 (2017) and Pope and Medzhitov, "Emerging Principles of Gene Expression Programs and Their Regulation," *Molecular Cell* 71:389-397 (2018), which are hereby incorporated by reference in their entirety. Instead of expressing actin polymerization genes, microglia now induce the expression of a wide array of cytokines and chemokines which would be expressed only modestly in a homeostatic state. The state space of the microglia completely changed in response to an external stimulus. Within this context, it is shown in Examples 2-5 that BET inhibition, rather than inducing a pathological attractor state, restrains inflammation and promotes a homeostatic state in microglia (FIG. 3B).

Example 14

Neuronal Survival as an Attractor State

In Examples 6-10 it is shown that BET proteins negatively regulate neuronal survival. BET inhibition induces protected neuronal state defined by low metabolic activity and high protein degradation remarkably similar to that induced by caloric restriction or mTOR inhibition (FIG. 10C). It is important to note that there are numerous examples of IBET858-mediated alterations that may increase neuronal survival on their own such as increased Sirt1 (Kim et al., "SIRT1 Deacetylase Protects Against Neurodegeneration in Models for Alzheimer's Disease and Amyotrophic Lateral Sclerosis," *The EMBO Journal* 26:3169-3179 (2007), which is hereby incorporated by reference in its entirety), Gdf11 (Katsimpardi et al., "Vascular and Neurogenic Rejuvenation of the Aging Mouse Brain by Young Systemic Factors," *Science* 344:630-634 (2014), which is hereby incorporated by reference in its entirety), or aspartate (Errico et al., "Free D-aspartate Regulates Neuronal Dendritic Morphology, Synaptic Plasticity, Gray Matter Volume and Brain Activity in Mammals," *Translational Psychiatry* 4:e417 (2014) and Krashia et al., "Persistent Elevation of D-Aspartate Enhances NMDA Receptor-Mediated Responses in Mouse Substantia Nigra Pars Compacta Dopamine Neurons," *Neuropharmacology* 103:69-78 (2016), which are hereby incorporated by reference in their entirety) or decreased CCR5 (Zhou et al., "CCR5 is a Suppressor for Cortical Plasticity and Hippocampal Learning and Memory," *eLife* 5:e20985 (2016), which is hereby incorporated by reference in its entirety). For the sake of brevity, a few of these changes are described to illustrate the depth/breadth of the pro-survival phenotype induced by IBET858 but did not provide an exhaustive list. Any one of these impacts is worthy of study in its own right however it is proposed that these changes are properties of an emergent, neuroprotective attractor state. Similar to the ASD attractor state, the hope is to focus on the totality of the cellular state rather than one particular gene or pathway. As such, this neuroprotective attractor state may explain how CR and rapamycin lead to the same cellular phenotype as IBET858 despite completely different mechanisms of action. Interestingly, removal of microglia or neuronal BET activity alone was not sufficient to prevent neurodegeneration and cognitive decline, suggesting that these states may synergize to afford protection. Therefore, observing the stable and perhaps additive convergence of two cellular states may also be being observed (e.g. decreased inflammation and increased neuronal resilience) in vivo that is required for complete rescue from neurode-generation.

The commonality of these states suggests that existing natural systems may employ mechanisms to alter BET activity as an endogenous strategy to promote survival. Supporting this, Brd2 is shuttled out of the nucleus in response to serum withdrawal in *Drosophila*. Guo et al., "Activation-induced Nuclear Translocation of RING3," *Journal of Cell Science* 113:Pt 1:3085-3091 (2000), which is hereby incorporated by reference in its entirety. BET protein expression is also highest in vulnerable neuron subpopula-tions including Purkinje Cells, cells in CA1, and L3/5 Cortex. The data suggests that high BET protein activity may contribute to the vulnerability of these cells by regu-lating metabolic gene expression. This suggests that there may in turn be protected neuronal populations which would predict to be low in BET expression. For example, it would be expected that the pacemaker cells that regulate breathing to be metabolically less active and show little to no BET expression. While more work is necessary to elucidate these mechanisms, it is highly possible that natural mechanisms exist to inhibit BET-dependent transcription in times of stress.

In conclusion the data elucidates previously unknown roles for BET proteins in the central nervous system and provide critical support to the idea that Autism Spectrum Disorders may arise from an epigenetic rather than synaptic mechanism. For the first time in neurons, the direct gene targets of Brd2 and Brd4 which likely have unique functions are identified. Lastly, this work identifies BET inhibition as a promising and multifunctional therapeutic strategy for neurodegenerative disease.

Example 15

Figure 16E:
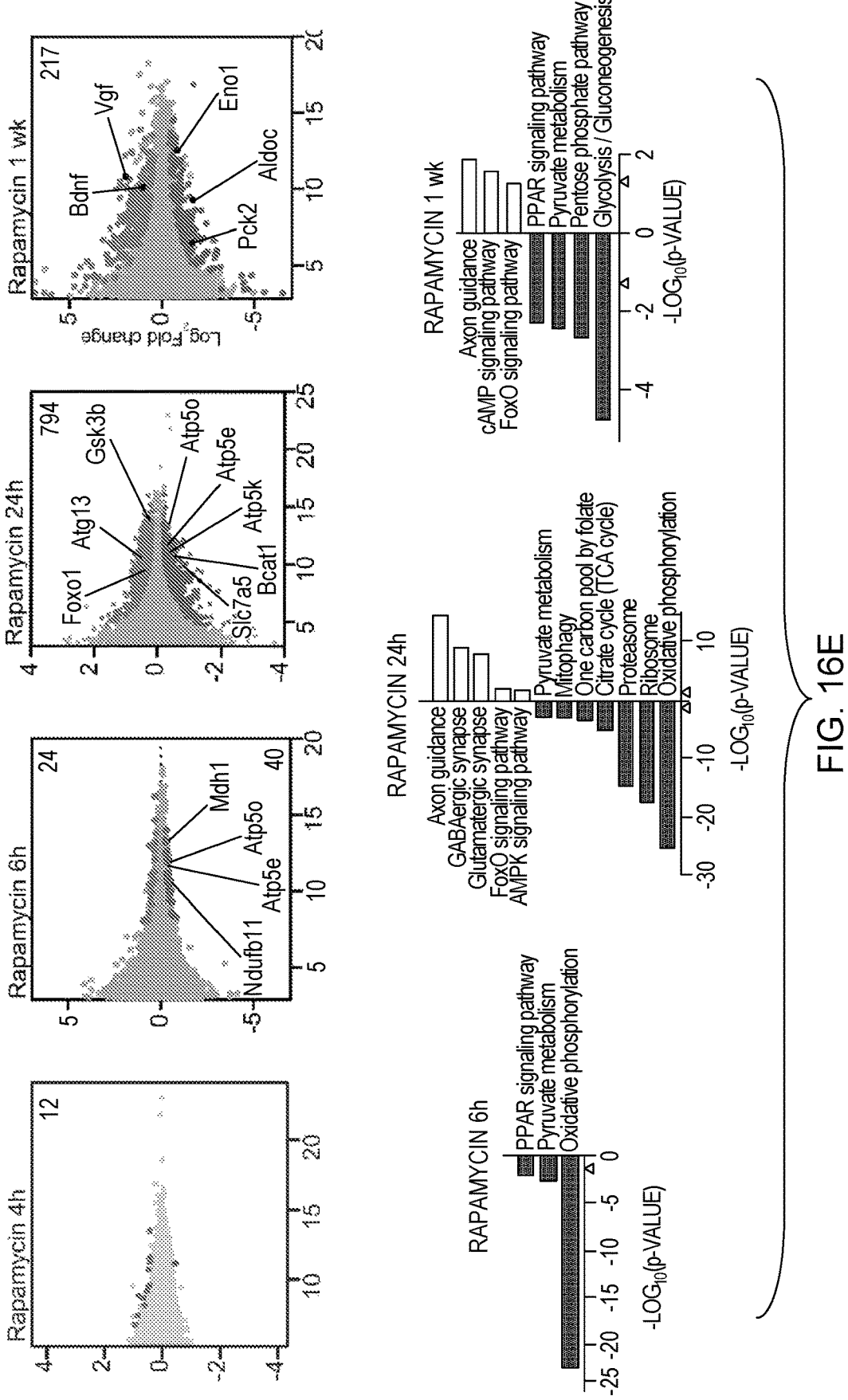
Figure 16F:
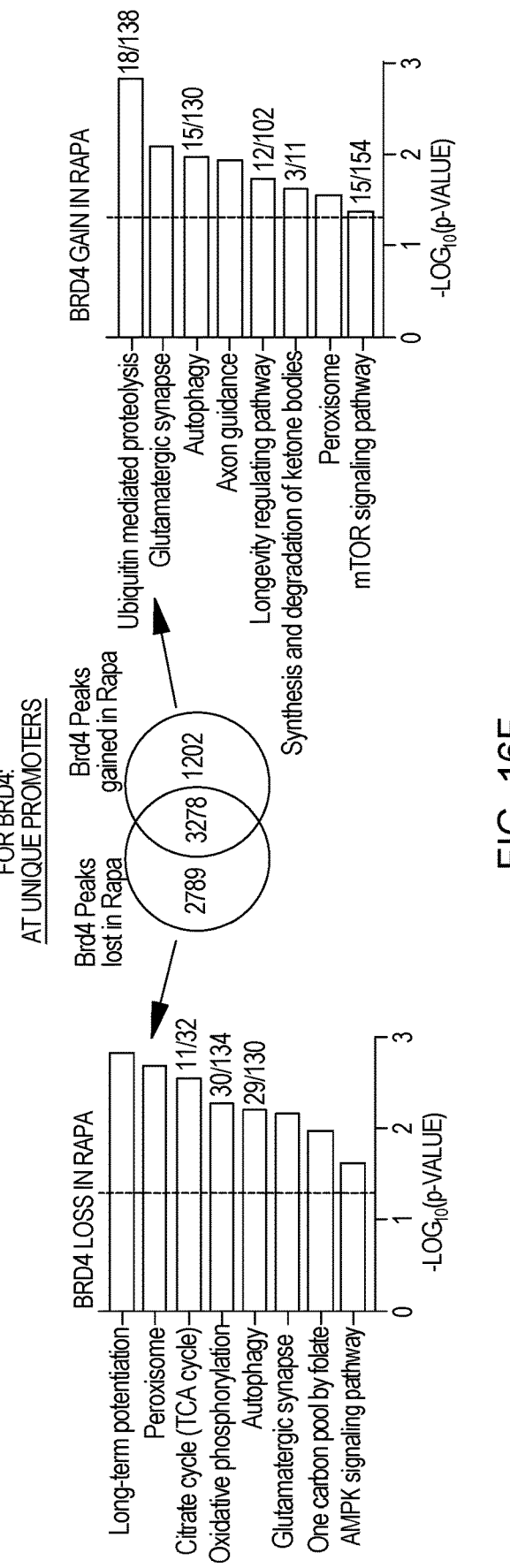

Rapamycin Treatment Promotes Neuronal Longevity/Survival and is Associated with Rapid Gene Expression Changes in Metabolic Genes that are Associated with a Displacement of BRDs from Chromatin Rapamycin has neuroprotective activity. Primary cortical neurons were treated with rapamycin (20 nM) at day 7 and propidium iodide (PI) staining was carried out every 3-4 days to evaluate the percentage of living cells (FIG. 16A). Two-way repeated measures ANOVA with multiple com-parisons, n=6 for each condition. As shown in FIG. 16B, the heatmap shows mean firing rate (Hz) normalized by column in neuronal cultures over time for rapamycin and control treated cells. Dot plots of the average mean firing rate (Hz) of control and rapamycin-treated neurons at day 7, 14 and day 28 are shown in FIG. 16C. Dot plots in FIG. 16D show the percentage of cells that are releasing LDH after 6 hours and 24 hours of exposure to 1 mM glutamate upon pre-treatment with either control or rapamycin for 1 week. It is confirmed that rapamycin triggers rapid changes in meta-bolic gene expression (FIGS. 16A-16D). MA plots and KEGG pathway enrichment for primary cortical neurons treated with rapamycin (20 nm) for 4 hours, 6 hours, 24 hours, and 1 week are shown in FIG. 16E. Rapamycin treatment leads to changes in Brd4 chromatin association associated with gene networks involved in metabolism (down) and neuronal longevity (up) (FIG. 16F). Brd4 Chip sequencing experiments have been performed in saline and rapamycin treated primary cortical neurons six hours after treatment.

Figures 17A, 17B, 17C, 17D, 17E:
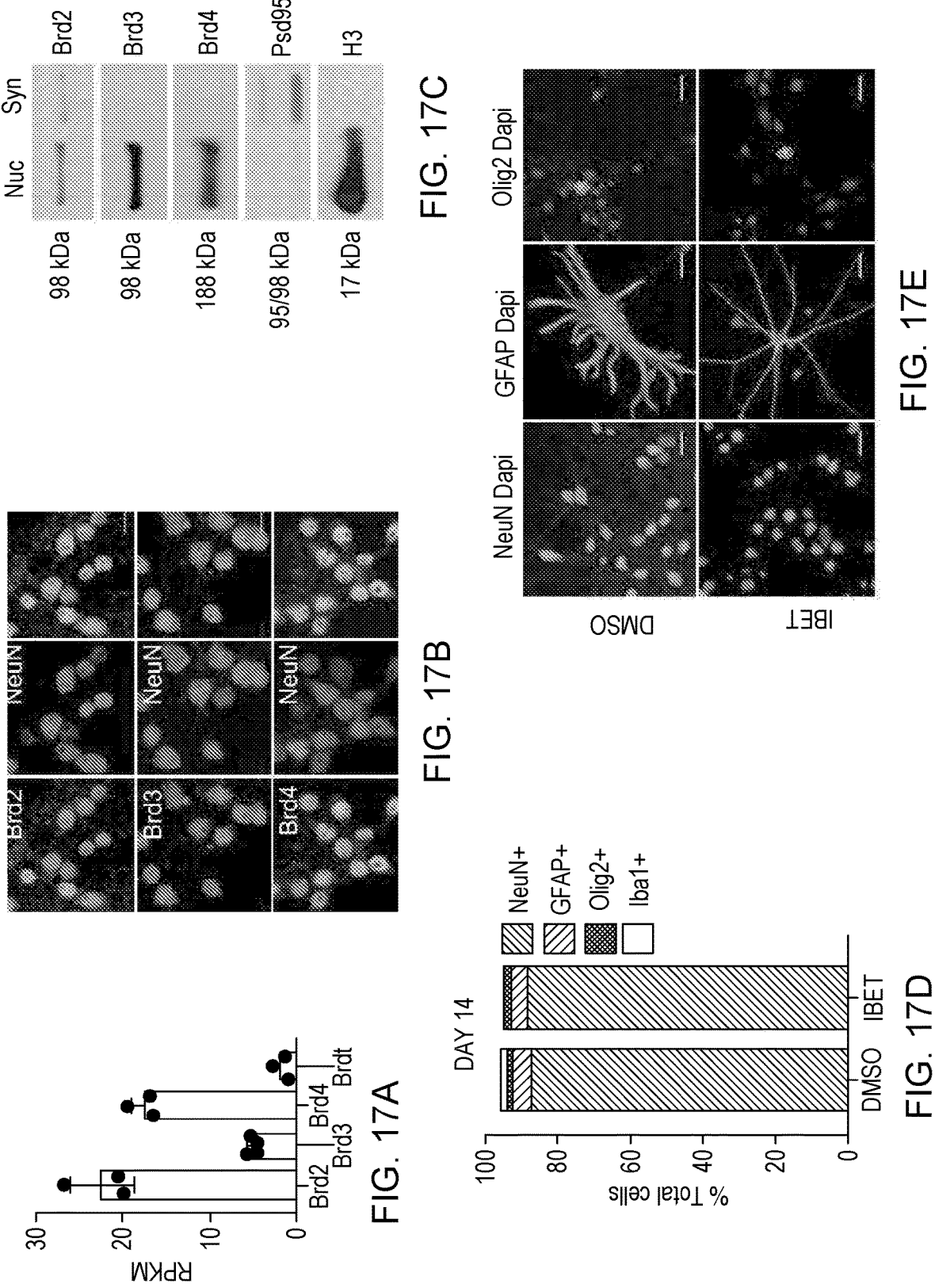
FIGS. 17A-17F show that primary cortical neurons express BRD2/3/4, with BRD2 and BRD4 being the most abundant, as confirmed by gene expression data (FIG. 17A), immunohistochemistry (FIG. 17B), and western blots (FIG. 17C). One week of IBET858 treatment of primary cortical neuron cultures does not change the cellular composition of the culture (FIGS. 17D-17E) or the expression profile of pan-neuronal, microglial, astrocyte, or oligodendrocyte identity genes (FIG. 17F).
Figure 17F:
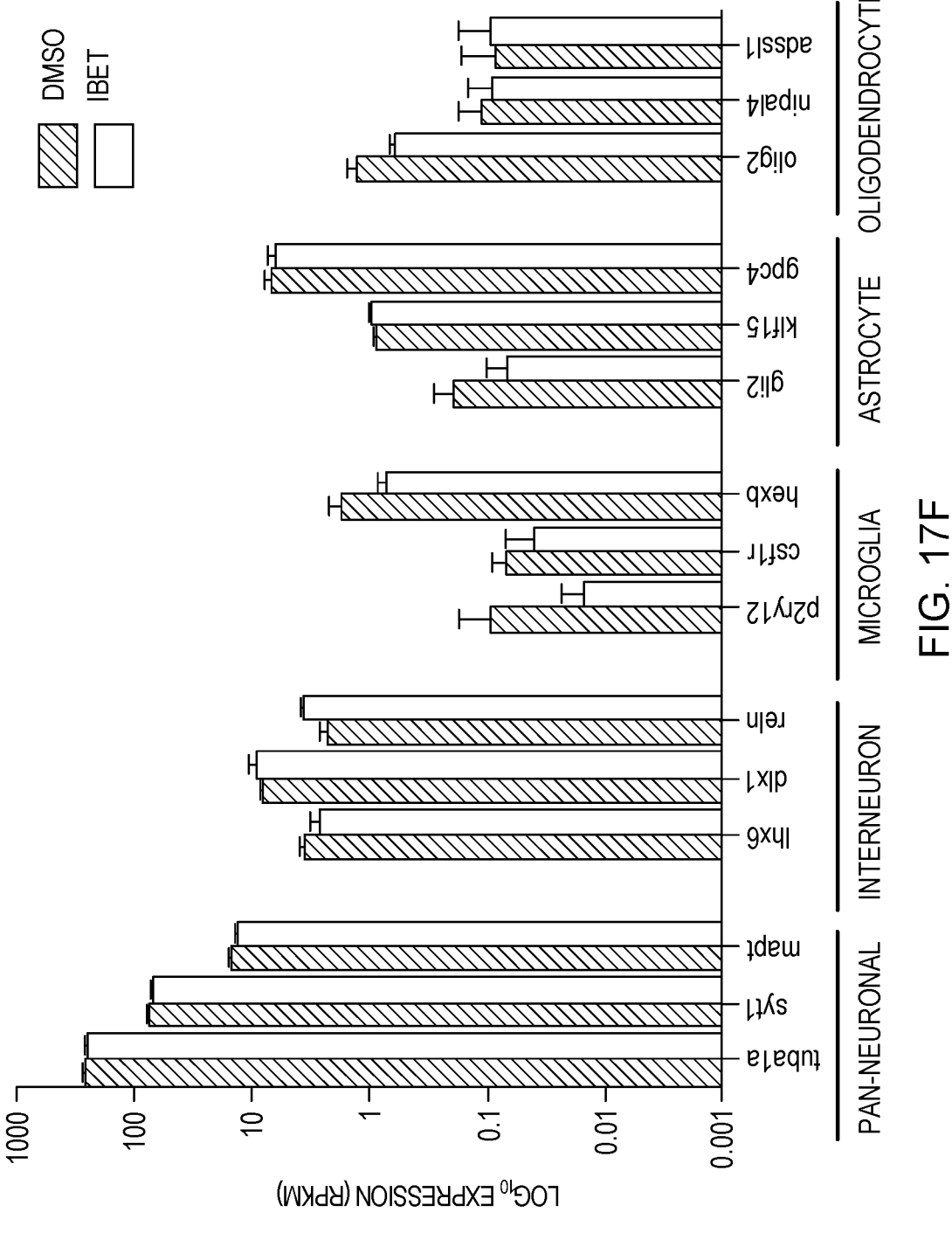

Primary cortical neurons express BRD2/3/4, with BRD2 and BRD4 being the most abundant, as confirmed by gene expression data (FIG. 17A), immunohistochemistry (FIG. 17B), and western blots (FIG. 17C). 1 week of IBET858 treatment of primary cortical neuron cultures does not change the cellular composition of the culture (as shown in FIGS. 17D and 17E) or the expression profile of pan-neuronal, microglial, astrocyte, or oligodendrocyte identity genes (FIG. 17F).

Example 16

Figure 18A:
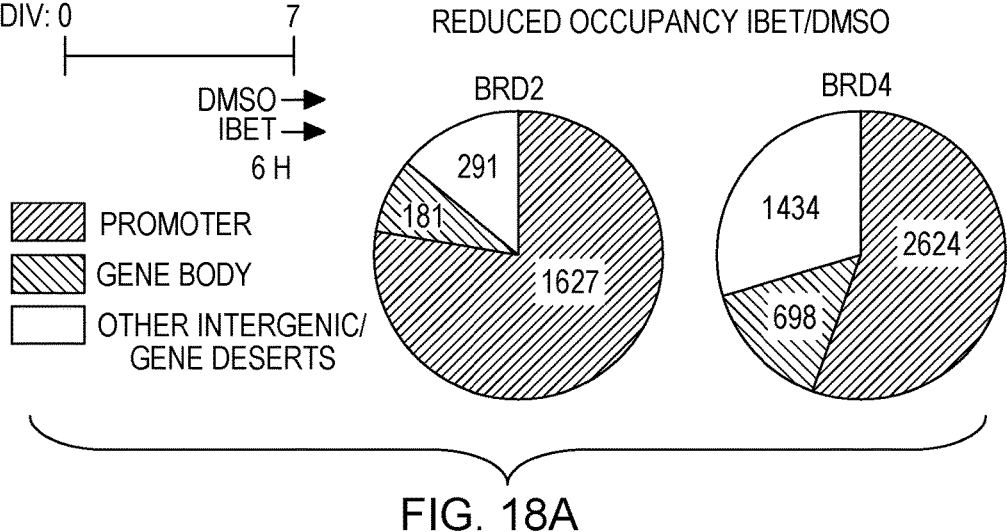
FIGS. 18A-18F show that treatment with a BET inhibitor (also interchangeably referred to herein as "IBET treatment" and "IBET") leads to changes of BRD2 and BRD4 binding on chromatin that mimic some of the changes seen in rapamycin treatment.
Figure 18B:
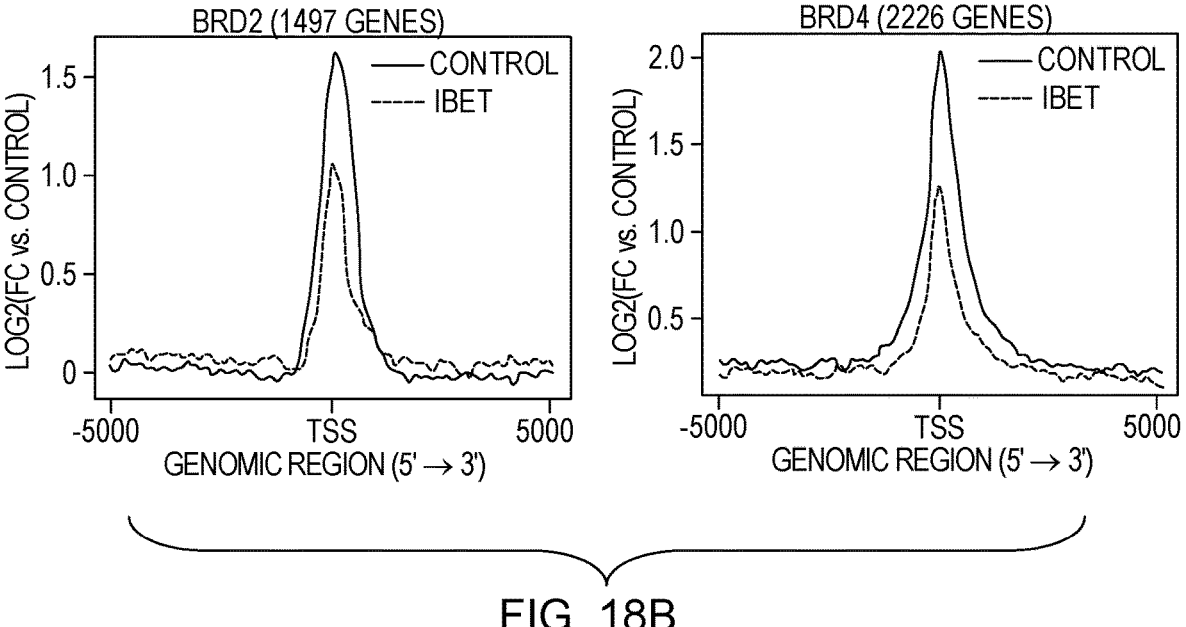
Figure 18C:
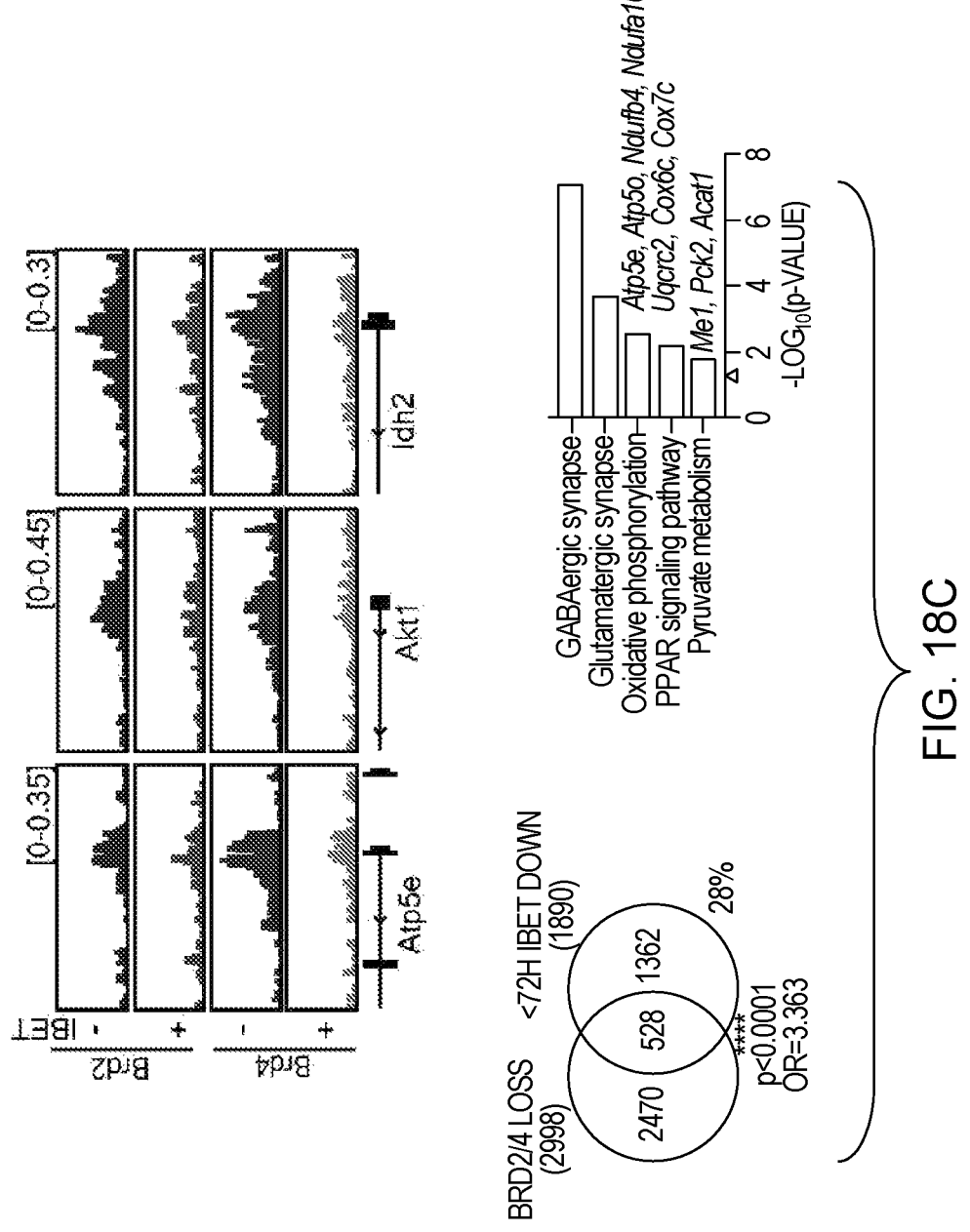
Figure 18D:
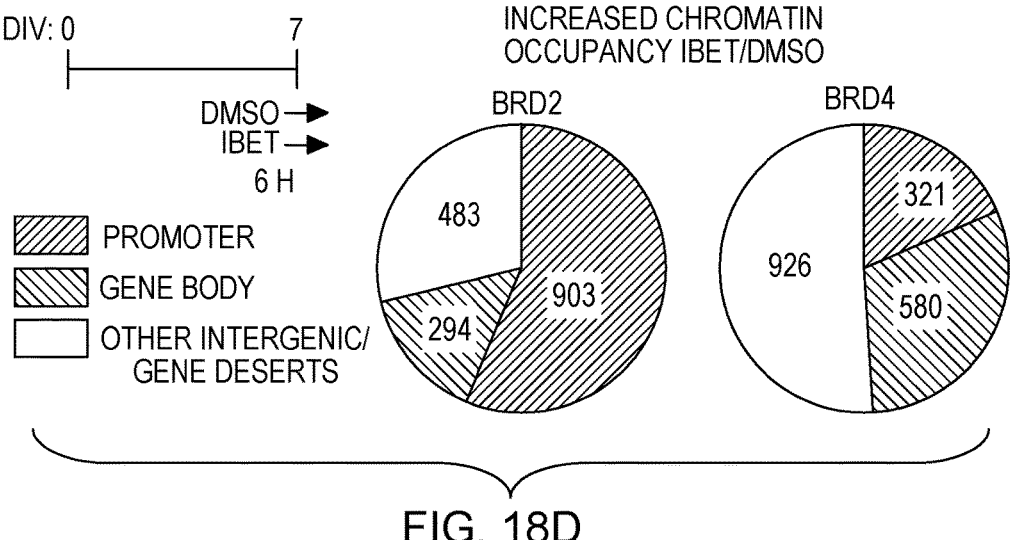
Figure 18E:
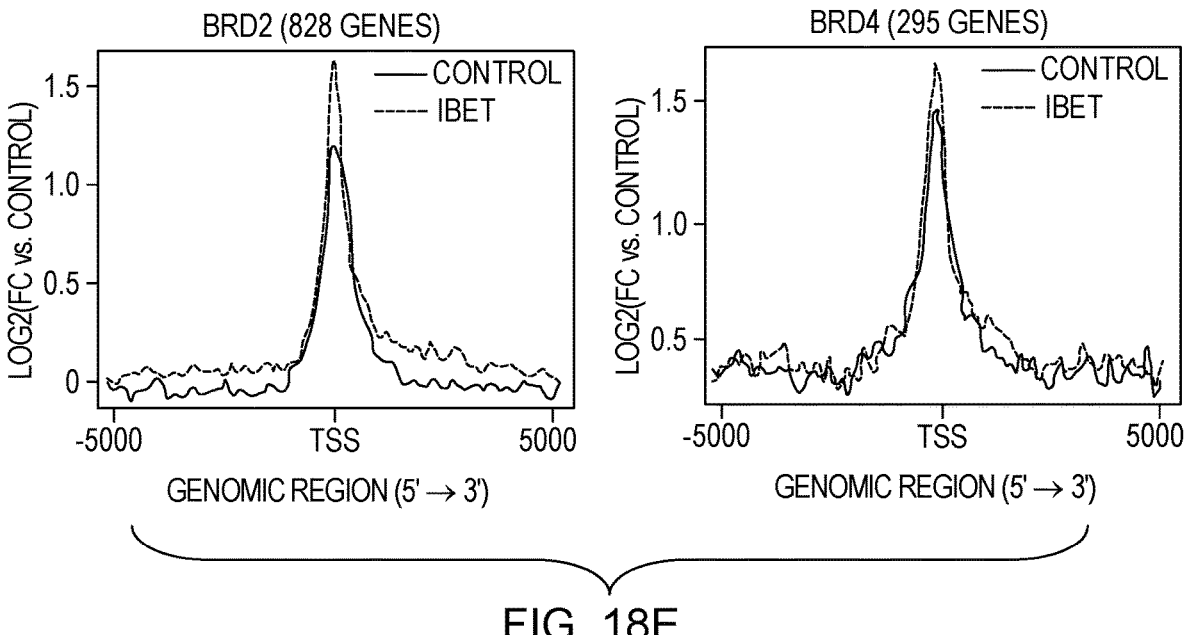
Figure 18F:
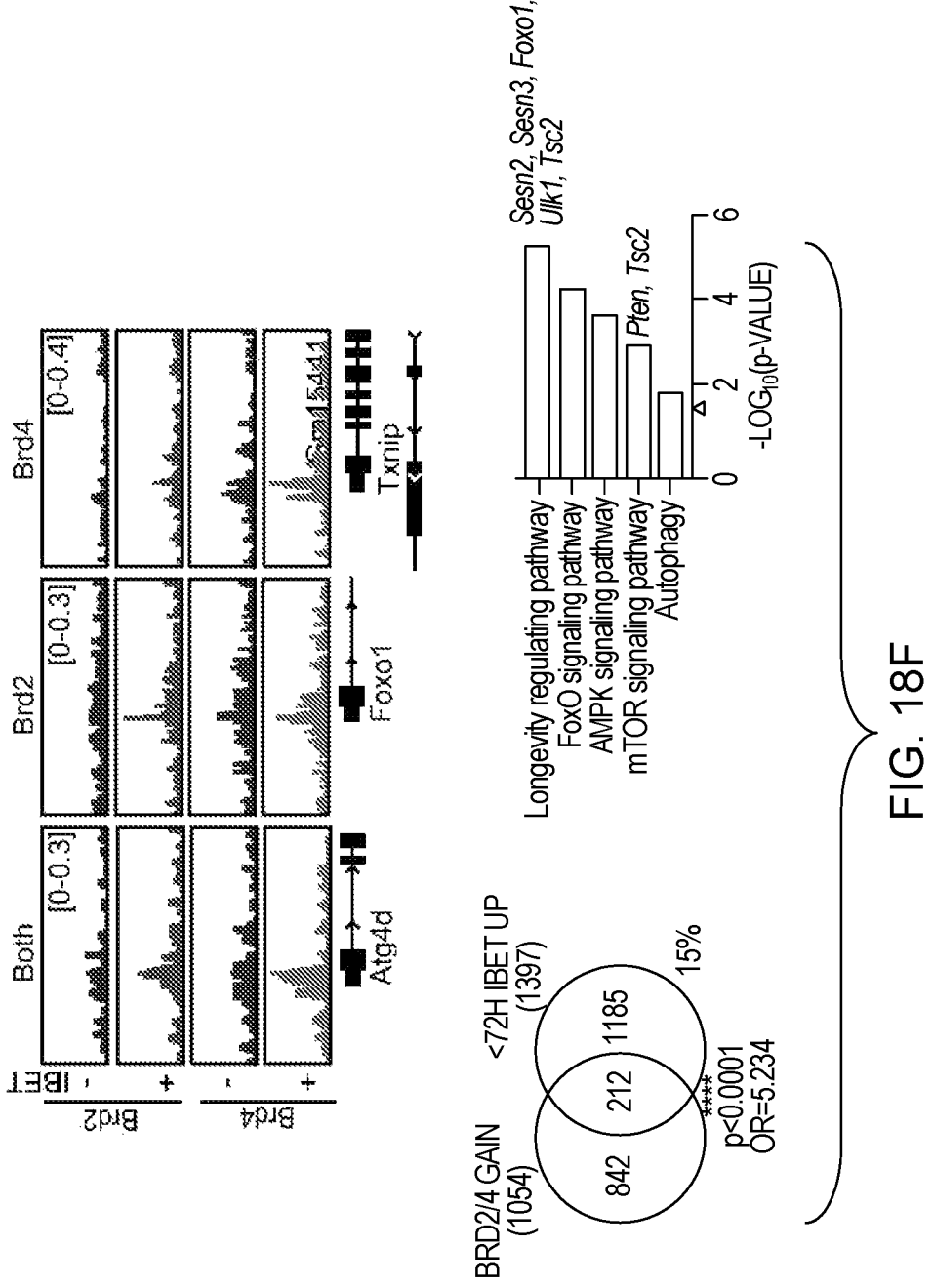

IBET Treatment Leads to Changes of BRD2 and BRD4 Binding on Chromatin that Mimic Some of the Changes Seen in Rapamycin Treatment Genomic distribution of loci that have reduced occupancy of BRD2 (2099 loci) or BRD4 (4756 loci) at DIV7 after 6 hours of IBET858 treatment as shown in FIG. 18A. IBET sensitive genes lose BRD2 and BRD4 at the transcriptional start site of 1497 and 2226 genes, respectively (FIG. 18B). Representative traces of three genes, Atp5e, Akt1, and Idh2, that lose both BRD2 and BRD4 at the transcriptional start site are shown in FIG. 18C. Of the genes that have reduced occupancy BRD2 or BRD4 at the promoter after 6 hours of IBET858, 528 are also transcriptionally downregulated and these overlapping genes are enriched (KEGG enrichment) for metabolic pathways including oxidative phosphory-lation, PPAR signaling, and pyruvate metabolism. Genomic distribution of loci that have increased occupancy of BRD2 (1680 loci) or BRD4 (1827 loci) at day 7 after 6 hours of IBET858 treatment is shown in FIG. 18D. As depicted in FIG. 18E, there is a gain of BRD2 at the transcriptional start sites of 828 genes and a gain of BRD4 at 295 genes. Representative traces of three genes, that gain both BRD2 and BRD4 (Atg4d), gain only BRD2 (Foxo1), or gain only BRD4, (Txnip) are shown in FIG. 18F. Of the genes that have increased occupancy of BRD2 or BRD4 at the pro-moter after 6 hours of IBET858, 212 are also transcription-ally upregulated and these overlapping genes are enriched for neuroprotective pathways including longevity regulating pathway, FoxO signaling, and autophagy (FIG. 18G).

Example 17

Figure 19:
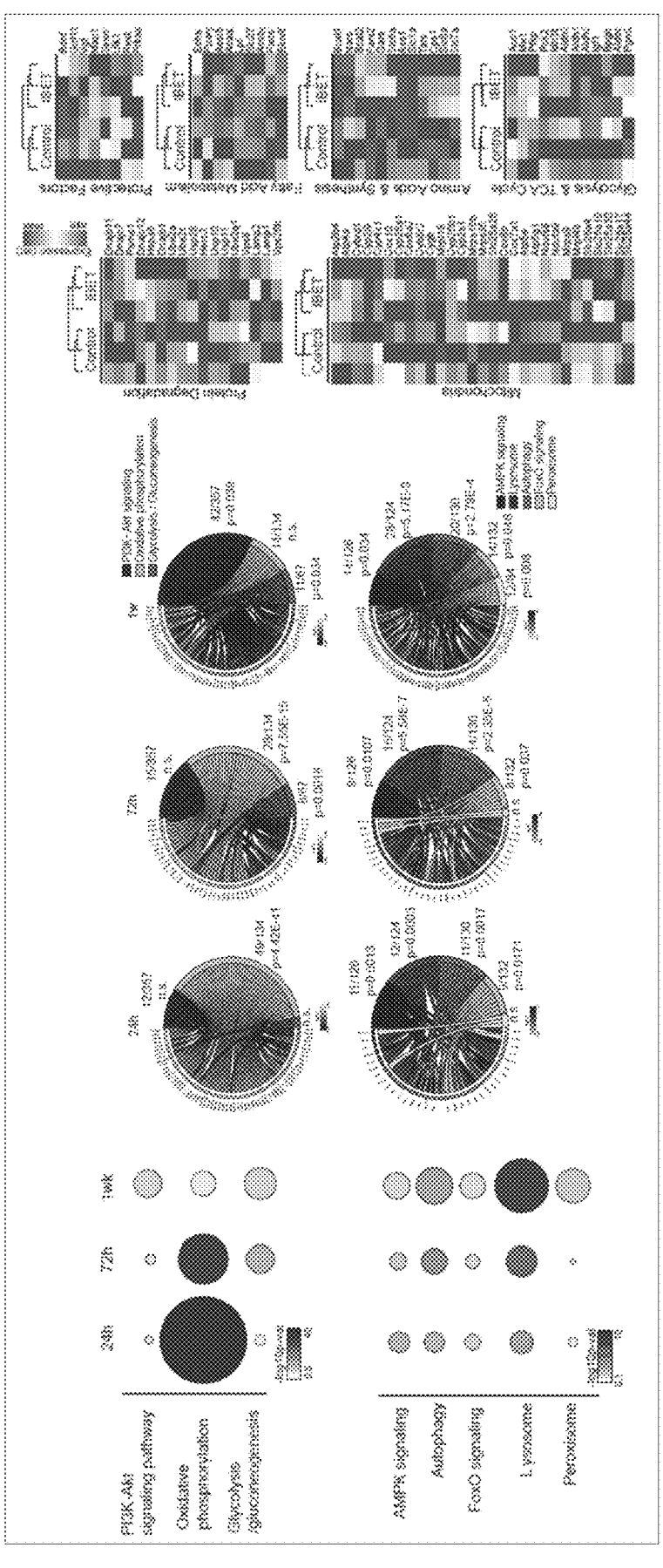
FIG. 19 shows that IBET858 treatment induces a switch towards a neuroprotective gene expression program in primary cortical neurons. Long term IBET858 treatment of primary cortical neurons induces a progressive metabolic switch characterized by early downregulation of genes that support oxidative phosphorylation at 24 h, followed by progressive downregulation of genes involved in PI3K-Akt signaling and glycolysis/gluconeogenesis at 72 hours to 1 week. By contrast, there is an early and stable induction of genes associated with neuroprotective (AMPK and FoxO signaling) and autophagy/lysosomal degradation pathways. Downregulated genes are indicated in blue, upregulated genes in red. Heatmaps highlighting the significant transcriptional downregulation of selected genes involved in anabolic and oxidative metabolism (mitochondria, glycolysis and tricarboxylic acid cycle (TCA cycle), amino acids and synthesis, fatty acid metabolism) and upregulation of selected genes associated with protein degradation and neuroprotection 1 week after IBET treatment.

IBET858 Treatment Induces a Switch Towards a Neuroprotective Gene Expression Program in Primary Cortical Neurons Long term IBET858 treatment of primary cortical neurons induces a progressive metabolic switch characterized by early downregulation of genes that support oxidative phos-phorylation at 24 hours, followed by progressive downregu-lation of genes involved in PI3K-Akt signaling and glyco-lysis/gluconeogenesis at 72 hours to 1 week (FIG. 19). By contrast, there is an early and stable induction of genes associated with neuroprotective (AMPK and FoxO signal-ing) and autophagy/lysosomal degradation pathways. Heat-maps in FIG. 19 highlight the significant transcriptional downregulation of selected genes involved in anabolic and oxidative metabolism (mitochondria, glycolysis and TCA cycle, amino acids and synthesis, fatty acid metabolism) and upregulation of selected genes associated with protein degradation and neuroprotection 1 week after IBET treatment.

Example 18

Figure 20A:
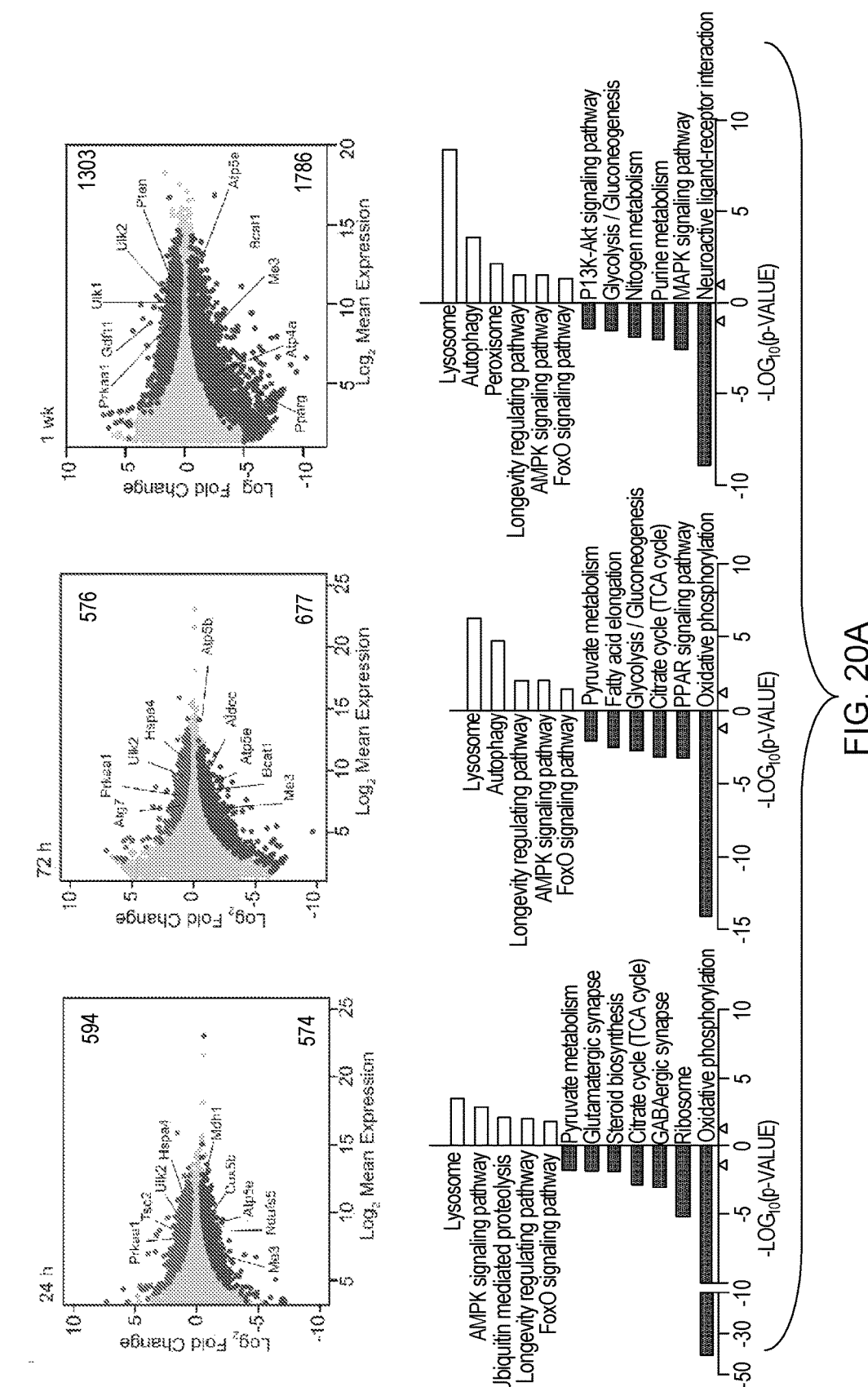
FIGS. 20A-20D depict that IBET858 treatment induces changes in gene expression that mimic transcriptional changes seen in response to rapamycin revealing a distinct set of genes that are likely to provide the neuroprotective effects seen by both treatments.
Figure 20B:
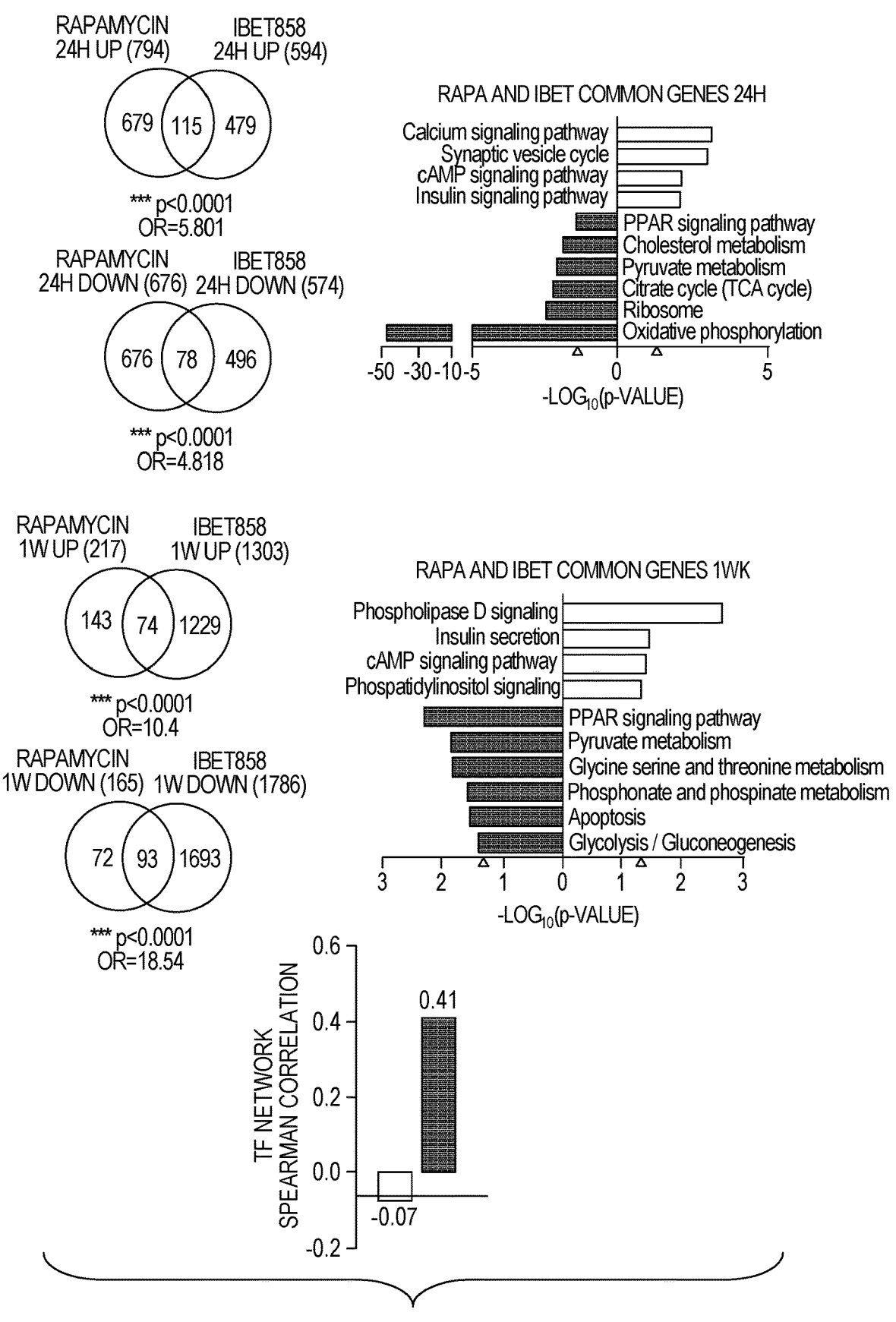
Figures 20C, 20D:
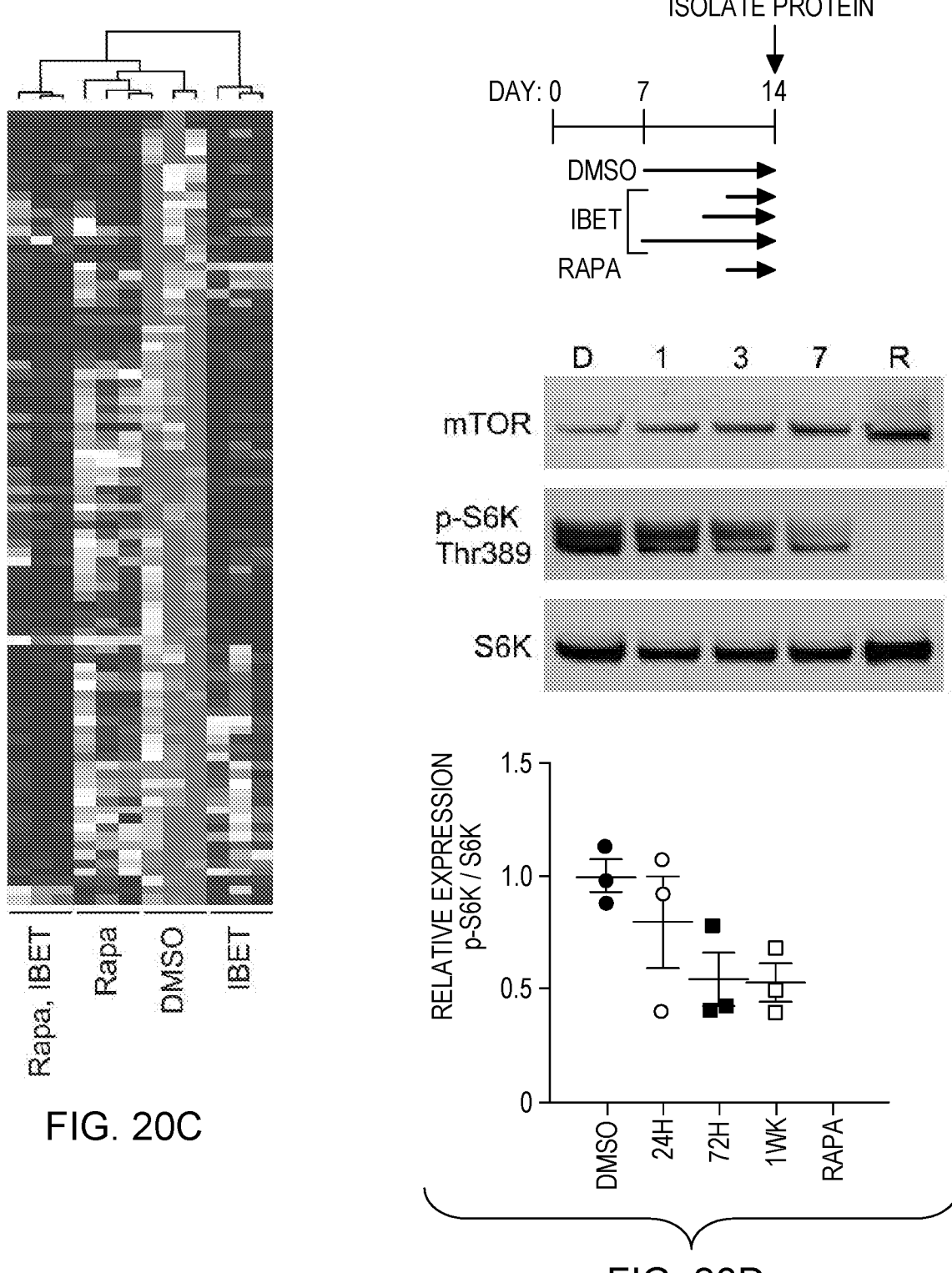

IBET858 Treatment Induces Changes in Gene Expression that Mimic Transcriptional Changes Seen in Response to Rapamycin Revealing a Distinct Set of Genes that are Likely to Provide the Neuroprotective Effects Seen by Both Treatments MA plots and KEGG pathway enrichment for primary cortical neurons treated with IBET858 for 24 hours, 72 hours, and 1 week are shown in FIG. 20A. Rapamycin and IBET control the expression of similar genes (FIG. 20B). The degree of overlap between rapamycin and IBET-induced gene expression changes at 24 hours and 1 week is significant (FIG. 20B). Genes that display equal downregulation by IBET and rapamycin and combined treatment has similar effect, suggesting that rapamycin-mediated suppression of these genes occurs via BRD displacement from chromatin (FIG. 20C). IBET treatment for one week induces changes in mTor activity as measured by S6K phosphorylation (FIG. 20D).

Example 19

IBET858 Treatment Induces a Metabolic Switch in Primary Cortical Neurons

Figure 21B:
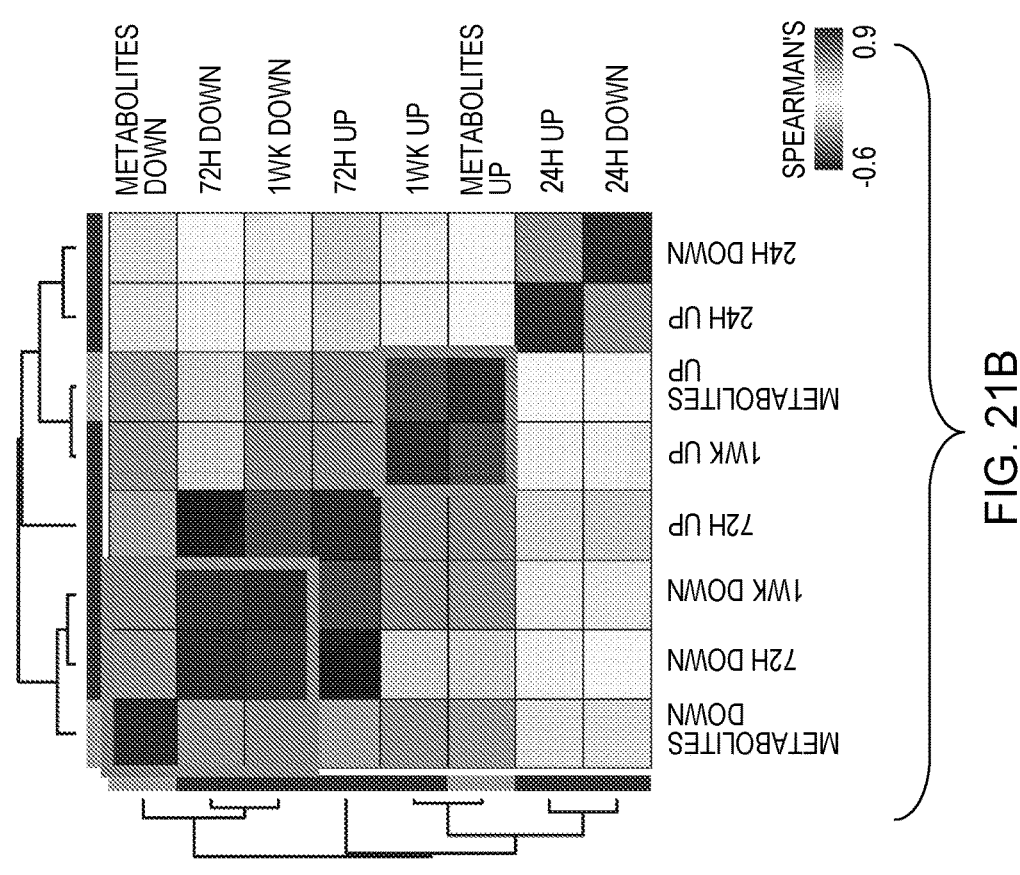
Figure 21A:
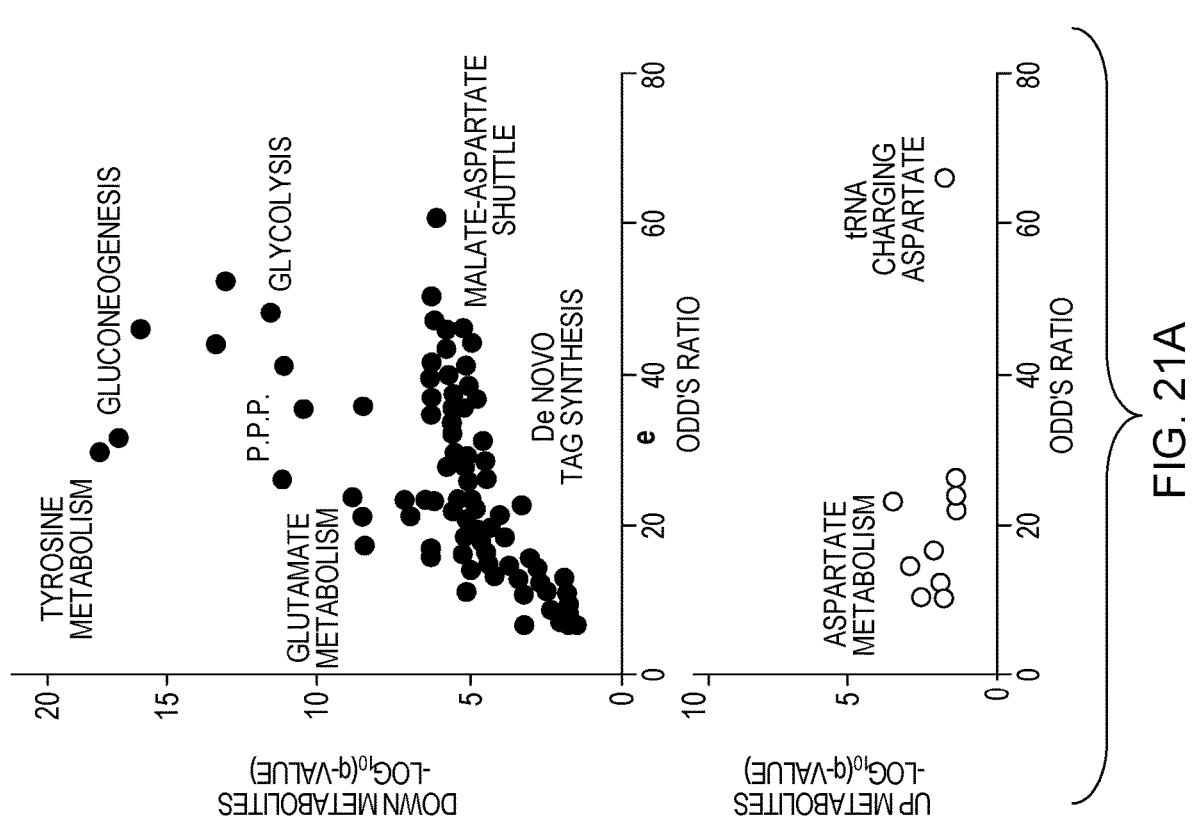
Figure 21C:
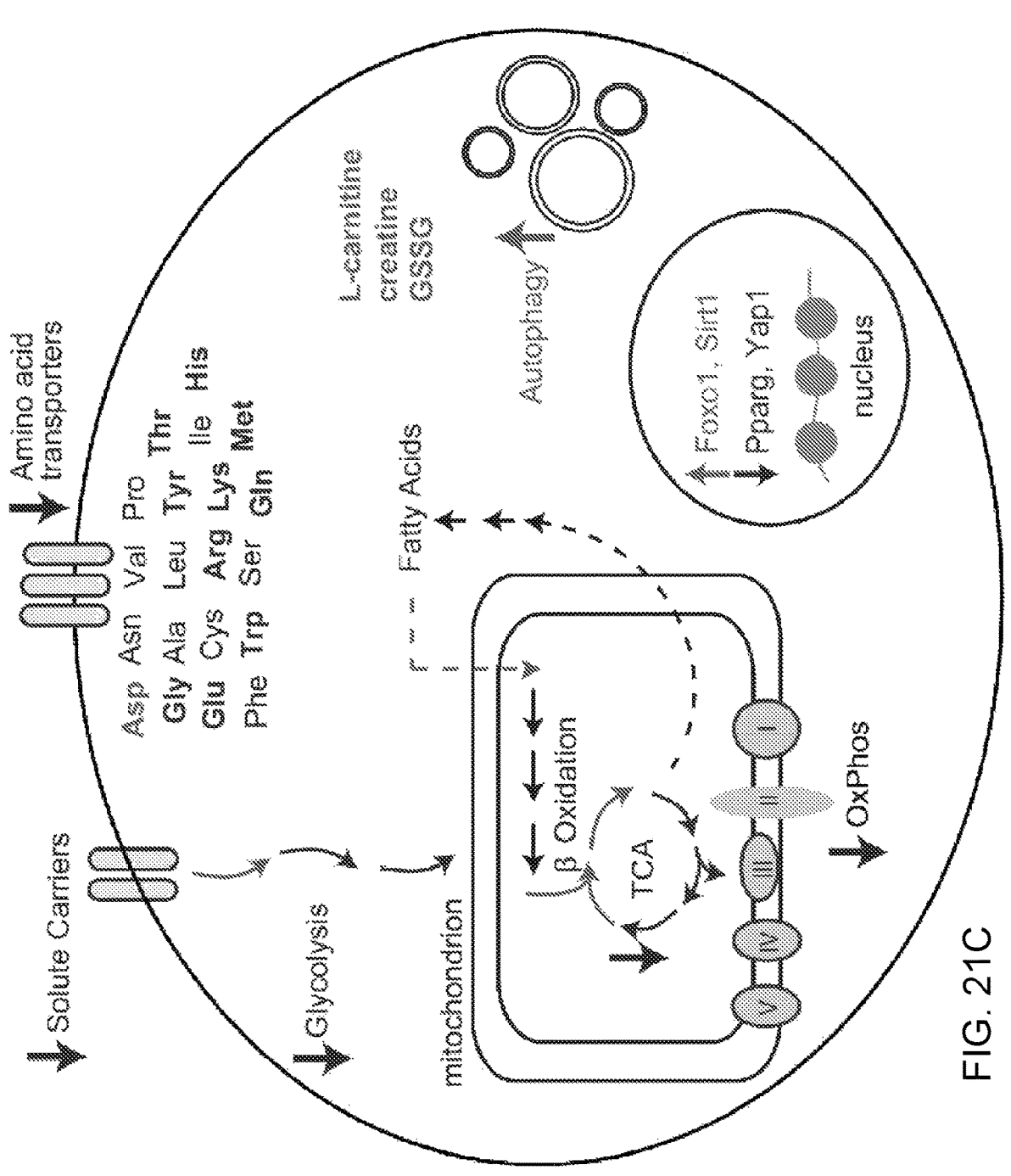
Figures 21D, 21E, 21F, 21G, 21H, 21I, 21J:
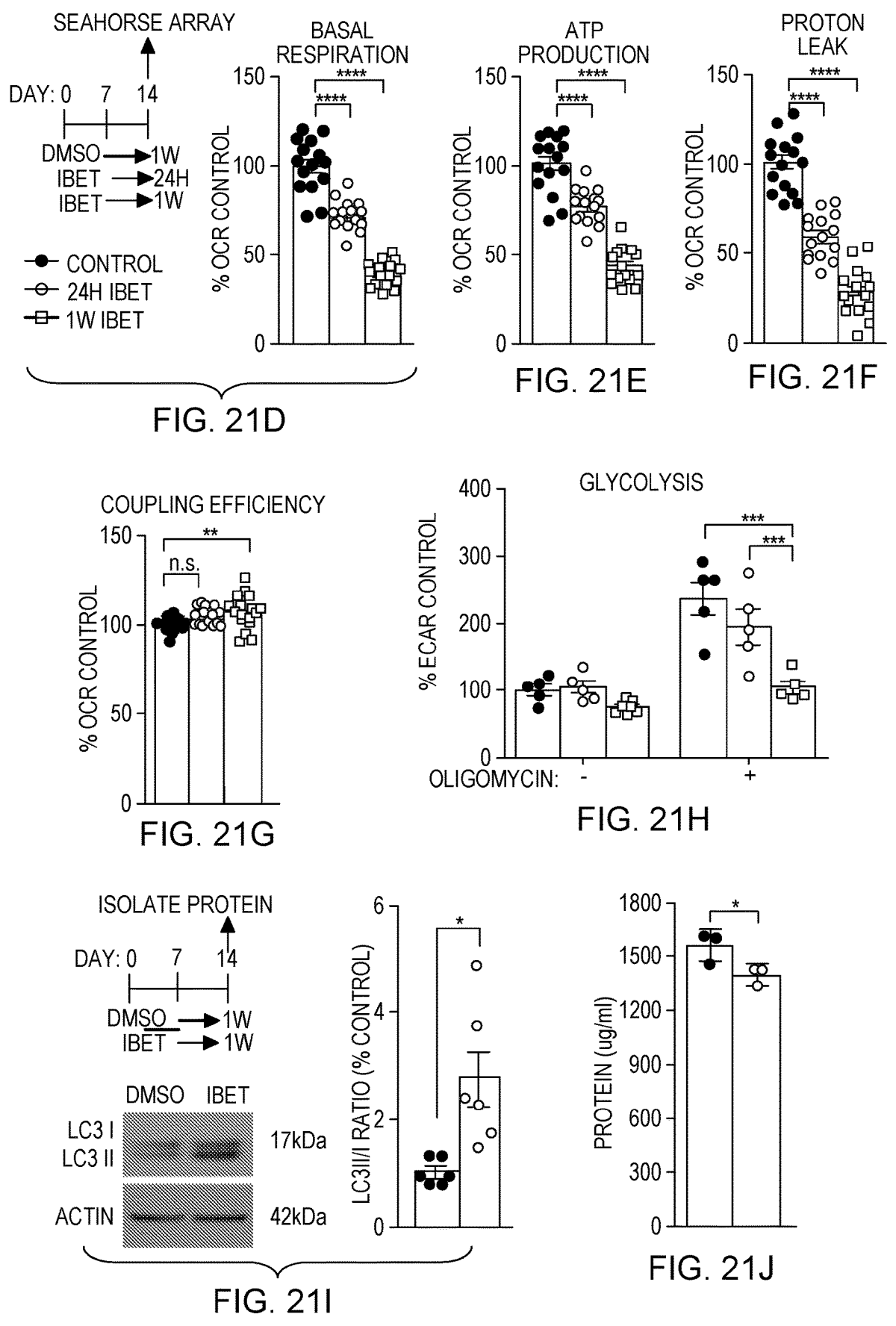
Figure 21K:
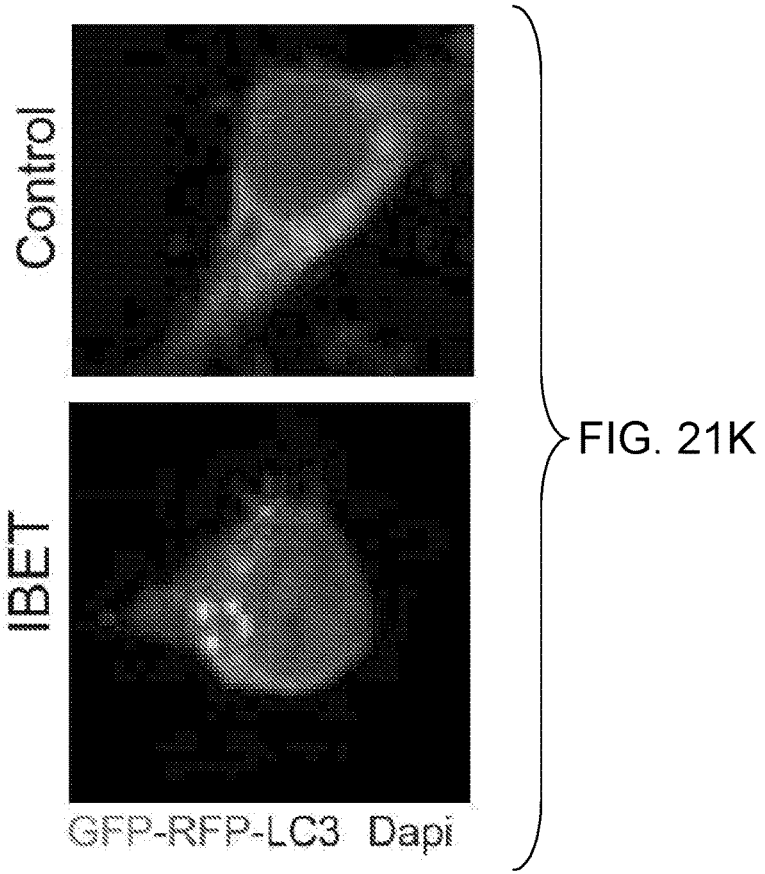
Figure 21L:
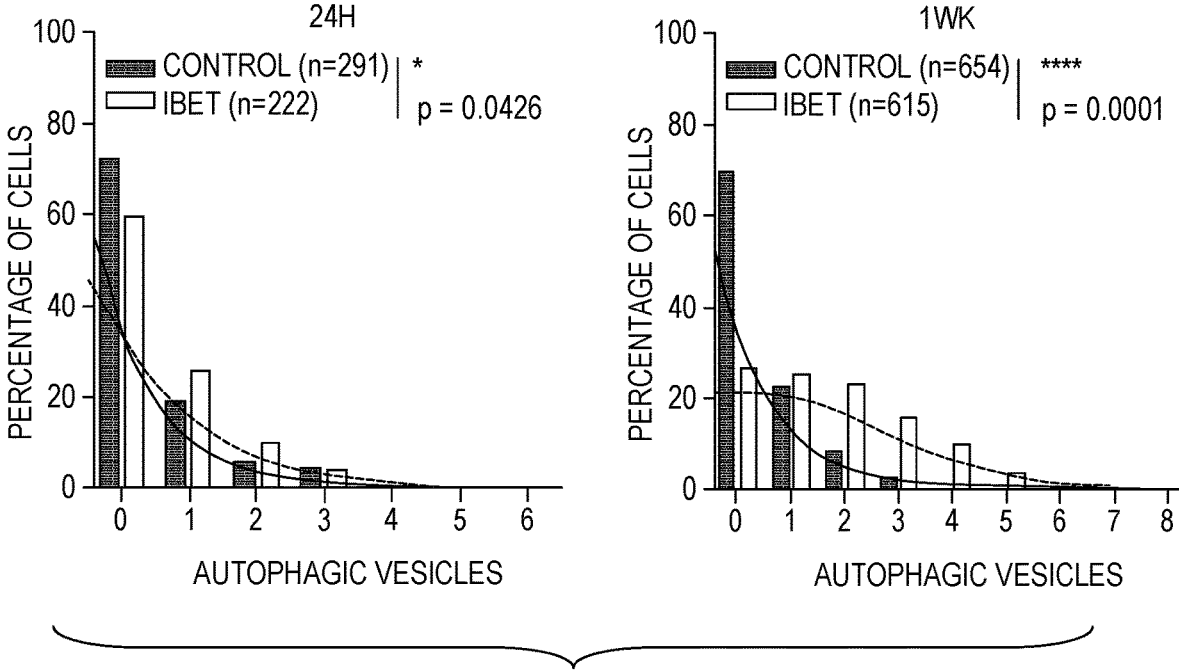

Primary cortical neurons treated with IBET858 for 1 week have decreased glycolysis and amino acid metabolites (FIG. 21A). There is significant correlation between the decreased metabolites and genes downregulated after 72 hours to 1 week of IBET858 treatment (FIG. 21B). A summary of gene expression and metabolite data highlighting downregulation of solute carriers and metabolites that support anabolic and oxidative metabolic programs and an upregulation of neuroprotective metabolites and programs, such as autophagy (FIG. 21C). The glycolytic capacity of primary cortical neurons treated with acute (24 hour) or chronic (1 week) of IBET858 (FIGS. 21D-21H). IBET treated neurons was evaluated using the Seahorse assay. A progressive decrease in basal mitochondrial respiration (FIG. 21D) and ATP production (FIG. 21E) was observed, suggesting a decreased reliance on energy production by the oxidative phosphorylation. The mitochondria also display decreased proton leak (FIG. 21F) and increased coupling efficiency (FIG. 21G), suggesting increased mitochondrial integrity. Further, the neurons display a decrease in glycolytic capacity as measured by the extracellular acidification rate (ECAR) (FIG. 21H). 1 week of IBET858 treatment increases autophagy as measured by an increase in the LC3 II/I ratio and a decrease in overall protein content by BCA assay (FIGS. 21I and 21J). CAG-RFP-EGFP-Map1lc3b mice expressing the LC3 protein together with RFP and a pH-dependent eGFP were used to evaluate the number of autophagic vesicles by immunofluorescence (FIGS. 21K and 21L). Primary cortical neurons of these mice were treated with IBET858 for 1 w and an increase in autophagic vesicles was observed (FIG. 21K). Frequency distribution of autophagic vesicles after 24 hours (left) or 1 week (right) treatment with IBET858 (FIG. 21L).

Example 20

Figure 22A:
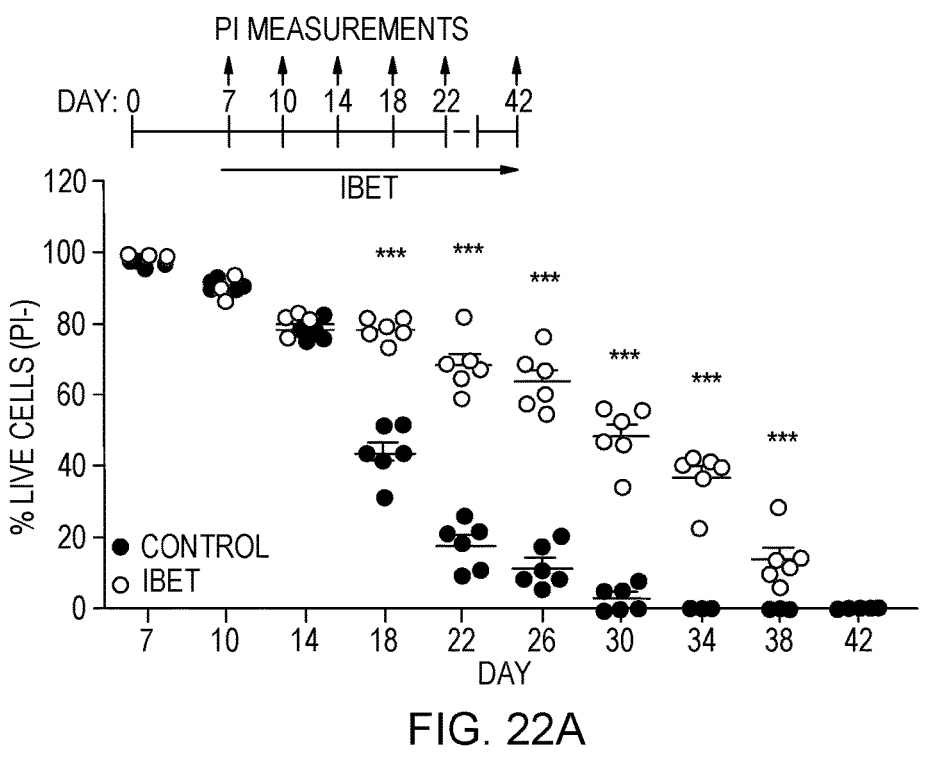
FIGS. 22A-22H show that IBET treatment promotes neuronal longevity and extended—but not acute—IBET pretreatment protects neurons from neurotoxin-induced cell death.

IBET Treatment Promotes Neuronal Longevity and Extended—but not Acute—IBET Pretreatment Protects Neurons from Neurotoxin-Induced Cell Death IBET promotes longevity of neurons in culture (FIG. 22A). Primary cortical neurons were treated with iBET858

Figure 22B:
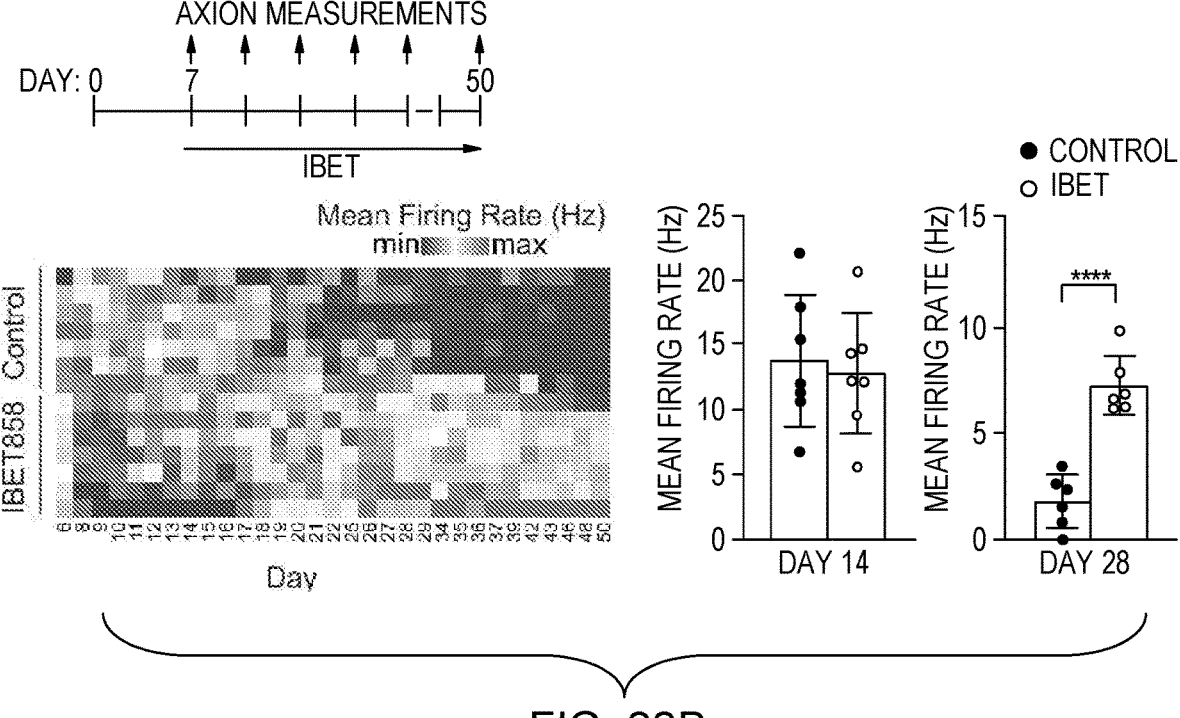

(1 uM) at day 7 and propidium iodide (PI) staining was carried out every 3-4 days to evaluate the percentage of living cells. Long-lived IBET treated neurons maintain normal activity patterns (FIG. 22B). Heatmap shows mean firing rate (Hz) normalized by column in neuronal cultures over time. Dot plots show the average mean firing rate (Hz) of control and IBET858-treated neurons at day 14 (left) and day 28 (right).

Figures 22C, 22D, 22E, 22F:
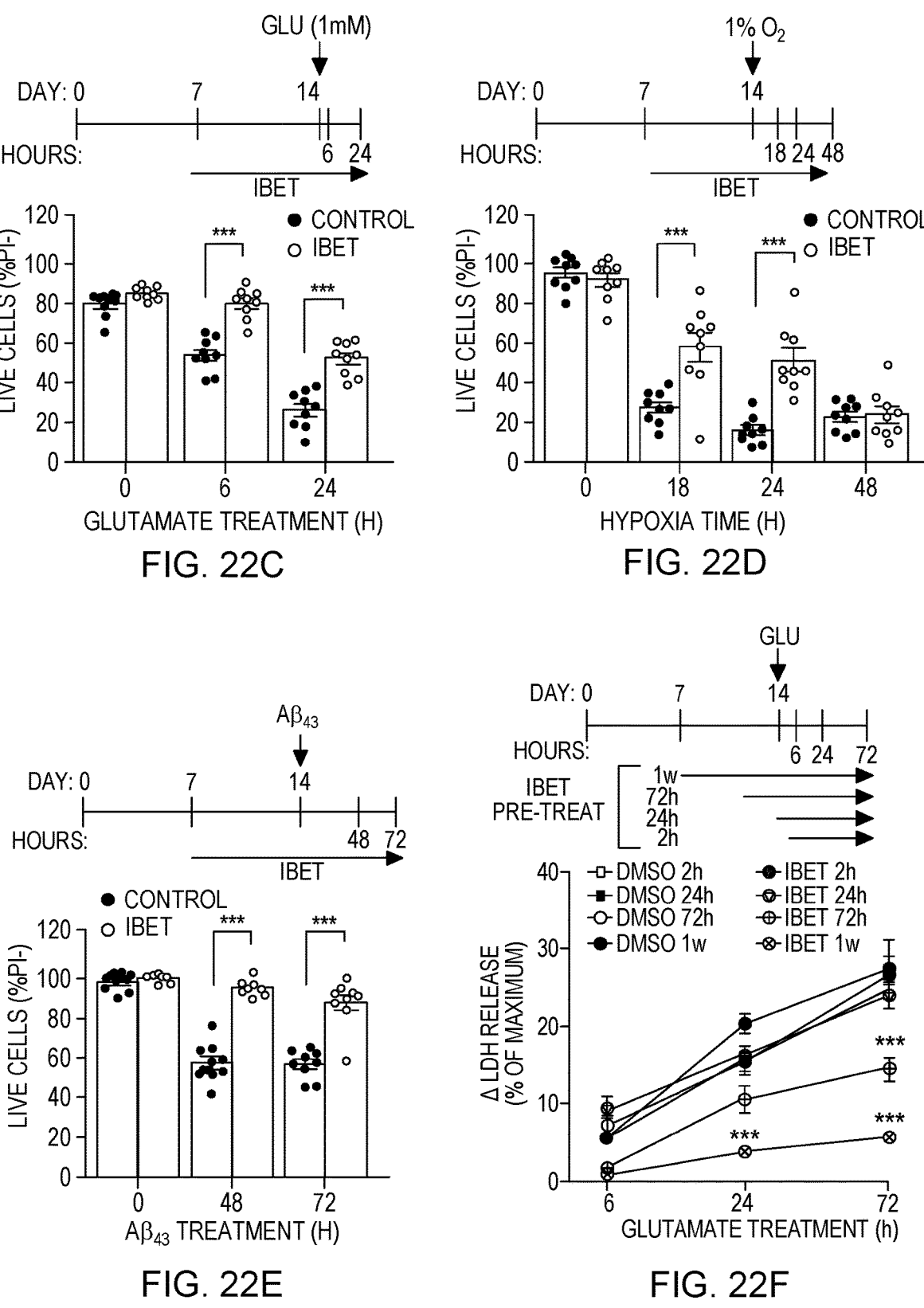

IBET treatment protects neurons from neurotoxin-induced cell death (FIGS. 22C-22E). Dot plots show the percentage of cells that are propidium iodide negative after different neurotoxic insults when pre-treated with either control or iBET for 1 week. 6 hours and 24 hours after 1 mM glutamate exposure are shown in FIG. 22C; 18 hours, 24 hours, and 48 hours of hypoxia (1% O2) are shown in FIG. 22D; and 48 hours and 72 hours of Aβ1-43 oligomer exposure (10 μM) are shown in FIG. 22E. Two-way repeated measures ANOVA with multiple comparisons, n=3 per group, ***p<0.001. Experiments were repeated a minimum of three times.

Figure 22G:
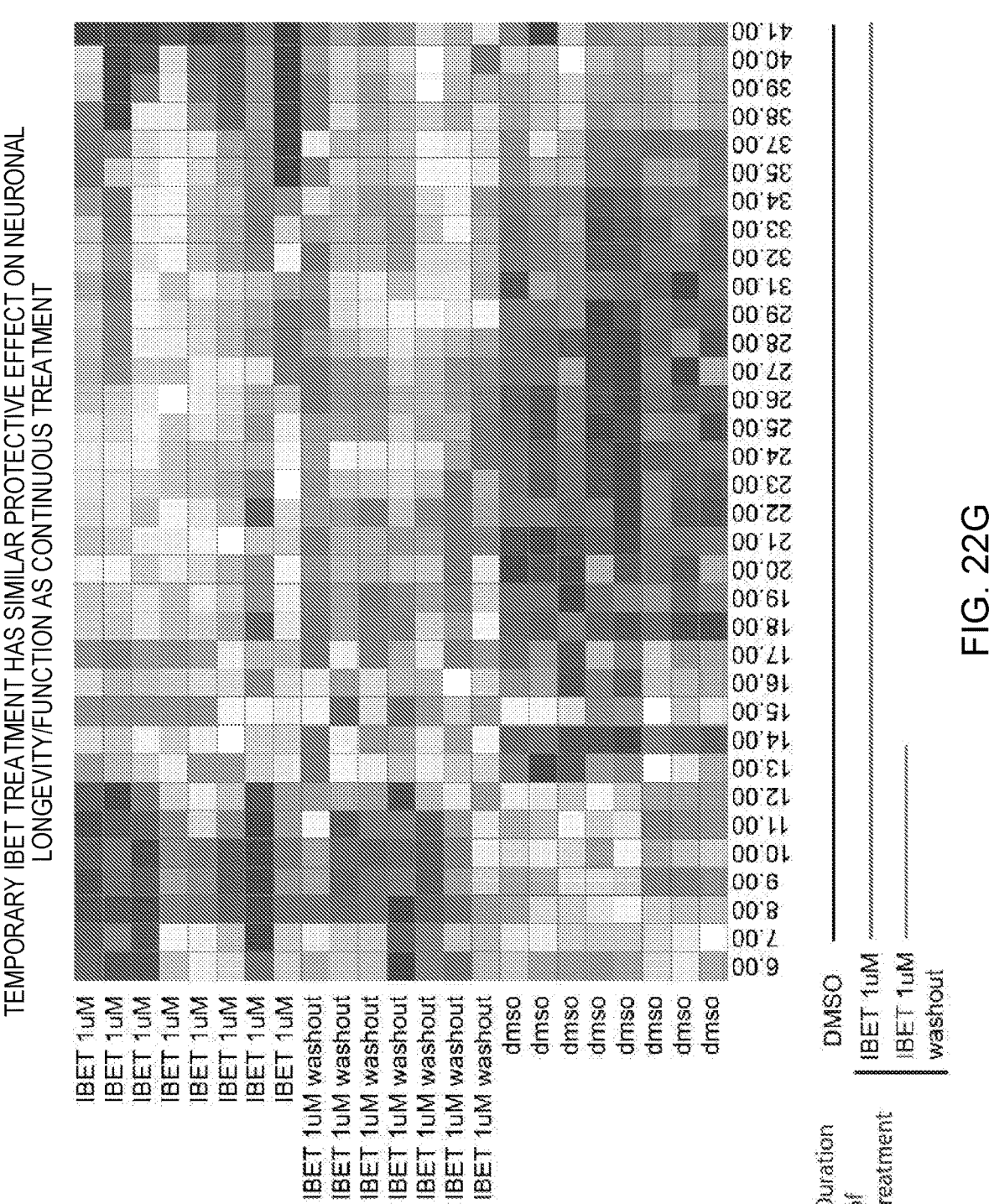
Figure 22H:
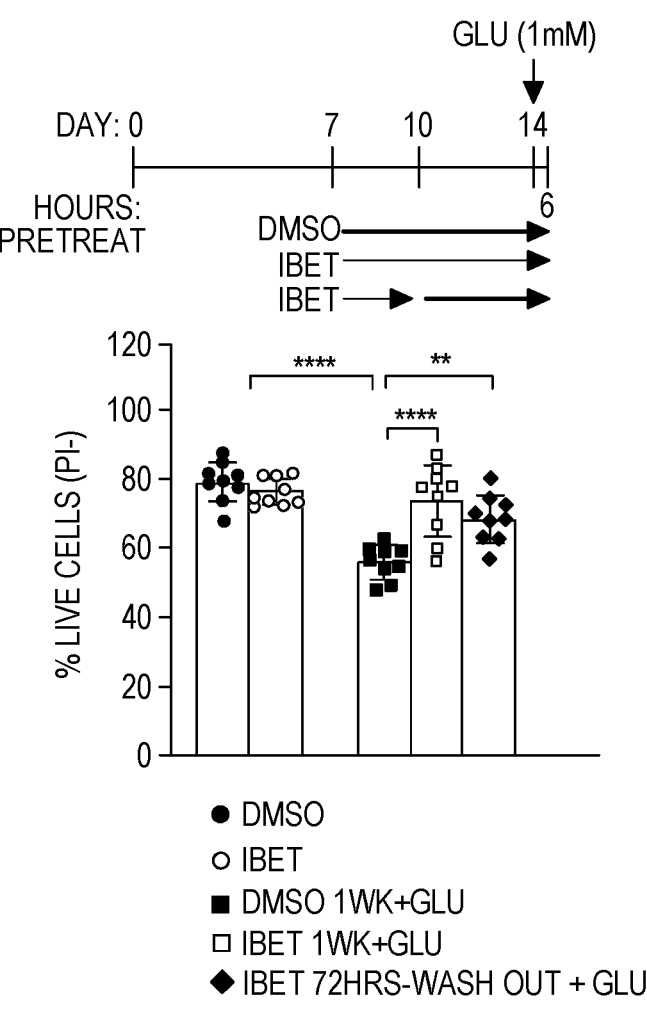

Extended—but not acute—IBET pre-treatment protects neurons from neurotoxin-induced cell death (FIG. 22F). Primary cortical neurons were pre-treated with either IBET858 (1 μM) or control for 2 hours, 24 hours, 72 hours, or 1 week before glutamate exposure (1 mM) at day 14. LDH release was measured 6 hours, 24 hours, and 72 hours after initial glutamate exposure. Temporary, one week of IBET treatment mediates prolonged neuronal survival that is maintained even in the absence of IBET (FIG. 22G). The heatmap in FIG. 22G shows mean firing rate (Hz) normalized by column in neuronal culture treated with control, IBET858 (1 uM) continuously and IBET858 (1 uM) for 1 week followed by washout at day 14, n=7-8. Temporary IBET pretreatment establishes a neuroprotective phenotype that is maintained even in the absence of IBET (FIG. 22H). Primary cortical neurons were pre-treated with either 1 week IBET858 (1 μM) or 72 hours or followed by wash out and 4 days on DMSO before glutamate exposure (1 mM) at day 14 (FIG. 22H).

Example 21

IBET858 Treatment Prevents Neurodegeneration In Vivo

Figure 23A:
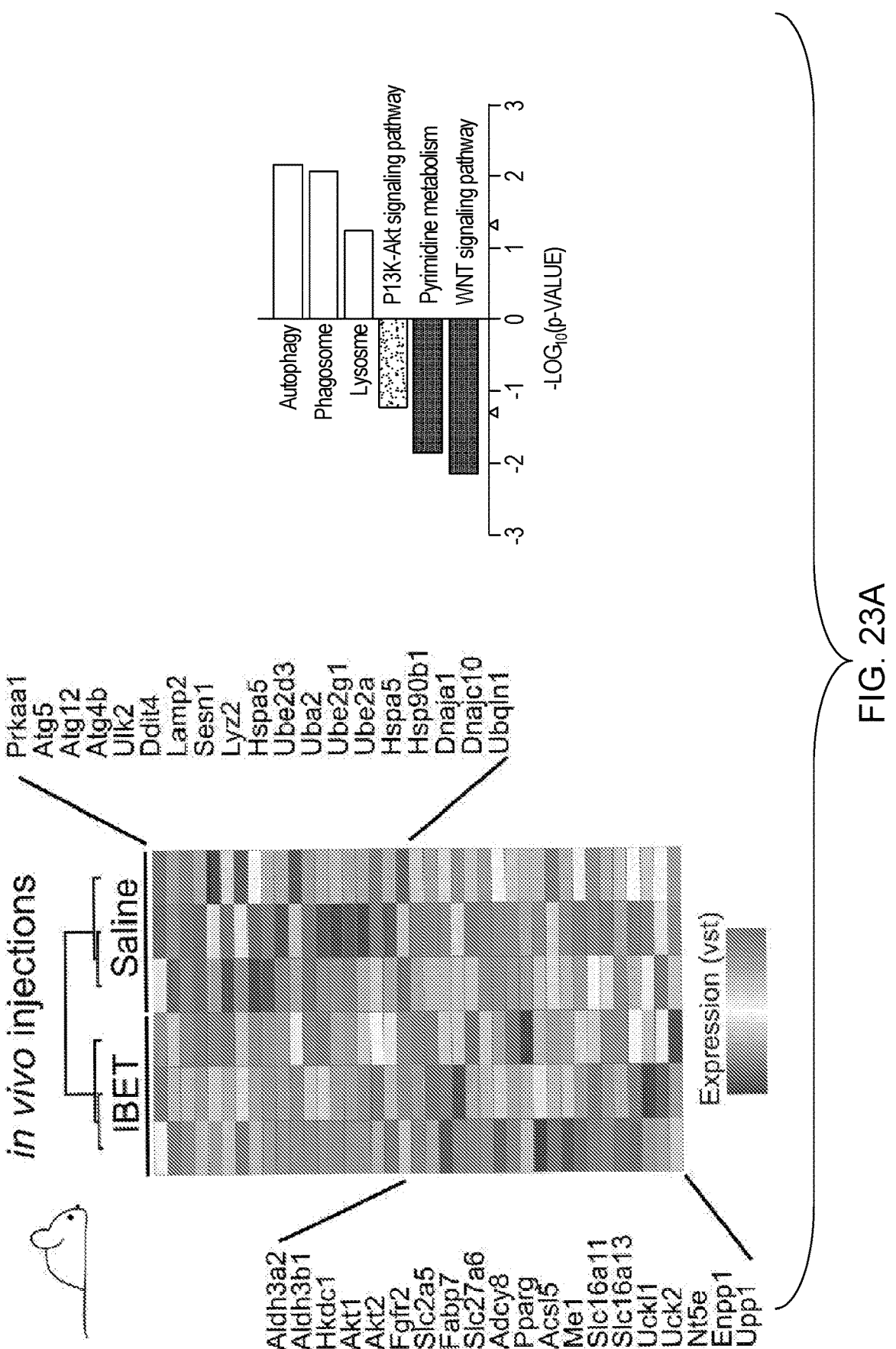
FIGS. 23A-23E show that IBET858 treatment prevents neurodegeneration in vivo.

IBET treatment induces neuroprotective gene expression changes in the hippocampus of mice in vivo (FIG. 23A). The heatmap in FIG. 23A shows gene expression analysis of striatum of IBET858 treated mice compared to vehicle. Autophagy and proteostasis genes are increased, while many genes involved in different metabolic pathways are downregulated.

Figure 23B:
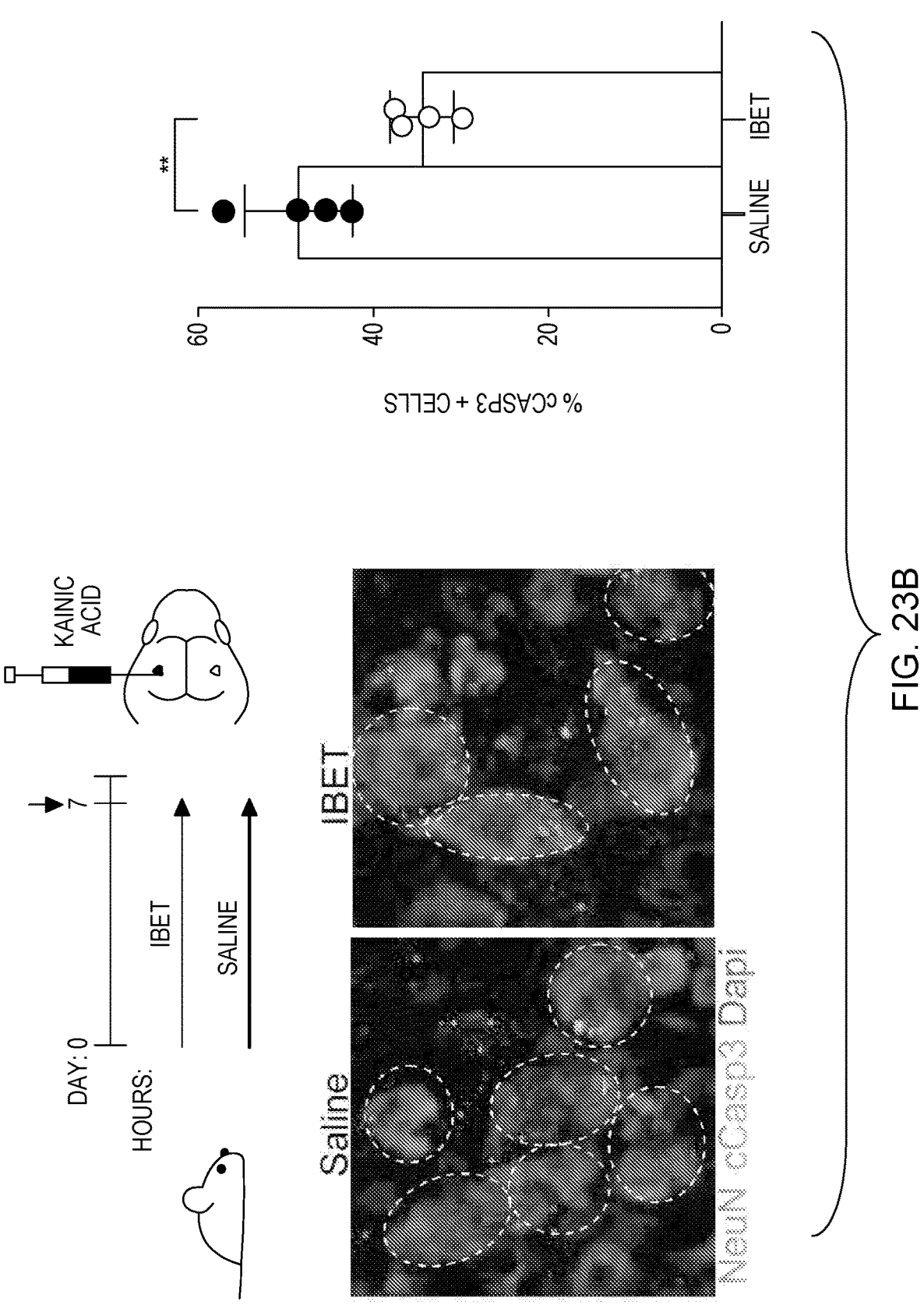

IBET treatment protects neurons from glutamate-induced toxicity in vivo (FIG. 23B). C57bl/6 mice were daily treated with IBET858 (30 mg/kg, i.p.) for 1 week, followed by stereotaxic injection of kainic acid in the hippocampus. Mice were perfused 24 hours after kainic acid injection and brains were immunostained for cCASP3 to identify dying cells.

Figure 23C:
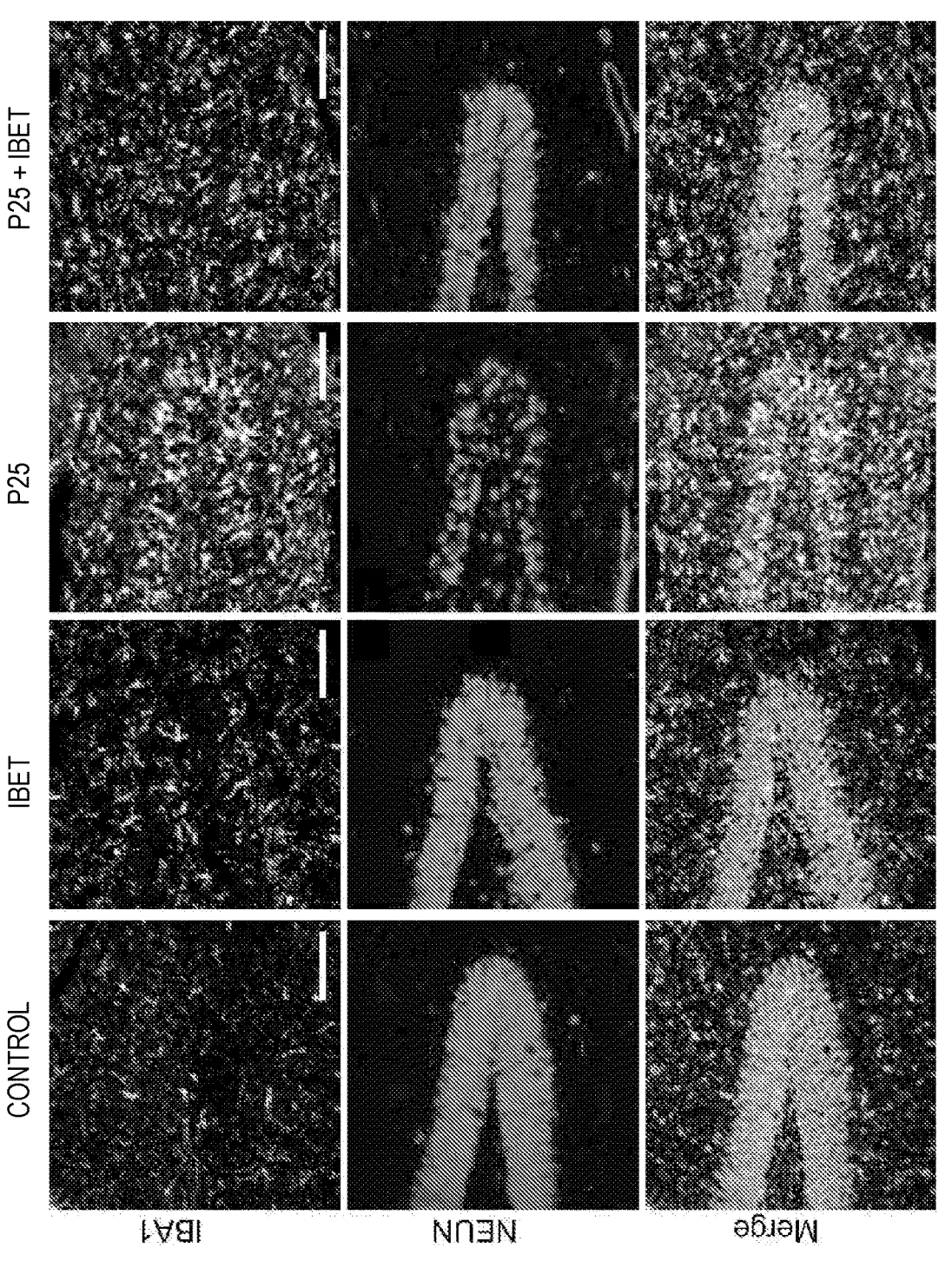
Figure 23D:
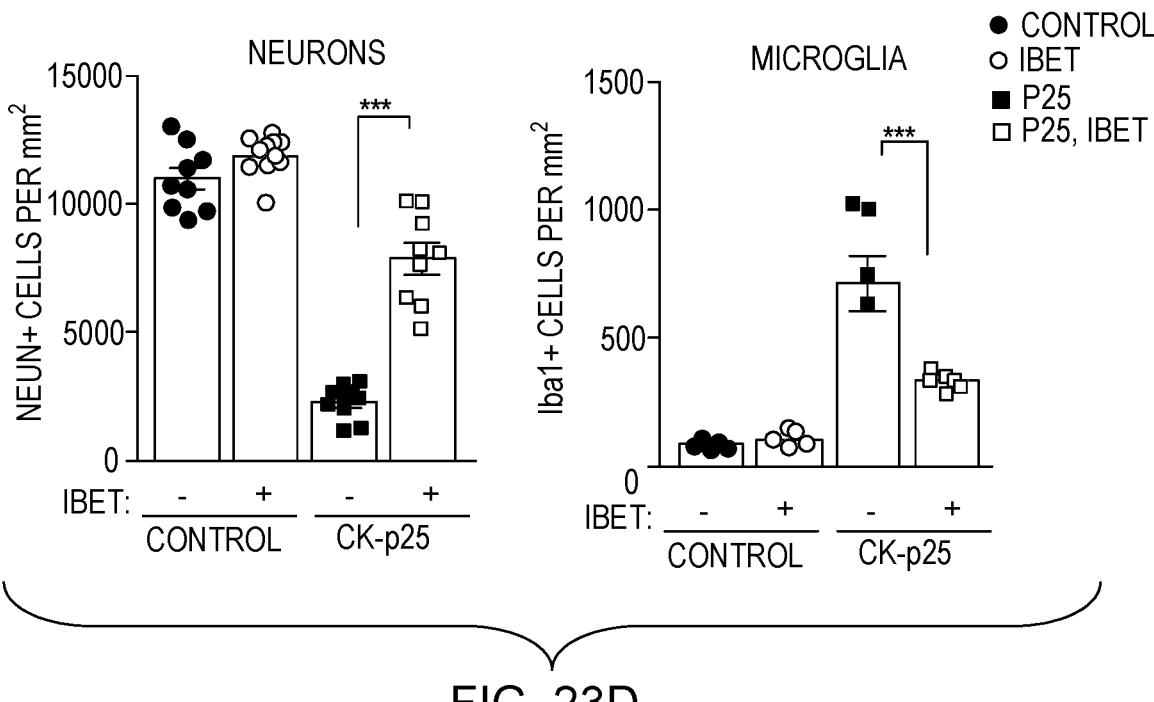

IBET treatment prevents neuronal death and neuroinflammation in a mouse model of Alzheimer disease (FIGS. 23C and 23D). Immunofluorescence of IBA1=microglia and NEUN=neurons in the dentate gyms after 7 weeks of P25 transgene expression shows a significant rescue of neuronal numbers and microglia activation in the hippocampus.

Figure 23E:
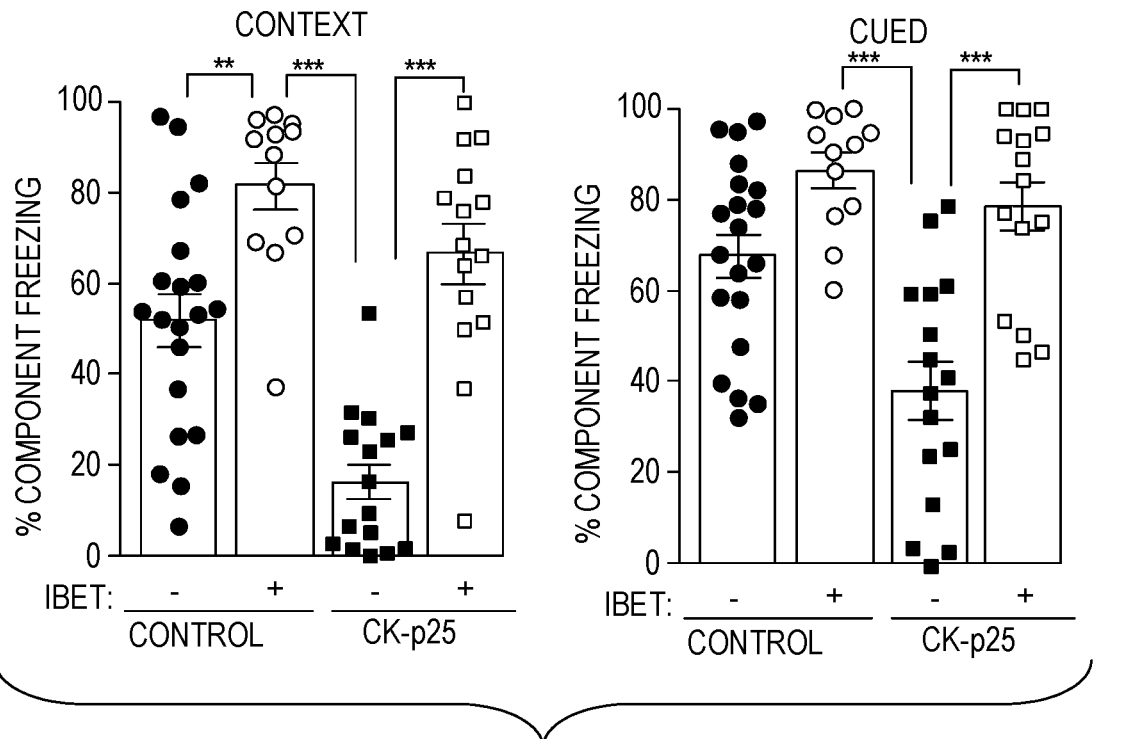

IBET treatment prevents loss of memory in a mouse model of Alzheimer disease (FIG. 23E). Classical fear conditioning assay was used to assess learning and memory in mice. Percent time freezing during contextual and cued recall one week after classic fear conditioning is shown.

Example 22

IBET858 Treatment Prevents Neurodegeneration In Vivo

Figures 24A, 24B, 24C, 24D:
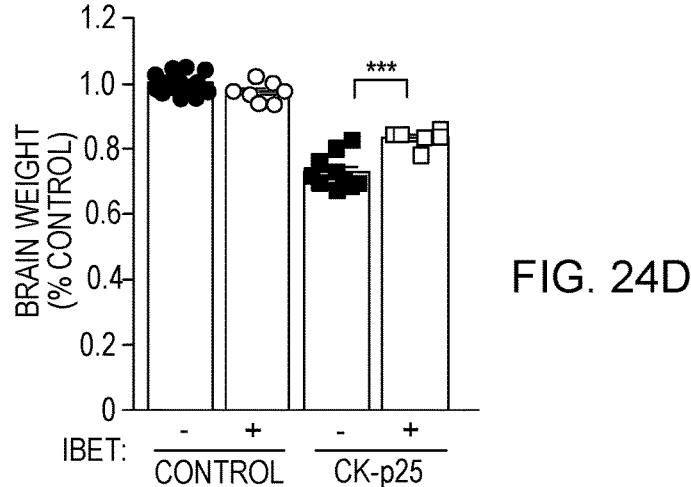
FIGS. 24A-24G illustrate that IBET858 treatment prevents neurodegeneration in vivo.

IBET treatment does not affect Caspase 3 expression (FIG. 24A). Gene expression levels for Casp3 are unaffected by 5 week IBET858 treatment in vivo. n=3, unpaired two-tailed t-test. IBET treatment does not affect p25 transgene expression (FIGS. 24B and 24C). Scheme of IBET treatment in P25 mouse is shown in FIG. 24B. To generate the p25 neurodegenerative mouse model, tetOCDK5R1/GFP were bred to CamK2a-tTA mice ("CK-p25"). Transgene overexpression was induced at 6 weeks of age by removing doxycycline from the diet. After two weeks, mice were daily injected with IBET858 (30 mg/kg, i.p.) or vehicle (FIG. 24C). Gene expression and protein levels of GFP reflecting transgene expression are unchanged.

Figure 24E:
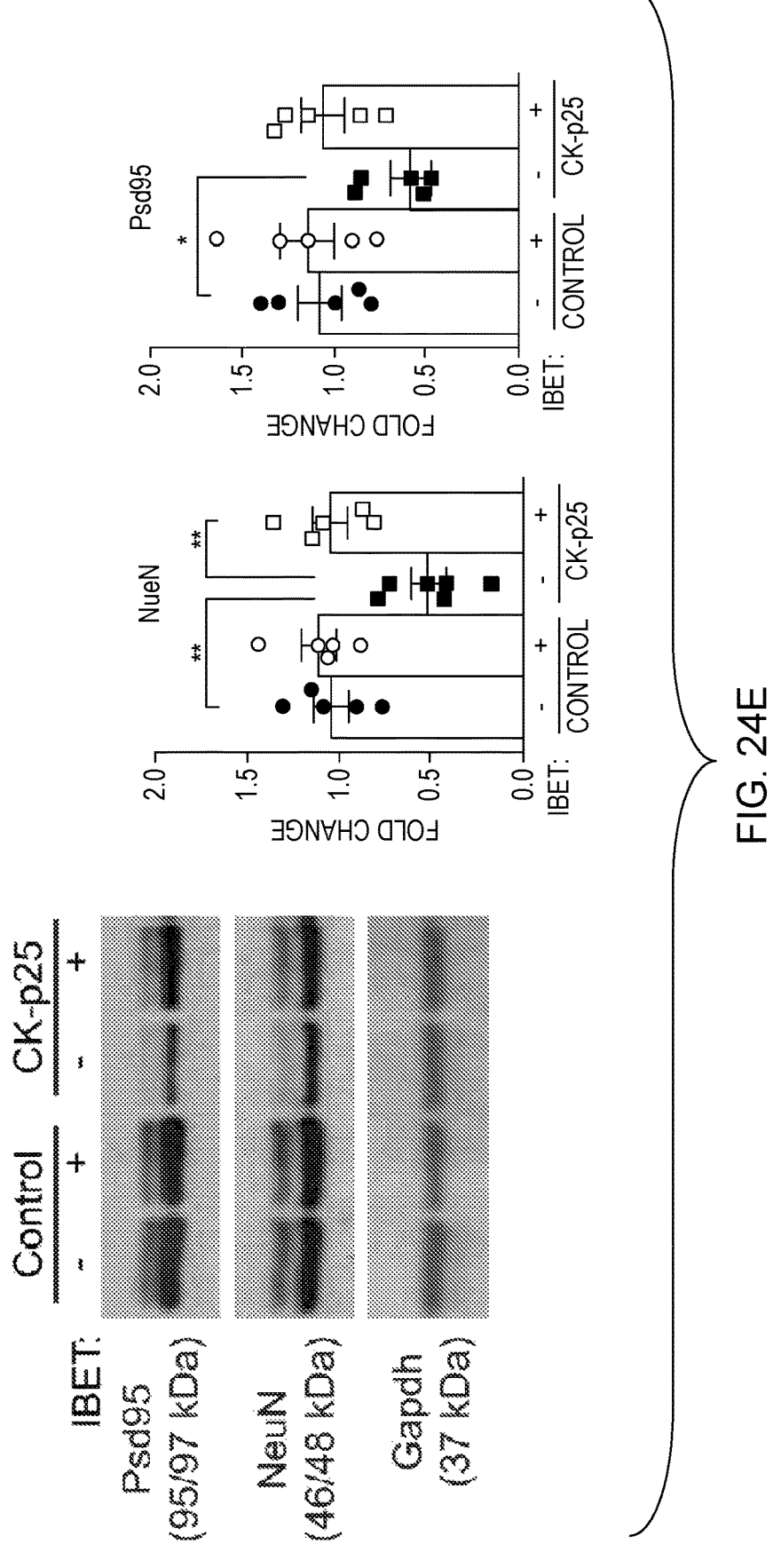

IBET treatment rescues neuronal loss in p25 model (FIG. 24D-24E). Brain weight of control and CKp25 mice treated with vehicle or IBET858 are shown as percentage of control brains (FIG. 24D). NEUN and PSD95 protein levels in the hippocampus of CK-p25 mice are restored by IBET858 treatment (FIG. 24E).

Figure 24F:
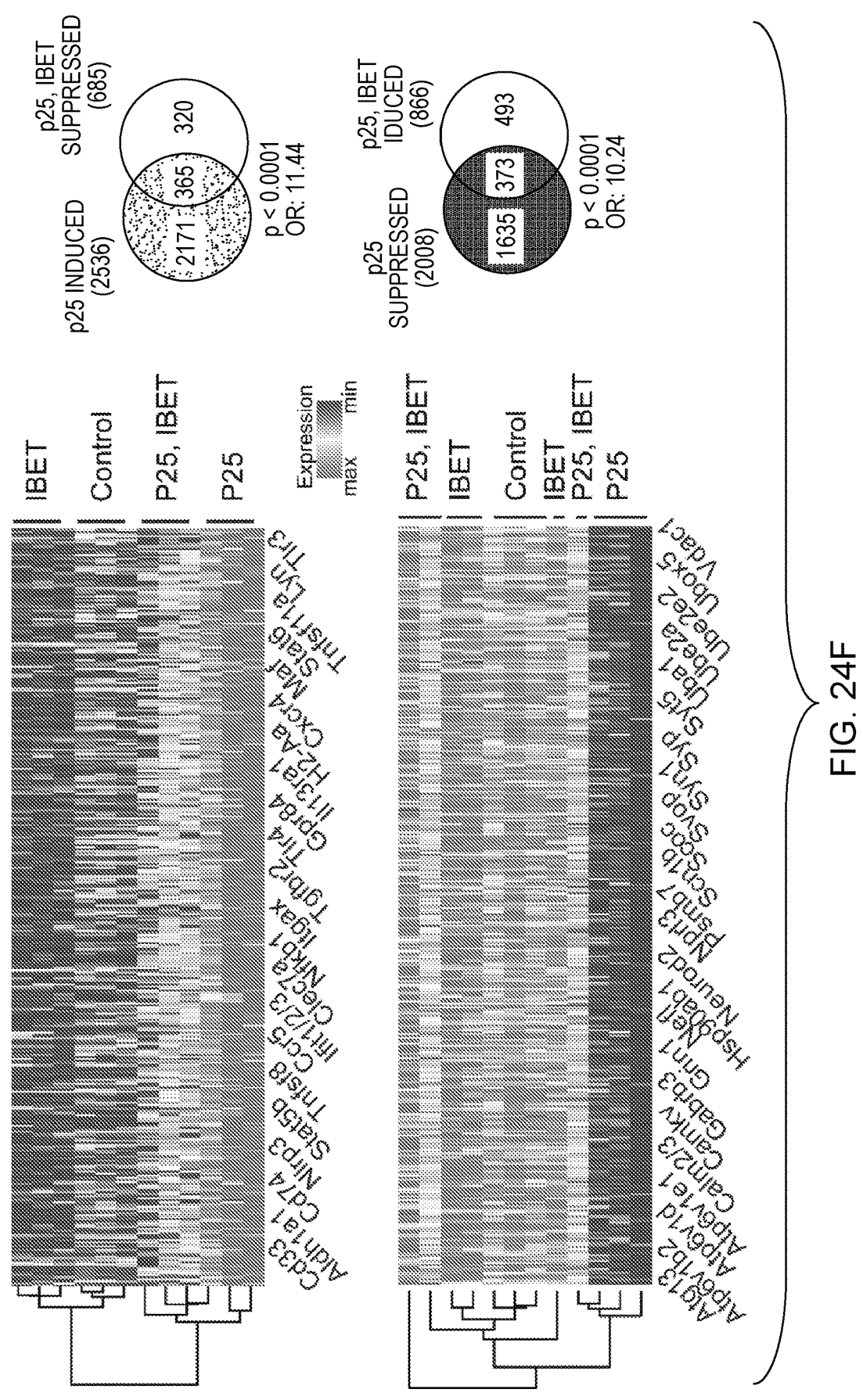

IBET treatment reduces inflammatory gene expression and rescues neuronal gene expression in p25 mice (FIG. 24F). Total RNA was isolated from the hippocampus of p25 overexpressing mice that were daily injected with IBET858 (30 mg/kg, i.p.) and sequenced (n=3 per group). Heatmaps shows normalized expression of 365 genes induced by P25 overexpression that are significantly suppressed by IBET858 and normalized expression of 373 genes suppressed by P25 overexpression that are significantly induced by IBET858.

Figure 24G:
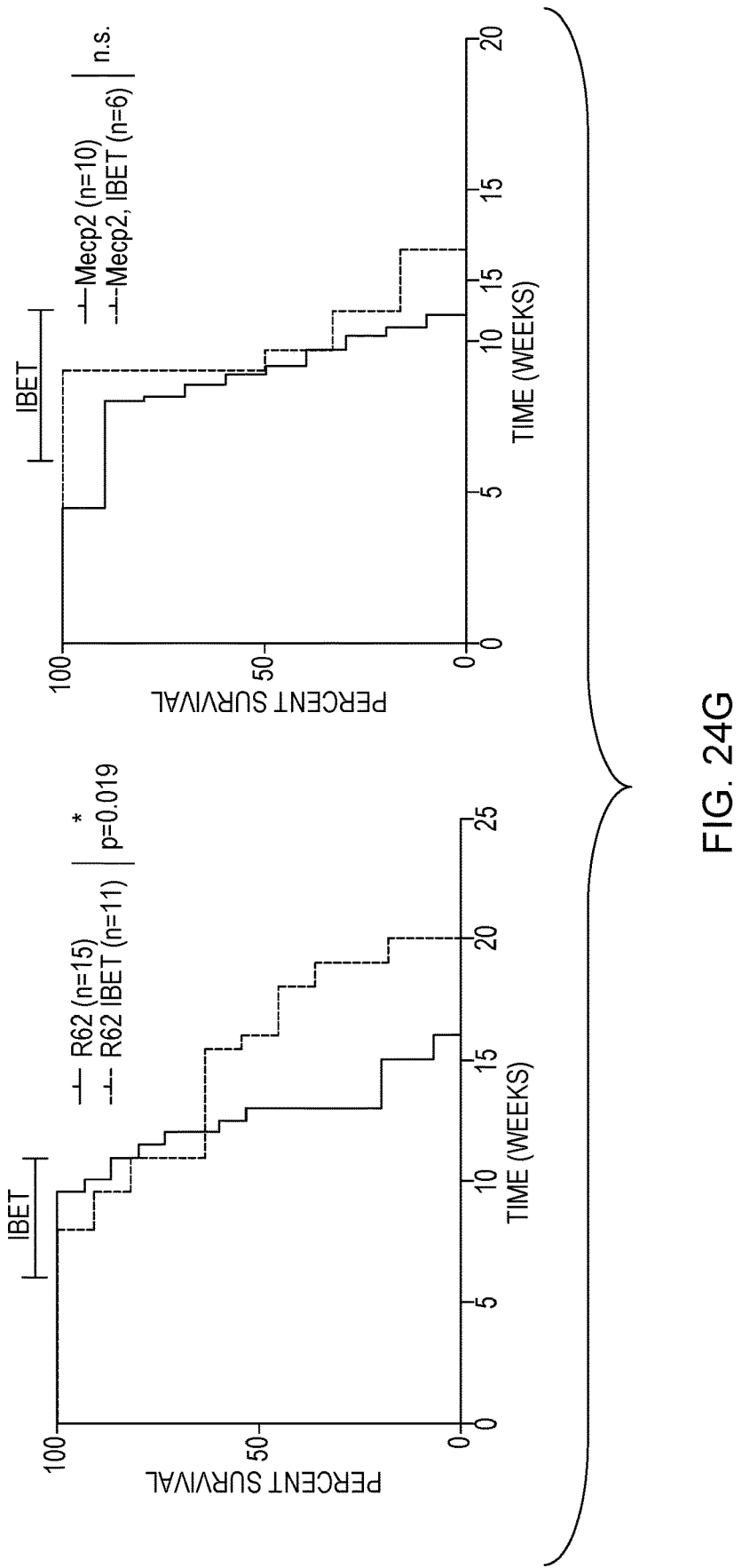

Temporary IBET treatment rescued survival in Huntington's (neurodegeneration) but not in Rett syndrome (neurodevelopmental syndrome) in mice (FIG. 24G). Survival graph of R6/2 mice treated daily with either vehicle or IBET858 (30 mg/kg, i.p.) at 6 weeks of age for 5 weeks. Survival graph of Mecp2 mice treated daily with either vehicle or IBET858 (30 mg/kg, i.p.) at 6 weeks of age for 5 weeks.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating Huntington's disease, the method comprising:
   administering IBET858 to a subject in need thereof.

2. The method of claim 1, wherein IBET858 is administered in an amount between about 10 mg/kg and about 100 mg/kg.

3. The method of claim 1, wherein IBET858 is administered once daily for about 1 week.

4. The method of claim 1, wherein said administering is carried out intraperitoneally, orally, parenterally, nasally, subcutaneously, intravenously, intramuscularly, intracerebroventricularly, intraparenchymally, by inhalation, intranasal instillation, by implantation, by intracavitary or intravesical instillation, intraocularly, intraarterially, intralesionally, transdermally, topically, intradermally, intrapleurally, intrathecally, or by application to mucous membranes.

* * * * *